US009834773B2

(12) United States Patent
Rigali et al.

(10) Patent No.: US 9,834,773 B2
(45) Date of Patent: Dec. 5, 2017

(54) METHODS AND MEANS FOR METABOLIC ENGINEERING AND IMPROVED PRODUCT FORMATION BY MICRO-ORGANISMS

(75) Inventors: Sebastien Rigali, Angleur (BE); Mannfred Friedrich Bruno Titgemeyer, Möhrendorf (DE); Gilles Philippus Van Wezel, Oegstgeest (NL)

(73) Assignees: Universiteit Leiden, Leiden (NL); University of Liège, Angleur (BE); Friedrich-Alexander-Universität Erlangen-Nürnberg, Erlangen (DE)

( * ) Notice: Subject to any disclaimer, the term of this patent is extended or adjusted under 35 U.S.C. 154(b) by 1682 days.

(21) Appl. No.: 12/224,050

(22) PCT Filed: Feb. 14, 2007

(86) PCT No.: PCT/NL2007/050061
§ 371 (c)(1),
(2), (4) Date: May 19, 2009

(87) PCT Pub. No.: WO2007/094667
PCT Pub. Date: Aug. 23, 2007

(65) Prior Publication Data
US 2011/0143394 A1 Jun. 16, 2011

(30) Foreign Application Priority Data
Feb. 14, 2006 (EP) .................................. 06075336

(51) Int. Cl.
*C12N 15/09* (2006.01)
*C12N 15/52* (2006.01)
*C07K 14/36* (2006.01)
*C12N 1/38* (2006.01)

(52) U.S. Cl.
CPC .............. *C12N 15/52* (2013.01); *C07K 14/36* (2013.01); *C12N 1/38* (2013.01)

(58) Field of Classification Search
USPC ....................................................... 536/23.7
See application file for complete search history.

(56) References Cited

FOREIGN PATENT DOCUMENTS

NL WO 2007/094667 A1 * 8/2007 ............. C12N 15/09
WO WO 2007/094667 A1 8/2007

OTHER PUBLICATIONS

Rigali et al in "Extending the classification of bacterial transcription factors beyond the helix-turn-helix motif as an alternative approach to discover new cis/trans relationships" (NAR, vol. 32, No. 11, Jun. 2004, pp. 3418-3426).*

Piette et al in "From Dormant to Germinating Spores of Streptomyces coelicolor A3(2): Niew Perspectives from the crp Null Mutant" (J of Proteome Research, 2005 vol. 4, No. 11, pp. 1699-1708.*
Rigali et al (J of Biol Chem, 2002 vol. 277; pp. 12507-12515.*
Cerdeno et al (Chemistry & Biology vol. 8 2001 pp. 817-829).*
Rigali et al "Extending the classification of bacterial transcription factors beyond the helix-turn-helix motif as an alternative approach to discover new cis/trans relationships" (Nucleic Acids Research, 2004, vol. 32, No. 11, pp. 3418-3426, published online Jun. 24, 2004).*
Zazopoulos et al "A genomics-guided approach for discovering and expressing cryptic metabolic pathways" (Nature Biotechnology, Feb. 2003 vol. 21, pp. 187-190).*
Zazopoulos et al Supplementary Methods, 2003.*
Piette et al., From dormant to germinating spores of Streptomyces coelicolor A3(2): New perspectives from the crp null mutant, Journal of Proteome Research, Oct. 1, 2005, pp. 1699-1708, vol. 4, No. 5.
Rigali, et al., Subdivision of the helix-turn-helix GntR family of bacterial regulators in the FadR, HutC, MocR, and YtrA subfamilies, Journal of Biological Chemistry, Apr. 12, 2002, pp. 12507-12515, vol. 277, No. 15.
Rigali et al., Extending the classification of bacterial transcription factors beyond the helix-turn-helix motif as an alternative approach to discover new cis/trans relationships, Nucleic Acids Research, Jun. 2004, pp. 3418-3426, vol. 32, No. 11.
PCT International Search Report, PCT/NL/2007/050061 dated Jun. 28, 2007.
Rigali et al., The sugar phosphotransferase system of Streptomyces coelicolor is regulated by the GntR-family regulator DasR and links N-acetylglucosamine metabolism to the control of development, Molecular Microbiology, Sep. 2006, pp. 1237-1251, vol. 61, No. 5.
Cerdeño et al., *Analysis of prodigine biosynthesis gene cluster of Streptomyces coelicolor A3(2): new mechanisms for chain initiation and termination in modular multienzymes*, Chem. & Bio. 8 (2001) 817-829.
Ley et al., Ecological and Evolutionary Forces Shaping Microbial Diversity in the Human Intestine, Cell (2006) 124, 837-848.

* cited by examiner

*Primary Examiner* — Catherine S Hibbert
(74) *Attorney, Agent, or Firm* — TraskBritt, P.C.

(57) ABSTRACT

Described are methods and means for metabolic engineering and improved product formation by a filamentous micro-organism or a low G+C gram-positive bacterium. Disclosed is that DasR and DasR binding sites play an important and universal role in the control of gene expression in micro-organisms. Based on this finding, provided are multiple useful applications, such as a method for regulating the expression of a gene of interest, a method for controlling metabolism, a method for decreasing undesired expression and many more. Moreover, provided are means that can be used to establish said methods: for example a micro-organism in which the DasR binding site in operable linkage with a particular gene has been modified to obtain increased or decreased expression of a protein (being a desired or undesired protein) encoded by said gene.

8 Claims, 32 Drawing Sheets

Figure 1A:
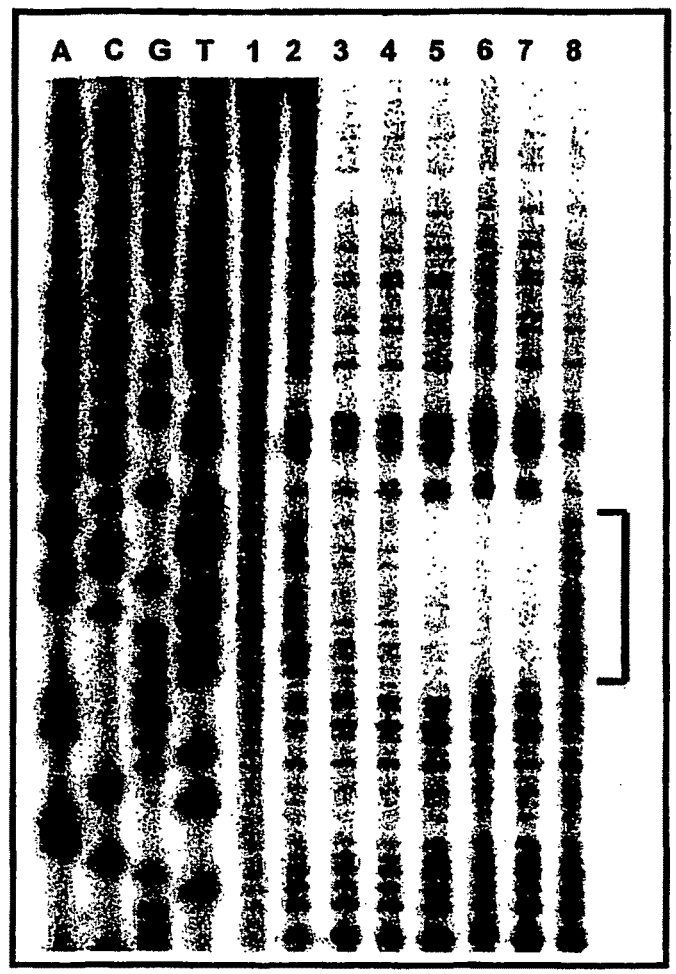

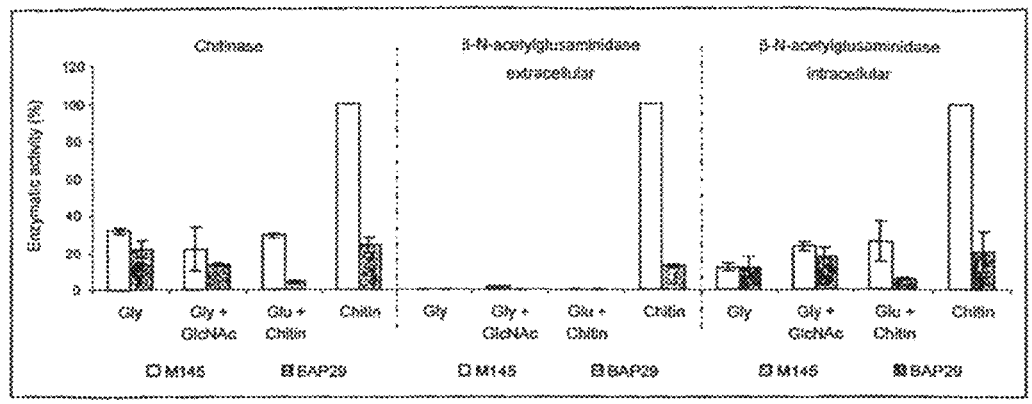
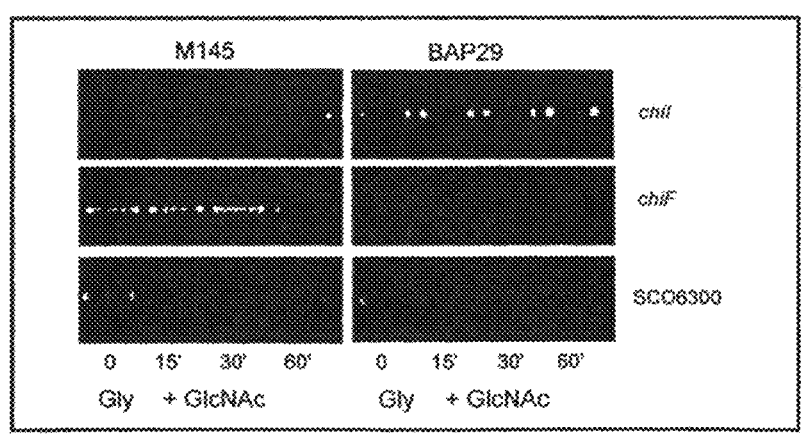
Figure 6

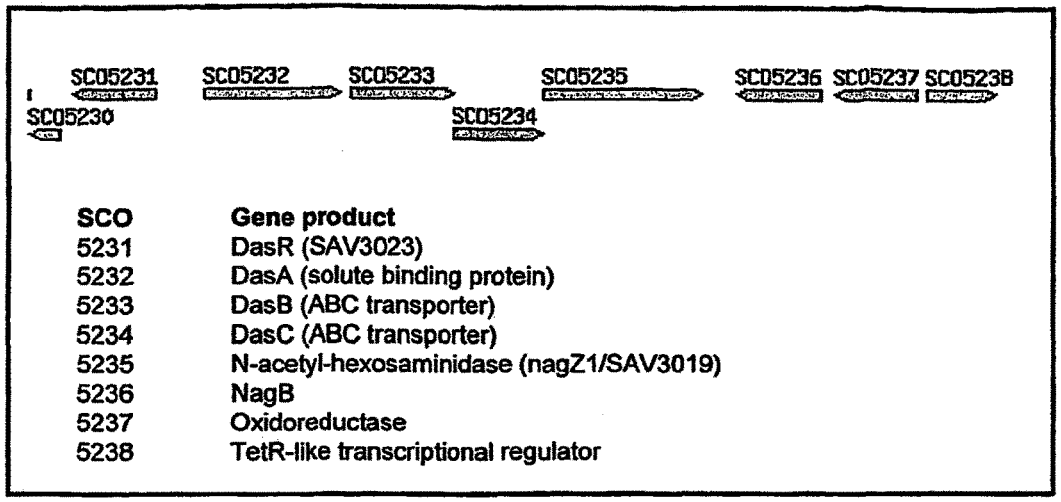
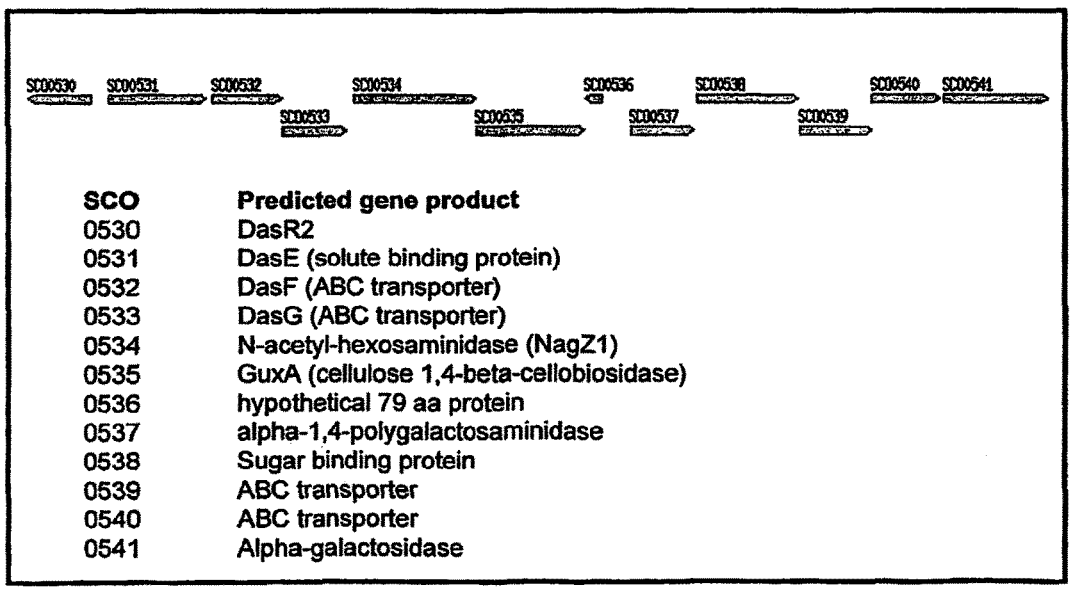
Figure 14C

19A

**DNA sequence of *S. clavuligerus* dasR**

ATGAGCACCGACGTCAGCAGTGCGGAGAACGAGGGTGGGGCGACCGTCCGTACCGCGCGCGT
GCCCAAGTACTACCGTCTGAAGAAGCATCTGCTCGACATGACCCGGACCCAGACGCCGGGCA
CACCGGTCCCGCCGGAGCGCACCCTGGCCGCCGAGTTCAACACCTCGCGCACGACGGTGCGC
CAGGCCCTGCAGGAGCTGGTGGTCGAGGGCCGCCTGGAGCGCATCCAGGGCAAGGGCACCTT
CGTCGCCAAGCCCAAGGTGTCGCAGGCGCTGCAACTCACCTCGTACACCGAGGACATGCGGG
CCCAGGGCCTCGAACCGACCTCTCAGCTGCTGGACATCGGCTACATCACCGCCGACGACCGG
CTCGCCGGGCTGCTGGACATCACGGCCGGCGGCCGGGTGCTGCGCATCGAGCGGCTGCGCAT
GGCCAACGGCGAGCCGATGGCCATCGAGACCACCCACCTCAGCGCGAAGCGCTTCCCCGCCC
TGCGCCGCTCCCTGGTGAAGTACACGTCCCTCTACACCGCGCTCGCCGAGGTGTACGACGTC
CATCTCGCCGAGGCCGAGGAGACCATCGAGACCTCCCTGGCCACCCCGCGCGAGGCCGGTCT
GCTCGGCACCGACGTCGGCCTGCCCATGCTGATGCTCTCCCGGCACTCCCAGGACCGCACCG
GCCAGCCGGTGGAGTGGGTCCGCTCGGTGTACCGGGGCGACCGCTACAAGTTCGTGGCCCGC
CTCAAGCGGCCCCAGGAC

19B

**Amino acid sequence of *S. clavuligerus* DasR**

```
  1 MSTDVSSAENEGGATVRTARVPKYYRLKKHLLDMTRTQTPGTPVPPERTL
 51 AAEFNTSRTTVRQALQELVVEGRLERIQGKGTFVAKPKVSQALQLTSYTE
101 DMRAQGLEPTSQLLDIGYITADDRLAGLLDITAGGRVLRIERLRMANGEP
151 MAIETTHLSAKRFPALRRSLVKYTSLYTALAEVYDVHLAEAEETIETSLA
201 TPREAGLLGTDVGLPMLMLSRHSQDRTGQPVEWVRSVYRGDRYKFVARLK
251 RPQD
```

Figure 19

```
              31              H    T    H              81
    scoel  LLDMTRTQTP GTPVPPERTL AAEFDTSRTT VRQALQELVV EGRLERIQGK
    saver  LLDMTETLPP GTPVPPERTL AAEFDTSRTT VRQALQELVV EGRLERIQGK
    sgris  LLDMTDTLPP GTPVPPERTL AAEFDTSRTT VPQALQELVV EGRLERIQGK
    scoll   LXMTETQAP GTPVPPERTL AAEFDTSRTT VRQALQELVV EGRLERIQGK
    svene     MTETLPP GTPVPPERTL AAEFDTSRTT VRQALQELVV EGRLERIQGK
    sgran     LTETLPP GTPVPPERTL AAEFDTSRTT VRQALQELVV EGRLERIQGK
    slimo        TLPP GTSVPPERTL AAKFDTSRTT VRQALQELVV EGRLERIQGK
    sdias           P GTPVPPERTL AAEFDTSRTT VRQALQELVV EGRLERIQGK
    scinn          PP GTPVPPERTL AAKGDTSRTT VRQALQELVV EGRLERIQGK
    sgold             GTPVPPERTL AAEFDTSRTT VRQALQELVV EGRLERIQGK
    sambo              TPVPPERTL PAEFDTSRTT VRQALQELVV EGRLERIQGK
```

Figure 20

US 9,834,773 B2

METHODS AND MEANS FOR METABOLIC ENGINEERING AND IMPROVED PRODUCT FORMATION BY MICRO-ORGANISMS

CROSS-REFERENCE TO RELATED APPLICATION

This is a national phase entry under 35 U.S.C. §371 of International Patent Application PCT/NL2007/050061, filed Feb. 14, 2007, published in English as International Patent Publication WO 2007/094667 A1 on Aug. 23, 2007, which claims the benefit under Article 8 of the Patent Cooperation Treaty to European Patent Application Serial No. 06075336.5, filed Feb. 14, 2006, the entire disclosure of each of which is hereby incorporated herein by this reference.

STATEMENT ACCORDING TO 37 C.F.R. §1.52(e)(5) SEQUENCE LISTING SUBMITTED ON COMPACT DISC

Pursuant to 37 C.F.R. §1.52(e), a compact disc containing an electronic version of the SEQUENCE LISTING has been submitted, the contents of which are hereby incorporated by reference. A second compact disk is submitted and is an identical copy of the first compact disc. The discs are labeled "Replacement Copy 1" and "Replacement Copy 2," respectively, and each disc contains one file entitled "P75940US00 revised.txt" which is 135 KB and was created on Aug. 9, 2010.

TECHNICAL FIELD

The invention relates to the field of biochemistry, molecular biology and microbiology. More specifically, the invention relates to methods and means for metabolic engineering and improved product formation by a filamentous microorganism or a low G+C gram-positive bacterium.

BACKGROUND

Filamentous micro-organisms are widely used as industrial producers of products such as antibiotics, anticancer agents, antifungicides and enzymes (Bennett, 1998; Demain, 1991; Hopwood et al., 1995). These organisms include the eukaryotic filamentous fungi (ascomycetes) and the prokaryotic actinomycetes (e.g. *Amycolatopsis, Nocardia, Thermobifido* and *Streptomyces*). The market capitalization for antibiotics and enzymes totals around 28 and 2 billion dollars per year, respectively. The soil-dwelling streptomycete *Streptomyces coelicolor* constitutes an important model system for the study of bacterial development and antibiotic production (Locci, 1986). *Streptomyces* colonies form a meshwork of vegetative mycelia from which aerial, spore-forming hyphae differentiate (Chater, 1998). Their morphogenesis is controlled by a complex, spatial and temporal genetic programming scheme that is switched on upon nutrient limitation (Schauer et al., 1988; Willey et al., 1991). Streptomycetes are principal protagonists in the recycling and mineralization of organic compounds of dead plants, fungi and insects, which are composed of the polysaccharides cellulose, xylan, and chitin, the most abundant carbon sources on earth (Hodgson, 2000). Hence, they also play a crucial role in our hunt for renewable sources. Interestingly, the study of genome sequences of actinomycetes has unveiled a surprisingly large number of cryptic antibiotic biosynthesis clusters and novel enzymes with industrial potential, thus offering new challenges for directed discovery of natural products, including drugs and enzymes (Hopwood, 2003). For example, a novel screening technique established that selective growth conditions can induce the normally dormant biosynthetic clusters for enediyne-type anti-tumour antibiotics (Zazopoulos et al., 2003).

Global regulation in bacteria involves the presence of pleiotropic-acting transcription factors that coordinate expression of genes, operons and regulons of diverse cellular processes (Martinez-Antonio and Collado-Vides, 2003). *Escherichia coli* has seven global transcription factors that together regulate approximately half of its genes. The most prominent one is the cyclic AMP receptor protein Crp directly controlling around 200 target genes (Bruckner and Titgemeyer, 2002; Gosset et al., 2004; Zhang et al., 2005). Crp represents the paradigm of a genetic regulator, its properties having attained textbook status and the Crp-cAMP mediated regulation of alternative carbon sources in *E. coli* is probably the most classical example to illustrate mechanisms that modulate genes expression. Uncovering such pleiotropic regulators is crucial for our understanding of the life style of bacteria and since the elucidation of the role of Crp in carbon catabolite repression (CCR), scientists devoted to carbon utilization always refers to this model to discuss the situation in other micro-organisms. Hence, the catabolite control protein CcpA is a similarly global regulator in low G+C Gram-positive bacteria, and controls more than 300 genes in *Bacillus subtilis* (Moreno et al., 2001; Titgemeyer and Hillen, 2002). CcpA controls genes involved in CCR, glycolysis, nitrogen assimilation, and phosphate metabolism (Bruckner and Titgemeyer, 2002).

So far, the study of carbon utilization in streptomycetes failed to discover a global regulator, and only resulted in examples of specific regulators controlling individual sugar regulons (Hindle and Smith, 1994; Parche et al., 1999; van Wezel et al., 1997). Interestingly, streptomycetes privileged another category of regulator/sensor element to globally mediate the shift from CCR to substrate induction, using MsiK as the master switch to provide energy to many sugar-specific ABC transporters (Hurtubise et al., 1995; Schlosser et al., 1997; Schlosser et al., 1999; Schlosser, 2000). However, a conserved regulatory motif identified upstream of few genes related to carbohydrate metabolism was still intriguing the research community devoted to carbon regulation, and maintained the idea that perhaps a global regulator would exist (Nothaft et al., 2003; Rigali et al., 2004; Studholme et al., 2004). Our in silico analysis of the helix-turn-helix GntR family (Rigali et al., 2002) recently identified new cis/trans regulatory codes that predict that DasR (SCO5231) regulates the phosphotransferase system specifically for the uptake of N-acetylglucosamine ($PTS^{Nag}$) (Rigali et al., 2004).

DISCLOSURE OF THE INVENTION

The present inventors disclose that the protein DasR is a regulatory master switch that is involved in multiple processes in micro-organisms.

In a first embodiment, the invention provides a method for identifying a gene which expression is controlled by a DasR-like protein, comprising comparing the DasR binding site consensus sequence with a candidate sequence and selecting the candidate sequence that has a matrix score of at least 5.0.

DasR proteins show a high homology in actinomycetes. All of these DasR proteins comprise a DNA binding motif, preferably a helix-turn-helix DNA binding motif. FIG. 14 shows an alignment of DasR homologues of actinomycetes. The DNA binding motif lies in roughly the first 80 amino acids of the protein (the most important signature is indicated by HTH, for Helix-turn-helix domain, in FIG. 14). FIG. 20 presents an alignment of DasR binding motifs from 10 different streptomycetes. The second part of the protein (roughly 80-255) has homology to the effector binding domain (EBD) of other GntR-type transcriptional regulators, and is therefore the place where binding of glucosamine-6-P is expected to take place.

A DasR-like protein is typically a DasR protein or a functional equivalent and/or a functional fragment thereof, preferably obtained/derived from an actinomycete, which DasR protein comprises the above outlined characteristics, i.e. comprising an DNA binding domain, an EBD and for example capable of binding to a (consensus) DasR binding site. Examples of DasR proteins are the DasR proteins presented in FIG. 14 (A or B or C). It is clear for the skilled person that for example a DasR protein from *Streptomyces coelicolor* can be modified without significantly changing the above outlined characteristics, for example, by introducing point mutations or (small) deletions. Hence, a DasR-like protein is a DasR protein, preferably obtained from for example *Streptomyces coelicolor, Streptomyces clavuligerus, Streptomyces avermitilis, Streptomyces griseus, Streptomyces scabies, Streptomyces* species 139 or *Thermobifido fusca*, possibly comprising mutations which do not interfere significantly with for example the binding of said DasR-like protein to a (consensus) DasR binding site (or DasR target site; the terms will be used interchangeable herein). The *Streptomyces clavuligerus* DasR sequence has been determined by the present inventors and the nucleic acid sequence as well as the amino acid sequence is depicted in FIG. 19. Hence, in yet another embodiment the invention provides an isolated or recombinant nucleic acid encoding the protein as depicted in FIG. 19B. In a preferred embodiment said nucleic acid is the nucleic acid as depicted in FIG. 19A.

To establish the degree of variation between the DNA binding motifs of DasR in various other streptomycetes, we determined the DNA sequence of the corresponding part of dasR from several other streptomycetes, and derived the amino acid sequence (FIG. 20). This shows that the DNA binding motif of *Streptomyces* dasR genes and their gene products are very highly conserved, and will bind the same binding sites in all streptomycetes. Therefore, in another preferred embodiment, the DNA binding motif of DasR matches that of the consensus sequence provided in FIG. 20.

Figure 14A:
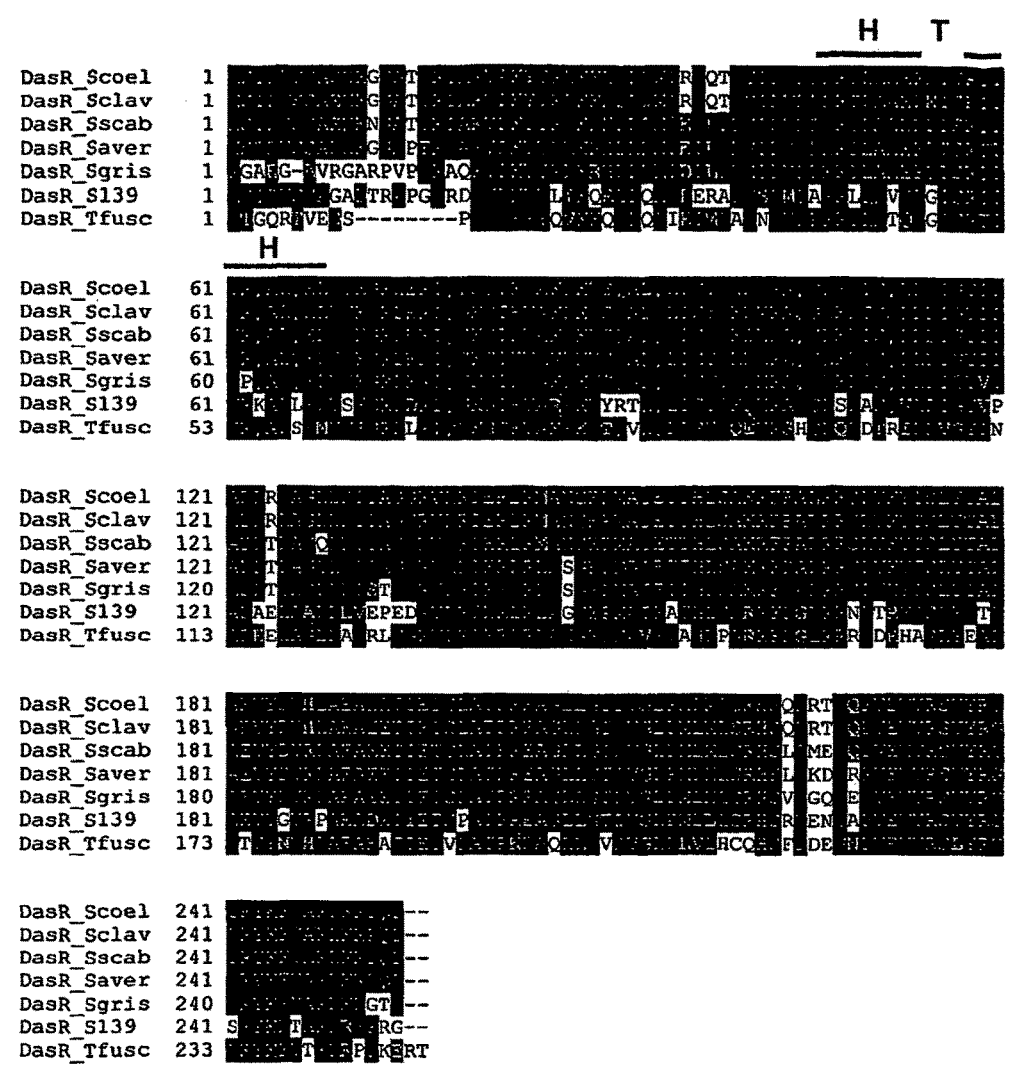
Figure 14B:
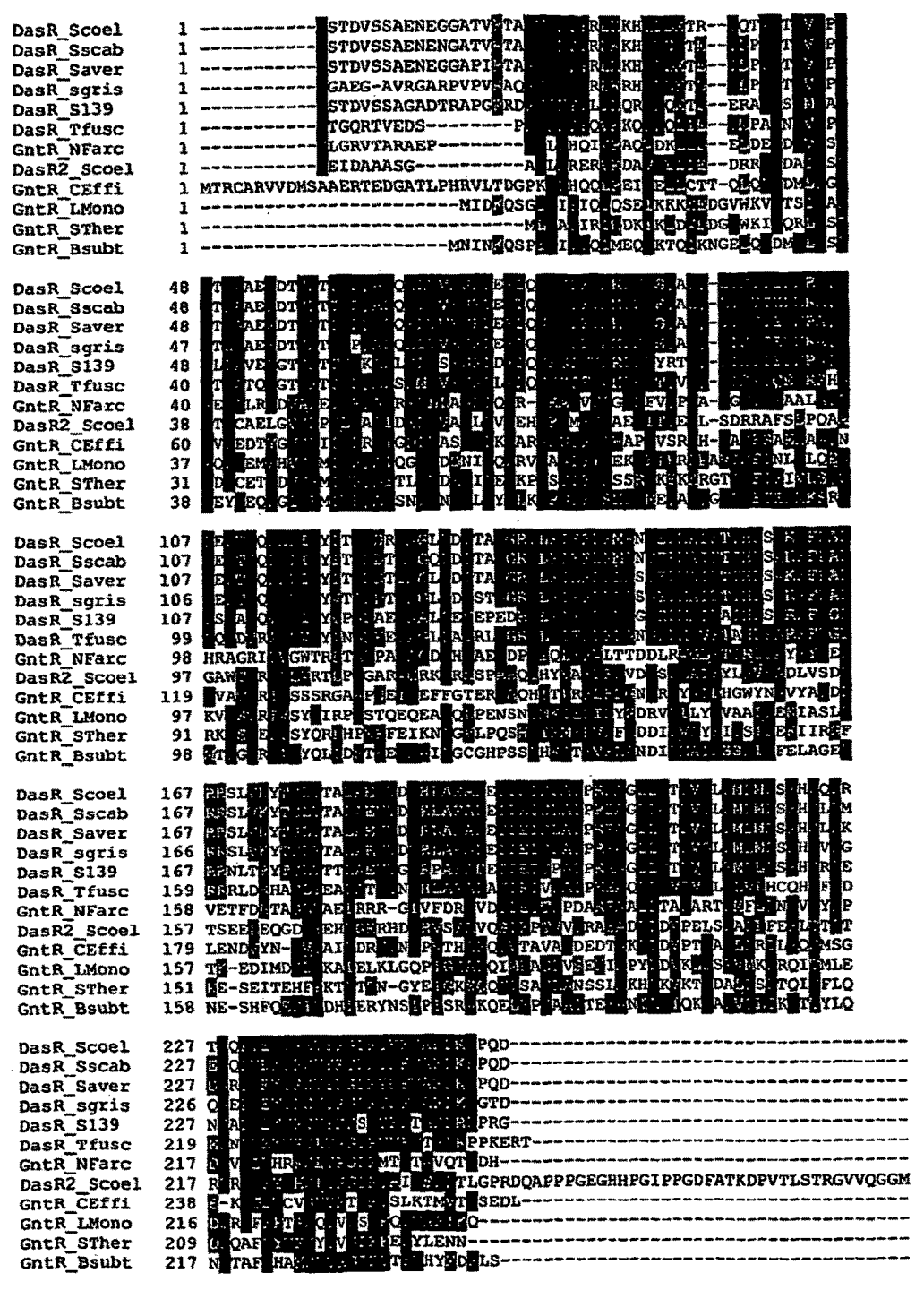

It is clear from FIG. 14A or B that a DasR-like protein cannot only be derived from an actinomycete, but also from a low G+C gram-positive bacteria, such as a *Streptococcus*. Moreover, from FIG. 14C it is clear that a method or a means according to the invention can also be performed/provided with a DasR homologue that was identified in *Streptomyces coelicolor*. Of course any suitable combination of these DasR-like proteins can also be made. Hence, the term DasR-like protein comprises not only a DasR protein from an actinomycete but also of a lower G+C gram-positive bacterium or a DasR homologue identified in any of the mentioned organisms.

The consensus sequence for the DasR binding site (dre) in actinomycetes is NN(T/A)GG(T/A)(C/G)T(A/G)N(A/T)C(C/A)(A/C)N (SEQ ID NO:1), where the most highly conserved nucleotides (occurring in more than 80% of all known DasR binding sites) are underlined. In a preferred embodiment, the consensus sequence is (A/T)N(T/A)GGTC TANACCAN (SEQ ID NO:2). In an even more preferred embodiment, the DasR binding site in actinomycetes is ACT GGTCTACACCA(G/C) NO:3. N can be any nucleotide (G, A, T or C) and two nucleotides between parentheses, for example (T/A) means that one of the mentioned nucleotides is present. In this particular example: T or A.

The consensus sequence for the DasR binding site in actinomycetes is also used to find sites in other bacteria, and preferably in other Gram-positive bacteria. The identified consensus sequence for *Bacillus* species is (A/G)N(T/A)(G/T)(G/A)T(C/A)TA(G/T)A(C/T)(C/A)(A/T)N(T/C) NO:4, that for *Lactococcus* species is A(T/A)(T/C)(G/A)(G/A) TATATA(C/T)(C/T)(A/G)(A/T)T NO:5, that for *Listeria* species is A(T/C)(T/C)(G/T)(G/A)T(A/C)TA(T/G)A(C/T)(C/A)(A/G)(A/G)T NO:6, and that for *Streptococcus* species is (A/T)(T/A)T(G/A)(G/T)(A/C)TA(T/G)N(C/A)(C/T)A(A/T)(T/A) NO:7. Again, N can be any nucleotide (G, A, T or C) and two nucleotides between parentheses, for example (A/G) means that one of the mentioned nucleotides is present. In this particular example: A or G. The invention thus provides a method for identifying a gene which expression is controlled by a DasR-like protein, comprising comparing the DasR binding site consensus sequence with a candidate sequence and selecting the candidate sequence that has a matrix score of at least 5.0, wherein said gene is present in an actinomycete, a bacillus, a lactococcus, a listeria or a streptococcus, preferably in combination with the corresponding identified DasR binding site consensus sequence.

Preferably, a candidate gene which expression is controlled by a DasR-like protein is determined by using a position weight matrix. The matrix score is determined according to the method described by Rigali et al. 2004 and in the materials and methods section of the present invention. In brief, a set of known DasR binding sites is used to perform a first search in the target organism, e.g. *Streptomyces coelicolor*. This results in new sites, which are experimentally validated. The obtained known targets are used to build a position weight matrix and this is used to predict the complete regulon of the target organism.

In a preferred embodiment, the candidate sequence has a matrix score of at least 7.0. Even more preferred is a score equal or higher than 9.0. All targets with a score above 9 that have been tested were found to be bound by DasR.

In yet an even more preferred embodiment, a method according to the invention further comprises testing whether the expression of said selected candidate sequence is indeed controlled by DasR. This is for example accomplished by testing the binding of a DasR-like protein to said selected identified candidate sequence.

The DasR binding sites are typically located upstream of the gene of interest. Table 2 shows the location of the DasR binding sites relative to the translational start site of the genes of interest. More specifically, in a non-limiting explanation, if the DasR binding site is located upstream of the promoter of the gene of interest, it is likely that it has an activating role on the transcription of said gene of interest. Conversely, if the DasR binding site overlaps the promoter or is located downstream of it, it is likely that it functions as a repressor of the transcription of said gene of interest. However, some proven DasR binding sites have been found inside a gene of interest. One example of this is the target gene malX2 of *S. olivaceoviridis* (Genbank Q8GBT8). In this case, the dre site (ACTGGTCTACACCACC) (SEQ ID NO:8) is almost identical to that of *S. coelicolor* malX2 (ACTGGTCTACACCAGT (SEQ ID NO:9); #3 in Table 2, matrix score of 16.2), but located between nt positions +36 and +51 downstream of the translational start site. Binding of DasR to this site was proven by EMSA on a double-stranded oligonucleotide. Therefore, it is clear that a DasR binding site can be functional both upstream and inside of a gene of interest.

With the above-described method, the present inventors have established (by using a novel and restrictive DasR binding site position weight matrix) that more than 200 genes are directly controlled by DasR, including regulons for central and secondary metabolism. These genes are derived from around 130 transcription units that are described in Table 2. The identified genes belong to different categories or kinds of genes, such as genes related to sugar or aminosugar metabolism or genes involved in polysaccharide degradation (summarised in FIG. 1B). The list of DasR targets also includes transcription factors and hence it is concluded that DasR is also involved in indirect transcriptional control. The diversity of genes that is controlled/regulated by DasR is large and hence the present inventors consider DasR to be a master switch in the regulation of gene expression in micro-organisms.

Now that the inventors have disclosed that DasR and DasR binding sites play such an important and universal role in the control of gene expression in micro-organisms, the invention provides multiple useful applications, such as a method for regulating the expression of a gene of interest, a method for controlling metabolism, a method for decreasing undesired expression and many more. Moreover, the invention also provides means that can be used to establish said methods: for example a micro-organism in which the DasR binding site in operable linkage with a particular gene has been modified to obtain increased or decreased expression of a protein (being a desired or undesired protein) encoded by said gene. Other examples of methods and means will be provided in the following description.

In one embodiment, the invention provides a method for regulating the expression of a gene of interest in a DasR-like protein comprising micro-organism, comprising providing said micro-organism with a compound capable of interfering with the binding of a DasR-like protein to a DasR-binding site in operable linkage with said gene of interest or a DasR-binding site in operable linkage with a gene whose product is involved in the expression of said gene of interest.

Said method for regulating the expression of a gene of interest may be a method for increasing the expression of a gene of interest or a method for decreasing the expression of a gene of interest. This is, amongst others, dependent on whether expression of said gene of interest is desired or undesired. In case expression of a gene of interest is desired, expression is preferably increased and in case expression of a gene of interest is not desired (i.e. is undesired), expression is preferably decreased. Whether the action of said compound capable of interfering with the binding of a DasR-like protein to a DasR-binding site must result in increased or decreased binding between said protein and said site, depends on whether expression of said gene of interest is, upon binding of a DasR-like protein to a DasR binding site, repressed or activated. It is clear from Table 2 (as well as from FIG. 4), that the expression of some genes is repressed upon binding of a DasR-like protein to a DasR-binding site (for example #1, 3, 5, or 7 of Table 2) and that expression of some other genes is activated upon binding of a DasR-like protein to a DasR-binding site (for example #13 of Table 2). All the necessary information to decide the right course of action is presented in the present application. Moreover, information on whether expression of a particular gene or operon is activated or repressed is expanded by using micro-array approaches. One example of such an experiment is the comparison of the expression of genes in a DasR-like protein comprising micro-organism to the expression of genes in a DasR-like protein (null) mutant comprising micro-organism. Another example is a comparison of the expression of genes in a DasR-like protein comprising micro-organism grown in the presence or absence of an inducer molecule (e.g. glucosamine-6-P). Yet another example is the use of the so-called ChIP-on-chip approaches, where DasR-like protein bound DNA fragments are hybridized to microarrays. This will identify the targets directly bound by DasR.

As will be discussed in more detail later, a DasR-like protein comprising micro-organism is a micro-organism that comprises a DasR-like protein or an organism that is capable of expressing said DasR-like protein from a nucleic acid encoding said protein. Moreover, said micro-organism may be an organism that is by nature capable of expressing said DasR-like protein or it may be a micro-organism which has been genetically modified to produce DasR-like protein. Moreover, it is also possible to provide a micro-organism that is already capable of expressing (endogenous) DasR-like protein with a further nucleic acid that enables production of more DasR-protein. Such an additional nucleic acid encoding a DasR-like protein may encode the endogenous DasR or it may encode a heterologous DasR-like protein.

As already outlined above the compound capable of interfering with the binding of a DasR-like protein to a DasR-binding site may result in increased or decreased binding of a DasR-like protein to said binding site, i.e. interfering must be understood to read on increasing the binding as well as on decreasing the binding between said protein and said binding site.

As also already outlined above, DasR-regulated genes are very diverse and may range from a gene involved, in for example, a metabolic process as well as a gene which is a transcription factor. Moreover, a lot of processes in an organism involve so-called cascades of (enzyme) reactions. Hence, the DasR-binding site may be in operable linkage with a particular gene of interest (i.e. the direct end product) or the DasR-binding site may be in operable linkage with a gene whose product is involved in the expression of said gene of interest (for example an intermediate in a cascade or a transcription factor involved in the gene expression of a gene of interest). Hence, a method according to the invention is capable of directly regulating expression of a gene of interest or a method according to the invention is capable of indirectly regulating expression of a gene of interest.

Direct regulation includes a situation in which the gene of interest is a single transcription unit or locus, or where the gene of interest is part of an operon.

Indirect regulation also includes a situation in which a DasR-like protein regulates the expression of a regulator (protein or nucleic acid) whereby the regulator is capable of regulating expression of another gene. Said regulator may be responsible for regulating expression of a target gene or a target operon or a target regulon. This part of the invention is supported by the finding that Table 2 also includes 16 transcription factors (#27, 31, 46, 51, 56, 62, 67, 71, 77, 81, 84, 105, 119, 129, 130 and 131), supporting an extensive level of indirect transcriptional control by DasR.

There are multiple ways in which a compound capable of interfering with the binding of a DasR-like protein to a DasR-binding site may be provided to a micro-organism. This is also dependent on the type of compound (which will be discussed in more detail hereunder). If the compound capable of interfering with the binding of a DasR-like protein to a DasR-binding site is for example a small and/or chemical compound which is taken up (for example via endocytosis or fagocytosis or actively transported across the membrane) by said micro-organism, said compound is simple added to the surroundings (for example growth medium) of said micro-organism. If the compound capable of interfering with the binding of a DasR-like protein to a DasR-binding site is a nucleic acid (DNA or RNA), said micro-organism is preferably provided (for example via transfection or transduction or transformation) with said nucleic acids with any of the well known techniques therefore.

As already mentioned the compound capable of interfering with the binding of a DasR-like protein to a DasR-binding site may be very diverse in nature, for example a small (chemical) molecule, metal or ion, a signalling molecule such as a γ-butyrolactone or of peptide origin, a non-ribosomal peptide, a protein or a nucleic acid. In one of the preferred embodiments, said compound is a genetic compound, i.e. a nucleic acid (DNA or RNA). One example of a suitable nucleic acid is a dasR nucleic acid, i.e. a nucleic acid encoding a DasR-like protein (or a functional fragment or derivative thereof). Even more preferably, such a dasR nucleic acid is under control of a strong or inducible promoter. If expression of a gene of interest in operable linkage with a DasR-binding site is normally activated upon binding of a DasR-like protein, the presence of more (for example over-expressed DasR) is capable of further inducing/increasing/activating expression of said gene of interest. If expression of a gene of interest in operable linkage with a DasR-binding site is normally repressed upon binding of a DasR-like protein and if expression of said gene of interest results in an undesired product, the presence of more (for example over-expressed DasR) is capable of further reducing/decreasing/repressing expression of said gene of interest and the amount of undesired product is at least in part (further) decreased. A second example of a suitable nucleic acid is a nucleic acid encoding a mutant DasR-like protein, for example a DasR-like protein with reduced binding capacity for a DasR-binding site or a DasR-like protein with improved binding capacity for a DasR-binding site or a DasR-like protein that is no longer capable of being activated by a so-called inducer (for example a DasR-like protein mutated in or lacking an effector binding domain). Based on the information provided in FIG. 14, a skilled person can easily determine which part of a DasR protein can be modified to obtain a certain result. For example, mutations (deletions, insertion, (point)mutations) in the DNA binding part will have an effect on the binding capacity of such a modified DasR-like protein to a DasR-binding sequence. The effect of provided mutations are easily tested by a binding assay. A third example of a suitable nucleic acid is a nucleic acid containing a modified DasR-binding site (either with decreased of increased DasR-protein binding capacity). Preferably such a nucleic acid is placed into the genome of a particular micro-organism in such a way that the DasR-binding site normally present in front of a gene of interest is exchanged with the modified binding site. Moreover, a gene of interest whose expression is not regulated by DasR can be modified to include a (modified) DasR-binding site upstream of or inside the gene. Optionally, the relevant micro-organism is further provided with DasR-like protein (as a protein or as a nucleic acid encoding said DasR-like protein) and the expression of said gene is now controlled by DasR. The use of a (modified) DasR-binding site typically involves a homologous recombination process. Techniques to obtain homologous recombination are known by the skilled person and hence no further details are provided on said subject matter. A fourth example of a suitable nucleic acid is a nucleic acid that represents a modified dasR promoter. The endogenous expression of DasR is autoregulated. If DasR protein is present in certain amounts it will auto-repress its own expression until the amount of DasR is below a certain threshold level. Modifying the DasR-promoter to a promoter which is not autoregulated increases the amount of available DasR protein and hence especially expression of a gene of interest which is increased upon binding of a DasR-like protein to a DasR binding site in operable linkage with said gene is increased. It is clear to a skilled person that the use of such a nucleic acid preferably involves a recombination process in which the originally present dasR promoter is (at least partly) exchanged for the modified dasR promoter. A fifth example of a suitable nucleic acid is related to the third example and comprises a nucleic acid which arranges for an additional or a deleted DasR binding site. The introduction of additional DasR binding sites in operable linkage with a gene of interest is especially useful in cases of gene expression which is activated upon DasR binding and the deletion of a DasR binding site is for example useful in cases of gene expression that are repressed upon DasR binding but whose expression is desired.

Yet another example of a very useful compound capable of interfering with the binding of a DasR-like protein to a DasR-binding site is an inducer. Such an inducer is very useful in case the expression of a gene of interest is repressed upon binding of a DasR-like protein to a DasR binding site in operable linkage with a gene of interest. Preferably, such an inducer is a derivative of a sugar. As will be disclosed within the experimental part, glucosamine-6-phosphate (the term glucosamine-6-P will be used interchangeably herein) is a very potent inducer of DasR-repressed gene expression. In a preferred embodiment, N-acetylglucosamine (or a derivative or a multimer thereof) is added to the environment of a micro-organism and said N-acetylglucosamine will be converted upon transport into said micro-organism, to glucosamine-6-phosphate. The use of such an inducer is extremely advantageous, because it does not involve any genetic manipulation of the micro-organism at all, but it simple involves manipulation from the outside (i.e. addition of N-acetylglucosamine or a derivative or a multimer thereof).

The present inventors have identified two possible transporters for N-acetylglucosamine, namely the adjacent genes nagE1 and nagE2. As described in the experimental part, mutants of these genes have been constructed and it turns out that nagE2 is the gene encoding a transporter for N-acetylglucosamine. This finding provides even more examples of useful compounds capable of interfering with the binding of a DasR-like protein to a DasR-binding site. For example, if a DasR-like protein comprising micro-organism as used in any of the methods of the invention is incapable of producing (functional) NagE2, said micro-organism is not capable of responding to externally provided and/or formed/produced N-acetylglucosamine (GlcNAc) and DasR will stay active (in case of a DasR repressed gene, DasR remains bound). In another example, the amount of GlcNAc transporter is increased, this is for example obtained by providing a micro-organism with a nucleic acid (preferably nagE2) encoding said GlcNAc transporter. In this case more GlcNAc will be transported into a cell and as a consequence more glucosamine-6-phosphate will be produced. As a result DasR-repressed expression will be decreased and expression of a gene which expression is normally repressed will be increased. In yet another example, the gene encoding the GlcNAc-transported is mutated such that only a variant of GlcNAc is transported into the cell.

Yet another example of a compound capable of interfering with the binding of a DasR-like protein to a DasR-binding site is the use of an antibody (or a fragment thereof, for example the binding part) that binds to either DasR or to the DasR binding site and thus at least in part blocks the binding of DasR to a DasR binding site.

It is clear to the skilled person, that any of the above-mentioned compound capable of interfering with the binding of a DasR-like protein to a DasR-binding site may optionally be combined.

As already described the kind of genes whose expression is regulated by DasR is very diverse. For a summary of the different categories of genes regulated by DasR see also FIG. 1B. One group of such genes, are genes that are involved in metabolic processes. Therefore, in yet another embodiment, the invention provides a method for controlling metabolism in a DasR-like protein comprising micro-organism, comprising regulating the binding of a DasR-like protein to a DasR-binding site in operable linkage with a gene whose product is part of a metabolic route. In a preferred embodiment, the binding of a DasR-like protein to a DasR-binding site in operable linkage with a gene whose product is part of a metabolic route is regulated by providing to said micro-organism a compound capable of interfering with the binding of said DasR-like protein to said DasR-binding site.

It is clear that the compound capable of interfering with the binding of a DasR-like protein to a DasR-binding site in operable linkage with a gene whose product is part of a metabolic route may be very diverse in nature (as already discussed above), for example a small (chemical) molecule, metal or ion, a signalling molecule such as a γ-butyrolactone or of peptide origin, a non-ribosomal peptide, or a protein or a nucleic acid. In one of the preferred embodiments, said compound is a genetic compound, i.e. a nucleic acid. Examples of suitable nucleic acids are already given above. In case expression of such a metabolic gene is decreased upon binding of DasR protein to a DasR binding site in operable linkage with said gene, it is also possible (as discussed above) to use an inducer, such as glucosamine-6-phosphate.

Depending on whether expression of said particular gene whose product is part of a metabolic route (or involved in metabolism) is repressed or activated upon binding of DasR to a DasR binding site in operable linkage with said particular gene, the skilled person is capable (based on the herein given guidance) to decide if the binding between DasR protein and a DasR binding site in front of said particular gene must be increased or decreased and moreover, the application provides multiple example of how to increase or decrease binding.

Examples of genes whose product are part of a metabolic route are not-limiting mentioned in Table 2. One example relates to genes involved in glutamate/glutamine metabolism. These are summarised in Table 4. These genes encode enzymes involved in the synthesis or degradation of Glu/Gln, but also tRNA molecules required for the translation of codons that specify incorporation of a Glu or Gln amino acid into a polypeptide synthesized by the ribosome.

Figure 5:
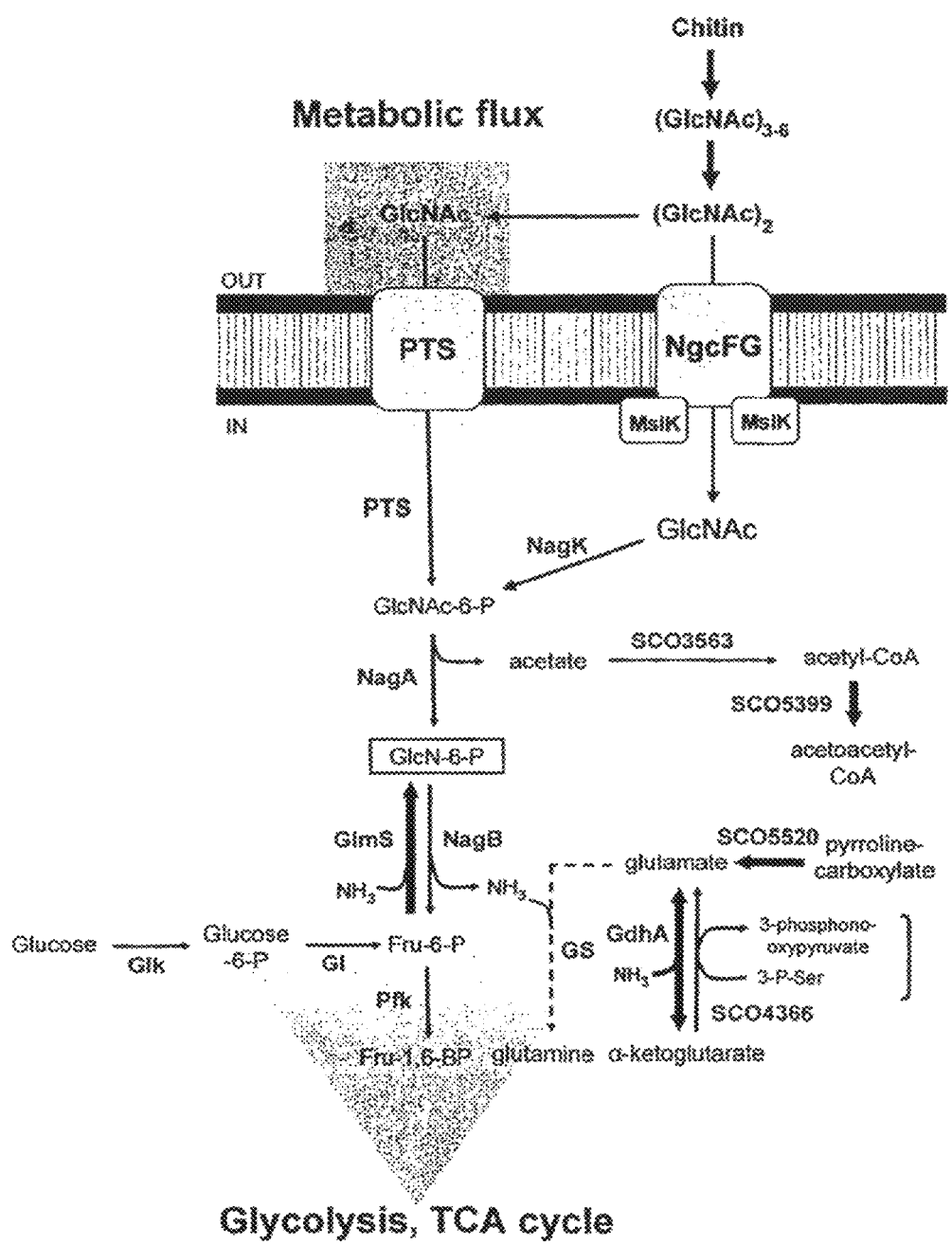

A second example involves the metabolism of N-acetylglucosamine and related molecules. The pathway for N-acetylglucosamine is linked to that of glutamate, as shown in FIG. 5. Examples include the chitinolytic genes that convert the polymer chitin into N-acetylglucosamine (e.g. #7, 11, 12, 14, 19, 23, 25, 26 in Table 2), the PTS that transports N-acetylglucosamine into the cell (e.g. #1, 2, 3, 5 in Table 2), and the metabolic genes nagK, nagA (#10, operon) and nagB (#15).

Another nucleic acid relating to glutamate and N-acetylglucosamine metabolism is an RNA ribozyme, which processes the glmS gene in *Bacillus subtilis* (Winkler et al., 2004), and therefore predictable in other gram-positive bacteria such as actinomycetes. The glmS gene is a target of regulation by DasR (#86 in Table 2), and its gene product GlmS uses glutamine and fructose-6-P to form glucosamine-6-P. Processing of the glmS transcript is required for activation of the mRNA. Excitingly, the ribozyme is activated by glucosamine-6-P, which is the metabolic product of the GlmS enzyme. We have shown here that glucosamine-6-P is also the inducer molecule of DasR. Additional data by Winkler et al. showed that the ribozyme responds to the metabolic state and represses the glmS gene in response to rising glucosamine-6-P concentrations.

A third example relates to energy provision, such as enzymes involved in glycolysis (e.g. phosphofructokinase, #74 in Table 2; see also fructose-1,6-bisphosphatase, fructose-1-phosphate kinase and phosphoenolpyruvate synthase in Table 8) and acetyl-CoA formation or processing (e.g. acetoacetyl-CoA synthetase, #12 Table 2; acyl-CoA dehydrogenase, #25 in Table 2; and acetoacetyl-CoA thiolase (ThiL; activated by DasR; FIG. 4). Acetyl CoA is a crucial starting compound of the TCA cycle. Surprisingly, DasR also controls energy provision directly via the control of the nuo operon encoding the subunits of NADH dehydrogenase (#104 in Table 2; two DasR binding sites). This enzyme is the first of the electron transport (redox) chain.

Many of the examples mentioned for Table 2 are also part of Tables 4-7 and 9 that refer to target genes occurring in low G+C Gram-positive bacteria. Therefore, the metabolic engineering approach also applies in a similar fashion to this important class of bacteria, which includes *Bacillus, Lactococcus, Lactobacillus, Streptococcus* and *Listeria*.

The metabolic processes or routes that may be influenced according to a method of the invention are amino acid metabolism, peptidoglycan degradation or synthesis, fatty acid biosynthesis, transport of metabolites, degradation of extracellular polysaccharides (preferably polymers of glucose, fructose, galactose, N-acetylglucosamine, glucosamine, mannose or chitobiose, or combinations thereof) or nitrogen metabolism.

In a preferred embodiment, the invention provides a method for controlling metabolism in a DasR-like protein comprising micro-organism, comprising regulating the binding of a DasR-like protein to a DasR-binding site in operable linkage with a gene whose product is part of a metabolic route, wherein the expression of said gene results in the presence of a corresponding product that directs the metabolism in said micro-organism to or from glycolysis or to or from the citric acid (TCA) cycle.

Figure 17:
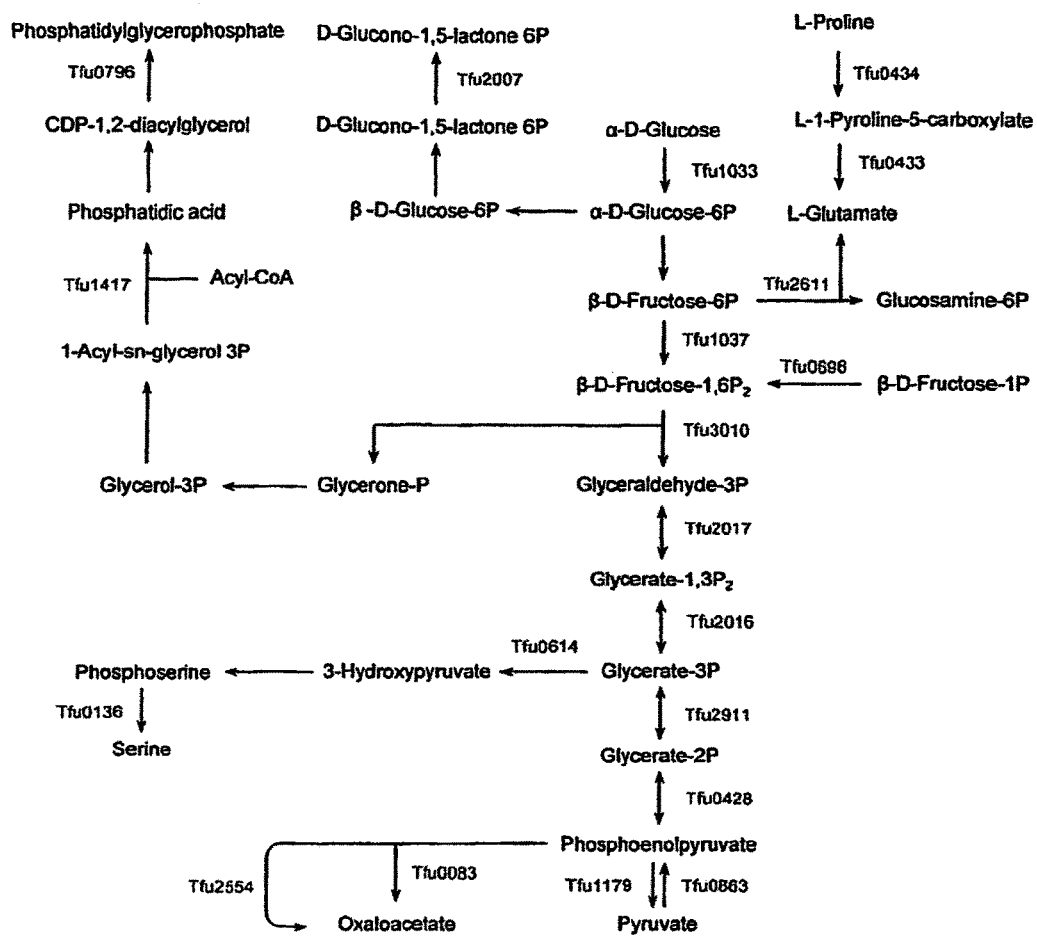

The inventors have identified a particularly surprising example of such metabolic control in *Thermobifido fusca*, where all the steps of glycolysis are controlled by a DasR-like protein (FIG. 17 and Table 9). Therefore, it is clear to the skilled person that modifying, for example, the activity of DasR will allow the control of glycolysis and TCA cycle in the microorganism.

Other DasR-regulated genes that are identified by the present inventors, include antibiotics or antibiotic clusters, (commercial interesting) enzymes and so on.

Therefore, the invention provides in yet another embodiment a method for obtaining expression of a product of interest in a DasR-like protein comprising micro-organism, comprising providing said micro-organism with a compound capable of interfering with the binding of a DasR-like protein to a DasR-binding site in operable linkage with a gene encoding said product of interest or a DasR-binding site in operable linkage with a gene involved in the production of said product of interest.

Interfering with the binding of a DasR-like protein to a DasR-binding site in operable linkage with a gene encoding said product of interest or a DasR-binding site in operable linkage with a gene involved in the production of said product of interest may be such that the binding is at least in part inhibited or it may be such that the binding is at least in part increased. With "at least in part" is meant that there is a detectable difference between the situation in which no compound is added and the situation in which said compound is added. In a preferred embodiment, the binding of a DasR-like protein to a DasR binding site is essentially completely inhibited or the binding is essentially irreversible.

Different compounds capable of influencing the binding between DasR protein and a DasR binding site in operable linkage with a gene that encodes a product of interest are already discussed above and include a genetic compound (i.e. a nucleic acid, optionally stably integrated in the genome of the corresponding micro-organism or existing as an episomal nucleic acid in said micro-organism) or a protein or a small hormone-like signalling molecule or for example a small (chemical) compound. In another preferred embodiment, said compound is an inducer of a DasR-regulated process. Such an inducer is especially useful in case of DasR-repressed expression. An example of such an inducer is glucosamine-6-phosphate or a functional equivalent or a functional fragment thereof. Preferably, N-acetylglucosamine (or a derivative or a multimer thereof) is provided to the medium of a micro-organism that is used for production of said product of interest.

A suitable compound is selected depending on the fact whether the expression of the gene corresponding to said product of interest is activated or repressed upon binding of a DasR-protein to a DasR binding site in operable linkage with said gene. In case expression is activated upon binding, it is desired to improve the binding of DasR protein to the binding site in operable linkage with the relevant gene, to enhance or improve or obtain expression. This is for example accomplished by adding DasR binding sites in operable linkage with the relevant gene, or by mutating the binding site (higher matrix score) to improve its interaction with DasR, or by adding DasR with improved binding capacity and so on. In case expression is repressed upon binding of DasR, it is desired to decrease binding of DasR to said binding site and thus to relieve said expression from repression. This is for example accomplished by deletion or mutation of the relevant DasR binding site.

In a preferred embodiment, said product of interest is a secondary metabolite. Examples of secondary metabolites are provided in Table 3 and include compounds such as clavulanic acid or butyrolactones.

Clavulanic acid is a very important inhibitor of beta-lactamase-type enzymes that are capable of inactivating penicillin and other beta-lactam-type antibiotics. Therefore, clavulanic acid is often administered to patients in combination with beta-lactam antibiotics such as penicillin when patients are expected to be infected with penicillin-resistant bacteria. Hence, a method according to the invention is also used to increase expression of clavulanic acid.

DasR also regulates genes involved in the biosynthesis of the hormone-like γ-butyrolactones, such as barB in *S. virginiae* (Table 3). These γ-butyrolactones are crucial signalling compounds that control antibiotic production and morphogenesis in actinomycetes (Horinouchi 2002; Beppu and Horinouchi, 1991; Horinouchi and Beppu, 1993; Horinouchi and Beppu, 1992).

For example, A-factor controls streptomycin production in *S. griseus*. Therefore, in another embodiment, the invention provides a method for indirectly regulating antibiotic production indirectly through the control of signalling molecules.

In yet another preferred embodiment, said product of interest is an antibiotic, an enzyme, a product from a cryptic gene cluster, an anti-tumor agent or an agricultural compound. Examples of enzymes are a cellulase, a pectinase, a lipase, an amylase, a chitinase, a mannanase, a xylanase, a protease, a peroxidase, a catalase, a laccase, or a sugar isomerase. Examples of antibiotics are the glycopeptide antibiotics, including vancomycin (produced by *Streptomyces toyocaensis* and *Amylocatopsis orientalis*), daptomycin (produced by *Streptomyces roseosporus*) and the teichoplanin-like compound A47934 (produced by *Streptomyces toyocaensis*), chloramphenicol (produced by *Streptomyces venezuelae*), streptomycin (produced by *Streptomyces griseus*), novobiocin (produced by *Streptomyces spheroides*), and also the well-studied model clusters for antibiotic production, namely actinorhodin and undecylprodigiosin of *Streptomyces coelicolor*. The latter two are controlled by the pathway-specific activator genes actII-ORF4 (#27 in Table 2) and redZ (#129 in Table 2), respectively. Also, the actinorhodin biosynthetic enzyme ActVA4 was strongly activated in the absence of DasR (FIG. 4). On the basis of our analysis of the known sequences related to antibiotic biosynthesis we surprisingly disclose that more than half of all known antibiotic biosynthesis clusters are regulated by DasR and hence intervention via DasR controlled expression provides a very useful means for modifying antibiotic production.

Moreover, the inventors also disclose that the actinorhodine biosynthese cluster is (indirectly) under control of DasR. As disclosed in FIG. 4B, a DasR null mutant secretes a considerable amount (approximately 95% of the total amount of secreted protein) of protein which is designated as SCO5074 (dehydratase). This dehydratase is part of the actinorhodine biosynthesis cluster and the dehydratase tailors the sectreted antibiotic. Hence, the invention further provides means and methods for controlling (preferably increasing) the amount of produced/secreted actinorhodine.

Both filamentous micro-organisms as well as low G+C gram-positive bacteria are examples of micro-organisms in which the methods according to the invention can be applied. However, using these micro-organisms in for example a method for obtaining expression of a product of interest can be accompanied by production of an undesired product. Some of these undesired products are now known to be regulated by DasR and the invention thus provides in yet another embodiment, a method for at least in part reducing production of an undesired product in a DasR-like protein comprising micro-organism, comprising providing said micro-organism with a compound capable of interfering with the binding of a DasR-like protein to a DasR-binding site in operable linkage with a gene encoding said undesired product or a DasR-binding site in operable linkage with a gene involved in the production of undesired product.

Interfering with the binding of a DasR-like protein to a DasR-binding site in operable linkage with a gene encoding said undesired product or a DasR-binding site in operable linkage with a gene involved in the production of said undesired product may be such that the binding is at least in part inhibited or it may be such that the binding is at least in part increased. With "at least in part" is meant that there is a detectable difference between the situation in which no compound is added and the situation in which said compound is added. In a preferred embodiment, the binding is essentially completely inhibited or is the binding is essentially irreversible.

Preferably, the binding of a DasR-like protein to a DasR-binding site is at least in part increased by providing said micro-organism with an increased amount of DasR-binding sites in operable linkage with a gene encoding said undesired product or in operable linkage with a gene involved in the production of said undesired product. In yet another preferred embodiment, the binding of a DasR-like protein to a DasR-binding site is at least in part decreased by removing at least one DasR binding site in said micro-organism that was originally in operable linkage with a gene encoding said undesired product or in operable linkage with a gene involved in the production of said undesired product.

As disclosed herein, the expression of some proteases are regulated by a DasR-like protein. Examples are provided in Table 2: #60 (metallopeptidase) or #109 (peptidase). In case a method of the invention is used to produce a proteinaceous product of interest, the expression of the mentioned peptidases can be influenced at the same time.

In a preferred embodiment, said undesired product is an undesired side product or an undesired shunt product.

It is clear to a skilled person that any of the methods according to the inventions can optionally be combined. For example a method for controlling metabolism combined with a method for at least in part reducing production of an undesired product. In a preferred embodiment, the invention provides a combination of a method for obtaining expression of a product of interest with a method for at least in part reducing production of an undesired product and hence, the invention provides a method for obtaining expression of a product of interest in a DasR-like protein comprising micro-organism as described above, further comprising providing said micro-organism with a compound capable of interfering with the binding of a DasR-like protein to a DasR-binding site in operable linkage with a gene encoding an undesired product or a DasR-binding site in operable linkage with a gene involved in the production of an undesired product.

For example if the product of interest is encoded by a gene whose expression is repressed upon binding by DasR to a DasR binding site in front of said gene, expression of this product of interest is at least in part increased by providing an inducer. If at the same time an undesired product is expressed which presence for example interferes with the isolation/purification of said product of interest and if this undesired product is activated upon binding of a DasR protein to the relevant DasR binding site, this binding site is for example genetically modified to at least in part block binding of a DasR protein to said relevant DasR binding site. Based on the present invention it is clear to the skilled person that various situations of DasR regulation of the product of interest and the undesired product are possible which may be solved via any one of the herein described options.

Examples of genes whose expression is regulated by DasR (either activated or repressed) are outlined in Table 2. It is clear to the skilled person that the invention also provides methods based on the specific properties of the products of these genes. Moreover, we also have observed that the absence of DasR results in aberrant growth behaviour on certain growth media. The following part of the description provides examples of uses based on the results as presented in Table 2 as well as uses based on the observation with a DasR null mutant.

One example is the observation that the absence of DasR (see the experimental part related to the DasR null mutant) or the enhanced expression of DasR results in aberrant growth behaviour. For example, a DasR null mutant grown on glucose results in fragmented growth of a filamentous micro-organism. In liquid cultures the absence of DasR results in enhanced branching (FIG. 16), while expression of DasR using a multi-copy plasmid reduces branching. Moreover, the inventors have identified genes that are related to the cytoskeleton or peptidoglycan. Hence, the invention further provides a method for obtaining a filamentous micro-organism with altered fragmentation and/or branching characteristics during growth comprising altering the expression of a DasR-regulated gene. Most filamentous micro-organisms (for example streptomycetes) only sporulate on solid media, while growth in a liquid culture is restricted to the formation of a vegetative mycelium. This typically develops into an intricate network of hyphae, among others resulting in pellet formation, with only the most outwardly oriented sections showing high physiological activity, resulting in reduced growth rate and low yield of the desired product per unit of biomass. Furthermore, because of their filamentous morphology, high density fermentations of biotechnologically interesting streptomycetes often are highly viscous, resulting in a low biomass accumulation due to for instance aeration and mixing problems. From this perspective it is desirable that fragmentation of the mycelium in submerged cultures is stimulated, that branching of the mycelium is reduced, and that in general the viscosity of the culture is reduced.

Another example is based on the observation that some of the identified DasR regulated genes are genes involved in protein secretion and/or protein folding. Examples are secE (#102 in Table 2) and secY (#100 in Table 2), which are essential membrane components of the Sec secretion system. In fact, repeated measurements of total secreted protein in large cultures revealed that in the absence of an active copy of DasR total amount of secreted protein was reduced by 50%. Hence, the invention also provides a method for regulating protein secretion and/or protein folding in a DasR-like protein comprising micro-organism, comprising providing said micro-organism with a compound capable of interfering with the binding of a DasR-like protein to a DasR-binding site in operable linkage with a gene involved in protein secretion and/or protein folding.

Yet another example is based on the observation that some of the identified DasR regulated genes are genes involved in transport of metal ions, such as copper, iron or zinc. Relevant genes are for example a cutC-type copper homeostasis gene (#30 in Table 2) and the iron regulatory gene desR that controls iron uptake (#62 in Table 2). Hence, the invention also provides a method for regulating transport of a metal ion in a DasR-like protein comprising micro-organism, comprising providing said micro-organism with a compound capable of interfering with the binding of a DasR-like protein to a DasR-binding site in operable linkage with a gene involved in the transport of said metal ion.

Another example is based on the observation that many of the identified DasR regulated genes are genes involved in transport of sugars. Non-limiting examples are provided in Table I, including the PTS genes (nagE1, nagE2, malX2, ptsH, ptsI, crr; #1, 2, 3, 5), ABC transporters (e.g. #4, 8, 17, 22, 33, 53, 66, 111, and 122 in Table 2) and MsiK (#38) which is the universal ATPase for ABC transporters in streptomycetes and hence essential for their transporting activity. Of these examples, the PTS, MsiK and several of the ABC transporters have been experimentally validated. Hence, the invention also provides a method for regulating transport of a sugar in a DasR-like protein comprising micro-organism, comprising providing said micro-organism with a compound capable of interfering with the binding of a DasR-like protein to a DasR-binding site in operable linkage with a gene involved in the transport of a sugar. For example N-acetylglucosamine by the PTS$^{NAG}$ and chitobiose by the ABC transporter NgcEFG (#33 in Table 2). The DasR-repressed MsiK is required for the activity of many ABC transporters, for example for transport of cellobiose (CebEFG), maltose (MalEFG) and xylobiose (BxlEFG).

Yet another example is based on the observation that the production of antibiotics in a dasR null mutant showed medium-dependent development: on some media development was enhanced, while on others it was completely abolished. Hence, the invention also provides a method for influencing antibiotic production in a (filamentous) micro-organism, comprising functionally impairing a dasR gene and further comprising selecting a sugar source suitable for a particular antibiotic. Examples of a suitable sugar source in combination with a particular antibiotic are provided in FIG. 11.

In any of the methods of the invention a DasR-like protein comprising micro-organism is a micro-organism that comprises a DasR-like protein or an organism that is capable of expressing said DasR-like protein from a nucleic acid encoding said protein. Moreover, said micro-organism may be an organism that is by nature capable of expressing said DasR-like protein or it may be a micro-organism which has been genetically modified to produce DasR-like protein. Moreover, it is also possible to provide a micro-organism that is already capable of expressing DasR-like protein with a further nucleic acid that enables production of more DasR-protein. Such an additional nucleic acid encoding a DasR-like protein may be identical to the already present nucleic acid encoding the endogenous DasR or it may be heterologous. In a preferred embodiment, a DasR-like protein comprising micro-organism is obtained by providing a micro-organism with a nucleic acid encoding a DasR-like protein. Even more preferably, said DasR-like protein is heterologous. A nucleic acid encoding a DasR-like protein may be provided to a micro-organism by any method known therefore. Moreover, said nucleic acid may be present in said micro-organism as an episomal element or integrated into the genome of said micro-organism.

Moreover, said gene of interest can be an endogenous gene as well as an exogenous gene and hence a method of the invention can further comprise providing a DasR-like comprising organism with a nucleic acid encoding a gene of interest.

A micro-organism used in any of the methods of the invention is preferably a bacterium from marine or soil origin. In another preferred embodiment, said micro-organism is a filamentous micro-organism. Examples of a filamentous micro-organism are an ascomycete, a basidomycete, or an actinomycete. Examples of a suitable actinomycete are a *Streptomyces*, a *Nocardia*, a *Thermobifido*, an *Amycolatopsis*, a *Planobispora*, a *Streptoverticillium*, a *Rhodococcus*, or a *Corynebacterium*.

In yet another embodiment of the invention, a micro-organism is a low G+C gram-positive bacterium, such a *Bacillus, Lactobacillus, Lactococcus, Streptococcus*, or *Listeria*. Surprisingly, the inventors disclose in the present invention the core gene cluster nagA-nagB-dasR (and the dre elements) is also widespread among low G+C Gram-positives, including *Bacillus, Lactococcus, Listeria* and *Streptococcus*. Not only the organization is conserved, but also the sequence of the dre sites, even though the G+C content of the DNA of *Bacillus* (43%) is around 30% lower than that of streptomycetes (72-73%). The dre sites of *Bacillus subtilis* and *Bacillus halodurans* are summarised in Table 5, those of *Lactococcus lactic* in Table 6, of *Streptococcus* species in Table 7, and of *Listeria innocua* and *Listeria monocytogenes* in Table 8.

Low G+C gram-positive bacteria are important in for example the production of many dairy products and moreover, these bacteria are often used as a probiotic.

It is clear from the Tables 4 to 7, that also in these bacteria processes such as sugar uptake, metabolism or bacteriocin production is influenced by any of the methods described herein.

Surprisingly, the invention also discloses the finding that a dasR mutant showed strongly enhanced production of antibiotic. Moreover, as identified in Table 3, multiple antibiotic (clusters) are under control of DasR. Also cryptic antibiotic (clusters) have been found to be under control of DasR (Table 3). The invention thus provides a method for regulating, obtaining or increasing the expression of an antibiotic in a DasR-like protein comprising micro-organism, comprising providing said micro-organism with a compound capable of interfering with the binding of a DasR-like protein to a DasR-binding site in operable linkage with a gene encoding said antibiotic or a DasR-binding site in operable linkage with a gene involved in the production of said antibiotic. Preferably, such a method is used for obtaining or increasing the expression of an antibiotic. Even more preferably, said antibiotic is part of a cryptic antibiotic or a cryptic antibiotic cluster. In a preferred embodiment, said compound capable of interfering with the binding of a DasR-like protein to a DasR-binding site is N-acetylglucosamine or a derivative or a multimer thereof.

In yet another embodiment, the invention provides an activated DasR-repressed cryptic gene (cluster), wherein said cryptic gene (cluster) is activated by influencing binding of a DasR-like protein to a DasR-binding site in operable linkage with said gene (cluster). Influencing the binding between said protein and said binding site may result in a decreased or an increased/improved binding. In a preferred embodiment, said gene (cluster) is an antibiotic gene (cluster).

In case the binding of DasR to the relevant binding site results in a repressed level of for example antibiotic production, production of said antibiotic is for example accomplished by mutating the DasR binding site in operable linkage with said antibiotic. The mutation is preferably such that a DasR protein is no longer capable of sufficiently binding to said binding site. In yet another embodiment an inducer such as N-acetylglucosamine (which is converted to glucosamine-6-P) is used to relieve repression.

The invention also provides a micro-organism that has been genetically engineered in such a way that the expression of at least one DasR regulated gene is modified.

One suitable example is a micro-organism comprising an activated cryptic cluster as described above, e.g. a micro-organism in which the DasR binding site in operable linkage with said cluster is mutated such that binding of a DasR-like protein is increased or decreased.

Another example is a micro-organism comprising a mutated binding site for a DasR-like protein. Said binding site is mutated such that binding of a DasR-like protein is increased or decreased. Alternatively, said binding site will be modified such that the genes are controlled by a different repressor protein (for example to specifically repress the genes whose expression is less desirable). A skilled person is aware that several DNA binding proteins exist that recognise only binding sites that do not naturally occur in a particular micro-organism. Examples of such proteins are TetR (recognizes the tetO operator) or Gal4 (recognizing the eukaryotic gal promoter).

Yet another example is a micro-organism comprising a mutant of a DasR-like protein. For example a mutant with improved binding capacity or with decreased binding capacity or a variant of DasR that is insensitive to induction by glucosamine-6-P (or similar compounds). Another example is an essentially non-functional mutant, for example a null mutant of a DasR-like protein. Yet another example is a DasR-like protein in which (part of) the effector binding domain has been mutated (for example deleted).

Another example is a micro-organism comprising increased expression of DasR. This is for example accomplished by providing a micro-organism with an (over) expression cassette for DasR. Such a cassette may comprise an endogenous or a heterologous dasR gene. If a micro-organism does already comprise the genetic information to encode DasR it is also an option to impair the autoregulation of DasR in said micro-organism.

Two other examples are a micro-organism which essentially grows vegetatively and which produces altered levels of a secondary metabolite or a micro-organism which essentially grows vegetatively and which produces a product from a cryptic gene cluster.

Preferably, any of the mentioned micro-organisms produces increased amounts of a product of interest (such as for example an enzyme or an antibiotic).

Even more preferably, a micro-organism according to the invention is a bacterium from marine or soil origin. In another preferred embodiment, said micro-organism is a filamentous micro-organism. Examples of a filamentous micro-organism are an ascomycete, a basidomycete, or an actinomycete. Examples of a suitable actinomycte are a *Streptomyces*, a *Nocardia*, a *Thermobifido*, an *Amycolatopsis*, a *Planobispora*, a *Streptoverticillium*, a *Rhodococcus*, or a *Corynebacterium*.

In yet another embodiment of the invention, a micro-organism is a low G+C gram-positive bacterium, such a *Bacillus*, *Lactococcus*, *Streptococcus*, or *Listeria*.

Although it is convenient to start any of the methods of the invention with a micro-organism that does already comprise a nucleic acid encoding a DasR-like protein as well as a nucleic acid in operable linkage with a DasR-binding site, it is also possible to use the methods of the invention with a micro-organism that does not comprise said nucleic acids. Hence, the invention further provides a method for regulating expression of a product of interest in a DasR-like protein comprising micro-organism, comprising providing a nucleic acid encoding said product of interest or a nucleic acid encoding a protein involved in the production of said product of interest with a binding site for a DasR-like protein and wherein said binding site is in operable linkage with said nucleic acid. In a preferred embodiment, said micro-organism is further provided with a nucleic acid encoding a DasR-like protein.

In yet another embodiment, the invention provides use a mutated DasR-binding site for regulating expression of a DasR-controlled gene or use of a mutated DasR-like protein for regulating expression of a DasR-controlled gene or use of DasR for regulating expression of a DasR-controlled gene or use of a DasR-inducer for regulating expression of a DasR-controlled gene.

Any of the herein-described methods may further comprise a purification step, for example purification of the product of a gene of interest or purification of a product of interest (such as an enzyme or an antibiotic). Moreover, a method according to the invention may be performed on a small-scale basis or on a large-scale basis.

In yet another embodiment, the invention provides a method for obtaining or improving production of a secondary metabolite in a micro-organism, comprising providing said micro-organism with N-acetylglucosamine or a derivative or a multimer thereof. Said secondary metabolite may be a known or unknown secondary metabolite and hence said method can be part of a screening method, for example a screening method for identification of a novel drug. In a preferred embodiment, said secondary metabolite is an antibiotic. In yet another preferred embodiment, the invention provides a method for awakening or enhancing expression from a cryptic (antibiotic) cluster in a micro-organism, comprising providing said organism with N-acetylglucosamine or a derivative or a multimer thereof. In another preferred embodiment, the used micro-organism comprises a DasR-like protein. In yet another preferred embodiment, the N-acetylglucosamine or a derivative or a multimer thereof is added to the growth medium of said micro-organism. In yet another preferred embodiment, said N-acetylglucosamine or a derivative or a multimer thereof is added to said growth medium at a concentration of at least or preferably above 10 mM.

In yet another preferred embodiment, the used micro-organism is a filamentous micro-organism, preferably an ascomycete, a basidomycete, or an actinomycete. A suitable example of an actinomycete is a *Streptomyces*, a *Nocardia*, a *Thermobifido*, an *Amycolatopsis*, a *Planobispora*, a *Nonomuria*, a *Streptoverticillium*, a *Rhodococcus*, or a *Corynebacterium*.

In yet another embodiment, the invention provides the use of N-acetylglucosamine or a derivative or a multimer thereof for awakening or enhancing a cryptic (for example antibiotic) cluster in a micro-organism.

The invention will be explained in more detail in the following description, which is not limiting the invention.

FIG. 1. Identification of the DasR-binding site and prediction of the DasR regulon. (A) DNase I footprint analysis of the DasR-binding site in the crr-ptsI promoter region (nt positions −202/+8 relative to the start of crr; SEQ ID NO:490). The crr-ptsI probe was incubated with DNase I (0.4 µg/ml) and increasing amounts of purified DasR (0, 10, 20, 40, 60, or 80 pmol of DasR in lanes 2-7, respectively). Additional controls: Lane 1, probe without DasR and without DNase I; lane 8, probe with DNase I and 350 pmol of non-specific protein (BSA). ACGT, DNA sequence lanes. The DNA sequence of the crr-ptsI probe is depicts the DasR-protected sequence (indicated with "FOOTPRINT"). The sequence that conforms to the DasR consensus (SEQ ID NO:491; below the target site) is highlighted in black, and the crr translational start codon in grey. (B) Pie chart showing categories and number of genes shown and/or predicted to be controlled by DasR (see Table 2).

FIG. 2. Effect of dasR on development and antibiotic production. (A) Antibiotic production by *S. coelicolor* M145 and its dasR mutant BAP29 on minimal medium agar plates with or without GlcNAc. The presence of GlcNAc is required for induction of the pigmented antibiotics actinorhodin and undecylprodigiosin in *S. coelicolor* M145, while the expression is constitutive in the dasR mutant. The latter is in line with our discovery that (i) ActV4A is enhanced in the mutant (FIG. 4) and (ii) the identification of a DasR-bound dre upstream of the pathway-specific activator genes actII-ORF4 for actinorhodin production and redZ for undecylprodigiosin production. Unexpectedly, the dasR mutant grown on minimal media with GlcNAc presents the expression of a yet unchartacterized green pigment. (B) Overexpression of DasR causes developmental arrest. Left, S. coelicolor M145 with control plasmid pUWL-KS; right, the same strain with a plasmid over-expressing dasR (grown for 4 days at 30° C.); note the almost complete lack of aerial hyphae (white) in the strain over-expressing DasR; (C) Scanning electron micrographs of aerial hyphae and spores of S. coelicolor M145 and the dasR mutant BAP29. Insert caption shows aberrant spores of the DasR mutant. Bars represent 5 μm. (D) Transmission electron micrographs of spores of M145 (left) and BAP29 (right). Arrows indicate the voids between the cell wall and the membrane. FD, full detachment; ID, incomplete detachment.

Figure 3A:
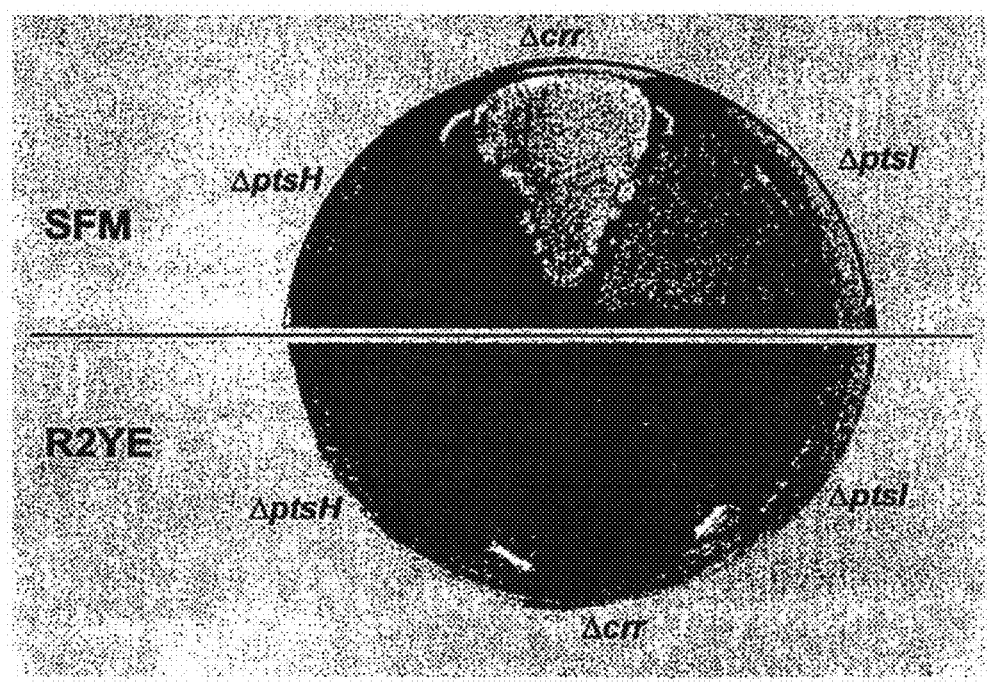
Figure 3B:
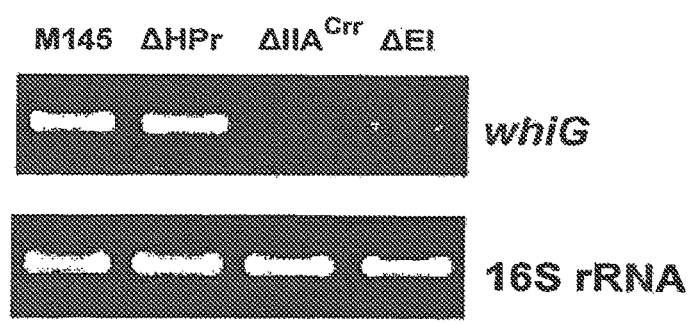
Figure 3C:
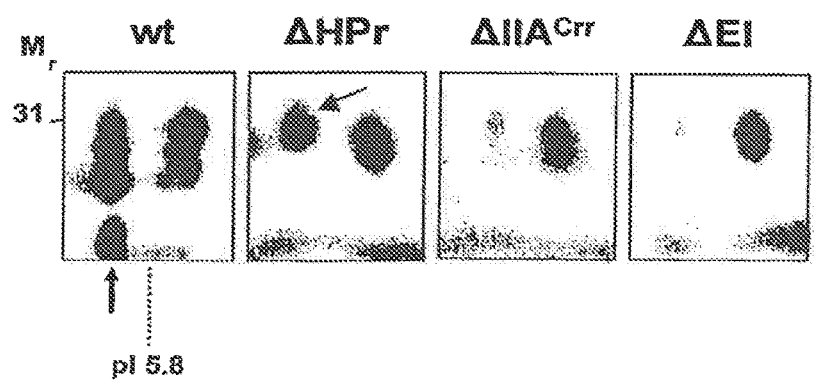

FIG. 3. Control of development via the PTS. (A) The PTS system is essential for correct development. Strains were grown for 5 days on SFM or R2YE agar plates. On SFM the crr mutant BAP2 produced a white aerial mycelium but failed to produce spores under these conditions, while deletion of ptsH (BAP1) or ptsI (BAP3) allowed the production of some grey-pigmented spores. Interestingly, on R2YE agar plates all three PTS mutants show vegetative arrest (so-called bald or bld phenotype). (B) PTS controls transcription of whiG. The figure shows a 1% agarose gel with amplification products from a semi-quantitative RT-PCR experiment. Total mRNA was prepared from exponentially grown mycelia of the wild-type and of PTS mutants BAP1 (ΔHPr), BAP2 (ΔIIA$^{Crr}$), and BAP3 (ΔEI). The figure shows that whiG-mRNA levels were diminished in the strains lacking the phophotransferases IIA$^{Crr}$ and EI. Results were reproduced in triplicate from mycelia harvested at different time points within the exponential growth phase. Detection of 16S rRNA served as a standard reference control. (C) Control of posttranslational modification of WhiG by HPr. two-dimensional gel electrophoresis was performed on total protein extracts from S. coelicolor M145 (wt), and its pts mutant derivatives lacking the genes for HPr kinase, Enzyme IIA (Crr) or Enzyme I, respectively. A close-up of the area around the WhiG protein is shown. Expectedly, the strongly reduced transcription (3B) resulted in very low concentrations of the WhiG protein band in the mutants lacking Enzyme IIA and Enzyme I. Surprisingly, several bands with lower molecular mass than WhiG but with the same isoelectric point were absent from the HPr mutant, strongly suggesting involvement of HPr in the posttranslational modification of WhiG. The exact nature of the modification is unknown, but considering that the effect is only on mass and not on pI we believe that this is due to processing of a WhiG pre-protein.

FIG. 4. Identification of DasR targets by proteome analysis. (A) Close-ups of protein spots whose intensity depends on DasR (greater than 2-fold). Arrows highlight the protein spots identified by mass spectrometry. Arrows highlight the protein spots identified by mass spectrometry. 1, ThiL (SCO5399), acetoacetyl-CoA thiolase; 2, GdhA (SCO4683), glutamate dehydrogenase; 3, SCO5520, pyrroline-5-carboxylate dehydrogenase; 4, ActV-A4 (SCO5079), member of the actinorhodin biosynthesis pathway with unknown function; 5, MsiK (SCO4240), multiple sugar import protein; 6, GpsI (SCO5737), guanosine pentaphosphate synthetase; 7, SCO4366, phosphoserine aminotransferase; 8, NagA (SCO4284), N-acetylglucosamine-6-phosphate deacetylase; 9, GalT (SCO3138), galactose-1-phosphate uridylyltransferase. Proteins: ThiL (SCO5399), acetoacetyl-CoA thiolase; GdhA (SCO4683), glutamate dehydrogenase; SCO5520, Δ-1-pyrroline-5-carboxylate dehydrogenase; MsiK (SCO4240), multiple sugar import protein; GpsI (SCO5737), guanosine pentaphosphate synthetase; SCO4366, phosphoserine aminotransferase; NagA (SCO4284), N-acetylglucosamine-6-P deacetylase; GalT (SCO3138), galactose-1-P uridylyltransferase. (B) One-dimensional PAGE gel showing secreted proteins isolated from the spent medium of liquid-grown cultures of S. coelicolor M145 and its dasR mutant BAP29. M, molecular size marker (n kDa). Note that a single protein—identified as SCO5074 and also known as ActVI-ORF3—is strongly over-expressed in the dasR mutant BAP29.

FIG. 5. Schematic representation of N-acetylglucosamine-related enzymatic reactions and central position of glucosamine-6-P. DasR target identification is indicated: Arrows: enhanced (thick arrow) or inhibited (thin arrow) in the dasR mutant. Extracellular chitin is hydrolysed and once incorporated into the cell, converted to N-acetylglucosamine (GlcNAc), which is then phosphorylated by NagK to GlcNAc-6-P. NagA deacetylates GlcNAc-6-P to GlcN-6-P, which occupies a central position between nitrogen metabolism, the TCA cycle, peptidoglycan precursor synthesis, and glycolysis via NagB (converts GlcN-6-P to fructose-6-phosphate (Fru-6-P)). This schematic representation highlights the central position of glucosamine-6-P, the effector molecule of the DasR regulon. The large vertical arrow highlights the (dasR-controlled) flux from extracellular (poly-)sugars towards glycolysis and TCA cycle The connected pathways can be retrieved from the KEGG database on the world wide web at (http://www.genome.ad.ip/kegg/pathway.html).

FIG. 6. DasR activates chitin-related genes. (A) Comparison of the global chitinase, extra- and intracellular β-N-acetylglucosaminidase activities between BAP29 and M145 after 48 h of growth in minimal medium supplemented with various carbon sources. Activities are expressed in percentage (%) compared to the parental strain M145 under inducing conditions. (B) RT-PCR on chiI, chiF, and SCO6300.

Figure 7:
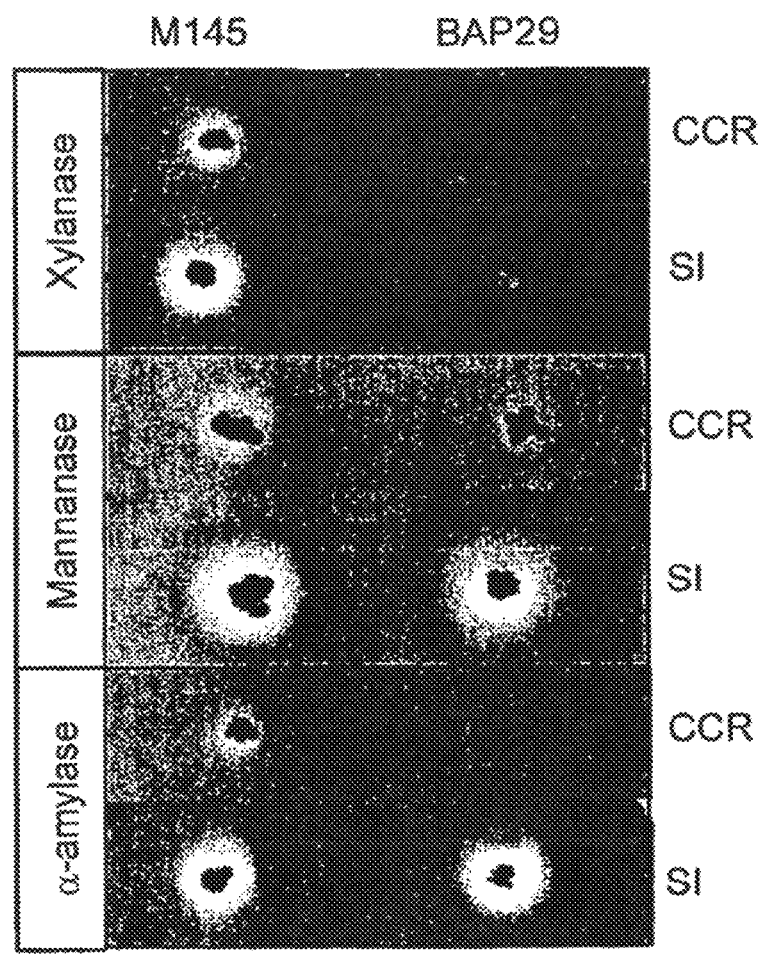

FIG. 7. DasR controls the expression of principal polysaccharides degrading systems. Enzymatic activity was measured as the size of the clearing zone produced around the colonies due to specific degrading activity. Left, M145; right, dasR mutant BAP29. Top, assay of xylanase activity; middle, mannanase activity; bottom, α-amylase activity. CCR, carbon catabolite repression induced by glucose; SI, substrate induction induced by xylan (top), mannan (middle) and starch (bottom). Note that in the absence of dasR xylanase expression could not be induced, while mannanase and α-amylase activities were overexpressed. In CCR conditions all systems show an enhanced glucose repression.

Figure 8:
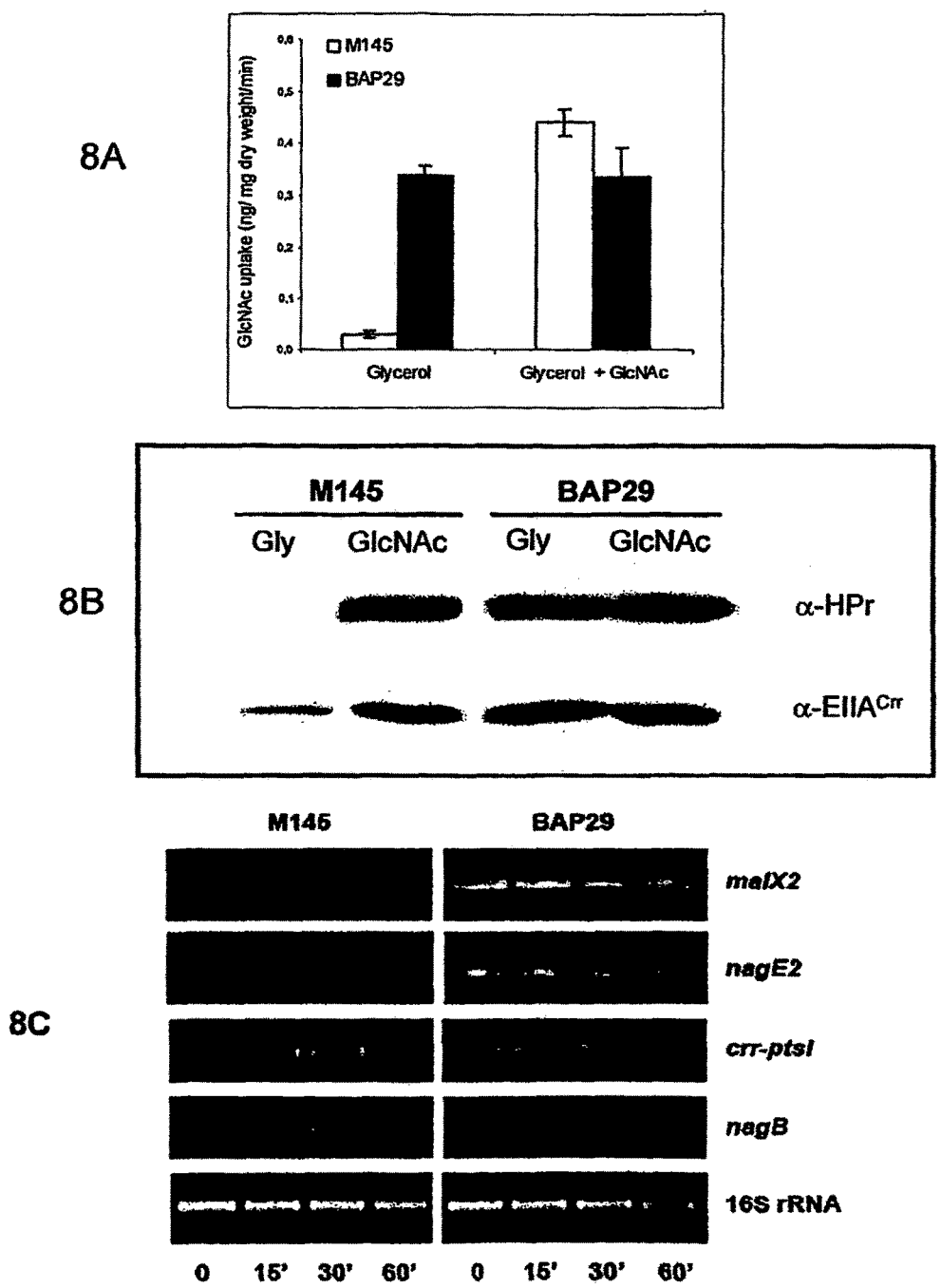

FIG. 8. DasR represses genes the N-acetylglucosamine regulon (A) Effect of deletion of dasR on the uptake of GlcNAc. Left, uptake in glycerol-grown cultures; right, uptake in cultures grown in glycerol and inducer (GlcNAc); note that expression was constitutive in BAP29. (B) Western blot analysis of HPr (top) and IIA$^{Crr}$ (bottom), showing that inducibility of these PTS proteins is controlled by DasR. (C) Transcriptional analysis of crr (for IIA$^{Crr}$), nagE2 (for IIC$^{GlcNAc}$), malX2 (for IIB$^{GlcNAc}$), nagB and chiF by semi-quantitative RT-PCR. Samples were collected before and 15, 30 and 60 min after the addition of GlcNAc to exponentially growing minimal medium glycerol cultures. 16S rRNA was used as control.

Figure 9:
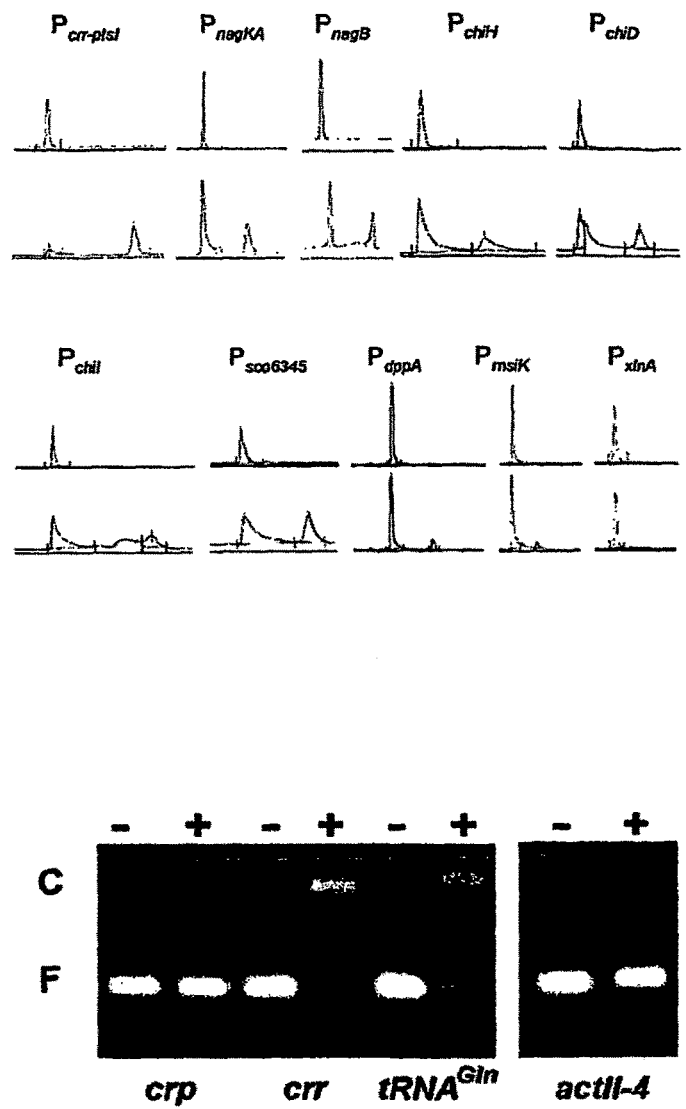

FIG. 9. cis/trans relationship between DasR and diverse target genes. Electromobility gel shift assays (EMSAs) are depicted that demonstrate binding of DasR to targets predicted in silico. Top: EMSAs were performed with 10 nM of fluorescent probe, without (upper plot) and with purified DasR (3 µM; lower plot) in the presence of 1000-fold excess of non-specific DNA. Bottom: EMSAs were conducted in a volume of 10 µl with 10 pmol of dre-containing DNA, a 1000-fold excess of non-specific DNA, and without (−) or with (+) 4 µg of purified DasR. DasR-dre complexes were resolved on 1% agarose gels in 1×TAE buffer. dre sites are indicated, where $P_{xlnA}$ and $P_{crp}$ served as negative controls and $P_{crr}$ as the positive control.

Figure 10:
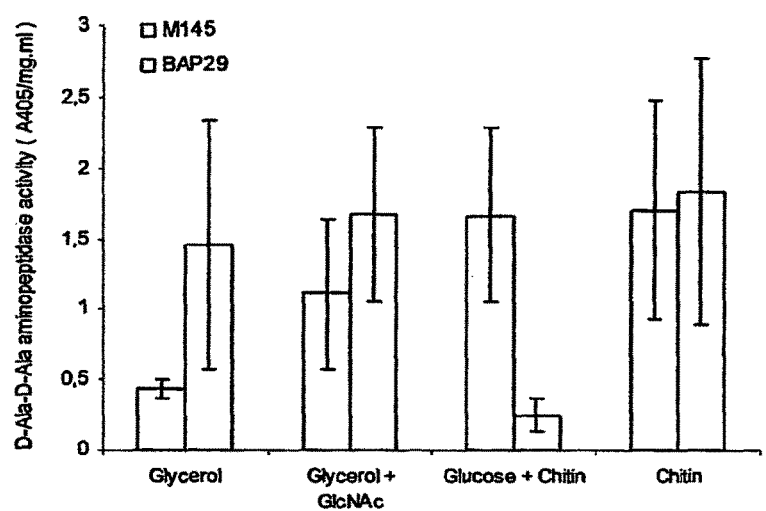

FIG. 10. DppA activity measurements. Production of DppA (D-Ala-D-Ala aminopeptidase) by *S. coelicolor* M145 and BAP29 (ΔdasR) was measured as intracellular activity of DppA. Cultures were grown for 24 h in liquid MM cultures with various (combinations of) carbon sources, namely glycerol, glycerol+N-acetylglucosamine, chitin or glucose+chitin.

Figure 11:
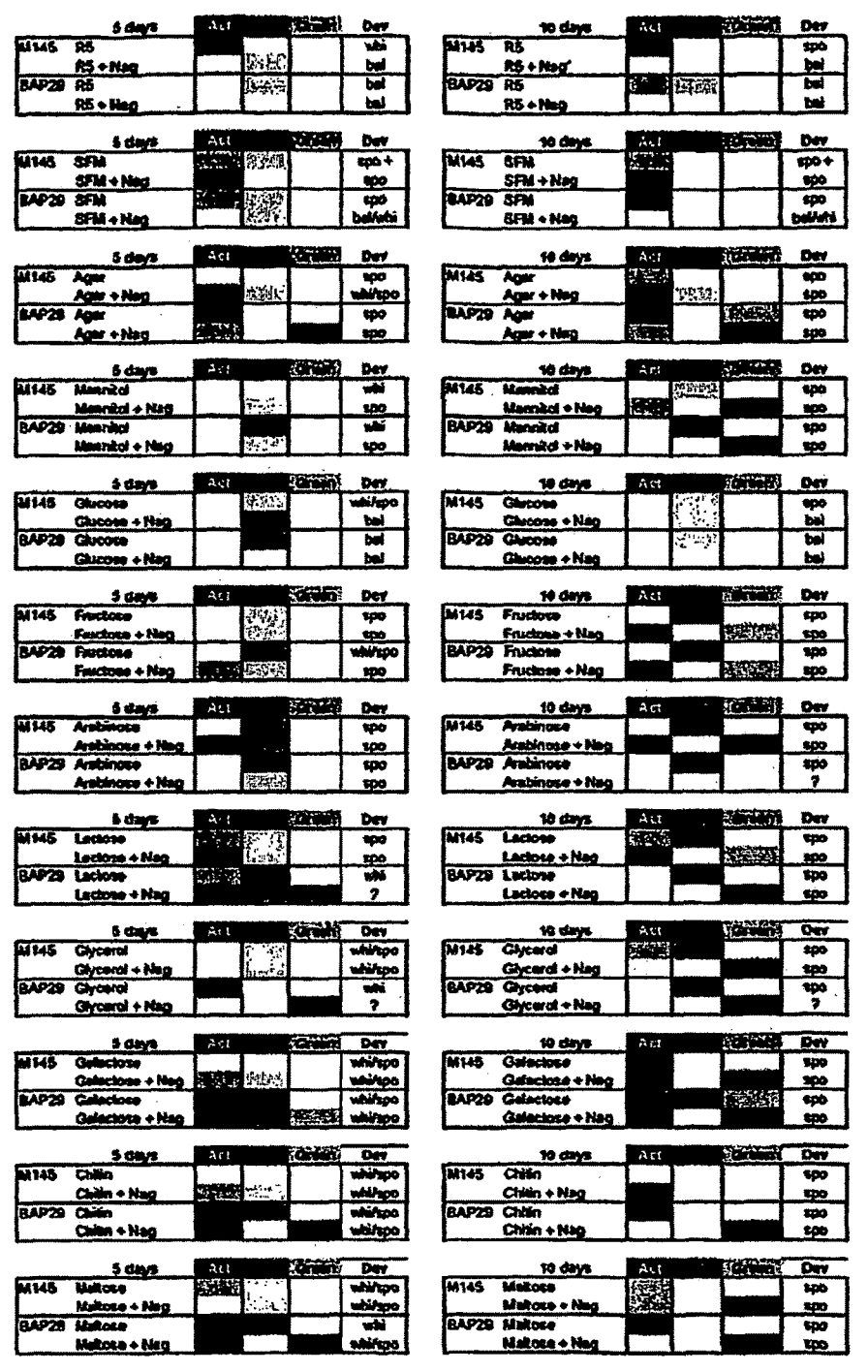

FIG. 11. Effect of sugars on antibiotic production in *streptomyces coelicolor* and effect of DasR. Act, actinorhodin (blue pigment); Red, undecylprodigiosin (red pigment); green, unknown new compound. Dev indicates developmental stage of the culture (bal, bald/vegetative phenotype; whi, white/aerial hyphae; spo, sporulation).

Figure 12:
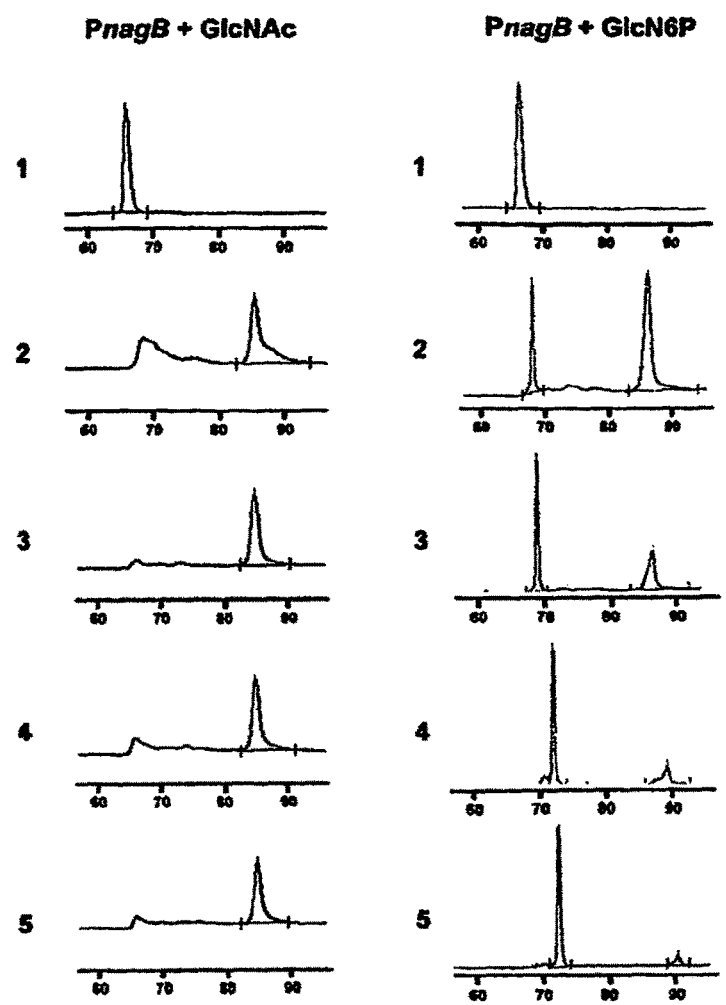

FIG. 12. DNA-binding by DasR is inhibited by glucosamine-6-P. The figure shows EMSAs of DasR binding to the nagB promoter. EMSAs were performed with 10 nM fluorescent probe, 3 µM purified DasR, and 500-fold excess of non-specific DNA. Plot 1 displays the control experiment on the nagB promoter (no DasR added); Plots 2-5, nagB promoter with DasR and 50, 100, 150, and 200 mM of GlcNAc (left panel, no effect) and GlcN-6-P (right panel, release of DasR from the dre site).

Figure 13:
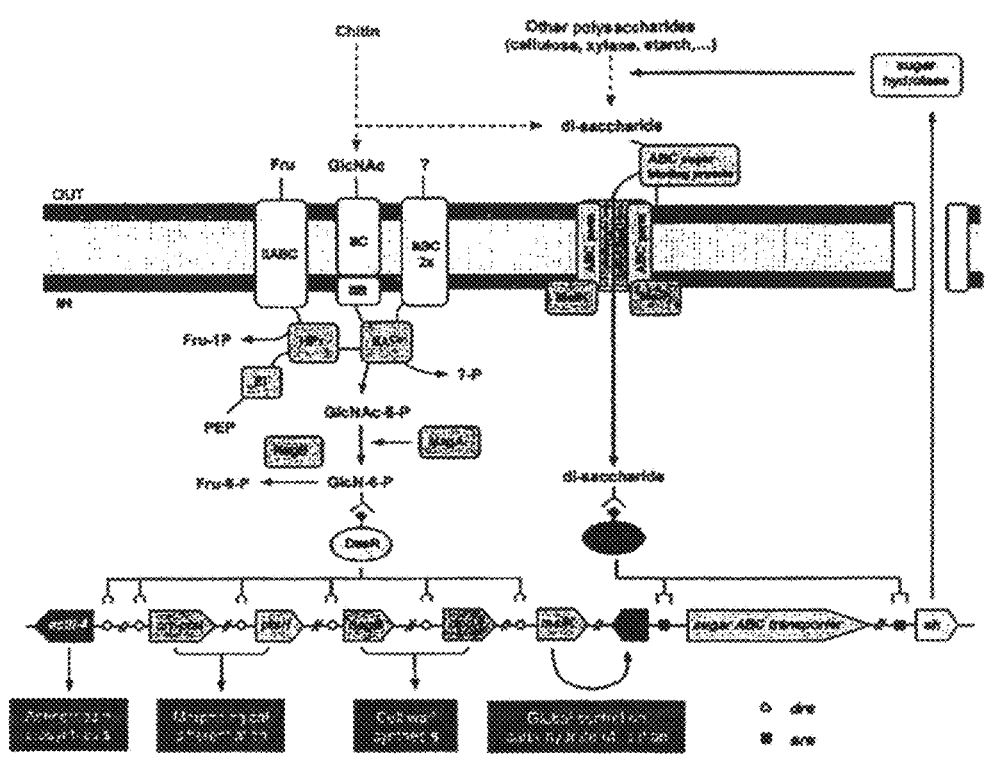

FIG. 13. Model for global control of carbon utilization by DasR. The model illustrates that abundant polysaccharidic carbon sources in the soil (cellulose, xylan, chitin, etc.) are degraded by extracellular hydrolases to the respective mono- and disaccharides. N-acetylglucosamine (GlcNAc) is transported by the PTS via sequential phosphoryl group transfer from PEP to enzyme I (EI, encoded by ptsI) to HPr (ptsH) to $EIIA^{Crr}$ (crr), which in turn phosphorylates the EIIB protein of the GlcNAc-specific permease EIIBC. DasR functions as a repressor of all genes of the $PTS^{GlcNAc}$. Other breakdown products are transported by ABC-permeases that are composed of two sugar-specific membrane proteins, a specific extracellular and a lipid-anchored sugar binding protein. Many of these ABC systems (more than 40 predicted) are assisted by the universal ATPase MsiK (multiple sugar import protein) that is regulated by DasR. The metabolic enzymes NagA and NagB (both genes controlled by DasR) convert GlcNAc-6-P to glucosamine-6-P (GlcN-6-P) and fructose-6-P. GlcN-6-P serves as an effector for DasR and thus provokes gene expression of pts genes and msiK. DasR-mediated control to nagB and to the dppA operon (D-Ala-D-Ala aminopeptidase) indicates its role in regulating cell wall synthesis. sh, sugar hydrolase gene; sr, gene for a specific regulator of an operon encoding an ABC permease and related extracellular sugar hydrolases. Yellow circles and red boxes on the fictive chromosome represent the DasR responsive elements and the sugar-specific regulator responsive elements, respectively.

FIG. 14. Alignment of DasR homologues from Gram-positive bacteria. (A) DasR homologues from actinomycetes. Homologues included in the pileup are DasR proteins from: Scoel, *Streptomyces coelicolor* (SCO5231) (SEQ ID NO:492); Sclav, *Streptomyces clavuligerus* (SEQ ID NO:493); Saver, *Streptomyces avermitilis* (SAV3023) (SEQ ID NO:495); Sgris, *Streptomyces griseus* (BAB79296) (SEQ ID NO:496); Sscab, *Streptomyces scabies* (SEQ ID NO:494); S139, *Streptomyces* species 139 (AAN04228) (SEQ ID NO:497); Tfusc, *Thermobifido fusca* (AAZ54592) (SEQ ID NO:498). (B) Comparison of DasR-like proteins from high and low G+C Gram-positive bacteria. Interestingly, *S. coelicolor* DasR (Scoel; SEQ ID NO:492) is around 40% identical to *Bacillus subtilis* GntR-type protein CAB 15508 (Bsubt, SEQ ID NO:504). Additional proteins are from Nfarc, *Nocardia farcinica* (SEQ ID NO:499); Ceffi, *Corynebacterium efficiens* (BAC19131) (SEQ ID NO:501); Lmono, *Listeria monocytogenes* (AAT03756) (SEQ ID NO:502); and Sther, *Streptococcus thermophilus* (AAV62475) (SEQ ID NO:503). Proteins represented in (A) that are also represented in (B) include Sscab (SEQ ID NO:494); Saver (SEQ ID NO:495); sgris (SEQ ID NO:496); 5139 (SEQ ID NO:497); and Tfusc (SEQ ID NO:498). A second DasR homologue (designated DasR2; SEQ ID NO:500) was found in *Streptomyces coelicolor* (SCO0530) and is included in the pileup. The only known target site is located immediately upstream of the ABC transporter operon SCO531-532-533. (C) The similarity between the genes SCO5231-5235 and SCO530-534 strongly suggests a gene duplication event.

Figure 15:
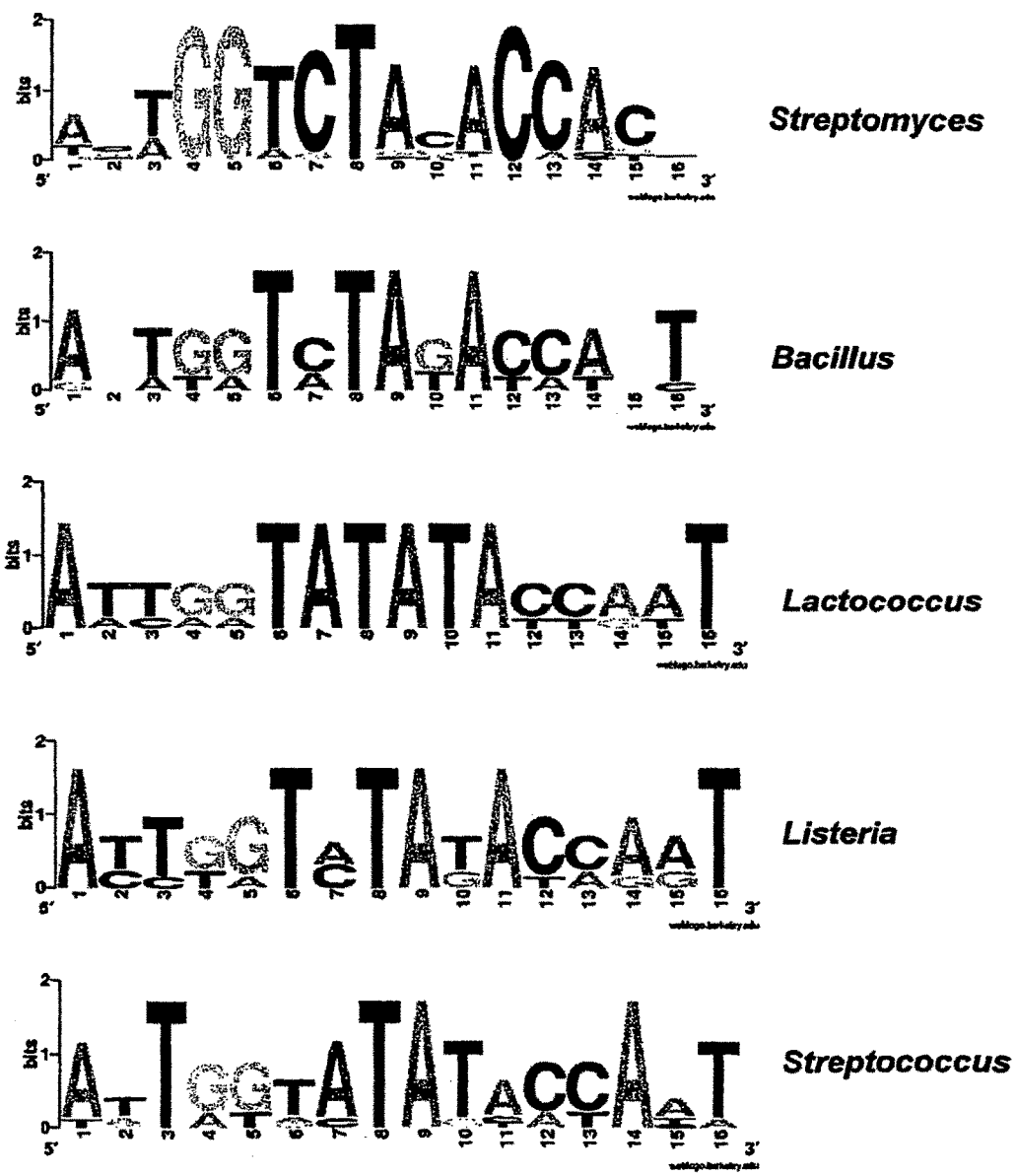

FIG. 15. Derived consensus sequences from *Streptomyces, Bacillus, Lactococcus, Listeria* and *Streptococcus*. The figures were prepared using the Logo software (Crooks et al., 2004). Large letters indicate high conservation, low letters indicate low conservation of the nucleotide position in all predicted DasR binding sites in the respective organisms. For these predictions we used the consensus DasR binding sequence from *S. coelicolor* to search for homologous sequences upstream of pts and nag genes in low G+C Gram-positive bacteria. The consensus sequences for the DasR binding sites in the respective organisms are, e.g.: *Streptomyces* (SEQ ID NO:1); *Bacillus* (SEQ ID NO:4); *Lactococcus* (SEQ ID NO:5); *Listeria* (SEQ ID NO:6); and *Streptococcus* (SEQ ID NO:7). The derived consensus sequences were then used to build a new matrix for putative DasR binding sites occurring in *Bacillus, Lactococcus, Listeria* and *Streptococcus*.

Figure 16:
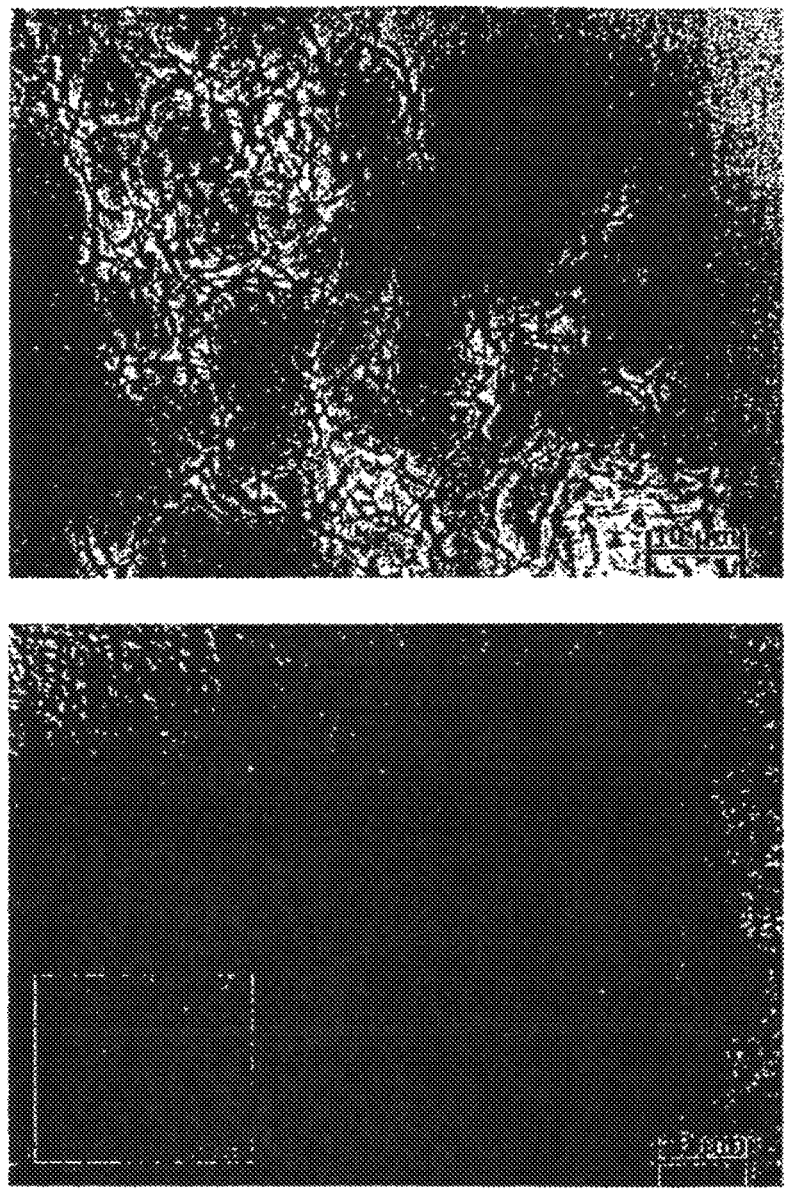

FIG. 16. Morphology and branching of *S. coelicolor* M145 and its dasR mutant in liquid-grown TSB cultures. While *S. coelicolor* M145 (top picture) shows typical occasional branching, deletion of the dasR gene results in strong increase in brancing (bottom picture). This suggests that modification of the expression level of dasR allows us to determine the branching frequency, which is important for the control of morphology and hence is a tool for improved growth behaviour in large scale fermentations. Bar=10 µm.

FIG. 17. Complete control of glycolysis and related pathways by DasR in *Thermobifido fusca*. Almost all steps in glycolysis and the connected pathways leading to oxaloacetate are predicted to be directly controlled by DasR. Database reference numbers for the respective genes are indicated. Note that every single step in glycolysis is predicted to be DasR-dependent.

Figure 18:
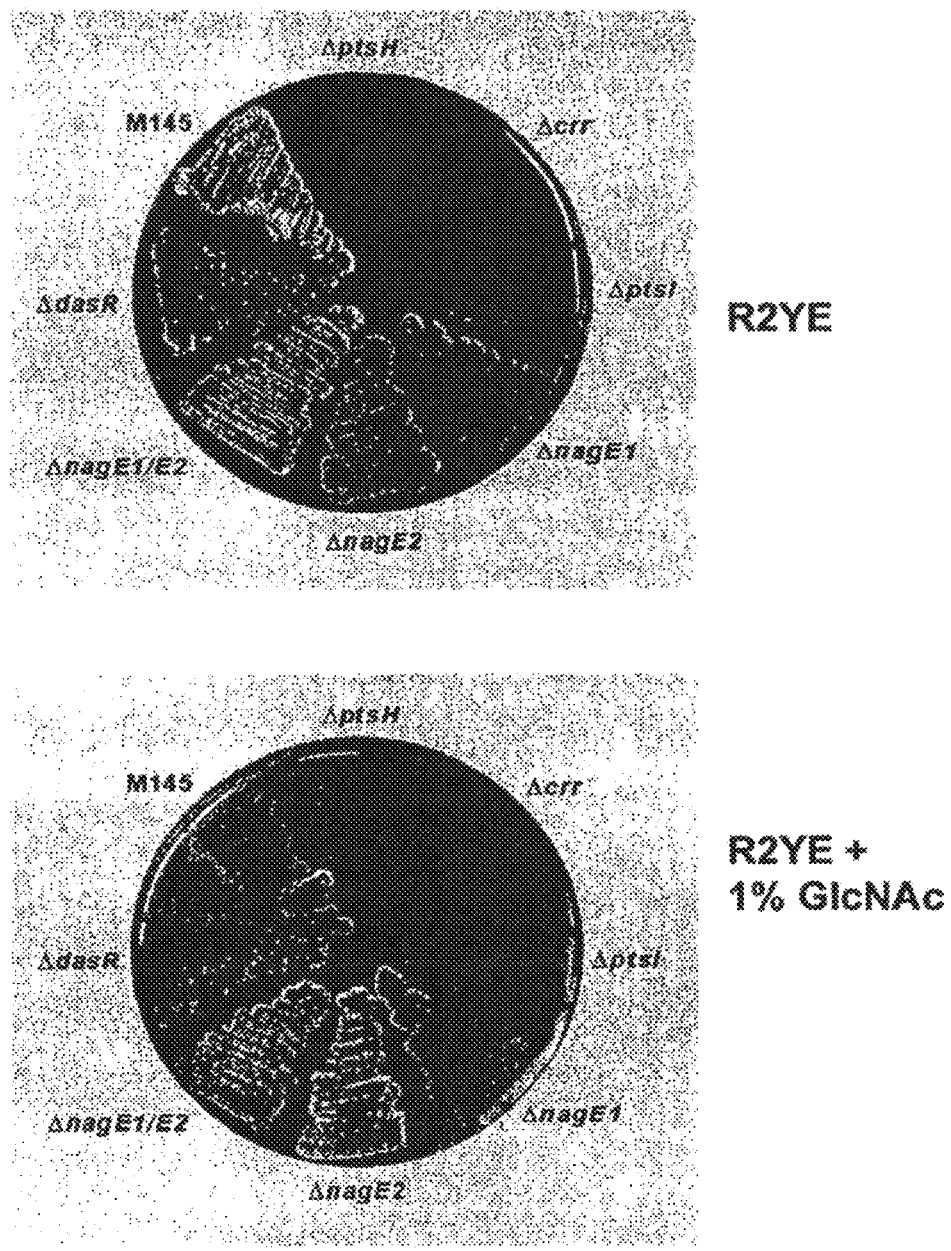

FIG. 18. N-acetylglucosamine is transported by NagE2 (SCO2907). Mutants deleted for the transport genes nagE1/(SCO2906), nagE2 (SCO2907), or both, were plated on R2YE agar plates with or without N-acetylglucosamine (1% w/v). Other strains on the agar plates are: *S.coelicolor* M145 (parent of all mutants), the dasR mutant BAP29 and the pts mutants ptsH (BAP1), crr (BAP2), and ptsI (BAP3). For phenotypes of the pts mutants see also FIG. 3A). Excitingly, in the absence of nagE2 (or nagE2 and nagE1)addition of N-acetylglucosamine has no effect on development, while the nagE1mutant and the parental strain S. coelicolor M145 become arrested in the vegetative state. This proves that indeed nagE2 is the transporter of N-caetylglucosamine and is essential for import of the inducer molecule for the DasR control system.

FIG. 19. The nucleic acid and amino acid sequence of S. clavuligerus dasR/DasR. A) The dasR nucleic acid sequence (SEQ ID NO:505). B) The DasR amino acid sequence (SEQ ID NO:506).

FIG. 20. Alignment of protein sequences corresponding to the helix-turn-helix DNA binding motif of DasR obtained from various Streptomyces species. Sambo, S. ambofaciens (SEQ ID NO:517); Saver, S. avermitilis (SEQ ID NO:508); Scinn, S. cinnamoneus (SEQ ID NO:515); Scoel, S. coelicolor (SEQ ID NO:507); Scoll, S. collinus (SEQ ID NO:510); Sdias, S. diastatochromogenes (SEQ ID NO:514); Sgran, S. granaticolor (SEQ ID NO:512); Sgold, S. goldeniensis (SEQ ID NO:516); Sgris, S. griseus (SEQ ID NO:509); Slimo, S. limosus (SEQ ID NO:513); and Svene, S. venezuelae (SEQ ID NO:511). Amino acid numbering corresponds to aa sequence of S. coelicolor DasR (SCO5231). Symbols HTH above the sequence refer to the Helix-Turn-Helix DNA binding signature.

Figure 21:
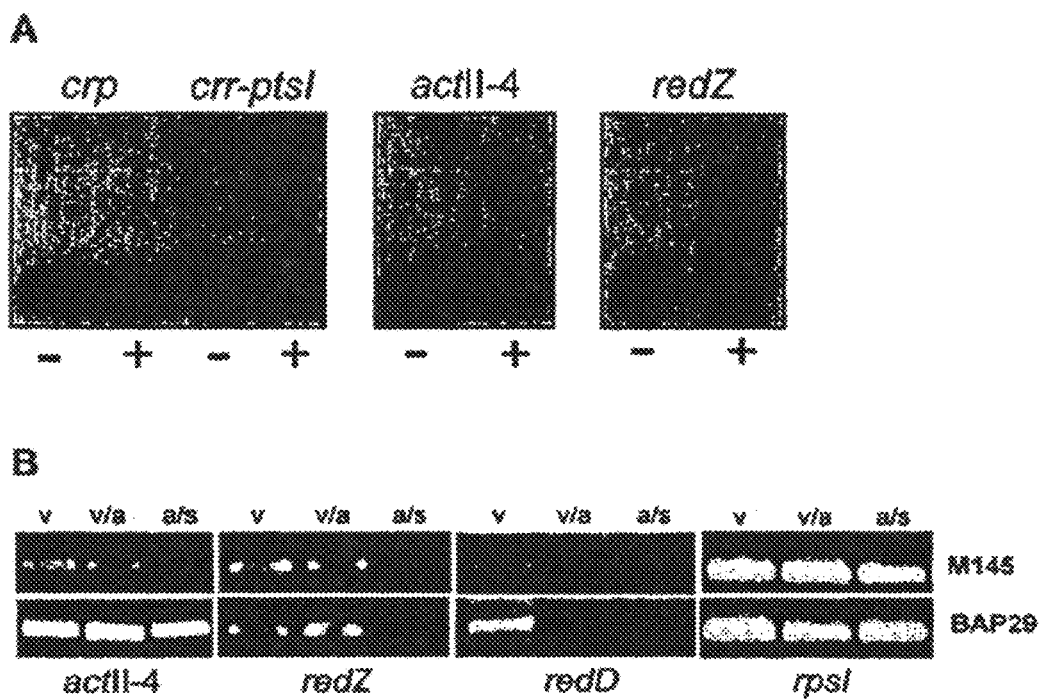

FIG. 21. DasR represses expression of Act and Red pathway-specific activators. (A) Electrophoretic mobility shift assays showing that DasR interacts with dre sites predicted upstream of actII-ORF4 and redZ. DNA probes encompassing dre sites found upstream of the crr-ptsI operon (encoding enzyme EIIA and enzyme EI of the PTS), actII-ORF4 and redZ were incubated with (+) or without (-) purified His-tagged DasR. The experimentally validated dre site upstream of the crr-ptsI operon (Rigali et al 2004) and the predicted cis-acting element of crp (Derouaux et al 2004) of S. coelicolor were used as positive and negative controls, respectively. (B). Transcriptional analysis of Act and Red pathway-specific activators by semi-quantitative RT-PCR. DasR directly represses transcriptional expression of actII-ORF4 and redZ. Samples were collected from S. coelicolor M145 and the dasR mutant grown on MM mannitol agar plates after 30 h (vegetative growth), 42 h (initiation of aerial growth), and 72 h (aerial growth and spores). v, vegetative mycelium; a, aerial hyphae; s, spores.

Figure 22:
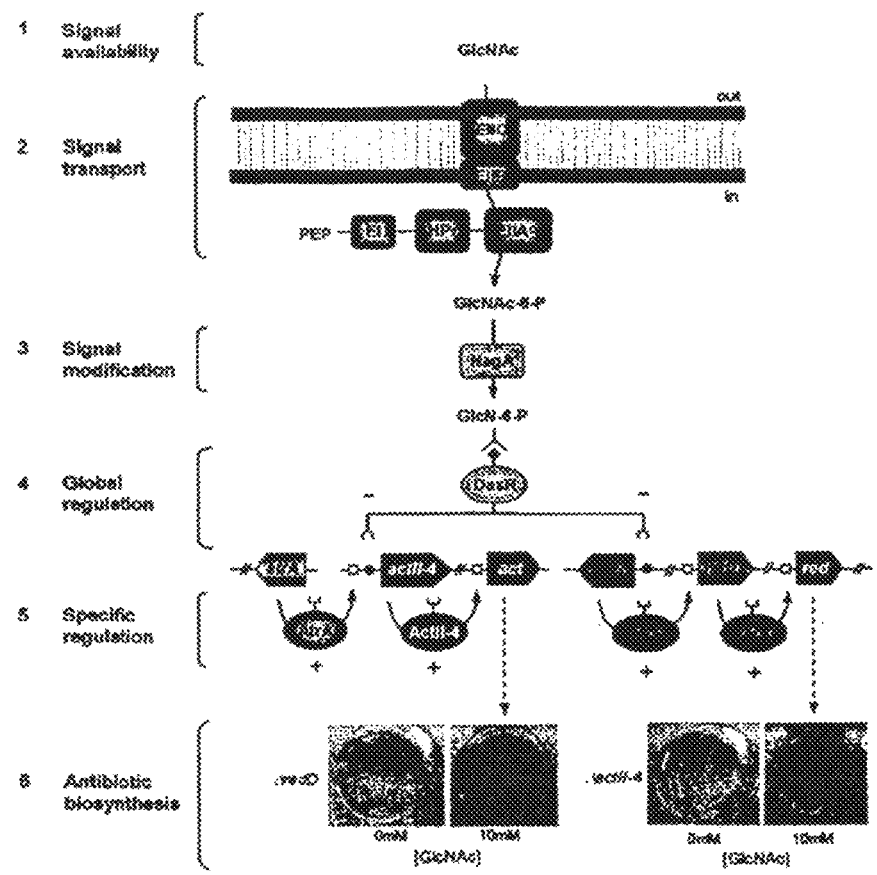

FIG. 22. N-acetylglucosamine-dependent signalling cascade of actinorhodin and undecylprodigiosin production in S. coelicolor. N-acetylglucosamine (GlcNAc) enters the cytoplasm and is subsequently phosphorylated via the GlcNAc-specific phosphoenolpyruvate-dependent phosphotransferase system, composed of intracellular general PTS proteins EI, HPr, and EIIA, and the GlcNAc-specific EIIB and EIIC components. N-acetylglucosamine-6-phosphate (GlcN-6P) is further deacetylated by NagA, the GlcN-6P deacetylase. The resulting glucosamine-6-phosphate (GlcN-6P) is a known allosteric effector of DasR able to inhibit its DNA-binding ability, resulting in loss of transcriptional repression of actII-ORF4 and redZ, which encode the pathway-specific transcriptional activators of the actinorhodin and undecylprodigiosin biosynthesis clusters, respectively. In support of the deduced antibiotic biosynthesis signalling cascade, GlcNAc induces Act and Red production in the S. coelicolor ΔredD (M510) and ΔactII-ORF4 (M511) mutants, respectively.

Figure 23:
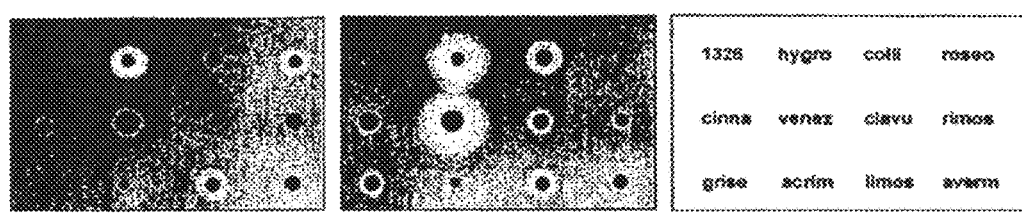

FIG. 23. Conservation of the GlcNAc-dependent antibiotic-inducing pathway amongst streptomycetes. Streptomycetes were grown on MM agar plates with 0.5% mannitol alone (left panel), or with added 1% GlcNAc (right panel), and an overlay was applied containing B. subtilis, allowing visualization of growth inhibition caused by antibiotic production. The tested streptomycetes were Streptomyces lividans 1326 (1326), Streptomyces hygroscopicus (hygro), Streptomyces collinus (colli), Streptomyces roseosporus (roseo), Streptomyces cinnamonensis (cinna), Streptomyces venezuelae (venez), Streptomyces clavuligerus (clavu), Streptomyces rimosus (rimos), Streptomyces griseus (grise), Streptomyces acrimycini (acrim), Streptomyces limosus (limos), and Streptomyces avermitilis (averm). See Materials and Methods section for exact nomenclature. The GlcNAc-triggering effect on antibiotic activity was most obvious for S. hygroscopicus, S. collinus, S. venezuelae, S. clavuligerus, S. rimosus, and S. griseus.

Figure 24:
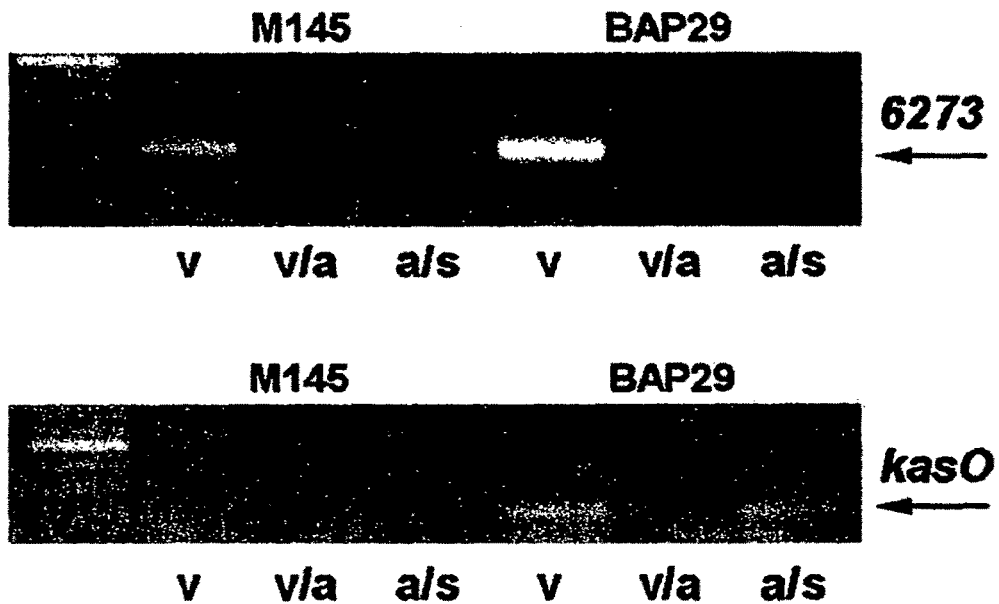

FIG. 24. DasR represses expression of the type I polyketide "cryptic" cluster. Transcriptional analysis of the cryptic type I polyketide cluster of S. coelicolor (SCO6273-SCO6288) by semi-quantitative RT-PCR. Inactivation of dasR results in the transcriptional "awakening" of the cryptic pathway-specific activator gene, kasO (SCO6280), and subsequently enhanced transcription of SCO6273, encoding a putative type I polyketide synthase, during vegetative growth. Samples were collected from S. coelicolor M145 and the dasR mutant BAP29 grown on MM mannitol agar plates after 30 h (vegetative growth), 42 h (initiation of aerial growth), and 72 h (aerial growth and spores). v, vegetative mycelium; a, aerial hyphae; s, spores.

DESCRIPTION OF TABLES

Table 1 Experimentally validated DasR binding sites used to build the matrix for consensus sequence.

Table 2 Non-limiting list of genes controlled by a DasR binding site in Streptomyces coelicolor.

Table 3 List of putative binding sites for DasR relating to secondary metabolism (cut-off score 5). A. Antibiotics and metabolites of known function produced by actinomycetes B. Known and cryptic biosynthesis clusters of Streptomyces coelicolor.

Table 4 DasR target genes related to glutamate and glutamine metabolism.

Table 5 DasR binding sites in Bacillus species A. B. subtilis B. B. halodurans.

Table 6 DasR binding sites in Lactococcus lactis.

Table 7 DasR binding sites in Streptococcus species A. S. pneumoniae B. S. pyogenes C. S mutans D. S. agalactiae.

Table 8 DasR binding sites in Listeria species. A. Listeria innocua B. Listeria monocytogenes.

Table 9 DasR binding sites in Thermobifido fusca. Metabolic genes corresponding to FIG. 17 are highlighted.

DETAILED DESCRIPTION OF THE INVENTION

Experimental Part
Materials and Methods
 Bacterial Strains.
 E. coli DH5α, and BL21(DE3) were used for subcloning and DasR overexpression experiments. S. coelicolor M145, M510 (M145 ΔredD), M511 (M145 ΔactII-IV) and M512 (M145 ΔactII-IV ΔredD) (Floriano and Bibb, 1996) and Streptomzyces lividans 1326 were all obtained from the John Innes Centre strain collection, Streptomyces avermitilis NRRL 8165 (MA-4680), Streptonzyces hygroscopicus ATCC27438, Streptomyces limosus ATCC 19778, Streptomyces rinzosus ATCC 10970, Streptonzyces roseosporus ATCC 31568 and Streptonzyces venezuelae ATCC15439 were obtained from the ATCC strain collection and *Streptomyces acrinzycini* DSM 40540, *Streptomyces cinnanzonensis* DSM 40467, *Streptomyces clavuligerus* NRRL 3585, *Streptomyces collinus* DSM 40733 and *Streptomyces griseus* NRRL B2682 from the DSMZ strain collection. The dasR mutant BAP29 (ΔdasR::accC4) was created by replacing the coding region of the gene by the apramycin resistance gene cassette, using plasmid pWHM3, according to a routine procedure (Nothaft et al., 2003). The same strategy was used to create the knock-out mutants for ptsH (BAP1), crr (BAP2), ptsI (BAP3), nagE1 (BAP4), nagE2 (BAP5), and nagE1/E2 (BAP6). BAP1-3 were published previously (Nothaft et al., 2003). *S. coelicolor* strains were grown at 28° C. using tryptic soy broth without dextrose as complex medium (TSB, Difco) or minimal medium (van Wezel et al., 2005). *E. coli* cultures were grown in Luria-Bertani broth (LB) at 37° C. Phenotypic characterization of mutants was done on minimal medium agar plates with various carbon sources as indicated in the text (Kieser et al., 2000). Quantification of Act and Red was performed as described previously (Martinez-Costa et al., 1996).

DNase I Footprinting.

A 222-bp DNA fragment corresponding to the −202/+8 region relative to the start of *S. coelicolor* crr gene (SCO1390) was chosen for DNase I footprinting. The DNA fragment was amplified from chromosomal DNA by PCR. 50 fmoles of $^{32}P$ end-labelled probe were incubated with the relevant proteins (DasR-(His)$_6$ and/or BSA) and DNaseI (0.4 µg/ml) as described (Sambrook et al., 1989).

Computational prediction. Multiple alignments and position weight matrices were generated as described previously (Rigali et al., 2004) by the Target Explorer automated tool on the world wide web at trantor.bioc.columbia.edu/Target Explorer!) (Sosinsky et al., 2003). The weight matrix was deposited as "DasR4".

Protein Purification and Western Blot.

Purification of recombinant histidine-tagged DasR (Rigali et al., 2004) and Western blot analysis with antibodies raised against HPr and IIA$^{Crr}$ have been described elsewhere (Nothaft et al., 2003).

RT-PCR.

RNA was isolated from mycelium of *S. coelicolor* M145 and BAP29. Minimal medium cultures containing 50 mM glycerol were inoculated with spores and grown until $OD_{550}$ of 0.6 (exponential growth). N-acetylglucosamine was added at 0.5% and samples were taken after 0, 15, 30 and 60 minutes. RT-PCR analyses were conducted with the Superscript III one-step RT-PCR Kit (Invitrogen). RT-PCRs without reverse transcription were used as control for absence of residual DNA. For semi-quantitative analysis, samples were taken at three-cycle intervals between cycles 18 to 35 to compare non-saturated PCR product formation (van Wezel et al., 2005). Data were verified in three independent experiments.

Oligonucleotides used for the RT-PCR experiments described in FIG. 21B were:

For redZ (5'-CGACATGAAAGTGCAGGTGG-3' (SEQ ID NO:518) and 5'-TCGGGCTFGGTCAGCAAAAGC-3' (SEQ ID NO:519)), for actII-ORF4 (5'-GCTGCAGACG-TACGTGTACCACAC-3' (SEQ ID NO:520) and 5'-GCGTCGATACGGAGCTGCATTCC-3' (SEQ ID NO:521)), for redD (5'-TCATGGGAGTGCGGA-GAACGCG-3' (SEQ ID NO:522) and 5'-CGCCCCACA-GTTCGTCCACCAG-3' (SEQ ID NO:523)), SCO6273 (5'-CGGGGGCGAACTCGTCAAGGTC-3' (SEQ ID NO:524) and 5'-GCCGAGATGTCGATGAGGACGCGG-3' (SEQ ID NO:525)), for kasO (5'-GCGGGATGCTCAGTGAG-CACGG-3' (SEQ ID NO:526) and 5'-GACGAGGTCGGC-GAGGACGGG-3' (SEQ ID NO:527)) and for rpsI (5'-GAGACCACTCCCGAGCAGCCGC-3' (SEQ ID NO:528) and 5'-GTAGCGGTTGTCCAGCTCGAGCA-3'(SEQ ID NO:529)).

Score matrix (DasR4)

| | | | | | | | | | | | | | | | | |
|---|---|---|---|---|---|---|---|---|---|---|---|---|---|---|---|---|
| A | 0.63 | −0.53 | −1.12 | −2.71 | −2.71 | −0.53 | −1.12 | −2.71 | 1.31 | −2.71 | 1.16 | −2.71 | −2.71 | 0.76 | −0.53 | −0.17 |
| C | −1.08 | −0.12 | −2.71 | −2.71 | −2.71 | −2.71 | 0.15 | −1.08 | −2.71 | −2.71 | −2.71 | 1.36 | 1.36 | −2.71 | 0.36 | −1.08 |
| G | −0.49 | 0.93 | −1.08 | 1.13 | 1.36 | −2.71 | 0.81 | −2.71 | −2.71 | 1.36 | −1.08 | −2.71 | −2.71 | −2.71 | 0.54 | −2.71 |
| T | 0.10 | −2.71 | 1.16 | −0.17 | −2.71 | 1.16 | −1.12 | 1.24 | −2.71 | −2.71 | −1.12 | −2.71 | −2.71 | 0.49 | −1.12 | 0.98 |

The minimum score obtained by a sequence scanned by matrix DasR4 is −38.55 and the maximum score is 17.25. According to the current experimental validations, a DasR-binding site could be defined as a sequence of 16 nucleotides that, when scanned by the DasR4 matrix, obtains a score comprised between higher than 6 (and up to 17.25). Illustratively, a truly and experimentally validated DasR-binding site with a score of only −2.97 has been found upstream of gdhA encoding a NADP-specific glutamate dehydrogenase.

Microscopy.

Transmission electron microscopy (TEM) for the analysis of thin sections of hyphae and spores was performed with a Philips EM410 transmission electron microscope (Mahr et al., 2000). Phase contrast micrographs were produced using a Zeiss standard 25 phase-contrast microscope, and a 5 megapixel digital camera.

Sugar Uptake.

Uptake assays with 20 µM N-[$^{14}C$]acetyl-D-glucosamine (6.2 mCi mmol$^{-1}$) into mycelia were performed as described (Nothaft et al., 2003).

Two-Dimensional Gel Electrophoresis and Protein Spot Identification.

Mycelia of *S. coelicolor* M145 and BAP29 were grown in minimal medium with 50 mM glycerol, harvested at different time points within exponential phase, washed, resuspended in 20 mM HEPES, pH7.5 and 50 mM $MgSO_4$ and sonicated; cell debris was removed after centrifugation. DNA and RNA were eliminated by DNase and RNase treatment. The proteins extracts were dialysed twice at 4° C. against water, followed by addition of 6 M solid urea and 2M thiourea, TritonX-100 (2.5% (v/v)) IPG buffer (0.5% (v/v)), DTT (25 mM) and bromophenolblue. Membrane proteins were removed by ultracentrifugation for 1 h at 65.000 g. 1.5 mg of the cytoplasmic protein fraction was applied on 24-cm IPG strips (pH range 4-7) on an IPGPhor unit (Amersham/Pharmacia). The IPG strips were subjected to 12.5% polyacrylamide gels that were run on the Ettan DALT II system (Amersham/Pharmacia). The gels were stained with PhastGel Blue R and scanned. Proteome patterns were compared using two gel sets derived from independent experiments. Protein intensities were analysed by densitometric gray scale analysis with TINA software (Raytest). Protein spots were excised, subjected to in-gel digestion with trypsin and analysed by liquid chromatography tandem mass spectrometry (LC-MS/MS) (Marvin-Guy et al., 2005).

Electromobility Gel Shift Assay (EMSA).

EMSAs were performed with fluorescent probes (10 nM) with an ALF express sequencer (Filee et al., 2001). Purified DasR (3 µM) and 1000-fold excess of non-specific DNA were used in the reaction mixture. Predicted cis-acting elements were taken from the promoter regions of actII-ORF4 (SCO5085; 5'-CACATTGAAATC TGTTGAGTAGGCCTGTTATTGTCGCCCC-3' (SEQ ID NO:530)), and redZ (SCO5881; 5'-ACAAGATCTTCT TGAGGTGGAAACCACTTTCGTATCAGTCT-3' (SEQ ID NO:531)). Known cis-acting elements upstream of crr (SCO1390; CCGTGAGGAG TGTGGTCTAGACCTCTAATCGGAACA-3' (SEQ ID NO:532)), and crp (SCO3571; 5'-TGCGGCATCCTTGT-GACAGATCACACTGTTTGGACT-3' (SEQ ID NO:533)) were used as positive and negative controls, respectively. The 16 nt dre sites are underlined.

Enzymatic Activities.

Chitinase activity was determined as described previously (Zhang et al., 2002) using a colorimetric assay with carboxymethylchitin-Remazol Brilliant Violet 5R (Loewe Biochemica GmbH, Germany) as substrate. D-Ala-D-Ala aminopeptidase measurements were performed with D-Ala-paranitroanilide as substrate (Cheggour et al., 2000). BCA protein assay (Pierce) was used for determining protein concentrations.

Global Antibiotic Activity Assays.

Samples (1 µl) of diluted spore suspensions were spotted on minimal medium plates containing 0.5% mannitol with or without 1% GlcNAc and incubated three days at 28° C. For the bioassay, we inoculated 10 ml of molten soft nutrient agar (SNA) with 500 µl of a Bacillus subtilis overnight culture ($OD_{600}$~1), and poured the mixture into square 12-cm-side Petri dishes. Plates were kept 2 h at 4° C. to solidify SNA and to allow diffusion of antibiotics produced, then incubated overnight at 30° C.

Experimental Part

Results

Prediction of the DasR Regulon.

To allow the S. coelicolor genome to be scrutinized for the occurrence of the DasR operator site, we performed DNaseI footprinting on the dre of the crr-ptsI operon, encoding the PTS enzyme IIA ($IIA^{Crr}$) and enzyme I (EI) (FIG. 1A). The protected sequence (TGTGGTCTAGACCTCT (SEQ ID NO:10)) corresponded to positions −130 to −115 relative to the start of crr, and had a 13 out of 16 by match to the derived DasR binding site consensus sequence (see below). This information was used to determine the dre sites of target genes that we had already validated (Table 1 and (Rigali et al., 2004)). Using this training set, we built a refined position weight matrix ("DasR4"; see materials and methods), resulting in an alignment matrix that was used to scan the complete S. coelicolor genome.

Figure 1B:
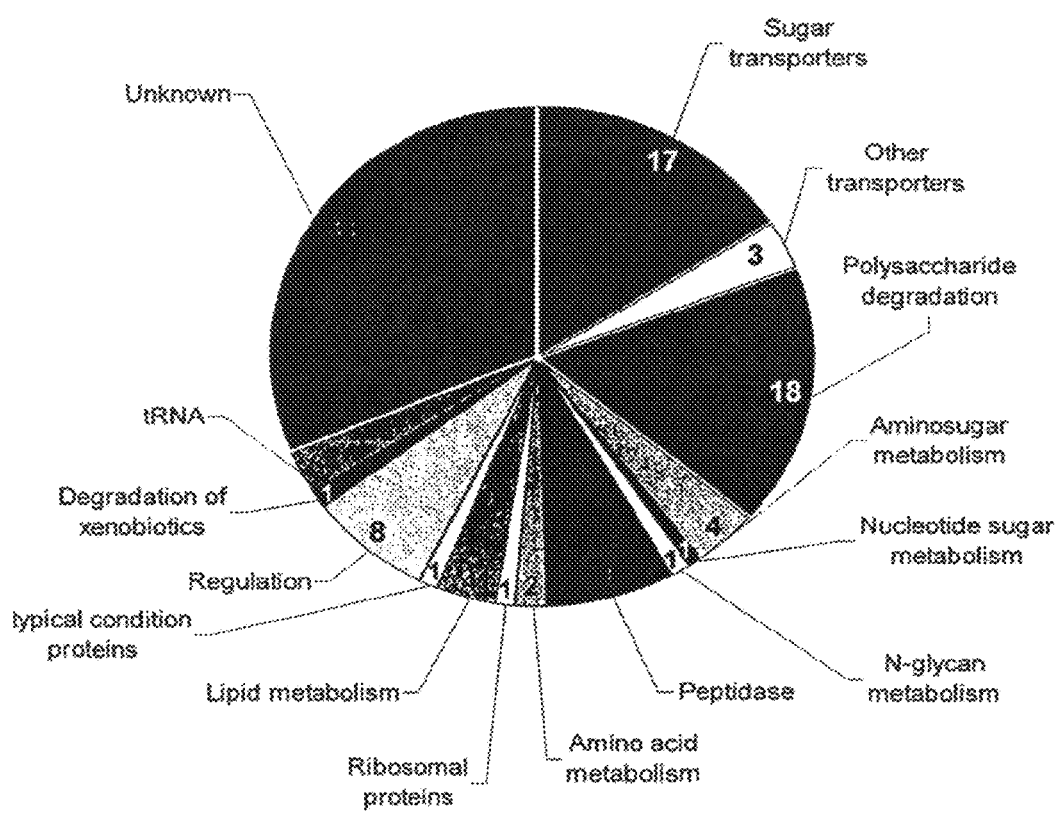

A genome scan revealed 160 dre sites for 131 transcription units, representing over 200 candidate genes. About 40% of the target genes are related to sugar or aminosugar metabolism, with N-acetylglucosamine (GlcNAc) as the central saccharidic component (FIG. 1B and Table 2). The relationship with GlcNAc also connects to the identification of cell wall-associated peptidases. The predicted DasR regulon further includes genes for nitrogen metabolism including genes related to glutamine/glutamate amino acid metabolism. The list of targets also includes 16 transcription factors (#27, 31, 46, 51, 56, 62, 67, 71, 77, 81, 84, 105, 119, 129, 130, and 131 in Table 2), suggesting an extensive level of indirect transcriptional control by DasR.

Phenotype of the dasR Mutant

A dasR null mutant (BAP29) was constructed by replacing almost the complete coding region (nt 14-635 out of 765) by the apramycin resistance cassette (aacC4), to study the role of DasR in vivo.

The dasR mutant of S. coelicolor showed medium-dependent development: on some media development was enhanced, while on others it was completely abolished. This is summarised in FIG. 11. This strongly suggests that the function of DasR depends on the carbon and nitrogen sources used.

Figure 2A:
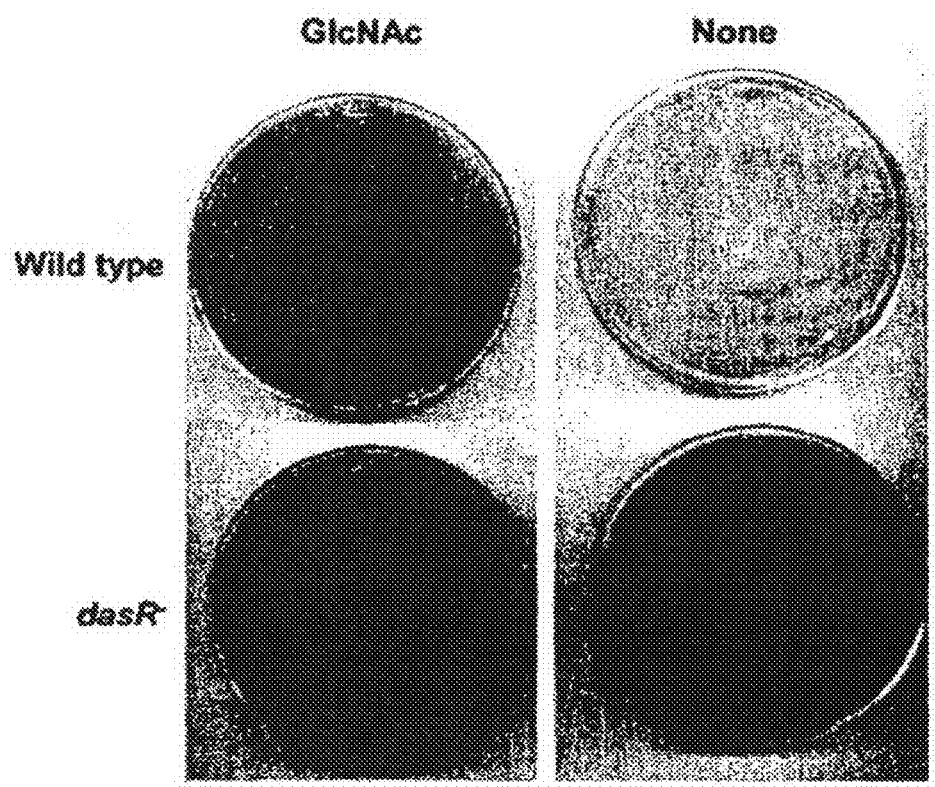
Figure 2B:
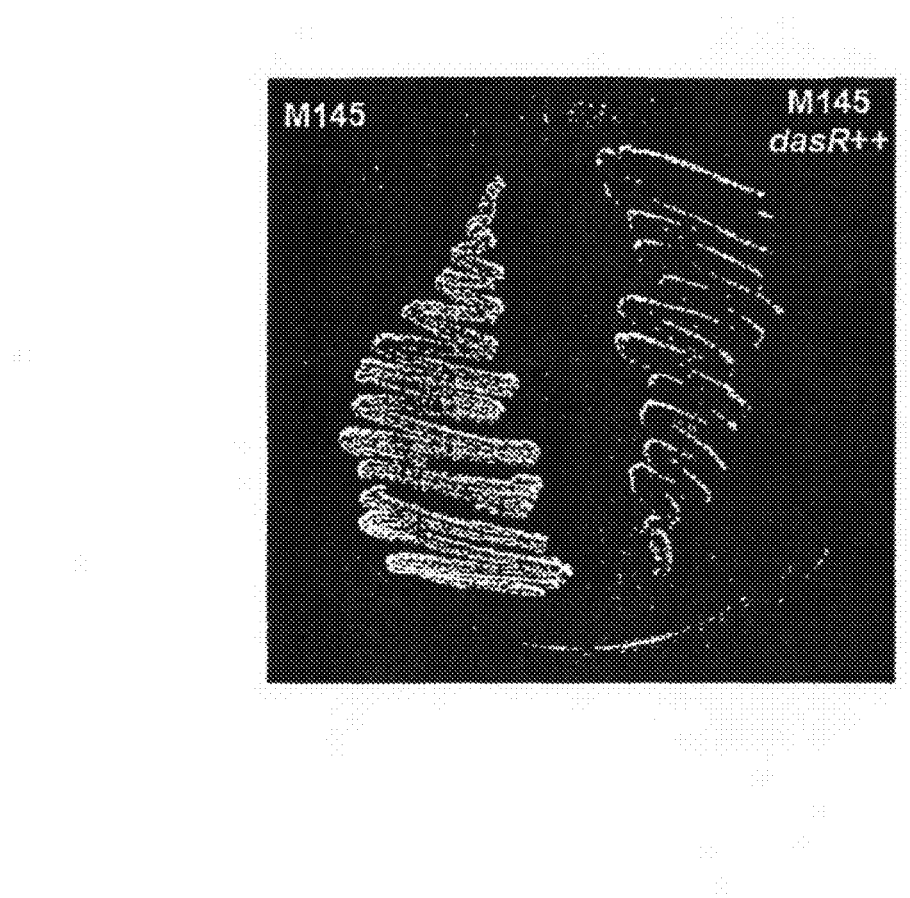
Figure 2C:
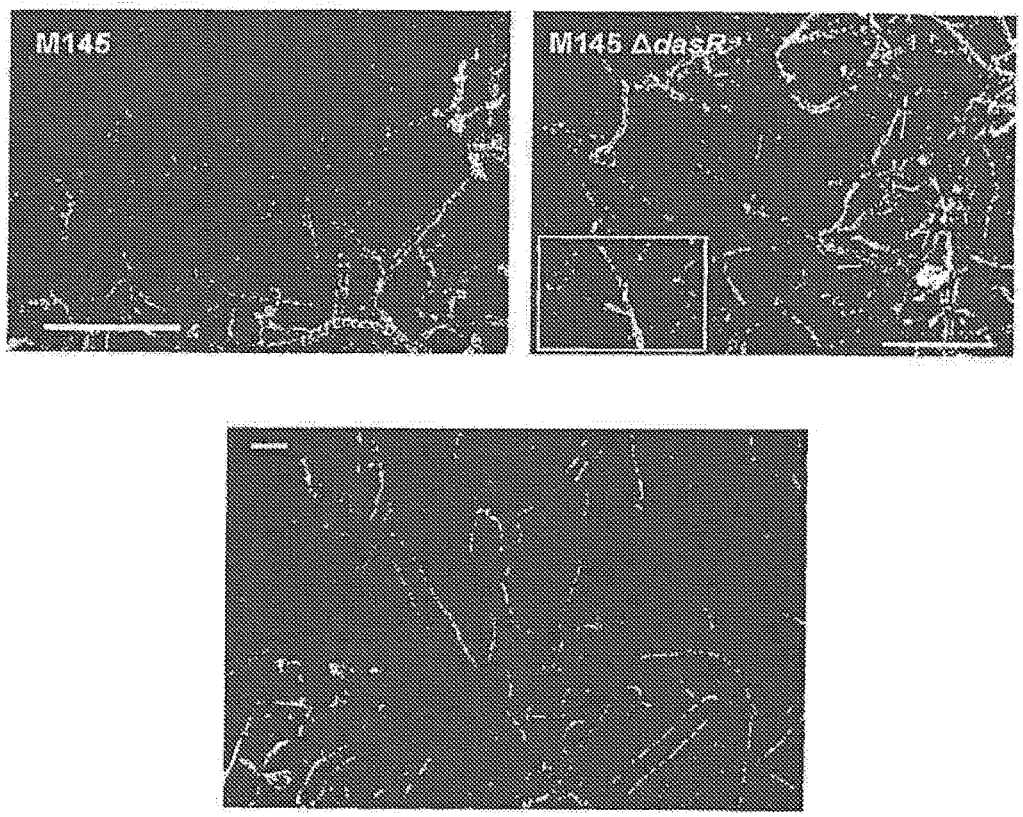
Figure 2D:
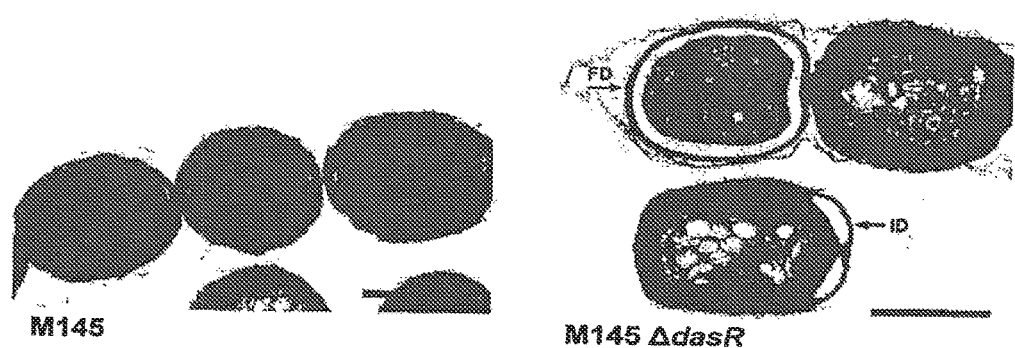

Surprisingly, the dasR mutant showed strongly enhanced antibiotic production (FIG. 2A). Overproduction of DasR in strain M145(pFT241 dasR$^+$) resulted in a reversed, non-sporulating bald (bld) phenotype (FIG. 2B). Closer inspection of the dasR mutant by cryo-scanning electron microscopy (cryo-SEM) showed that spores were almost completely absent in the dasR mutant, and aerial hyphae collapsed readily during sample preparation (FIG. 2C). Analysis at high resolution by Transmission EM of cross-sections from S. coelicolor M145 and BAP29 revealed that while M145 produced normal spores, the dasR mutant produced many spores (approximately 30%) with smaller or larger voids close to the spore wall (FIG. 2D; voids indicated by arrows), suggesting extensive detachment of the cytoplasmic membrane from the spore wall. Additionally, spore morphologies were significantly more heterogeneous; while wild-type spores typically have a size of 0.6 by 0.8 µm, the dasR mutant showed an unusually strong variation in spore sizes (0.5-1.4 µm in length, but with the same width of 0.8 µm). In addition, many mutant spores had a wall with a thickness similar to that of aerial hyphae, failing to create the typical thick spore wall. These observations connect well to our in silico predictions (Table 2) that dasR controls genes involved in the fate of peptidoglycan, including the genes for the metabolism of the precursor N-acetyglucosamine.

DasR and the Control of Development

How does DasR control the switch to development? Inclusion of pts genes in the dasR regulon allowed us to propose that at least one link is through the DasR-mediated control of the PTS. In a previous publication (Nothaft et al., 2003), we described normal but retarded development for the individual pts knock-out mutants, namely BAP1 (ΔptsH, the gene for HPr), BAP2 (Δcrr, the gene for $IIA^{Crr}$), and BAP3 (ΔptsI, the gene for enzyme I (EI)). More detailed phenotypic analysis of the PTS mutants revealed that while eventually all of the pts mutants were on some media able to produce spores, morphogenesis was significantly delayed on diverse complex and minimal media agar plates with the strongest differences when grown in the presence of mannitol and arabinose. Strains were grown for 5 days on SFM or R2YE agar plates. As shown in FIG. 3A, On SFM the crr mutant BAP2 produces a white aerial mycelium but failed to produce spores under these conditions, while deletion of ptsH (BAP1) or ptsI (BAP3) allowed the production of some grey-pigmented spores.

Interestingly, on R2YE agar plates all three PTS mutants show vegetative arrest (so-called bald or bld phenotype).

We recently discovered in a proteomics screen of these mutants that the expression patterns (in BAP2 and BAP3) or the modification patterns (in BAP1) of the WhiG protein, a key developmental σ factor for early aerial growth (Chater et al., 1989), strongly differed from those in the parental strain M145. To establish the expression of whiG, its transcription was analysed in all three mutants and in M145. Interestingly, whiG transcription was strongly reduced in the BAP2 and BAP3 mutants (FIG. 3B), providing a likely explanation for their failure to complete sporulation, since whiG mutants have a characteristic non-sporulating phenotype.

Hence, we propose that DasR acts as the nutrient sensor, and translates this through control of the PTS, which in turn controls whiG and—in view of the developmental arrest of the pts mutants—most likely at least one or more other early developmental genes. It might be noteworthy that the phosphotransferases EI, HPr, and IIA$^{Crr}$ provide a perfect signalling system through reversible metabolite-dependent phosphorylation, which in other bacteria is used for diverse but always carbon-related responses (Brückner and Titgemeyer, 2002).

Proteome Analysis

Figure 4A:
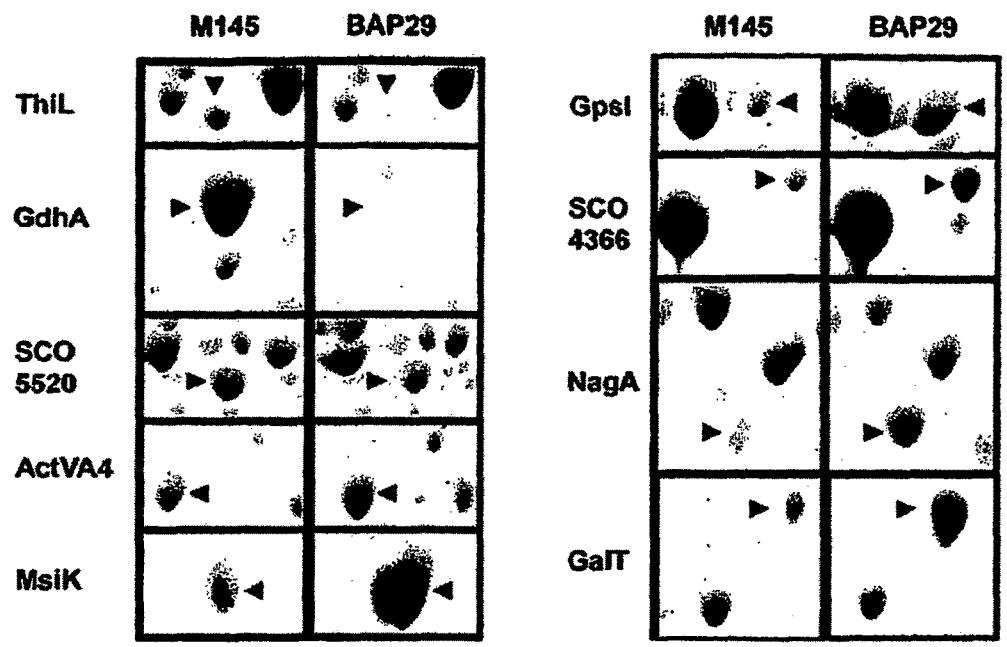

To obtain an assessment of the effect of DasR, we compared the protein profiles of BAP29 and its parent M145. Protein extracts were prepared from mycelia grown in the presence of glycerol (a neutral carbon source) and analyzed by two-dimensional gel electrophoresis. About 4% of the protein spots on the Coomassie-Brilliant-Blue-stained gels were altered in intensity by more than two-fold and eight were identified by mass spectrometry (FIG. 4A). 11 of the most spectacular differences between M145 and BAP29 were analyzed, and of these we could positively identify nine proteins by mass spectrometry (FIG. 4A). Two of the proteins were predicted in our in silico screen, namely the multiple sugar import protein MsiK and NagA (N-acetylglucosamine-6-P deacetylase). Only nagA and msiK were included in Table 2 and contained predicted dre sites. The others could be related to central and to secondary metabolism (see below and FIG. 5). Binding of DasR to the dre in the msiK promoter region was demonstrated by EMSA (see below). According to a role of MsiK in the uptake of inducers of polysaccharides-degrading systems, the induction of these enzymatic arsenals (about a hundred of genes) should be also affected due to the dasR deletion (see Discussion).

The lack of a dre upstream of the other seven genes suggests indirect control of these genes by DasR. Visualising the metabolic pathways related to proteins identified by proteome analysis revealed that most gravitate around GlcNAc and glutamate metabolism, fitting well with the in silico and in vitro data presented above (FIG. 5).

DasR Controls Secondary Metabolism and Antibiotic Production in Actinomycetes

Interestingly, two of the targets identified in our proteomics screen, namely ActVA4 and GpsI, which are both up-regulated in the dasR mutant, are involved in the production of the antibiotic γ-actinorhodin (Bibb, 2005) which correlated well with the early an activated production of blue γ-actinorhodin in the dasR mutant (FIG. 2A). GpsI is the guanosine pentaphosphate (pppGpp) synthetase that synthesizes the ppGpp precursor. It has been established that the stringent factor ppGpp has a causal role in activating actII-ORF4 transcription (Hesketh et al., 2001). The high amount of GpsI in BAP29 suggests an increased pool of ppGpp precursors and therefore early and enhanced production of actinorhodin. The function of ActVA4 is unknown but the gene is included in the cluster responsible for actinorhodin production (20 genes) and depending on the transcriptional activator actII-ORF4 (Arias et al., 1999). As follows from Table 2, actII-ORF4 features among the predicted DasR target genes. Direct binding of purified DasR to the dre upstream of this gene is substantiated by our observation that DasR protein directly binds to a double-stranded oligonucleotide containing the dre element found in the actII-ORF4 promoter region (FIG. 9). This proves that indeed DasR controls actinorhodin production by binding to the pathway-specific activator gene for the synthesis of this exciting compound, suggesting that DasR plays a crucial role in the control of antibiotic production in actinomycetes.

Figure 4B:
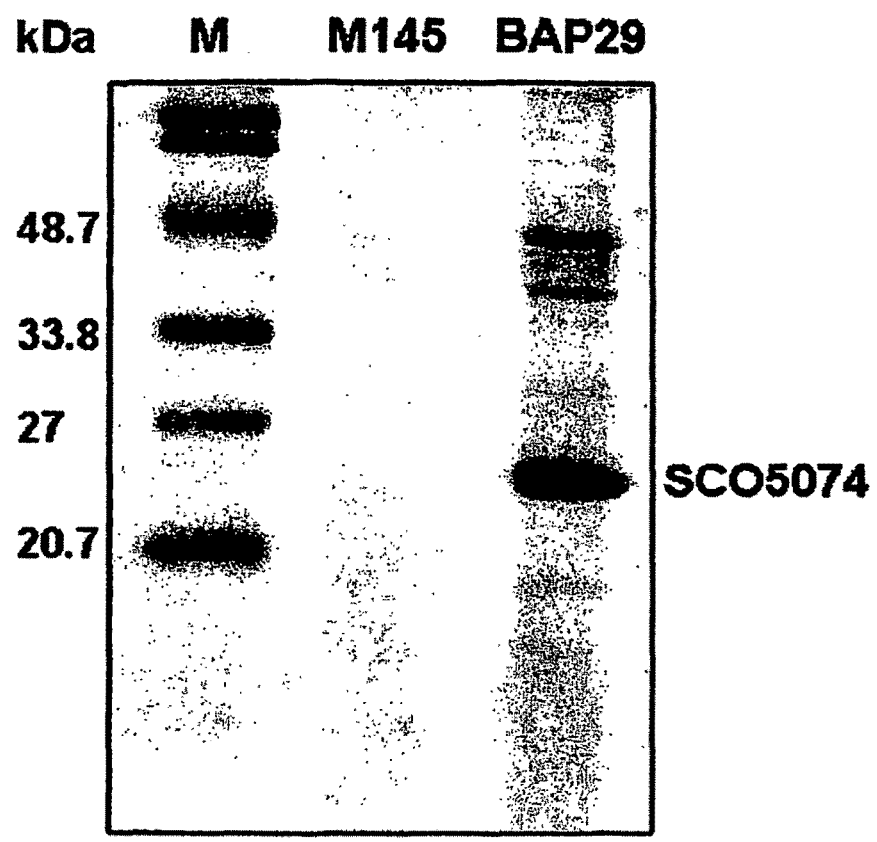

Excitingly, comparison of the secreted proteins in abstracts of the dasR mutant and its parent S. coelicolor M145 by one-dimensional gel electrophoresis showed that one single protein was extraordinarily highly over-expressed in the dasR mutant (FIG. 4B). This protein was identified by Mass spectrometry as SCO5074. This protein was recently shown to be part of the actinorhodin biosynthesis cluster, and is a secreted dehydratase that is most likely responsible for tailoring of the secreted antibiotic (Hesketh & Chater 2003; Taguchi et al, 2000). The gene product most likely assists cyclisation-dehydration of the alcohol in the actinorhodin precursor to give the pyran ring, a reaction that can proceed spontaneously but far less efficiently without it. As described in Taguchi et al. (2000), the actVI-ORF3 disruption mutant produces less (about half as much) actinorhodin as the parent. This is in line with our observation that while the wild-type strain produced a blue pigment, the dasR mutant produced a purple/violet pigment, most likely a variant of actinorhodin due to the extreme over-expression of SCO5074.

Also highly interesting is that using the novel bioinformatics techniques described above, we identified dre sites upstream of many more genes involved in the regulation and/or production of antibiotics. These targets are summarised in Table 3.

Control of Enzyme Production

With 16 predicted genes, chitin-related (chi) genes constitute a large subset of potential DasR targets, including chitinases, chitin binding proteins, extracellular β-N-acetylglucosaminidases (convert chito-oligosaccharides into GlcNAc and chitobiose), and intracellular β-N-acetylglucosaminidases (hydrolyse chitobiose to GlcNAc). To substantiate this, we determined the overall chitinolytic activity of BAP29 and M145 grown under inducing (chitin) or repressing (glycerol, glycerol plus GlcNAc, and glucose plus chitin) conditions. As depicted in FIG. 6A, we observed a strongly reduced chitinolytic activity in BAP29, when cells were grown on chitin in the presence or absence of glucose. Similar observations were made when total β-N-acetylglucosaminidase activities were assayed FIG. 6A).

Seven examples were selected to validate the predicted cis-trans relationship between DasR and chi genes, for the chitinolytic system that is required for the utilization of chitin, a polymer of N-acetylglucosamine that is the one but most abundant carbon source on earth. Positive DNA-DasR interactions were observed for all tested promoters (FIG. 9), although some had low binding efficiency. The transcription of three chitinase genes was monitored by RT-PCR on RNA isolated from cultures grown under conditions inducing (glycerol and GlcNAc) or not inducing (glycerol) the uptake of GlcNAc (FIG. 6B). The genes analysed were chiI (SCO1444), chiF (SCO7263), and SCO6300, encoding a putative secreted β-N-acetylglucosaminidase. As deduced from the global chitinolytic activity, a basal expression was observed for all three genes in cultures grown solely on glycerol. For chiI and SCO6300, there was no significant difference in transcript levels between M145 and BAP29. Excitingly, chiF transcription was fully dependent on DasR: while we failed to detect any transcript in RNA preparation from BAP29, there was strong chiF transcription in the RNA samples of the wild type. These data suggest that DasR positively controls the chitinolytic system, in contrast to its repressing function towards genes for GlcNAc transport and its subsequent intracellular catabolism (see below).

Other extracellular enzymes are also controlled by DasR (FIG. 7). Indeed, we found that besides the chitinolytic system also the activity of mannanases, α-amylases, xylanases depend on DasR (FIG. 7). All of these polysaccharide-degrading systems were in fact affected in both substrate induction and glucose control by dasR, underlining its crucial position in the control mechanisms for enzyme secretion.

DasR-Mediated Control of Sugar Transport

Since many of the predicted DasR targets were involved in the fate of carbon sources (Table 2), we analyzed the effects of the dasR mutation on sugar import. Transport assays revealed that PTS-mediated internalization of GlcNAc had become constitutive in BAP29, while in the parent M145 uptake was induced by GlcNAc (FIG. 8A). This correlated to constitutive protein levels of the universal PTS phosphotransferases HPr and IIA$^{Crr}$ (FIG. 8B), and was supported by RT-PCR of the respective genes (malX2, nagE2, crr-ptsI and ptsH; FIG. 8C) that encode the PTS permease complex (IIB$^{GlcNAc}$, IIC$^{GlcNAc}$, IIA$^{Crr}$, EI, HPr).

As shown above, in silico prediction and proteome analysis identified msiK (SCO4240), encoding the universal ATPase MsiK, as a target for DasR (FIG. 4). DNA binding experiments showed that DasR directly binds to the dre present in the msiK promoter region (FIG. 9), showing that DasR is involved in the regulation of MsiK-dependent ABC-type (ATP-binding cassette) transporters, which include those for uptake of cellobiose, trehalose, maltose, xylobiose, chitobiose, and probably another further 20 to 30 carbohydrates (Bertram et al., 2004). An obvious consequence of DasR-dependent control of MsiK is that DasR indirectly controls the availability of sugar operon inducers, thus affecting the expression of all extracellular sugar hydrolases. This corresponds well to our discovery that besides the chitinolytic system also the expression of mannanases, α-amylases, xylanases depends on DasR (FIG. 7).

DasR-Dependent Peptidoglycan-Associated Proteins

The observed cell-wall anomalies in the dasR mutant (FIG. 2D) are at least in part explained by the finding that several genes encoding peptidoglycan-associated peptidases are included in the list of potential DasR targets (Table 2). In fact, a site has been predicted 71 bp upstream a five-membered dppA operon (SCO6486-6490). dppA itself encodes a putative binuclear zinc-dependent, D-specific aminopeptidase (pfam 04951), 30% identical and 50% similar to DppA of Bacillus subtilis (DppA$^{Bsu}$) (Cheggour et al., 2000); DppA$^{Bsu}$ is only active on D-Ala-D-Ala and D-Ala-Gly-Gly substrates. The physiological role of DppA$^{Bsu}$, is probably an adaptation to nutrient deficiency by hydrolysing the D-Ala-D-Ala dipeptide required in peptidoglycan biosynthesis (Cheggour et al., 2000). An other orf of the dppA operon (SCO6489) is also involved in peptidoglycan precursors or peptidoglycan degradation products catabolism. The predicted gene product of SCO6489 is 32% identical and 47% similar to LdcA (L,D-carboxypeptidase A) from E. coli that hydrolyses the peptide bond between the di-basic amino acid and the C-terminal D-alanine in the tetrapeptide moiety in peptidoglycan (Templin et al., 1999). The inactivation of ldcA in E. coli results in a dramatic decrease in the overall cross-linkage of peptidoglycan.

To assess whether DasR controls the expression of the dppA operon, we performed DNA binding studies with purified His-tagged DasR and a fragment corresponding to 193 by upstream of dppA. Analysis using EMSAs established a weak but significant interaction of DasR with the dppA promoter (FIG. 9). To further substantiate a regulatory role for DasR on the expression of dppA, the intracellular D-Ala-D-Ala (SEQ ID NO:) aminopeptidase activity was measured in mutant BAP29 and compared to the parental strain S. coelicolor M145. Both strains were grown for 24 hours in MM supplemented with various carbon sources (FIG. 10). We failed to detect substantial variation in the total D-ala-D-Ala (SEQ ID NO:) aminopeptidase activity between M145 grown in chitin. However, in glucose+chitin we measured an average 85% of loss of activity in mutant BAP29 compared to M145. In glycerol and glycerol+GlcNAc the dasR mutant had about 70% and 33% increased activity, respectively, thus revealing an opposite effect. These experiments show that DasR controls dppA activity according to the culture conditions and therefore modulates the D-Ala-D-Ala pool required for peptidoglycan precursors biosynthesis.

DasR and Central Metabolism

Considering the large number of N-acetylglucosamine-related genes in the list of predicted dre sites, we investigated the impact of DasR on the regulation of the nag metabolic genes. EMSAs were conducted using purified DasR protein and DNA fragments encompassing the predicted dre sites for nagB (Glucosamine-6-P isomerase) and the nagKA operon (GlcNAc kinase, and GlcNAc-6-P deacetylase). In both cases a DasR-dre complex could be demonstrated (FIG. 9). This is consistent with our proteome analysis on NagA (FIG. 4), and with RT-PCR analysis of nagB, which is constitutively expressed in the dasR mutant (FIG. 8C). The DasR regulon further focuses on the fate of N-acetylglucosamine through control of genes for nitrogen metabolism, including aminosugar and glutamine/glutamate metabolism. Our proteome analysis revealed glutamate dehydrogenase (GdhA; completely dependent on DasR) and phosphoserine aminotransferase (SCO4366, repressed) as targets, which catalyse opposite reactions (Altermann and Klaenhammer, 2005) (FIGS. 4 & 5). Acetate that is liberated from N-acetylglucosamine by NagA is converted by acyl-CoA synthetase (strong dre site upstream of SCO3563 and confirmed by EMSA) to acetyl-CoA, the precursor of the TCA cycle. Acetyl-CoA is alternatively converted by a thiolase (ThiL; a target detected by proteomics, FIG. 4) to acetoacetyl-CoA to enter fatty acid metabolism. This may well extend to an unusual type of control at the translational level, as the last two genes in the operon containing all major tRNAs for Gln (anticodon CUG) and Glu (anticodon CUC)—in the order tRNA$^{Gln}$-tRNA$^{Glu}$-tRNA$^{Glu}$-tRNA$^{Gln}$-tRNA$^{Glu}$— are predicted to be regulated by DasR, while the first three are not, suggesting fine-tuning of tRNA availability by DasR. Supporting evidence for such control at the level at tRNA abundance comes from the presence of a predicted dre site upstream of Glu-tRNA$^{Gln}$ amidotransferase (Table 2).

Hence, a picture emerges of a hyper-controlled core network of the DasR regulon, crucial for the cell's energy balance and revolving around the triangle GlcNAc-Gln/Glu-Acetyl-CoA, with almost complete control of all metabolic steps involved. Thus, DasR plays a particularly prominent role in the control of central metabolism and is a very attractive target for metabolic engineering. All targets relating to N-acetylglucosamine and glutamate metabolism are highlighted in Table 4.

Amazingly, our analysis of the Thermobifido fusca genome showed that in fact every single step of glycolysis is controlled by DasR, with highly reliable dre sites located upstream of the respective enzyme-encoding genes (Table 9 and FIG. 17). The implications of this are truly daunting, as it means that in this industrially relevant actinomycete the flux through glycolysis can be easily controlled by the enhanced or reduced expression (or inactivation) of DasR.

Glucosamine-6-P is an Effector of DasR

A pivotal question is what is the effector molecule that modulates DasR? As shown in here, many of the targets for DasR relate to the generation (chitinolytic system), transport ($PTS^{GlcNAc}$), and metabolism (glycolysis via fructose 6-P) of N-acetylglucosamine. We therefore looked for the inducer among the intermediate molecules that gravitate around aminosugar metabolism. A binding interference experiment was set up where the ability of compounds to interfere with binding of dasR to the nagB and crr promoters was tested. These compounds were: N-acetylglucosamine, N-acetylglucosamine-6-P, glucosamine-6-P, glutamate, glutamine, acetyl-CoA, and fructose 6-P. These binding interference experiments identified glucosamine-6-P as the inducer/effector molecule, as it was the only of the compounds tested that prevented the formation of a complex of DasR with the nagB (FIG. 12) and crr promoter regions (not shown). The finding that glucosamine-6-P serves as an effector of DasR is explained by its central position at the metabolic crossroads between $(GlcNAc)_n$ extracellular degradation, N-acetylglucosamine transport and intracellular metabolism, lipid and nitrogen metabolism, glycolysis, and peptidoglycan synthesis (FIG. 13).

N-Acetylglucosamine is Transported by the NagE2 Transporter

Two possible transporters for N-acetylglucosamine were identified on the *S. coelicolor* genome, namely the adjacent genes nagE1 (SCO2906) and nagE2 (SCO2907). Mutants were created for both genes by replacing the entire gene by the apramycin resistance cassette aacC4. A double mutant was also produced (BAP6). The method used to do this was by using pWHM3, as described previously (Nothaft et al., 2003). Mutants deleted for the transport genes nagE1 (BAP4), nagE2 (BAP5), or both (BAP6), were plated on R2YE agar plates with or without N-acetylglucosamine (1% w/v). Other strains on the agar plates are: *S.coelicolor* M145 (parent of all mutants), the dasR mutant BAP29 and the pts mutants ptsH (BAP1), crr (BAP2), and ptsI (BAP3). For phenotypes of the pts mutants see also FIG. 3A). Excitingly, in the absence of nagE2 (or nagE2 and nagE1) addition of N-acetylglucosamine has no effect on development, while the nagE1 mutant and the parental strain *S. coelicolor* M145 become arrested in the vegetative state. This proves that indeed nagE2 is the transporter of N-acetylglucosamine and is essential for import of the inducer molecule for the DasR control system.

Clearly, influencing the activity of NagE2 (positively or negatively) will have a strong effect on the amount of inducer molecules introduced into the *Streptomyces* cell, and therefore will strongly effect the DasR regulatory system.

The Full Scale of the DasR Regulon

While we describe here around 200 targets (Table 2), the true number is without doubt much larger; for example, we used a highly restrictive dre position weight matrix to avoid false positives, but we have evidence that by doing so many true dre sites have been obscured. Additionally, we identified at least eight transcription factor genes in the list of predicted DasR targets. DasR controls many sensing/transport elements and the expression of Glu- and Gln-tRNAs. This suggests that DasR may be receptive to diverse environmental changes and governs many other regulons, and most likely at both the transcriptional and at the translational level. This multi-level control by DasR is summarized in FIG. 13.

Besides the absolute size of the regulon, a prerequisite for a global-acting regulator is further that it should act in concert with single-acting transcription factors (Moreno et al., 2001). Indeed, DasR controls chi-related genes, which are also regulated by the ChiS/ChiR two-component system (Kormanec et al., 2000) and by a third unknown DNA-binding protein identified recently (Fujii et al., 2005), suggesting a multi-partner control of the chitinolytic system. Another example arises from our studies on the regulation of the PTS, where we observed that besides DasR also SCO6008, encoding a ROK-family regulator (Titgemeyer et al., 1994), is required for activation of pts genes.

The Wide-Spread DasR Regulon is a Target for Novel Screening Procedures

Excitingly, the DasR regulatory network is highly conserved in *S. avermitilis* and *S. scabies*, with more than 75% of the dre sites predicted in *S. coelicolor* also found upstream of the orthologous genes in *S. avermitilis*, providing a strong phylogenetic argument for the presented predictions. The strong conservation of the dasR regulon in other actinomycetes also suggests that DasR may control many genes for natural products and enzymes in this class of bacteria. The conservation of the DasR regulon is underlined by the high conservation of DasR proteins (FIG. 14).

Considering the predicted control of clavulanic acid production in *S. clavuligerus* (Table 3), we cloned the dasR gene by PCR using oligonucleotides matching the −50/−30 and +900/+920 regions of *S. coelicolor* dasR, with nt positions relative to the start of the gene. The clone was sequenced, and the predicted gene product differed in a single amino acid position, namely an Asn55 in *S. clavuligerus* DasR and Asp55 in *S. coelicolor* DasR. On this basis it is obvious that the DasR binding site in *S. clavuligerus* is highly similar to that in *S. coelicolor*. The corresponding nucleic acid and amino acid sequence are disclosed in FIG. 19.

Surprisingly, we recently discovered that the core gene cluster nagA-nagB-dasR (and the dre elements) is also widespread among low G+C Gram-positives, including *Bacillus, Lactococcus, Listeria* and *Streptococcus*. Not only the organization is conserved, but also also the sequence of the dre sites, even though the G+C content of the DNA of *Bacillus* (43%) is around 30% lower than that of streptomycetes (72-73%). The dre sites of *Bacillus subtilis* and *Bacillus halodurans* are summarised in Table 5, those of *Streptococcus* species in Table 7, of *Lactococcus lactis* in Table 6, and of *Listeria innocua* and *Listeria monocytogenes* in Table 8. The derived consensus sequences for DasR binding sites in these species are summarised in cartoons in FIG. 15.

From this we conclude that the DasR core regulon is a very important concept, as its presence in such divergent micro-organisms means that the DasR control system has survived at least half a billion years of evolution. Finding a tool to manipulate the activity of DasR is therefore very important, as it will allow controlling the expression of many industrially and medically relevant compounds (enzymes, antibiotics, anti-tumor agents, agricultural compounds, and other secondary metabolites) from the outside rather than by genetic engineering. This is for example a prerequisite for setting up novel screening strategies, as individual strain manipulation is not an option. Addition of inducer (notably N-acetylglucosamine and derivatives) will trigger or at least enhance the expression of a wide range of natural products, allowing more ready screening. An obvious example is the control of cryptic clusters, which are silenced and therefore cannot be identified by activity-based screening assays. We show that antibiotic biosynthesis clusters are activated by the removal or reduced activity of DasR, and we anticipate that addition of inducer will relieve these clusters and thus boost the potential of novel screening procedures.

Detailed Analysis of Effect of DasR on Act and Red Production

As shown above, on media that do allow development (e.g. mannitol-containing solid media) the dasR mutant showed enhanced production of the pigmented antibiotics actinorhodin (Act) and undecylprodigiosin (Red). The relative increase in antibiotic production in the dasR mutant was quantified by determining Act and Red concentrations in the spent agar of solid-grown cultures (MM without any added carbon source). Under these conditions S. coelicolor grows solely on agar, enabled by induction of the DagA agarase (Buttner et al., 1987). Spectroscopic measurements showed that Act and Red production were consistently enhanced in BAP29 by factors of 3.2 (±0.2) and 3.9 (±0.3), respectively (averages of three independent experiments). As shown in FIG. 4, in further support of enhanced Act production by the dasR mutant, preliminary proteome analysis of extracellular fractions of M145 and BAP29 identified two proteins encoded by genes in the act cluster that were strongly up-regulated in the dasR mutant, namely ActVI-ORF3, encoded by SCO5074, a secreted protein involved in stereospecific pyran ring formation of actinorhodin (Hesketh and Chater, 2003; Ichinose et al., 1999), and ActVA-ORF4, the product of SCO5079 (Caballero et al., 1991)), a conserved hypothetical cytoplasmic protein.

We observed putative dre sites upstream of actII-ORF4 and redZ encoding transcriptional activators of the act and red gene clusters, respectively (for dre sites see Table 2). The dre site upstream of actII-ORF4 (nt positions −59/−44 relative to the translational start site) lies precisely between the canonical −35 and −10 sequences of the promoter, a position strongly suggesting that DasR should function as a transcriptional repressor. The dre site upstream of redZ (nt positions −201/186 relative to the translational start site) lies around 50 bp upstream of the −35 sequence of the redZ promoter.

Electrophoretic mobility gel shift assays (EMSAs) with purified His$_6$-tagged DasR and double-stranded oligonucleotide probes showed direct binding to the predicted dre sites of redZ and actII-ORF4 and to the positive control (dre site of crr-ptsI), while DasR did not bind to the cis-acting element of crp, which lacks similarity to the dre element and was therefore used as the negative control (FIG. 21A). No free template was found when DasR was bound to the crr fragment, while over 50% of the redZ probe was bound, and only around 10% of the probe containing the actII-ORF4 dre site. Hence, we established direct binding of the DasR protein to the predicted dre sites, with binding efficiencies corresponding to their 'statistical strength'.

The role of DasR in the control of actII-ORF4, redZ and redD was further assessed by semi-quantitative RT-PCR on RNA samples collected from the parental strain (M145) and the dasR mutant (BAP29) grown on MM mannitol agar plates for 30 h (vegetative growth), 42 h (initiation of aerial growth), and 72 h (aerial growth and spores). RT-PCR analysis revealed strongly enhanced transcription of actII-ORF4 at all time points in the dasR mutant and a discrete but significantly enhanced transcription of redZ (FIG. 21B). Apparently, not only does the degree of DasR-dependent transcriptional repression relate to the strength of the DNA-protein interactions, but the relative positioning of the dre site with respect to the promoter consensus sequence is also an important factor. It was shown previously that enhanced expression of redZ strongly induces redD transcription, even by-passing the block in antibiotic production in bldA mutants (Guthrie et al., 1998). Indeed, the enhanced expression of redZ was reflected in a clearly enhanced expression of the red pathway-specific activator gene redD. In conclusion, the known activator genes of the red cluster are negatively controlled by DasR, explaining the enhanced production of Red in a dasR mutant. For the act cluster, DasR competes with the transcriptional activator AtrA for binding to the promoter region of actII-ORF4, and inactivation of DasR—either through modulation of its in vivo activity or through gene inactivation—then results in enhanced Act production.

More Evidence that N-Acetylglucosamine Targets DasR to Unlock Antibiotic Production A signalling cascade from initial detection of the nutritional status of the environment to the onset of physiological and chemical differentiation should contain at least the following steps: (1) availability and sensing of an extracellular signal; (2) transport of 'signalling nutrients' into the cell; (3) their intracellular modification into an inducer molecule; (4) its binding to a global regulator, which is the checkpoint for (5) signalling the information to pathway-specific activators and (6) the switch to development and antibiotic production. Our experiments suggest that the GlcNAc sensory cascade controlled by DasR is a global system that triggers antibiotic production in direct response to nutrients (FIG. 22). The steps are: (1) sensing of GlcNAc; (2) transport via the PTS$^{GlcNAc}$; (3) conversion by NagA to glucosamine-6-P; (4) binding of the signalling molecule to DasR, thus inhibiting its repressing activity on actII-ORF4 and redZ and activating the pathways for biosynthesis of actinorhodin and undecylprodigiosin.

Arguing from the regulatory pathway deduced from the newly extended characterization of the DasR regulon (FIG. 22), we anticipated that DasR-dependent transport and phosphorylation of GlcNAc via the PTS could be a decisive signal to trigger actinorhodin and undecylprodigiosin biosynthesis in S. coelicolor. This hypothesis was tested by plating S. coelicolor M510 (ΔredD), M511 (ΔactII-ORF4) and M512 (ΔredD, ΔactII-ORF4) on MM agar plates with or without GlcNAc. As a consequence of the deletion of the respective pathway-specific activators, S. coelicolor M510 cannot produce the red-pigmented undecylprodigiosin and M511 fails to produce the blue-pigmented actinorhodin, while M512 produces neither antibiotic. These strains allowed us to specifically monitor each of the antibiotics, which is a necessary control because their pigmentation is pH-dependent, and biosynthetic derivatives show varying colours (Bystrykh et al., 1996; Ichinose et al., 1999). Neither strain produced significant amounts of actinorhodin or undecylprodigiosin when grown for five days on MM with agar as the sole carbon source. In the presence of GlcNAc (10 mM), production of Act or Red was induced in S. coelicolor M510 and M511, respectively (FIG. 22). No pigmented antibiotic was observed for M512, as expected (not shown). Thus, under starvation conditions production of Act and Red is induced both in response to increased levels of GlcNAc and by the absence of DasR.

Application of GlcNAc for Drug Discovery

Is the GlcNAc-mediated control of antibiotic production a more widespread phenomenon in streptomycetes? To assess this, we evaluated the effect of GlcNAc on total antimicrobial activity (bactericidal and bacteristatic) of several streptomycetes, using *Bacillus subtilis* as the indicator strain. The tested strains were spotted on minimal medium containing mannitol (0.5%) with or without GlcNAc (1%). Excitingly, growth inhibition zones indicative of antibiotic production were much larger for *Streptomyces clavuligerus* (a producer of cephamycin), *Streptomyces collinus* (produces kirromycin), *Streptomyces griseus* (streptomycin producer), *Streptomyces hygroscopicus* (produces hygromycin), *Streptomyces rimosus* (produces oxytetracycline), and *Streptomyces venezuelae* (chloramphenicol, methymycin) (FIG. 23). N-acetylglucosamine did not seem to affect antibiotic activity against *B. subtilis* in *Streptomyces acrimycini*, *Streptomyces avermitilis Streptomyces cinnamonensis*, *Streptomyces limosus*, and *Streptomyces lividans*. Interestingly, we observed a repressing effect in *Streptomyces roseosporus*. These results suggest that the relief of antibiotic production by GlcNAc (and through DasR) is a common control mechanism in streptomycetes.

In order to assess if DasR plays a role in silencing cryptic secondary metabolite clusters in streptomycetes, we analysed the expression level of a putative antibiotic biosynthetic cluster for a hypothetical type I polyketide (SCO6273-6288), the only cryptic cluster studied so far. Induction of this biosynthetic pathway depends on a pathway-specific activator, KasO (SCO6280), which is in turn repressed by the γ-butyrolactone (SCB1) binding protein ScbR (Takano et al., 2005). Repression of kasO is relieved by production of SCB1. To test the possible "awakening" of this cluster by the absence of dasR we performed semi-quantitative RT-PCR on RNA samples collected from the parental strain (M145) and the dasR mutant (BAP29) grown on MM mannitol agar plates for 30 h (vegetative growth), 42 h (initiation of aerial growth), and 72 h (aerial growth and spores). Excitingly, kasO transcripts were detected in the 30-h and 72-h RNA samples of BAP29, but were not seen in M145 in any of the samples (FIG. 24). Most likely as a result of the induction of kasO, transcription of SCO6273, the last ORF of the biosynthetic cluster and encoding a putative type I polyketide synthase, was dramatically increased (FIG. 24). The enhanced expression of SCO6273 was observed only during vegetative growth. No dre site was predicted upstream of kasO, and the cis-trans relationship between DasR and this cryptic cluster is under investigation.

Involvement of DasR in the Control of Cell Wall Lysis

Chitin is the main form of storage of GlcNAc and the second most abundant polymer on earth, and as such is of immense importance for soil-dwelling bacteria. GlcNAc is a rich N- and C-source and, with its metabolic products acetate, ammonia and fructose-6-P, stands at the crossroads of the major primary metabolic pathways. This underlines the selective advantage of being able to colonise different types of chitin-containing substrates (Saito et al., 2003; Schrempf, 2001). Our experiments suggest that GlcNAc can provide opposite signals, namely expansion (growth and developmental block) under nutrient-rich conditions and growth cessation followed by development (antibiotic production; sporulation) under nutrient-limited conditions. There are two major sources of GlcNAc: chitin and the bacterium's own cell wall, and they may trigger opposite responses. Bacterial chitinases mainly generate chito-oligosaccharides and N,N'-diacetylchitobiose (GlcNAc)$_2$ from chitin, and little GlcNAc. Also, dasR mutants have a fivefold lower chitinolytic activity than the parental strain (Colson et al., 2007), but overproduce antibiotics, suggesting that chitinases do not produce the signal. The 'GlcNAc effect' was observed only at higher concentrations (>5 mM). Perhaps the most likely natural source would be autolysis of the bacterial cell wall. Large amounts of GlcNAc were found to accumulate locally after programmed cell lysis, when general nutrient limitation necessitates development of an aerial mycelium at the expense of the vegetative hyphae (Miguelez et al., 2000). Since we show that nutrient sensing, cell wall lysis and proteolysis and secondary metabolism (in particular antibiotic production) are all linked directly to the function of DasR, there is a highly suggestive clustering within a single regulon of genes involved in the catabolism of peptidoglycan precursors, together with antibiotic pathway-specific activators.

The contrast between the large number of secondary metabolites produced by streptomycetes and the relatively limited knowledge on the global regulatory mechanisms that trigger their production implies that much is to be gained in terms of drug discovery by learning from the organism itself. We propose a signalling cascade from nutrient stress to antibiotic production. Our deduced pathway proposes GlcNAc as an important signalling molecule for streptomycetes, allowing them to determine the nutritional status of the habitat. The signal that is transported by the PTS$^{GlcNAc}$ is metabolized to glucosamine-6-P, inactivating DasR, which in turn is responsible for suppression of antibiotic production and development under nutrient-rich conditions. Besides the PTS$^{GlcNAc}$, DasR controls many more ABC sugar transporters and the functions of several of these are currently under investigation. The observation that antibiotic production can be awakened and/or enhanced by interfering with the DasR-mediated control system opens new perspectives for screening programmes directed at the discovery of novel natural products. Conceivably, the producing potential of thousands of strains could be boosted by addition of GlcNAc, and we have strong evidence that in many cases this makes the difference between a hit and a miss. This will improve the success rate of screening procedures aimed at the discovery of drugs for the treatment of infectious diseases caused by the recurring multi-drug resistant strains (such as MDR- and XDR-*Mycobacterium tuberculosis*, methicillin-resistant *Staphylococcus aureus* (MRSA), and vancomycin-resistant *Enterococcus faecalis* (VRE)) but also of specific cancers.

REFERENCES

Altermann, E., and Klaenhammer, T. R. (2005) Pathway-Voyager: pathway mapping using the Kyoto Encyclopedia of Genes and Genomes (KEGG) database. *BMC Genomics* 6: 60.

Ameisen, J. C. (2002) On the origin, evolution, and nature of programmed cell death: a timeline of four billion years. *Cell Death Differ* 9: 367-393.

Arias, P., Fernandez-Moreno, M. A., and Malpartida, F. (1999) Characterization of the pathway-specific positive transcriptional regulator for actinorhodin biosynthesis in *Streptomyces coelicolor* A3(2) as a DNA-binding protein. *J Bacteriol* 181: 6958-6968.

Baumann, S., Krueger, A., Kirchhoff, S., and Krammer, P. H. (2002) Regulation of T cell apoptosis during the immune response. *Curr Mol Med* 2: 257-272.

Bennett, J. W. (1998) Mycotechnology: the role of fungi in biotechnology. *J Biotechnol* 66: 101-107.

Bentley, S. D., Chater, K. F., Cerdeno-Tarraga, A. M., Challis, G. L., Thomson, N. R., James, K. D., Harris, D. E., Quail, M. A., Kieser, H., Harper, D., Bateman, A., Brown, S., Chandra, G., Chen, C. W., Collins, M., Cronin, A., Fraser, A., Goble, A., Hidalgo, J., Hornsby, T., Howarth, S., Huang, C. H., Kieser, T., Larke, L., Murphy, L., Oliver, K., O'Neil, S., Rabbinowitsch, E., Rajandream, M. A., Rutherford, K., Rutter, S., Seeger, K., Saunders, D., Sharp, S., Squares, R., Squares, S., Taylor, K., Warren, T., Wietzorrek, A., Woodward, J., Barrell, B. G., Parkhill, J., and Hopwood, D. A. (2002) Complete genome sequence of the model actinomycete *Streptomyces coelicolor* A3(2). *Nature* 417: 141-147.

Beppu, T., and Horinouchi, S. (1991) Molecular mechanisms of the A-factor-dependent control of secondary metabolism in *Streptomyces*. *Planta Med* 57: S44-47.

Bertram, R., Schlicht, M., Mahr, K., Nothaft, H., Saier, M. H., Jr., and Titgemeyer, F. (2004) In silico and transcriptional analysis of carbohydrate uptake systems of *Streptomyces coelicolor* A3(2). *J Bacteriol* 186: 1362-1373.

Bibb, M. (1996) 1995 Colworth Prize Lecture. The regulation of antibiotic production in *Streptomyces coelicolor* A3(2). *Microbiology* 142: 1335-1344.

Bibb, M. J. (2005) Regulation of secondary metabolism in streptomycetes. *Curr Opin Microbiol* 8: 208-215.

Bruckner, R., and Titgemeyer, F. (2002) Carbon catabolite repression in bacteria: choice of the carbon source and autoregulatory limitation of sugar utilization. *FEMS Microbiol Lett* 209: 141-148.

Brückner, R., and Titgemeyer, F. (2002) Carbon catabolite repression in bacteria: choice of the carbon source and autoregulatory limitation of sugar utilization. *FEMS Microbiol Lett* 209: 141-148.

Buttner, M. J., Fearnley, I. M., and Bibb, M. J. (1987) The agarase gene (dagA) of *Streptomyces coelicolor* A3(2): nucleotide sequence and transcriptional analysis. *Mol Gen Genet* 209: 101-109.

Bystrykh, L. V., Fernandez-Moreno, M. A., Herrema, J. K., Malpartida, F., Hopwood, D. A., and Dijkhuizen, L. (1996) Production of actinorhodin-related "blue pigments" by *Streptomyces coelicolor* A3(2). *J Bacteriol* 178: 2238-2244.

Caballero, J. L., Martinez, E., Malpartida, F., and Hopwood, D. A. (1991) Organisation and functions of the actVA region of the actinorhodin biosynthetic gene cluster of *Streptomyces coelicolor*. *Mol Gen Genet* 230: 401-412.

Challis, G. L., and Hopwood, D. A. (2003) Synergy and contingency as driving forces for the evolution of multiple secondary metabolite production by *Streptomyces* species. *Proc Natl Acad Sci USA* 100 Suppl 2: 14555-14561.

Chater, K. F., and Merrick, M. J. (1979) *Streptomycetes*. Oxford: Blackwell.

Chater, K. F., Bruton, C. J., Plaskitt, K. A., Buttner, M. J., Mendez, C., and Helmann, J. D. (1989) The developmental fate of *S. coelicolor* hyphae depends upon a gene product homologous with the motility sigma factor of *B. subtilis*. *Cell* 59: 133-143.

Chater, K. F., and Losick, R. (1997) Mycelial life style of *Streptomyces coelicolor* A3(2) and itrs relatives. In *Bacteria as multicellular organisms*. Shapiro, J. A. and Dworkin, M. (eds). New York: Oxford University Press, pp. 149-182.

Chater, K. F. (1998) Taking a genetic scalpel to the *Streptomyces* colony. *Microbiology* 144: 1465-1478.

Cheggour, A., Fanuel, L., Duez, C., Joris, B., Bouillenne, F., Devreese, B., Van Driessche, G., Van Beeumen, J., Frere, J. M., and Goffin, C. (2000) The dppA gene of *Bacillus subtilis* encodes a new D-aminopeptidase. *Mol Microbiol* 38: 504-513.

Colson, S., Stephan, J., Hertrich, T., Saito, A., van Wezel, G. P., Titgemeyer, F., and Rigali, S. (2007) Conserved cis-Acting Elements Upstream of Genes Composing the Chitinolytic System of Streptomycetes Are DasR-Responsive Elements. *J Mol Microbiol Biotechnol* 12: 60-66.

Crooks, G. E., Hon, G., Chandonia, J. M., and Brenner, S. E. (2004) WebLogo: A sequence logo generator. *Genonze Research* 14: 1188-1190.

Demain, A. L. (1991) Production of beta-lactam antibiotics and its regulation. *Proc Natl Sci Counc Repub China B* 15: 251-265.

Feitelson, J. S., Malpartida, F., and Hopwood, D. A. (1985) Genetic and biochemical characterization of the red gene cluster of *Streptomyces coelicolor* A3(2). *J Gen Microbiol* 131: 2431-2441.

Filee, P., Delmarcelle, M., Thamm, I., and Joris, B. (2001) Use of an ALFexpress DNA sequencer to analyze protein-nucleic acid interactions by band shift assay. *Biotechniques* 30: 1044-1048, 1050-1041.

Fleury, C., Pampin, M., Tarze, A., and Mignotte, B. (2002) Yeast as a model to study apoptosis? *Biosci Rep* 22: 59-79.

Floriano, B., and Bibb, M. (1996) afsR is a pleiotropic but conditionally required regulatory gene for antibiotic production in *Streptomyces coelicolor* A3(2). *Mol Microbiol* 21: 385-396.

Fujii, T., Miyashita, K., Ohtomo, R., and Saito, A. (2005) DNA-binding protein involved in the regulation of chitinase production in *Streptomyces lividans*. *Biosci Biotechnol Biochem* 69: 790-799.

Gosset, G., Zhang, Z., Nayyar, S., Cuevas, W. A., and Saier, M. H., Jr. (2004) Transcriptome analysis of Crp-dependent catabolite control of gene expression in *Escherichia coli*. *J Bacteriol* 186: 3516-3524.

Gramajo, H. C., White, J., Hutchinson, C. R., and Bibb, M. J. (1991) Overproduction and localization of components of the polyketide synthase of *Streptomyces glaucescens* involved in the production of the antibiotic tetracenomycin C. *J Bacteriol* 173: 6475-6483.

Guthrie, E. P., Flaxman, C. S., White, J., Hodgson, D. A., Bibb, M. J., and Chater, K. F. (1998) A response-regulator-like activator of antibiotic synthesis from *Streptomyces coelicolor* A3(2) with an amino-terminal domain that lacks a phosphorylation pocket. *Microbiology* 144: 727-738.

Hesketh, A., and Chater, K. F. (2003) Evidence from proteomics that some of the enzymes of actinorhodin biosynthesis have more than one form and may occupy distinctive cellular locations. *J. Ind. Microbiol. Biotechnol.* 30: 523-529.

Hesketh, A., Sun, J., and Bibb, M. (2001) Induction of ppGpp synthesis in *Streptomyces coelicolor* A3(2) grown under conditions of nutritional sufficiency elicits actII-ORF4 transcription and actinorhodin biosynthesis. *Mol Microbiol* 39: 136-144.

Hindle, Z., and Smith, C. P. (1994) Substrate induction and catabolite repression of the *Streptomyces coelicolor* glycerol operon are mediated through the GylR protein. *Mol Microbiol* 12: 737-745.

Hodgson, D. A. (2000) Primary metabolism and its control in streptomycetes: a most unusual group of bacteria. *Adv Microb Physiol* 42: 47-238.

Hopwood, D. A., and Wright, H. M. (1983) CDA is a new chromosomally-determined antibiotic from *Streptomyces coelicolor* A3(2). *J Gen Microbiol* 129 (Pt 12): 3575-3579.

Hopwood, D. A., Chater, K. F., and Bibb, M. J. (1995) Genetics of antibiotic production in *Streptomyces coelicolor* A3(2), a model streptomycete. *Biotechnology* 28: 65-102.

Hopwood, D. A. (1999) Forty years of genetics with *Streptomyces*: from in vivo through in vitro to in silico. *Microbiology* 145: 2183-2202.

Hopwood, D. A. (2003) The *Streptomyces* genome—be prepared! *Nat Biotechnol* 21: 505-506.

Hopwood, D. A. (2007) *Streptomyces in nature and medicine: the antibiotic makers*. New York: Oxford University Press.

Horinouchi, S., and Beppu, T. (1992) Autoregulatory factors and communication in actinomycetes. *Annu Rev Microbiol* 46: 377-398.

Horinouchi, S., and Beppu, T. (1993) A-factor and streptomycin biosynthesis in *Streptomyces griseus*. *Antonie Van Leeuwenhoek* 64: 177-186.

Horinouchi, S. (2002) A microbial hormone, A-factor, as a master switch for morphological differentiation and secondary metabolism in *Streptomyces griseus*. *Front Biosci* 7: d2045-2057.

Huang, J., Lih, C. J., Pan, K. H., and Cohen, S. N. (2001) Global analysis of growth phase responsive gene expression and regulation of antibiotic biosynthetic pathways in *Streptomyces coelicolor* using DNA microarrays. *Genes Dev* 15: 3183-3192.

Hurtubise, Y., Shareck, F., Kluepfel, D., and Morosoli, R. (1995) A cellulase/xylanase-negative mutant of *Streptomyces lividans* 1326 defective in cellobiose and xylobiose uptake is mutated in a gene encoding a protein homologous to ATP-binding proteins. *Mol Microbiol* 17: 367-377.

Ichinose, K., Surti, C., Taguchi, T., Malpartida, F., Booker-Milburn, K. I., Stephenson, G. R., Ebizuka, Y., and Hopwood, D. A. (1999) Proof that the ACTVI genetic region of *Streptomyces coelicolor* A3(2) is involved in stereospecific pyran ring formation in the biosynthesis of actinorhodin. *Bioorg Med Chem Lett* 9: 395-400.

Ikeda, H., Ishikawa, J., Hanamoto, A., Shinose, M., Kikuchi, H., Shiba, T., Sakaki, Y., Hattori, M., and Omura, S. (2003) Complete genome sequence and comparative analysis of the industrial microorganism *Streptomyces avermitilis*. *Nat Biotechnol* 14: 14.

Kieser, T., Bibb, M. J., Buttner, M. J., Chater, K. F., and Hopwood, D. A. (2000) Practical streptomyce genetics. *The John Innes Foundation, Norwich, United Kingdom*.

Kormanec, J., Sevcikova, B., and Homerova, D. (2000) Cloning of a two-component regulatory system probably involved in the regulation of chitinase in *Streptomyces coelicolor* A3(2). *Folia Microbiol (Praha)* 45: 397-406.

Locci, R. (1986) *Streptomycetes* and related genera. In *Bergey's Manual of Systematic Bacteriology*, vol. 2, pp. 2451-????, Edited by P. H. A. Sneath, N. S. Mair, M. E. Sharpe & J. G. Holt Baltimore: Williams & Wilkins.

Mahr, K., van Wezel, G. P., Svensson, C., Krengel, U., Bibb, M. J., and Titgemeyer, F. (2000) Glucose kinase of *Streptomyces coelicolor* A3(2): large-scale purification and biochemical analysis. *Antonie Van Leeuwenhoek* 78: 253-261.

Manteca, A., Fernandez, M., and Sanchez, J. (2005) A death round affecting a young compartmentalized mycelium precedes aerial mycelium dismantling in confluent surface cultures of *Streptomyces antibioticus*. *Microbiology* 151: 3689-3697.

Manteca, A., Mader, U., Connolly, B. A., and Sanchez, J. (2006) A proteomic analysis of *Streptomyces coelicolor* programmed cell death. *Proteomics* 6: 6008-6022.

Martinez-Costa, O. H., Arias, P., Romero, N. M., Parro, V., Mellado, R. P., and Malpartida, F. (1996) A relA/spoT homologous gene from *Streptomyces coelicolor* A3(2) controls antibiotic biosynthetic genes. *J Biol Chem* 271: 10627-10634.

Miguelez, E. M., Hardisson, C., and Manzanal, M. B. (2000) Streptomycetes: a new model to study cell death. *Int Microbiol* 3: 153-158.

Moreno, M. S., Schneider, B. L., Maile, R. R., Weyler, W., and Saier, M. H., Jr. (2001) Catabolite repression mediated by the CcpA protein in *Bacillus subtilis*: novel modes of regulation revealed by whole-genome analyses. *Mol Microbiol* 39: 1366-1381.

Nothaft, H., Dresel, D., Willimek, A., Mahr, K., Niederweis, M., and Titgemeyer, F. (2003) The phosphotransferase system of *Streptomyces coelicolor* is biased for N-acetylglucosamine metabolism. *J Bacteriol* 185: 7019-7023.

Parche, S., Schmid, R., and Titgemeyer, F. (1999) The phosphotransferase system (PTS) of *Streptomyces coelicolor*: identification and biochemical analysis of a histidine phosphocarrier protein HPr encoded by the gene ptsH. *Eur J Biochem* 265: 308-317.

Rice, K. C., and Bayles, K. W. (2003) Death's toolbox: examining the molecular components of bacterial programmed cell death. *Mol Microbiol* 50: 729-738.

Rigali, S., Derouaux, A., Giannotta, F., and Dusart, J. (2002) Subdivision of the helix-turn-helix GntR family of bacterial regulators in the FadR, HutC, MocR, and YtrA subfamilies. *J Biol Chem* 277: 12507-12515.

Rigali, S., Schlicht, M., Hoskisson, P., Nothaft, H., Merzbacher, M., Joris, B., and Titgemeyer, F. (2004) Extending the classification of bacterial transcription factors beyond the helix-turn-helix motif as an alternative approach to discover new cis/trans relationships. *Nucleic Acids Res* 32: 3418-3426.

Rudd, B. A., and Hopwood, D. A. (1979) Genetics of actinorhodin biosynthesis by *Streptomyces coelicolor* A3(2). *J Gen Microbiol* 114: 35-43.

Saito, A., Fujii, T., and Miyashita, K. (2003) Distribution and evolution of chitinase genes in *Streptomyces* species: involvement of gene-duplication and domain-deletion. In *Antonie Van Leeuwenhoek*. Vol. 84, pp. 7-15.

Sambrook, J., Fritsch, E. F., and Maniatis, T. (1989) *Molecular cloning: a laboratory manual*. Cold Spring Harbor, N.Y.: Cold Spring Harbor Laboratory Press.

Schauer, A., Ranes, M., Santamaria, R., Guijarro, J., Lawlor, E., Mendez, C., Chater, K., and Losick, R. (1988) Visualizing gene expression in time and space in the filamentous bacterium *Streptomyces coelicolor*. *Science* 240: 768-772.

Schlosser, A., Kampers, T., and Schrempf, H. (1997) The *Streptomyces* ATP-binding component MsiK assists in cellobiose and maltose transport. *J Bacteriol* 179: 2092-2095.

Schlosser, A., Jantos, J., Hackmann, K., and Schrempf, H. (1999) Characterization of the binding protein-dependent cellobiose and cellotriose transport system of the cellulose degrader *Streptomyces reticuli*. *Appl Environ Microbiol* 65: 2636-2643.

Schlosser, A. (2000) MsiK-dependent trehalose uptake in *Streptomyces reticuli*. *FEMS Microbiol Lett* 184: 187-192.

Schrempf, H. (2001) Recognition and degradation of chitin by streptomycetes. In *Antonie Van Leeuwenhoek*. Vol. 79, pp. 285-289.

Sosinsky, A., Bonin, C. P., Mann, R. S., and Honig, B. (2003) Target Explorer: An automated tool for the identification of new target genes for a specified set of transcription factors. *Nucleic Acids Res* 31: 3589-3592.

Studholme, D. J., Bentley, S. D., and Kormanec, J. (2004) Bioinformatic identification of novel regulatory DNA sequence motifs in *Streptomyces coelicolor*. *BMC Microbiol* 4: 14.

Taguchi et al. (2000) Chemical characterisation of disruptants of the *Streptomyces coelicolor* A3(2) actVI genes involved in actinorhodin biosynthesis. *J Antibiot*. 53: 144-152.

Takano, E., Gramajo, H. C., Strauch, E., Andres, N., White, J., and Bibb, M. J. (1992) Transcriptional regulation of the redD transcriptional activator gene accounts for growth-phase-dependent production of the antibiotic undecylprodigiosin in *Streptomyces coelicolor* A3(2). *Mol Microbiol* 6: 2797-2804.

Takano, E., Kinoshita, H., Mersinias, V., Bucca, G., Hotchkiss, G., Nihira, T., Smith, C. P., Bibb, M., Wohlleben, W., and Chater, K. (2005) A bacterial hormone (the SCB1) directly controls the expression of a pathway-specific regulatory gene in the cryptic type I polyketide biosynthetic gene cluster of *Streptomyces coelicolor*. *Mol Microbiol* 56: 465-479.

Tan, K., Moreno-Hagelsieb, G., Collado-Vides, J., and Stormo, G. D. (2001) A comparative genomics approach to prediction of new members of regulons. *Genome Res* 11: 566-584.

Templin, M. F., Ursinus, A., and Holtje, J. V. (1999) A defect in cell wall recycling triggers autolysis during the stationary growth phase of *Escherichia coli*. *Embo J* 18: 4108-4117.

Titgemeyer, F., Reizer, J., Reizer, A., and Saier, M. H., Jr. (1994) Evolutionary relationships between sugar kinases and transcriptional repressors in bacteria. *Microbiology* 140: 2349-2354.

Titgemeyer, F., and Hillen, W. (2002) Global control of sugar metabolism: a gram-positive solution. *Antonie Van Leeuwenhoek* 82: 59-71.

van Loo, G., Saelens, X., van Gurp, M., MacFarlane, M., Martin, S. J., and Vandenabeele, P. (2002) The role of mitochondrial factors in apoptosis: a Russian roulette with more than one bullet. *Cell Death Differ* 9: 1031-1042.

van Wezel, G. P., White, J., Young, P., Postma, P. W., and Bibb, M. J. (1997) Substrate induction and glucose repression of maltose utilization by *Streptomyces coelicolor* A3(2) is controlled by malR, a member of the lacl-galR family of regulatory genes. *Mol Microbiol* 23: 537-549.

van Wezel, G. P., Mahr, K., König, M., Traag, B. A., Pimentel-Schmitt, E. F., Willimek, A., and Titgemeyer, F. (2005) GlcP constitutes the major glucose uptake system of *Streptomyces coelicolor* A3(2). *Mol Microbiol* 55: 624-636.

Wright, L. F., and Hopwood, D. A. (1976) Identification of the antibiotic determined by the SCP1 plasmid of *Streptomyces coelicolor* A3(2). *J Gen Microbiol* 95: 96-106.

Willey, J., Santamaria, R., Guijarro, J., Geistlich, M., and Losick, R. (1991) Extracellular complementation of a developmental mutation implicates a small sporulation protein in aerial mycelium formation by *S. coelicolor*. *Cell* 65: 641-650.

Winkler, W. C., Nahvi, A., Roth, A., Collins, J. A., and Breaker, R. R. (2004) Control of gene expression by a natural metabolite-responsive ribozyme. *Nature* 428: 281-286.

Zazopoulos, E., Huang, K., Staffa, A., Liu, W., Bachmann, B. O., Nonaka, K., Ahlert, J., Thorson, J. S., Shen, B., and Farnet, C. M. (2003) A genomics-guided approach for discovering and expressing cryptic metabolic pathways. *Nat Biotechnol* 21: 187-190.

Zhang, H., Huang, X., Fukamizo, T., Muthukrishnan, S., and Kramer, K. J. (2002) Site-directed mutagenesis and functional analysis of an active site tryptophan of insect chitinase. *Insect Biochem Mol Biol* 32: 1477-1488.

Zhang, Z., Gosset, G., Barabote, R., Gonzalez, C. S., Cuevas, W. A., and Saier, M. H., Jr. (2005) Functional interactions between the carbon and iron utilization regulators, Crp and Fur, in *Escherichia coli*. *J Bacteriol* 187: 980-990.

TABLE 1

Experimentally validated DasR binding sites used to build the matrix for consensus sequences.

| | | | |
|---|---|---|---|
| malX2Sco | ACTGGTGTAGACCAGT | (SEQ ID NO: 11) | score = 16.20 |
| nagE2Sco(1) | CAAGGTGTAGACCTCT | (SEQ ID NO: 12) | score = 11.35 |
| nagE2Sco(2) | AGTGGTGTAGACCTGT | (SEQ ID NO: 13) | score = 16.98 |
| nagE2Sco(3) | AGTGGTGTAGACCACC | (SEQ ID NO: 14) | score = 15.01 |
| ptsHSco(1) | AGTTGTCTAGACCAGT | (SEQ ID NO: 15) | score = 15.29 |
| ptsHSco(2) | TCTTGTCTAGACCAGT | (SEQ ID NO: 16) | score = 13.71 |
| crr-ptsISco(1) | TGTGGTCTAGACCTCT | (SEQ ID NO: 17) | score = 15.61 |
| msiKSco | GGTGGTGTAGTCCACA | (SEQ ID NO: 18) | score = 12.52 |
| nagBSco | TGTGGTTTAGACCAAT | (SEQ ID NO: 19) | score = 13.72 |
| nagKASco(1) | GGTGGTGTAGACCTTA | (SEQ ID NO: 20) | score = 13.05 |
| nagKASco(2) | AGTGGACTAGACCTCT | (SEQ ID NO: 21) | score = 14.45 |
| chiFSco(1) | AAGGGTGTAGACCAGT | (SEQ ID NO: 22) | score = 13.55 |
| chiFSco(2) | ACTGGTACAGACCAAA | (SEQ ID NO: 23) | score = 9.73 |
| actII-4 | TGTTGAGTAGGCCTGT | (SEQ ID NO: 24) | score = 11.22 |

TABLE 2

| # | Evidence[1] | Target gene | Known or predicted function | dre | Pos[2] | Score[3] | co-transcribed gene[4] | Known or predicted function |
|---|---|---|---|---|---|---|---|---|
| 1 | ERA- | SCO2907, nagE2 | PTS EIIC component, N-acetylglucosamine uptake | ACAGGTCTACACCACT AGTGGTGTAGACCACC CAAGGTGTAGACCTCT (SEQ ID NO: 25) | -49 -32 -236 | 16.98 15.01 11.35 | — | — |
| 2 | | SCO2906, nagE1 | PTS EIIC component, not functional | ACTGGTCTACACCAGT (SEQ ID NO: 26) | -41 | 16.2 | — | — |
| 3 | ERA- | SCO2905c, malX2 | PTS EIIB component, N-acetylglucosamine uptake | ACTGGTCTACACCAGT (SEQ ID NO: 26) | -134 | 16.2 | — | — |
| 4 | E | SCO5232, dasA | ABC sugar transporter, sugar binding protein | ACTGGTCTACACCATT CTTGGTCTAGTCCATA (SEQ ID NO: 27) | -106 -322 | 15.79 8.15 | SCO5233, dasB/SCO5234, dasC/SCO5235 | ABC sugar transporter membrane protein/ABC sugar transporter membrane protein/putative intracellular Beta-N-acetylglucosaminidase |
| 5 | ERA- | SCO1390, crr | PTS EIIA$^{crr}$ component, N-acetylglucosamine uptake | TGTGGTCTAGACCTCT (SEQ ID NO: 28) | -130 | 15.61 | SCO1391, ptsI | PTS EI component, phosphoenolpyruvate-protein phosphatase |
| 6 | E | SCO5842 | putative acetyl-coenzyme A synthetase | AGTTGTCTAGACCAGT TCTTGTCTAGACCAGT (SEQ ID NO: 29) | -168 -153 | 15.29 13.71 | — | — |
| 7 | ERA- | SCO5841c | PTS Hpr, N-acetylglucosamine and fructose uptake | AGTTGTCTAGACCAGT TCTTGTCTAGACCAGT (SEQ ID NO: 29) | -51, -66 | 15.29 13.71 | — | — |
| 8 | E | SCO4286 | ABC sugar transporter, sugar binding protein | AGAGGTCTAGTCCACT GGTGGTGTAGACCTTA (SEQ ID NO: 30) | -81, -63 | 14.45 13.05 | hypothetical | hypothetical protein, unknown function |
| 9 | ER- | SCO4285c, nagK | NagK, N-acetylglucosamine kinase | AGAGGTCTAGTCCACT GGTGGTGTAGACCTTA (SEQ ID NO: 30) | -83, -101 | 14.45 13.05 | SCO4284c, nagA | NagA, N-acetylglucosamine-6-phosphate deacetylase |
| 10 | E | SCO5239 | Two-component sensor histidine kinase | AGTGGTCTAGTCCACA (SEQ ID NO: 31) | -335 | 14.19 | — | — |
| 11 | ER- | SCO5236c, nagB | NagB, probable glucosamine phosphate isomerase | TGTGGTTTAGACCAAT (SEQ ID NO: 32) | -68 | 13.72 | — | — |
| 12 | E | SCO3563, acsA | acetoacetyl-coenzyme A synthetase | ACAGGTCTAAACCATT (SEQ ID NO: 33) | -102 | 13.59 | — | — |
| 13 | ER+ | SCO7263, chiF | ChiF chitinase | ACTGGTCTACACCCTT ACTGGTACACAGACCAAA (SEQ ID NO: 34) | -172 -155 | 13.55 9.73 | SCO7264 | probable NADPH dependent oxidoreductase, Aldo/keto reductase |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 14 | E | SCO7225 | secreted chitinase | TATGGTCTAGACCTGA TCAGGTCTAGACCTGT CCTTGTCTAGACCAAT (SEQ ID NO: 35) | −55 −34 −168 | 13.18 12.46 11.46 | — | — |
| 15 | E | SCO7224c | possible integral membrane protein, DoxX family, unknown function | | −272, −293 −159 | | — | — |
| 16 | E | SCO1444, chiI | ChiI chitinase | ACTGGTCTAGTCCTCT ATTGGTCCATACCTAT (SEQ ID NO: 36) | −53 −75 | 12.81 5.22 | — | — |
| 17 | EP- | SCO4240c, msiK | MsiK, multiple sugar import protein, ABC transporter ATP-binding protein | GGTGGTGTAGTCCACA (SEQ ID NO: 37) | −75 | 12.52 | — | — |
| 18 | E | SCO5004 | hypothetical protein, unknown function | GGTGGTCCAGACCAAT (SEQ ID NO: 38) | −258 | 12.08 | — | — |
| 19 | E | SCO5003c, chiA | ChiA chitinase | | −77 | | — | — |
| 20 | E | SCO7056c | GntR-family transcriptional regulator (new subfamily) | ATTGGTCTAAACCAGC GCAGGTCTGGTCCTCC (SEQ ID NO: 39) | −79 −282 | 12.08 6.85 | — | — |
| 21 | EA- | SCO6486, dppA | DppA, D-alanyl-aminopeptidase | AGTGGTCCAGACCACC (SEQ ID NO: 40) | −71 | 12.03 | SCO6487, SCO6488, SCO6489, SCO6490 | possible aminoacylase/putative acyl-peptide hydrolase/LD-carboxypeptidase/ putative alanine acetyltransferase |
| 22 | E | SCO2672 | membrane protein, ABC transporter, FtsX cell division permease family, unknown function | AGAGGTCTGGACAACA (SEQ ID NO: 41) | −32 | 11.99 | — | — |
| 23 | E | SCO2503, chiJ | ChiJ putative chitinase | AAAGGTCTGGACCACA CTTGGTCCAGACCTCT TCTGGACCACAGCACT (SEQ ID NO: 42) | −78 −99 −73 | 11.81 8.47 5.73 | — | — |
| 24 | E | SCO1429, chiD | ChiD chitinase | ACTGGTCTAGTCCTCC AATGGTCCGAACCATT (SEQ ID NO: 43) | −96 −118 | 11.5 5.86 | — | — |
| 25 | E | SCO1428c, acd | acyl-CoA dehydrogenase | | −312 −290 | | — | — |
| 26 | E | SCO3679 | hypothetical protein, sigma factor PP2C-like phosphatase | TGTTGTCTAGTCCAAT (SEQ ID NO: 44) | −314 | 11.41 | — | — |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 27 | ER- | SCO5085, actII-4 | actinorhodin cluster activator protein | TGTTGAGTAGGCCTGT (SEQ ID NO: 45) | -59 | 11.22 | — | — |
| 28 | E | SCO6013 | probable 1-deoxyxylulose-5-phosphate synthase | AATGGTCTGGACCAGA GGTGGACTGGACCACC ATGGGACTAGACCAAT (SEQ ID NO: 46) | -274 -201 -258 | 11.03 8.63 7.95 | — | — |
| 29 | E | SCO6012c, chiH | ChiH chitinase | | -111, -184, -127 | | — | — |
| 30 | | SCO4315 | possible copper homeostasis protein, CutC family | ATTGGACTAGACCTGT (SEQ ID NO: 47) | -39 | 10.99 | — | — |
| 31 | E | SCO4671c | LysR-family regulatory protein | GCTGGTACAGACCAGT (SEQ ID NO: 48) | -55 | 10.83 | — | — |
| 32 | E | SCO6300c | probable secreted Beta-N-acetylglucosaminidase | AGAGGTCTAGACAAAA ATAGGTCTAGACCAAA (SEQ ID NO: 49) | -116 -131 | 10.67 9.78 | — | — |
| 33 | E | SCO6005, ngcE | ABC sugar transporter, sugar binding protein, NgcE | AGTGGACTATACCTGT (SEQ ID NO: 50) | -334 | 10.56 | SCO6006, SCO6007, ngcF/ngcG | ABC sugar transporter membrane protein, NgcF/ABC sugar transporter membrane protein, NgcG |
| 34 | E | SCO6004c | putative alpha-1,2-mannosidase | AGTGGACTATACCTGT (SEQ ID NO: 51) | -244 | 10.56 | — | — |
| 35 | E | SCO5376c, chiC | ChiC chitinase | AAAGGTCTGGACCATA ATAGGTCTGGACCAAT (SEQ ID NO: 52) | -88 -109 | 10.35 9.29 | SCO5375c | possible secreted protein, unknown function |
| 36 | E | SCO6345 | chitinase | TAAGGTCTAGACCTGC GTAGGTCTAGACCTGC (SEQ ID NO: 53) | -114, -94 -133, -153 | 9.99 8.74 | — | — |
| 37 | E | SCO6344c | putative secreted amidase | | | | — | — |
| 38 | E | SCO1212 | putative Mur like ligase | TGAGGTCCACACCACG (SEQ ID NO: 54) | -76 -5 | 9.92 | SCO1213 | conserved hypothetical protein |
| 39 | E | SCO1211c | putative polypeptide deformylase | | | | — | — |
| 40 | E | SCO1083c | putative flavin-dependent reductase | TGTGGAGAAGACCTCA (SEQ ID NO: 55) | -129 | 9.48 | — | — |
| 41 | E | SCO1433 | hypothetical protein, unknown function | ATTGGTGTCGACCACT (SEQ ID NO: 56) | -205 | 9.41 | — | — |
| 42 | E | SCO1432c | possible membrane protein, unknown function | ATTGGTGTCGACCACT (SEQ ID NO: 57) | -86 | | SCO1431c | possible membrane protein, unknown function |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 43 | E | SCO5266 | putative membrane protein | CATGGTGCAGACCTCC (SEQ ID NO: 58) | −139 | 9.25 | — | — |
| 44 | | SCO5265c | hypothetical protein | CATGGTGCAGACCTCC (SEQ ID NO: 59) | 38 | 9.25 | SCO5264c | hypothetical protein SC7G11.26c |
| 45 | E | SCO0481, chb3 | putative secreted chitin binding protein | TATGGTCTAGTCCAAC (SEQ ID NO: 60) | −201 | 9.19 | — | — |
| 46 | E | SCO2753 | LacI-family transcriptional regulator, NagR | GGTGGTCTGGACAAGA (SEQ ID NO: 61) | −120 | 9.15 | — | — |
| 47 | E | SCO2752c | possible oxidoreductase, unknown | GGTGGTCTGGACAAGA (SEQ ID NO: 61) | −127 | 9.15 | SCO2751c, SCO2750c | hypothetical protein/putative isomerase, unknown function |
| 48 | E | SCO7250c | putative N-acetylmuramoyl-L-alanine amidase | AGTGGCGTACACCTGT (SEQ ID NO: 62) | −213 | 9.04 | — | — |
| 49 | E | SCO5673, chiB | ChiB chitinase | ATTGGTCTGGACCAAA (SEQ ID NO: 63) | −63 | 9.03 | — | — |
| 50 | | SCO7699 | putative nucleotide-binding protein, sporulation-specific protein p3 (S. griseus) | GAGGGTCCAGACCTCT (SEQ ID NO: 64) | −245 | 9.0 | SCO7700/SCO7701 | putative cyclase/putative methyltransferase |
| 51 | | SCO7698c | putative merR-family transcriptional regulator | | −19 | | — | — |
| 52 | E | SCO2833c, chb | secreted chitin binding protein | GCAGGTCTAGACCAAG (SEQ ID NO: 65) | −70 | 8.91 | — | — |
| 53 | E | SCO2946c | ABC sugar transporter, sugar binding protein | AGAGGTCTGAACCAAT (SEQ ID NO: 66) | −112 | 8.91 | SCO2945c, SCO2944c, SCO2943c | ABC sugar transporter membrane protein, ABC sugar transporter membrane protein, putative intracellular beta-N-acetylglucosaminidase |
| 54 | E | SCO1117c | putative 3-carboxymuconate cyclase | CGCGGTCTAGACCAAA (SEQ ID NO: 67) | −131 | 8.79 | — | — |
| 55 | E | SCO5230c | integral membrane protein, putative sensory protein | TCTGGTCTAGTCCTGG (SEQ ID NO: 68) | −118 | 8.77 | SCO5229c | probable permease, sodium:solute symporter family |
| 56 | | SCO6149 | putative ATP GTP-binding protein | GGAGGTGTCGACCAAT (SEQ ID NO: 69) | −140 | 8.76 | SCO6150, CO6151 | putative ADA-like regulatory protein/putative methylated-DNA-protein-cysteine methyltransferase |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 57 | | SCO6319 | putative lipoprotein | ATTGGTCTGAACCATG (SEQ ID NO: 70) | −30 | 8.76 | — | — |
| 58 | | SCO6033 | hypothetical protein SC1C3.21 | CTTGGTCTAGTCCATT (SEQ ID NO: 71) | −278 | 8.68 | — | — |
| 59 | | SCO6032c | beta-N-acetylglucosaminidase | | −154 | 8.65 | — | — |
| 60 | E | SCOEc, chiE | ChiE chitinase and metallopeptidase | CTTGGTCCAGACCTGT (SEQ ID NO: 72) | −188 | | — | — |
| 61 | | SCO4394, desR | iron repressor | TGCGGTCTGGACCAGT ACTGATCGACCACG (SEQ ID NO: 73) | −184, +9 | 8.42 7.45 | — | — |
| 62 | | SCO4393c | Possible phosphosugar isomerase | | −247, −55, | | — | — |
| 63 | | SCO6084 | putative DNA polymerase | GAGGGTGGAGACCACT GGTGGTCCAGTCCTAC (SEQ ID NO: 74) | −292, −49 | 8.3 8.13 | — | — |
| 64 | | SCO5046, wblI | hypothetical protein | TCAGGAGTAGACCCGT (SEQ ID NO: 75) | −14 | 8.23 | — | — |
| 65 | | SCO1954 | hypothetical protein | GGATGTGAAAGACCTCT (SEQ ID NO: 76) | −101 | 8.15 | SCO1952c, SCO1951c, SCO1950c | hypothetical protein/conserved hypothetical protein/ hypothetical protein |
| 66 | | SCO1953c | ABC excision nuclease subunit C | | −268 | | | |
| 67 | | SCO5231c, dasR | DasR, gntR-family transcriptional regulator | CTTGGTCTAGTCCATA (SEQ ID NO: 77) | −150 | 8.15 | — | — |
| 68 | | SCO4506 | conserved hypothetical protein | AGAGGTCAAGATCACT (SEQ ID NO: 78) | −103 | 8.05 | SCO4507 | putative serine/threonine protein kinase |
| 69 | | SCO4505c, scoF2 | cold shock protein | | −206 | | — | — |
| 70 | | SCO3152c | hypothetical protein SCE87.03c | AGTGGACTCCTCCACC (SEQ ID NO: 79) | −50 | 8.03 | SCO6233 | — |
| 71 | | SCO6232 | putative beta-mannosidase | TCAGGACTAGACCGGT (SEQ ID NO: 80) | −86 | 7.97 | SCO6233 | putative transcriptional regulator |
| 72 | | SCO6231c | probable sugar transport system sugar-binding lipoprotein SC2H4.13c | | −202 | | — | — |
| 73 | E | SCO1906c | putative secreted protein, unknown function | ACTGGCGGAGACCTCT (SEQ ID NO: 81) | −128 | 7.93 | — | — |
| 74 | | SCO2119c, pfkA | 6-phosphofructokinase | GGTGGTTGAGGCCACT (SEQ ID NO: 82) | −40 | 7.83 | — | — |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 75 | | SCO1971 | conserved hypothetical protein | TGTGGTCGAGACGTGT (SEQ ID NO: 83) | -172 | 7.77 | SCO1972 | putative sugar kinase |
| 76 | | SCO1970c | putative dioxygenase | | 30 | | | — |
| 77 | | SCO1289 | putative gntR-family regulatory protein | CGTGGTGCAGACGTGA (SEQ ID NO: 84) | -36 | 7.73 | — | — |
| 78 | | SCO1288c | putative integral membrane protein | | -143 | | SCO1287c | hypothetical protein |
| 79 | | SCO0073 | hypothetical protein | CCAGGTTCAGACCTGT (SEQ ID NO: 85) | -219 | 7.69 | SCO0074, SCO0075 | hypothetical protein/ hypothetical protein |
| 80 | | SCO0072c | putative wall associated protein | | -309 | | — | — |
| 81 | | SCO5463 | putative MerR-family transcriptional regulator | ACTGGCCCGCACCACC (SEQ ID NO: 86) | 39 | 7.55 | SCO5464 | — |
| 82 | | SCO5462c | hypothetical protein SC3D11.19c | | -103 | | — | — |
| 83 | | SCO5016c | putative integral membrane protein | GGTGGAGCAGACCGGA (SEQ ID NO: 87) | -280 | 7.5 | — | — |
| 84 | E | SCO3975c | putative regulator | TGTGGTCGAGACCGGA (SEQ ID NO: 88) | -86 | 7.49 | — | — |
| 85 | | SCO5366, atpI | ATP synthase protein I | AGAGGTAAAGACCTCA (SEQ ID NO: 89) | -172 | 7.49 | — | — |
| 86 | | SCO2787 | conserved hypothetical protein SCC105.18 | ACGGGTGCGGACCACT (SEQ ID NO: 90) | -61 | 7.44 | SCO2788, SCO2789, glmS2 | hypothetical protein SCC105.19/glucosamine-fructose-6-phosphate aminotransferase |
| 87 | | SCO2786c | beta-N-acetylhexosaminidase | | -70 | | — | — |
| 88 | | SCO4442 | hypothetical protein SCD6.20 | ATTGGCGTAAACCACA (SEQ ID NO: 91) | -41 | 7.41 | — | — |
| 89 | | SCO1752 | putative integral membrane protein | TGTGGCATGCACCACT (SEQ ID NO: 92) | -80 | 7.29 | — | — |
| 90 | | SCO1751c | putative transmembrane transport protein | | -198 | | — | — |
| 91 | | SCO6003c | putative DNA-binding protein | GCCGGTGAAGACCAGT (SEQ ID NO: 93) | -235 | 7.26 | — | — |
| 92 | E | SCO5716c | putative peptide transport system secreted peptide binding protein | ATTGGCGCAGACCACT (SEQ ID NO: 94) | -197 | 7.24 | — | — |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 93 | | SCO5330 | hypothetical protein SC6G9.03c | GCTGGCGTAGCCCACT (SEQ ID NO: 95) | −54 | 7.16 | — | — |
| 93 | | SCO5430c | putative extracellular solute-binding lipoprotein | AATGGTCTAGTCAGGT (SEQ ID NO: 96) | −81 | 7.02 | SCO5429c, SCO5428c | putative integral membrane transport protein/putative integral membrane transport protein |
| 94 | | SCO2685c | putative ATP-binding protein SCC61A.06c | AGTGGACAACACCCGA (SEQ ID NO: 97) | −142 | 6.95 | SCO2684c | putative ATP-binding membrane protein |
| 96 | E | SCO4516c | hypothetical protein SCD35.23c | ACTGGTCTGGATCCGT (SEQ ID NO: 98) | −20 | 6.91 | SCO4515c | putative membrane protein |
| 97 | | SCO7054 | conserved hypothetical protein | TGTGGAGTAGAGTAGT (SEQ ID NO: 99) | −47 | 6.89 | SCO7055 | putative methyltransferase |
| 98 | | SCO7053c | hypothetical protein | | −50 | | — | — |
| 99 | E | SCO4735 | 30S ribosomal protein S9 | CGTGGGCCGAGACCACT (SEQ ID NO: 100) | −1 | 6.88 | — | — |
| 100 | | SCO4722, secY | preprotein translocase SecY subunit | GCTCGTCTGAACCACT (SEQ ID NO: 101) | −266 | 6.87 | SCO4723 | adenylate kinase |
| 101 | | SCO7509c | conserved hypothetical protein | GCGGGTGAAGACCAGC (SEQ ID NO: 102) | 20 | 6.83 | — | — |
| 102 | | SCO4646, secE | preprotein translocase SecE subunit | ACTGGTCTCCAAAACC (SEQ ID NO: 103) | −156 | 6.81 | SCO4647 | transcription antitermination protein |
| 103 | | SCO4645c | aspartate aminotransferase | ACTGGTCTCCAAAACC (SEQ ID NO: 104) | −281 | 6.81 | — | — |
| 104 | | SCO4562 | NuoA, NADH dehydrogenase subunit | GGTGGTGGAGATCACA (SEQ ID NO: 105) | −206 | 6.78 | SCO4563-SCO4575 (nuoBCDEFGHIJKLMN) | NADH dehydrogenase subunits NuoA-NuoN |
| 105 | | SCO1692c | putative oxidoreductase | CGCGGTTCTACTCCATT (SEQ ID NO: 106) | −116 | 6.76 | SCO1691c | putative tetR transcriptional regulator |
| 105 | | SCO4904c | putative integral membrane protein | TGAGGCCTGCGCCACA (SEQ ID NO: 107) | −72 | 6.69 | — | — |
| 107 | | SCO5954 | chitinase (putative secreted protein) | ATTGGTTCCAGACCTTC (SEQ ID NO: 108) | −95 | 6.64 | — | — |
| 108 | | SCO5805, nrdJ | ribonucleotide reductase | AGTGAACAAGACCTGT (SEQ ID NO: 109) | −117 | 6.61 | — | — |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 109 | | SCO4609 | putative peptidase | CCTGGCGTTGACCAGT (SEQ ID NO: 110) | −136 | 6.6 | SCO4610/SCO4611 | putative integral membrane protein/hypothetical protein SCD39.11 |
| 110 | | SCO2547c | putative hydrolase | GGTGGTCCGGTCCTGT (SEQ ID NO: 111) | −24 | 6.58 | SCO2546c | probable adenosine deaminase |
| 111 | | SCO4963 | putative ABC transporter ATP-binding protein | CCTGGTGAAGACCTTC (SEQ ID NO: 112) | 27 | 6.55 | SCO4964 | putative integral membrane transport protein |
| 112 | | SCO2037c, trpB | tryptophan synthase beta subunit | GGTGGATCAGACCGCT (SEQ ID NO: 113) | −69 | 6.54 | SCO2036c | tryptophan synthase alpha subunit |
| 113 | | SCO0915 | hypothetical protein SCM10.03 | TTTGGTATGGACCATT (SEQ ID NO: 114) | −98 | 6.52 | — | — |
| 114 | | SCO0914c | putative lipoprotein | | −127 | | — | — |
| 115 | | SCO2802 | putative secreted protein | AGAGGACTCGTCCACG (SEQ ID NO: 115) | 16 | 6.51 | — | — |
| 116 | | SCO6914 | hypothetical protein SC1B2.20 | GGTGCTGGAGACCTCA (SEQ ID NO: 116) | −133 | 6.51 | SCO6915 | hypothetical protein SC1B2.21 |
| 117 | E | SCO5609c | hypothetical protein SC2E1.26c | ACTGGTCAGGACCGCT (SEQ ID NO: 117) | −133 | 6.38 | — | — |
| 118 | | SCO3261 | putative ATP-binding protein | ACCGGGCTACACACCT (SEQ ID NO: 118) | −284 | 6.37 | SCO3262 | hypothetical protein |
| 119 | | SCO5636c, korSA | transcriptional regulator | ACTGGACGAGACCCCG (SEQ ID NO: 119) | −187 | 6.34 | — | — |
| 120 | E | SCO7070 | chitosanase | ACAGGTCCGGACCAAT (SEQ ID NO: 120) | −50 | 6.34 | — | — |
| 121 | E | SCO7069c | chitinase | | −61 | 6.32 | — | — |
| 122 | | SCO1558c | putative ABC transporter permease protein | GGAGGCCTGCTCCAGC (SEQ ID NO: 121) | 11 | 6.32 | — | — |
| 123 | | SCO5717c | conserved hypothetical protein SC3C3.03c | CCGGGTGTAGCCCAGC (SEQ ID NO: 122) | 31 | 6.32 | — | — |
| 124 | | SCO3510c | putative DNA methylase | CGGGGTCTGGACCTGC (SEQ ID NO: 123) | −42 | 6.29 | — | — |

TABLE 2-continued

| # | Evidence[1] | Target gene | Known or predicted function | dre | Pos[2] | Score[3] | co-transcribed gene[4] | Known or predicted function |
|---|---|---|---|---|---|---|---|---|
| 125 | | SCO4811 | putative integral membrane protein | CGTGATCCAGACCACC (SEQ ID NO: 124) | 9 | 6.25 | — | — |
| 126 | | SCO3560 | putative ATP-binding protein | AGTGGTCTTCTTCACC (SEQ ID NO: 125) | −61 | 6.24 | — | — |
| 127 | | SCO3559c | putative oxidoreductase | | −58 | 6.24 | — | — |
| 128 | | SCO5276 | conserved hypothetical protein | ACGGGTCCACTCAACA (SEQ ID NO: 126) | −56 | 6.24 | SCO5277, SCO5278, SCO5279, SCO5280 | putative magnesium chelatase/putative magnesium chelatase/hypothetical protein SCCB12.03/putative ATP-binding protein |
| 129 | R− | SCO5881c, redZ | Undecylprodigiosine activator | AGTGGTTTCCACCTCA (SEQ ID NO: 127) | −201 | 6.24 | — | — |
| 130 | | SCO1262c | putative gntR-family transcriptional regulator | CTTGGTCAAGACCAAT (SEQ ID NO: 128) | −113 | 6.22 | — | — |
| 131 | | SCO2141 | putative small secreted hydrophilic protein | ATCGGCCTGGACAACT (SEQ ID NO: 129) | −167 | 6.19 | SCO2142, SCO2143, SCO2144, SCO2145 | putative two component sensor kinase/putative two component system response regulator/putative integral membrane transporter/putative glycerate kinase |

[1] If confirmed target, method is indicated: E, EMSA (target site bound by DasR), A, enzyme Assay, R, RT PCR. "+" means shown to be activated by DasR, "−", shown to be repressed by DasR.
[2] Position is last nucleotide position of the dre target site relative to the translational start site of the gene.
[3] Weighed matrix score of the dre site. Cut-off of 6.00 was taken as bottom limit. Higher score means better fit to the consensus sequence.
[4] If genes are known or predicted to be in an operon (generally because there is no or almost no intergenic region), the presumed co-transcribed genes are shown.

TABLE 3

List of putative binding sites for DasR relating to secondary metabolism (cut-off score 5)

A. Antibiotics and metabolites of known function produced by actinomycetes

| Secondary metabolite | Streptomyces strain | dre sequence | | Target | Function | score |
|---|---|---|---|---|---|---|
| Clavulanic acid | S. clavuligerus | attggagtagacctct | (SEQ ID NO: 130) | pcbR | PBP; β-lactam resistance | 11.47 |
| | | ggagggctgaccagc | (SEQ ID NO: 131) | pcbR | PBP; β-lactam resistance | 5.72 |
| Actinorhodin | S. coelicolor | tgttgagtaggctgt | (SEQ ID NO: 132) | actII-ORF4 | pathway-specific activator | 11.22 |
| Undecylprodigiosin | S. coelicolor | gcaggtgagaccacc | (SEQ ID NO: 133) | redZ | pathway-specific activator | 6.61 |
| | | tgaggtgaaaccact | (SEQ ID NO: 134) | redZ | pathway-specific activator | 6.24 |
| Valanimycin | S. viridifaciens | ctctgagtaggcctgt | (SEQ ID NO: 135) | vlmM | Valanimycin transferase | 8.01 |
| Daptomycin | S. filamentosus | actggtcgaccagc | (SEQ ID NO: 136) | dptD | peptide synthetase 3 | 10.12 |
| | | ggaggtcgaccagt | (SEQ ID NO: 137) | dptP | hypothetical | 9.24 |
| | | tgaggtgacgccacc | (SEQ ID NO: 138) | AAX31564 | Putative phosphatase | 6.59 |
| | | tgaggtcgaggccacc | (SEQ ID NO: 139) | dptD | peptide synthetase 3 | 5.98 |
| | | agtggtctgaccacc | (SEQ ID NO: 140) | dptP | hypothetical | 5.97 |
| | | cgtgatctacacctcc | (SEQ ID NO: 141) | dptBC | peptide synthetase 2 | 5.91 |
| | | cgtgatctacacctcc | (SEQ ID NO: 142) | dptBC | peptide synthetase 2 | 5.91 |
| | | acaagtccacacccc | (SEQ ID NO: 143) | dptA | peptide synthetase 1 | 5.53 |
| | | cgaggctagaactgg | (SEQ ID NO: 144) | AAX31565 | metalloprotease | 5.43 |
| | | cgtggctggacctca | (SEQ ID NO: 145) | dptBC | peptide synthetase 2 | 5.39 |
| | | ggtggtcctcaccacg | (SEQ ID NO: 146) | dptBC | peptide synthetase 2 | 5.33 |
| | | actggagtccacctga | (SEQ ID NO: 147) | AAX31520 | ATP-dependent helicase | 5.00 |
| | | cgaggcctacaccctc | (SEQ ID NO: 148) | AAX31577 | hypothetical | 6.05 |
| Novobiocin | S. spheroides | ggaggtgagatcaca | (SEQ ID NO: 149) | novH | Peptide synthase | 8.45 |
| Actinomycin | S. anulatus | ggaggtgagatcaca | (SEQ ID NO: 150) | acmC | peptide synthase III | 8.45 |
| | | | | acmC | peptide synthase III | |
| A47934 (teichoplanin) | S. toyocaensis | ggaggtgagatcaca | (SEQ ID NO: 151) | staC | peptide synthetase | 8.45 |
| | | tctggtgagaccttc | (SEQ ID NO: 152) | staP | membrane protein | 7.73 |
| | | actggtctgctgatg | (SEQ ID NO: 153) | staN | ion transporter | 6.23 |
| | | gctggtccaggcccct | (SEQ ID NO: 154) | dpgB | enhancer of Dihydroxyphenylacetyl-CoA synthetase activity | 6.21 |
| | | ggtggtcccagcctc | (SEQ ID NO: 155) | vanSst | histidine kinase | 5.87 |
| | | gctggtccgaccctc | (SEQ ID NO: 156) | vanSst | histidine kinase | 5.76 |
| | | catggtccgtccagc | (SEQ ID NO: 157) | staF | P450-related oxidase | 5.06 |
| Streptomycin | S. griseus | ggggtgtcgaccagc | (SEQ ID NO: 158) | CAH94374 | hypothetical | 7.81 |
| | | cgtggcgagtccaca | (SEQ ID NO: 159) | CAH94409 | methyltransferase | 5.74 |
| | | cctggtcttcacccg | (SEQ ID NO: 160) | strZ | transmembrane protein | 5.66 |
| | | agtggtcgcgatgc | (SEQ ID NO: 161) | apbE | thiamine biosynthesis lipoprotein | 5.13 |
| | | tgactgtcactcctc | (SEQ ID NO: 162) | CAH94395 | PqrB-type multidrug efflux protein | 5.03 |
| | | ggtgggcagaccatc | (SEQ ID NO: 163) | strB1 | Amidinotransferase I | 6.22 |
| | | agtgtcgagcgggt | (SEQ ID NO: 164) | strZ | transmembrane protein | 6.09 |
| | | attggcctgcaccgcg | (SEQ ID NO: 165) | strU | NAD(P) dependent oxidoreductase | 6.04 |

TABLE 3-continued

List of putative binding sites for DasR relating to secondary metabolism (cut-off score 5)

| | | | | | |
|---|---|---|---|---|---|
| Chloramphenicol | S. venezuelae | acgggtcttacacctcc (SEQ ID NO: 166) | papD | p-aminobenzoic acid synthase ORFIV | 10.38 |
| | | gctggtgtcgaccatc (SEQ ID NO: 167) | papA | 4-amino-4-deoxychorismate synthase | 7.34 |
| | | cgaggtggagacctac (SEQ ID NO: 168) | papA | 4-amino-4-deoxychorismate synthase | 5.91 |
| | | cgaggtggagacctac (SEQ ID NO: 169) | papAB | p-aminobenzoate synthase | |
| Butyrolactone | S. virginiae | actggtgtcgaccag (SEQ ID NO: 170) | barB | hormone-like γ-butyrolactone biosynthesis | 10.12 |

B. Known and cryptic biosynthesis clusters of Streptomyces coelicolor

| metabolite | gene | function | dre | position | score | co-transcribed | function |
|---|---|---|---|---|---|---|---|
| actinorhodin | SCO5085 | actinorhodin cluster activator protein | TGTTGAGTAGGCCTGT (SEQ ID NO: 171) | -59 | 11.22 | — | — |
| actinorhodin | SCO5090 | actinorhodin polyketide synthase bifunctional cyclase/dehydratase | GGTGGTCCACACCCTG (SEQ ID NO: 172) | 24 | 5.58 | SCO5091/SCO5092 | cyclase/actinorhodin polyketide putative dimerase |
| Prodigiosin | SCO5879 | acyl-coa dehydrogenase RedW | ACAGGTCTACGGCACG (SEQ ID NO: 173) | -324 | 7.33 | SCO5880 | RedY protein |
| Prodigiosin | SCO5881c | RedZ response regulator | AGTGGTTTCCACCTCA (SEQ ID NO: 174) | -201 | 6.24 | — | — |
| Prodigiosin | SCO5883c | hypothetical protein SC3F7.03c | GTTGCCTGCTCCAGG (SEQ ID NO: 175) | -252 | 5.11 | — | — |
| CDA (calcium-dependent antibiotic) | SCO3237c | conserved hypothetical protein | GTAGGTCTCGACCTCC (SEQ ID NO: 176) | -151 | 5.84 | — | — |
| CDA (calcium-dependent antibiotic) | SCO3226 | two component system response regulator | AGCGGTCTGCTCGACT (SEQ ID NO: 177) | -99 | 5.75 | — | — |
| CDA (calcium-dependent antibiotic) | SCO3234 | putative phosphotransferase | CGATCGTCCAGACCGGT (SEQ ID NO: 178) | 15 | 5.51 | — | — |

TABLE 3-continued

List of putative binding sites for DasR relating to secondary metabolism (cut-off score 5)

| | | | | | |
|---|---|---|---|---|---|
| Isorenieratine | SCO0188 | putative methylesterase | GCAGGACTACACCGTG (SEQ ID NO: 179) | -168 | 5.6 | — |
| Tetrahydroxynaphtalene (melanine) | SCO1206 | putative polyketide synthase | GCTGGTGGAGACCCGC (SEQ ID NO: 180) | -274 | 5.6 | SCO1207/SCO1208 putative cytochrome P450/hypothetical protein |
| Unknown | SCO0387 | putative bi-domain oxidoreductase | GGTTGTGCAGAACTAC (SEQ ID NO: 181) | -4 | 5.04 | SCO0388/SCO0389/ hypothetical protein SCF62.14/putative SCO0390/SCO0391/ lipoprotein/putative membrane protein/putative SCO0392/SCO0393/ transferase/putative methyltransferase/ SCO0394/SCO0395/ putative transferase/hypothetical protein SCO0396/SCO0397/ SCF62.20/putative epimerase/dehydratase/ SCO0398/SCO0399/ hypothetical protein SCF62.22/putative SCO0400/SCO0401 integral membrane protein/putative glycosyl transferase/putative membrane protein/ putative epimerase/putative aminotransferase |
| Unknown | SCO0388 | hypothetical protein SCF62.14 | GCTGGTCGCCACCACG (SEQ ID NO: 182) | -87 | 5.51 | SCO0389/SCO0390/ putative lipoprotein/putative membrane SCO0391/SCO0392/ protein/putative transferase/putative SCO0393/SCO0394/ methyltransferase/putative transferase/ SCO0395/SCO0396/ hypothetical protein SCF62.20/putative SCO0397/SCO0398/ epimerase/dehydratase/hypothetical protein SCO0399/SCO0400/ SCF62.22/putative integral membrane SCO0401 protein/putative glycosyl transferase/putative membrane protein/putative epimerase/ putative aminotransferase |
| Unknown | SCO6282c | putative 3-oxoacyl-[acyl-carrier protein] reductase | GCTGGACGAGTCCACC (SEQ ID NO: 183) | -262 | 5.42 | — |

TABLE 4

DasR target genes related to glutamate metabolism. Targets, validation (experimental or in silico) and gene function are presented. For meaning and deduction of the score, see text.

| # | Gene | Known or predicted gene product | Evidence dre | Score |
|---|---|---|---|---|
| 1 | tRNA Gln | tRNA Gln anticodon CTG. | S | ACTGGTCTAAACCACA (SEQ ID NO: 184) 14.43 |
| 2 | tRNA Glu | tRNA Glu anticodon CTC. | S | ACTGGTCTAAACCACA (SEQ ID NO: 185) 14.43 |
| 3 | SCO4285c, nagK | N-acetylglucosamine kinase. ATP + N-acetyl-D-glucosamine = ADP + N-acetyl-D-glucosamine-6-phosphate | S, E | AGAGGTCTAGTCCACT GGTGGTGTAGACCTTA (SEQ ID NO: 186) 12.82 8.00 |
| 4 | SCO4284c, nagA | N-acetylglucosamine-6-phosphate deacetylase. CoA + N-acetyl-D-glucosamine 6-phosphate = acetyl-CoA + D-glucosamine-6-phosphate | S, E, P | AGAGGTCTAGTCCACT GGTGGTGTAGACCTTA (SEQ ID NO: 187) 12.82 8.00 |
| 5 | SCO5236c, nagB | Glucosamine-6 phosphate isomerase. L-glutamine + D-fructose 6-phosphate = L-glutamate + D-glucosamine-6-phosphate | S, E | TGTGGTTTAGACCAAT (SEQ ID NO: 188) 11.36 |
| 6 | CO6344 | Glu-tRNAGln amidotransferase A subunit. ATP + glutamyl-tRNA(Gln) + L-glutamine = ADP + phosphate + glutaminyl-tRNA(Gln) + L-glutamate | S | TAAGGTCTAGACCTGC (SEQ ID NO: 189) 9.99 |
| 7 | SCO5520 | pyrroline-5-carboxylate dehydrogenase. 1-pyrroline-5-carboxylate + NAD+ + H2O = L-glutamate + NADH + H+ | P | — | — |
| 8 | SCO4683 | GdhA, NADP-specific glutamate dehydrogenase. L-glutamate + H2O + NAD+ = 2-oxoglutarate + NH3 + NADH + H+ | P | — | — |
| 9 | SCO4366 | phosphoserine aminotransferase. O-phospho-L-serine + 2-oxoglutarate = 3-phosphonooxypyruvate + L-glutamate | P | — | — |

S, predicted in silico;
E, experimentally validated in vitro;
P, deduced from proteomics experiments;
dre, DasR responsive element.
Scores are expressed in unit of bits.

TABLE 5

DasR binding sites in Bacillus species.

A. B. subtilis

| Score | Position | Site | Gene | Synonym | COG | Product |
|---|---|---|---|---|---|---|
| 4.70572 | −121 | AGTGATCTATATACCAAT (SEQ ID NO: 190) | yflG | Bsu0769 | COG0024 | similar to methionine aminopeptidase |
| 4.70572 | −67 | ATTGTATAGATCATCACT (SEQ ID NO: 191) | yflF | Bsu0770 | COG1264 | similar to phosphotransferase system enzyme II |
| 4.54507 | −60 | AACGGTCTAGACAAAT (SEQ ID NO: 192) | yxaG | Bsu3995 | — | yxaG |
| 4.47401 | −127 | AGTGATCTAGACCAGC (SEQ ID NO: 193) | yvoB | Bsu3497 | COG1493 | similar to hypothetical proteins |
| 4.47401 | −71 | GCTGGTCTAGATCACT (SEQ ID NO: 194) | nagA | Bsu3498 | COG1820 | N-acetylglucosamine-6-phosphate deacetylase |
| 4.41253 | −44 | AGTTGTATATACAAGT (SEQ ID NO: 195) | treP | Bsu0780 | COG1264 | phosphotransferase system (PTS) trehalose-specific enzyme IIBC component |
| 4.41253 | −165 | ACTTGTATATACAACT (SEQ ID NO: 196) | yfkQ | Bsu0779 | — | similar to spore germination response |
| 4.3857 | −174 | ATATGTTAGACCTGT (SEQ ID NO: 197) | yqjU | Bsu2373 | — | yqjU |
| 4.3246 | −326 | ATCTGTCTATACCTAT (SEQ ID NO: 198) | yomE | Bsu2140 | — | yomE |
| 4.28564 | −82 | AATAGTATAGACTATT (SEQ ID NO: 199) | pckA | Bsu3051 | COG1866 | phosphoenolpyruvate carboxykinase |
| 4.25776 | −320 | TTTTGTATATACCATT (SEQ ID NO: 200) | ydbO | Bsu0454 | COG0053 | similar to hypothetical proteins |
| 4.25776 | −61 | AATGGTATATACAAAA (SEQ ID NO: 201) | ydbN | Bsu0453 | — | ydbN |
| 4.25487 | −68 | AGTGGTCTAAACTCCT (SEQ ID NO: 202) | bofA | Bsu0023 | — | integral membrane protein |
| 4.24264 | −226 | AATGGTATATATCATA (SEQ ID NO: 203) | yodL | Bsu1963 | — | yodL |
| 4.23975 | −346 | ATGGCTCTACACCATT (SEQ ID NO: 204) | ylaD | Bsu1476 | — | ylaD |
| 4.23813 | −2 | AATGGAATATACCAGT (SEQ ID NO: 205) | yhdN | Bsu0953 | COG0667 | similar to aldo/keto reductase |
| 4.23813 | −211 | ACTGGTATATTCCATT (SEQ ID NO: 206) | yhdM | Bsu0952 | COG1595 | similar to RNA polymerase ECF-type sigma factor |
| 4.23131 | −190 | ATTGGTTTAGACAACA (SEQ ID NO: 207) | tenI | Bsu1167 | COG0352 | transcriptional regulator |
| 4.23065 | −91 | ACATTTCTATACCATT (SEQ ID NO: 208) | hemE | Bsu1012 | COG0407 | uroporphyrinogen III decarboxylase |
| 4.20249 | −113 | AATTATATATACAATT (SEQ ID NO: 209) | rbsR | Bsu3589 | COG1609 | transcriptional regulator (LacI family) |
| 4.20249 | −46 | AATGTTATATAACATT (SEQ ID NO: 210) | yurO | Bsu3257 | COG1653 | similar to multiple sugar-binding protein |
| 4.20249 | −115 | AATGGTATATAATATT (SEQ ID NO: 211) | yndL | Bsu1783 | — | similar to phage-related replication protein |

TABLE 5-continued

DasR binding sites in Bacillus species.

| Score | Position | Site | Gene | Synonym | COG | Product |
|---|---|---|---|---|---|---|
| 4.19036 | −170 | ATTCGTATAAACAAGT (SEQ ID NO: 212) | yeeA | Bsu0677 | COG1002 | similar to hypothetical proteins |
| 4.19036 | −10 | AATGGTTTATATGAAT (SEQ ID NO: 213) | yqeK | Bsu2559 | COG1713 | similar to hypothetical proteins |
| 4.19036 | −237 | ACTTGTTTATACGAAT (SEQ ID NO: 214) | yefB | Bsu0675 | — | similar to site-specific recombinase |

B. B. halodurans

| Score | Position | Site | Gene | Synonym | COG | Product |
|---|---|---|---|---|---|---|
| 4.62842 | −168 | ATTTGTATATACCAAT (SEQ ID NO: 215) | BH0422 | BH0422 | COG1263 | PTS system, N-acetylglucosamine-specific enzyme II, ABC component |
| 4.62842 | −88 | ATTGATATATACCAAT (SEQ ID NO: 216) | BH3323 | BH3323 | COG2188 | transcriptional regulator (GntR family) |
| 4.62842 | −155 | ATTGGTATATACAAAT (SEQ ID NO: 217) | nagA | BH0421 | COG1820 | N-acetylglucosamine-6-phosphate deacetylase |
| 4.62842 | −231 | ATTGGTATATATCAAT (SEQ ID NO: 218) | BH3324 | BH3324 | COG1208 | glucose-1-phosphate thymidylyltransferase |
| 4.54325 | −152 | ATTGGTATAGACATTT (SEQ ID NO: 219) | BH0419 | BH0419 | COG2188 | transcriptional regulator (GntR family) |
| 4.54325 | −103 | AAATGTCTATACCAAT (SEQ ID NO: 220) | BH0418 | BH0418 | COG0500 | BH0418~unknown conserved protein in others |
| 4.5403 | −155 | TATGGTATAGACCACT (SEQ ID NO: 221) | BH2230 | BH2230 | — | BH2230~unknown |
| 4.50391 | −214 | ATTGGTATAAACAAAT (SEQ ID NO: 222) | BH1924 | BH1924 | COG1653 | sugar transport system (sugar-binding protein) |
| 4.48969 | −175 | ATTCGTTTAGACCAAT (SEQ ID NO: 223) | BH0593 | BH0593 | — | BH0593~unknown |
| 4.45248 | −41 | ATTGTTCTAGACCCTT (SEQ ID NO: 224) | BH2561 | BH2561 | COG3879 | BH2561~unknown conserved protein in bacilli |
| 4.41889 | −63 | ACTTGTATATACAAAT (SEQ ID NO: 225) | BH2216 | BH2216 | COG1264 | PTS system, trehalose-specific enzyme II, BC component |
| 4.41579 | −316 | AATGGTCTACACCAAG (SEQ ID NO: 226) | BH1484 | BH1484 | COG3595 | BH1484~unknown conserved protein in others |
| 4.41579 | −302 | CTTGGTGTAGACCATT (SEQ ID NO: 227) | BH1482 | BH1482 | COG0517 | BH1482~unknown conserved protein in B. subtilis |
| 4.40381 | −99 | ACTTGTATATACAAGT (SEQ ID NO: 228) | treA | BH0872 | COG0366 | alpha,alpha-phosphotrehalase |
| 4.40367 | −81 | AAAGGTGTAGATCATT (SEQ ID NO: 229) | BH0661 | BH0661 | — | response regulator aspartate phosphatase |
| 4.37739 | −104 | AATGATTTAGATCAAT (SEQ ID NO: 230) | BH0786 | BH0786 | COG1940 | transcriptional regulator |

TABLE 5-continued

DasR binding sites in Bacillus species.

| Score | Position | Site | | Gene | Synonym | COG | Product |
|---|---|---|---|---|---|---|---|
| 4.33078 | −136 | TATGGTCTATATCATT | (SEQ ID NO: 231) | BH0464 | BH0464 | COG1968 | bacitracin resistance protein (undecaprenol kinase) |
| 4.29237 | −81 | AATAGTATAGACTATT | (SEQ ID NO: 232) | pckA | BH3302 | COG1866 | phosphoenolpyruvate carboxykinase |
| 4.25057 | −344 | ACAGGTGTAGACATTT | (SEQ ID NO: 233) | BH3024 | BH3024 | COG0745 | BH3024~unknown |
| 4.22134 | −148 | AGTTGTTTAGACCAGA | (SEQ ID NO: 234) | BH2314 | BH2314 | COG0191 | fructose bisphosphate aldolase |
| 4.21655 | −71 | ATTGATCTATACAAAC | (SEQ ID NO: 235) | BH3244 | BH3244 | — | general stress protein |
| 4.21022 | −216 | ATTGATATAGATGAGT | (SEQ ID NO: 236) | BH2450 | BH2450 | — | BH2450~unknown |
| 4.19716 | −314 | AATGGTGTATAGAAAT | (SEQ ID NO: 237) | BH3530 | BH3530 | — | BH3530~unknown |
| 4.19716 | −145 | ATTGATTTATAGCATT | (SEQ ID NO: 238) | BH4039 | BH4039 | COG0582 | BH4039~unknown conserved protein |
| 4.1957 | −3 | ACATGTCTATACATCT | (SEQ ID NO: 239) | BH3678 | BH3678 | COG2972 | two-component sensor histidine kinase |
| 4.16786 | −302 | AATGGTGTAGAGGATT | (SEQ ID NO: 240) | rpoB | BH0126 | COG0085 | DNA-directed RNA polymerase beta subunit |
| 4.15636 | −186 | ATTGGTTTATATATAT | (SEQ ID NO: 241) | BH2699 | BH2699 | COG1136 | ABC transporter (ATP-binding protein) |
| 4.13718 | −216 | ATTGATCTAGAGCATA | (SEQ ID NO: 242) | spoVFA | BH2403 | — | dipicolinate synthase subunit A |
| 4.13468 | −241 | ATCGGTTTACACAATT | (SEQ ID NO: 243) | rplC | BH0134 | COG0087 | 50S ribosomal protein L3 |

TABLE 6

DasR binding sites in *Lactococcus lactis*

| Score | Position | Site | Gene | Synonym | COG | Product |
|---|---|---|---|---|---|---|
| 5.86694 | -36 | ATTGATATATACCAAT (SEQ ID NO: 244) | nagB | L14408 | COG0363 | glucosamine-6-P isomerase (EC 5.3.1.10) |
| 5.58801 | -72 | ATTGGTATATACTGTT (SEQ ID NO: 245) | nagA | L173068 | COG1820 | N-acetylglucosamine-6-phosphate deacetylase (EC 3.5.1.25) |
| 5.4239 | -40 | ATTGGTATATAAAAAT (SEQ ID NO: 246) | yxfB | L141634 | COG0500 | HYPOTHETICAL PROTEIN |
| 5.3542 | -215 | AACGGTATATACGATT (SEQ ID NO: 247) | yveE | L127921 | — | UNKNOWN PROTEIN |
| 5.24344 | -173 | AACAGTATATATCATT (SEQ ID NO: 248) | pi228 | L51784 | — | prophage pi2 protein 28 |
| 5.18192 | -37 | AGTGGTATATATTGTT (SEQ ID NO: 249) | rgrB | L0151 | COG2188 | GntR family transcriptional regulator |
| 5.16551 | -279 | AATGATATATATCTTT (SEQ ID NO: 250) | ymgC | L61341 | COG2936 | conserved hypothetical protein |
| 5.11627 | -170 | ACTTGTATATACTTAT (SEQ ID NO: 251) | rplJ | L0407 | COG0244 | 50S ribosomal protein L10 |
| 5.03205 | -164 | ATGGGTAGATAACAAT (SEQ ID NO: 252) | pi234 | L57508 | — | prophage pi2 protein 34 |
| 5.03205 | -1 | AATGAGATATATCAAT (SEQ ID NO: 253) | zitQ | L166512 | COG1121 | zinc ABC transporter ATP binding protein |
| 4.95193 | -261 | ATTGGTTTATACCGAC (SEQ ID NO: 254) | dexC | L128694 | COG0366 | neopullulanase (EC 3.2.1.135) |
| 4.95193 | -123 | GTCGGTATAAACCAAT (SEQ ID NO: 255) | malE | L128695 | COG2182 | maltose ABC transporter substrate binding protein |
| 4.92129 | -265 | ATTGGTATACAATATT (SEQ ID NO: 256) | yviA | L163025 | COG2323 | HYPOTHETICAL PROTEIN |
| 4.92129 | -118 | ATTAGTCTATATCTAT (SEQ ID NO: 257) | tra983B | L0444 | COG2826 | transposase of IS983B |
| 4.92129 | -189 | ATAAATAAATACCAAT (SEQ ID NO: 258) | yrjB | L174321 | COG0247 | oxidoreductase |
| 4.91311 | -348 | AATGGGATATACTGGT (SEQ ID NO: 259) | yqeL | L22900 | COG1161 | GTP-binding protein |
| 4.89476 | -286 | ATTGATATATATGTCT (SEQ ID NO: 260) | ycbC | L11986 | — | HYPOTHETICAL PROTEIN |
| 4.89476 | -314 | ACGAGTATATATAAAT (SEQ ID NO: 261) | yliA | L179789 | — | positive transcriptional regulator |
| 4.88629 | -220 | ATTGGTATAGGTCAAT (SEQ ID NO: 262) | ybhE | L176316 | COG3589 | HYPOTHETICAL PROTEIN |
| 4.88246 | -50 | ATAAGTATATACATCT (SEQ ID NO: 263) | yfhF | L174076 | — | HYPOTHETICAL PROTEIN |
| 4.8617 | -262 | AATGGAAGATACCATT (SEQ ID NO: 264) | ywaH | L191704 | — | UNKNOWN PROTEIN |
| 4.85976 | -241 | ACTTGTATTTATCAAT (SEQ ID NO: 265) | ps208 | L106731 | — | prophage ps2 protein 08 |

TABLE 7

DasR binding sites in Streptococcus species

A. S. pneumoniae TIGR4

| Score | Position | Site | Gene | Synonym | COG | Product |
|---|---|---|---|---|---|---|
| 4.56012 | -264 | AGTGGTGTATGCCAAT (SEQ ID NO: 266) | — | SP0571 | COG2184 | cell filamentation protein Fic-related protein |
| 4.52678 | -49 | ATTGGTCTATACCATA (SEQ ID NO: 267) | — | SP1415 | COG0363 | glucosamine-6-phosphate isomerase |
| 4.52678 | -118 | TATGGTATAGACCAAT (SEQ ID NO: 268) | — | SP1416 | COG0809 | S-adenosylmethionine:tRNA ribosyltransferase-isomerase |
| 4.50546 | -56 | ATTAGACTATACCAAT (SEQ ID NO: 269) | — | SP0266 | COG0449 | glucosamine--fructose-6-phosphate aminotransferase, isomerizing |
| 4.45088 | -9 | AGTGGAATATGACAGT (SEQ ID NO: 270) | — | SP0856 | COG0115 | branched-chain amino acid aminotransferase |
| 4.444 | -69 | ATTATAATATTCCAAT (SEQ ID NO: 271) | — | SP1211 | — | hypothetical protein |
| 4.444 | -296 | ATTATAATATTCCAAT (SEQ ID NO: 272) | — | SP1210 | — | hypothetical protein |
| 4.41439 | -134 | ATTATTATATAGCAAT (SEQ ID NO: 273) | — | SP2103 | COG0500 | rRNA (guanine-N1-)-methyltransferase |
| 4.41439 | -1 | ATTGCTATATATAAT (SEQ ID NO: 274) | — | SP2102 | — | hypothetical protein |
| 4.41439 | -314 | ATTGCTATATAATAAT (SEQ ID NO: 275) | — | SP2101 | COG2217 | cation-transporting ATPase, EI-E2 family |
| 4.3461 | -68 | ACTGTTATATAATACT (SEQ ID NO: 276) | — | SP0088 | COG0840 | hypothetical protein |
| 4.3461 | -19 | AGTATTATATAACAGT (SEQ ID NO: 277) | — | SP0087 | — | hypothetical protein |
| 4.32609 | -290 | AGTGGTCTATTCGAAT (SEQ ID NO: 278) | — | SP1249 | COG0516 | conserved hypothetical protein |
| 4.27568 | -345 | CTTGGGATAAACCACT (SEQ ID NO: 279) | — | SP1702 | COG0653 | preprotein translocase, SecA subunit |
| 4.27445 | -316 | ATTAGATATATAAAAT (SEQ ID NO: 280) | — | SP1956 | — | hypothetical protein |
| 4.27389 | -93 | ATAGGTCTATACCATT (SEQ ID NO: 281) | — | SP2056 | COG1820 | N-acetylglucosamine-6-phosphate deacetylase |
| 4.25853 | -232 | AGTGTTGTATGCCAGT (SEQ ID NO: 282) | — | SP0056 | COG0015 | adenylosuccinate lyase |
| 4.25658 | -35 | TTTGGAGTATTCCAAT (SEQ ID NO: 283) | — | SP1319 | COG1527 | v-type sodium ATP synthase, subunit C |
| 4.24921 | -212 | AAGGATATATACCAAT (SEQ ID NO: 284) | — | SP1431 | COG2189 | type II DNA modification methyltransferase, putative |
| 4.24425 | -46 | AGTGGTATATTTAATT (SEQ ID NO: 285) | — | SP0474 | COG1455 | PTS system, cellobiose-specific IIC component |
| 4.24425 | -138 | AATTAAATATACCACT (SEQ ID NO: 286) | — | SP0473 | COG1940 | ROK family protein |

TABLE 7-continued

DasR binding sites in Streptococcus species

| Score | Position | Site | | Gene | Synonym | COG | Product |
|---|---|---|---|---|---|---|---|
| 4.24051 | −42 | AATGGTATAATTCATT | (SEQ ID NO: 287) | — | SP1810 | — | hypothetical protein |
| 4.23862 | −94 | TATACTATATACCATT | (SEQ ID NO: 288) | — | SP0839 | COG1072 | pantothenate kinase |
| 4.23862 | −112 | AATGGTATATAGTATA | (SEQ ID NO: 289) | — | SP0840 | — | hypothetical protein |
| 4.23664 | −76 | ATTGGCATATCAGACT | (SEQ ID NO: 290) | — | SP1264 | COG1808 | conserved domain protein |
| 4.2252 | −87 | AATGTGATATAATAGT | (SEQ ID NO: 291) | — | SP1421 | COG1488 | conserved hypothetical protein |
| 4.21304 | −40 | CTTTGTATATACTAGT | (SEQ ID NO: 292) | — | SP0394 | COG2213 | PTS system, mannitol-specific IIBC components |
| 4.21243 | −149 | ATGGGGATATAACATT | (SEQ ID NO: 293) | — | SP2159 | — | fucolectin-related protein |
| 4.20615 | −50 | AGTGTGATATATAGT | (SEQ ID NO: 294) | — | SP0499 | COG0126 | phosphoglycerate kinase |
| 4.20387 | −42 | ACTAGTATAGCACAAT | (SEQ ID NO: 295) | — | SP1011 | — | GtrA family protein |

B. *S. pyogenes*

| Score | Position | Site | | Gene | Synonym | COG | Product |
|---|---|---|---|---|---|---|---|
| 4.95709 | −66 | AGTGGTATATACCATT | (SEQ ID NO: 296) | nagA | SPy1694 | COG1820 | putative N-acetylglucosamine-6-phosphate deacetylase |
| 4.76896 | −156 | TATGGTATATACCAAT | (SEQ ID NO: 297) | queA | SPy1400 | COG0809 | putative S-adenosylmethionine-tRNA ribosyltransferase-isomerase |
| 4.76896 | −62 | ATTGGTATATACCATA | (SEQ ID NO: 298) | nagB | SPy1399 | COG0363 | putative N-acetylglucosamine-6-phosphate isomerase |
| 4.57524 | −163 | ATTAGCATATCCCAAT | (SEQ ID NO: 299) | — | SPy0433 | — | hypothetical protein |
| 4.45835 | −148 | ATTAGACTATACCAAT | (SEQ ID NO: 300) | glmS | SPy1280 | COG0449 | putative L-glutamine-D-fructose-6-phosphate amidotransferase |
| 4.31846 | −123 | ATTGTGATATAATAAT | (SEQ ID NO: 301) | gatC | SPy1772 | COG0721 | putative Glu-tRNA Gln amidotransferase subunit C |
| 4.29471 | −2 | AATGATATATAATAAT | (SEQ ID NO: 302) | — | SPy0045 | COG0534 | conserved hypothetical protein |
| 4.2322 | −131 | AATTGGATATCACCAAT | (SEQ ID NO: 303) | — | SPy0593 | — | conserved hypothetical protein |
| 4.21387 | −155 | AGTTTAATATCCCAAT | (SEQ ID NO: 304) | lysS | SPy0595 | COG1190 | putative lysyl-tRNA synthetase |
| 4.21387 | −35 | ATTGGGATATTAAACT | (SEQ ID NO: 305) | — | SPy0596 | COG1011 | conserved hypothetical protein |
| 4.21271 | −144 | TATGGAATATTACACT | (SEQ ID NO: 306) | hasB | SPy2201 | COG1004 | UDP-glucose 6-dehydrogenase |

TABLE 7-continued

DasR binding sites in Streptococcus species

| Score | Position | Site | Gene | Synonym | COG | Product |
|---|---|---|---|---|---|---|
| 4.20978 | −301 | ACTTGTATATGCCAAG (SEQ ID NO: 307) | accD | SPy1744 | COG0777 | putative acetyl-CoA carboxylase beta subunit |
| 4.20304 | −170 | ACTGTTATATAGTATT (SEQ ID NO: 308) | acoA | SPy1026 | COG1071 | putative acetoin dehydrogenase (TPP-dependent) alpha chain |
| 4.2014 | −69 | ATTGTATTATAACAAT (SEQ ID NO: 309) | — | SPy1884 | COG0330 | similar to several eukaryotic hypersensitive-induced response proteins |
| 4.17464 | −139 | AGTGGCATAACACAAT (SEQ ID NO: 310) | fabG | SPy1749 | COG1028 | putative beta-ketoacyl-ACP reductase |
| 4.16261 | −165 | TGTTGGATATTCCAAT (SEQ ID NO: 311) | — | SPy1253 | — | conserved hypothetical protein |
| 4.1621 | −17 | ATTCGGATATAACAAA (SEQ ID NO: 312) | — | SPy1297 | COG1609 | putative transcription regulator (LacI family) |
| 4.14754 | −111 | ATTAGTATAGGCTACT (SEQ ID NO: 313) | — | SPy1437 | — | hypothetical protein |
| 4.13534 | −279 | ATTGGGATATGCAACA (SEQ ID NO: 314) | pyrR | SPy0830 | COG2065 | putative pyrimidine regulatory protein |
| 4.12956 | −148 | AATTGTATAGACCAAC (SEQ ID NO: 315) | — | SPy0539 | — | hypothetical gene |
| 4.1271 | −161 | AATGAAATATTCAAAT (SEQ ID NO: 316) | — | SPy2099 | COG2188 | putative transcriptional regulator (GntR family) |
| 4.1271 | −66 | ATTTGGATATATTCATT (SEQ ID NO: 317) | — | SPy2097 | COG1264 | putative PTS system enzyme II |
| 4.12284 | −105 | ATTGTGCTAGACCATT (SEQ ID NO: 318) | — | SPy1494 | — | hypothetical protein |
| 4.10357 | −100 | ATTGGAATATGATAAA (SEQ ID NO: 319) | — | SPy1249 | COG1393 | conserved hypothetical protein |
| 4.10336 | −42 | AATAGTATATTAGATT (SEQ ID NO: 320) | — | SPy0338 | COG1327 | conserved hypothetical protein |
| 4.09424 | −271 | ATTGGTACATGTCAAT (SEQ ID NO: 321) | glpF.2 | SPy1854 | COG0580 | putative glycerol uptake facilitator protein |

C. S. mutans

| Score | Position | Site | Gene | Synonym | COG | Product |
|---|---|---|---|---|---|---|
| 4.71268 | −42 | TTTGGTATATACCATT (SEQ ID NO: 322) | — | SMU.435 | — | putative N-acetylglucosamine-6-phosphate deacetylase |
| 4.56555 | −17 | ATTGGAATACACCAAT (SEQ ID NO: 323) | — | SMU.284 | — | hypothetical protein |
| 4.39528 | −69 | ATTAGACTATACCAAT (SEQ ID NO: 324) | glmS | SMU.1187 | — | glucosamine-fructose-6-phosphate aminotransferase |
| 4.35759 | −36 | ACTGGTATAAACCAAA (SEQ ID NO: 325) | gtfA | SMU.881 | — | sucrose phosphorylase, GtfA |
| 4.31505 | −125 | AATGTTATATTACAGT (SEQ ID NO: 326) | — | SMU.995 | — | putative ABC transporter, permease protein; possible ferrichrome transport system |

TABLE 7-continued

DasR binding sites in *Streptococcus* species

| Score | Position | Site | Gene | Synonym | COG | Product |
|---|---|---|---|---|---|---|
| 4.28134 | −295 | AATGGGAAATACCATT (SEQ ID NO: 327) | rexA | SMU.1499 | — | putative exonuclease RexA |
| 4.27644 | −101 | ATTGGAATATAAGACT (SEQ ID NO: 328) | — | SMU.458 | — | putative ATP-dependent RNA helicase |
| 4.26492 | −195 | ATTAGTATAAAACAAT (SEQ ID NO: 329) | — | SMU.1912c | — | hypothetical protein |
| 4.23783 | −238 | ATTGATATATTTCAAT (SEQ ID NO: 330) | mleS | SMU.137 | — | malolactic enzyme |
| 4.21286 | −67 | AATAGTTTATACTAAT (SEQ ID NO: 331) | — | SMU.753 | — | conserved hypothetical protein |
| 4.19185 | −199 | AGTTTTATATAACAAT (SEQ ID NO: 332) | — | SMU.1145c | — | putative histidine kinase; homolog of RumK and ScnK |
| 4.14917 | −331 | TATGGAATATATAATAAT (SEQ ID NO: 333) | parC | SMU.1204 | — | topoisomerase IV, subunit A |
| 4.14346 | −39 | AATAGTTTATACTACT (SEQ ID NO: 334) | — | SMU.1349 | — | hypothetical protein |
| 4.14346 | −330 | AGTAGTATAAACTATT (SEQ ID NO: 335) | — | SMU.1348c | — | putative ABC transporter, ATP-binding protein |
| 4.11591 | −270 | ATTGATATAGAACAGT (SEQ ID NO: 336) | pstS | SMU.1138 | — | putative ABC transporter, phosphate-binding protein |
| 4.11572 | −161 | GGTGGAATAGTCCAAT (SEQ ID NO: 337) | glgB | SMU.1539 | — | putative 1,4-alpha-glucan branching enzyme |
| 4.10525 | −298 | TGTGGCCTATGCCAAT (SEQ ID NO: 338) | — | SMU.166 | — | hypothetical protein |
| 4.10485 | 3 | AATGGTATAAAAAAAT (SEQ ID NO: 339) | msmE | SMU.878 | — | multiple sugar-binding ABC transporter, sugar-binding protein precursor MsmE |
| 4.10136 | −341 | ATTAGAATATGCCAGT (SEQ ID NO: 340) | hprT | SMU.14 | — | putative hypoxanthine-guanine phosphoribosyltransferase |
| 4.10001 | −125 | ATTAGAATATACCTCT (SEQ ID NO: 341) | — | SMU.1908c | — | hypothetical protein |
| 4.0932 | −38 | ATTGGTATATTAAAAA (SEQ ID NO: 342) | — | SMU.1764c | — | conserved hypothetical protein |
| 4.0924 | −252 | AAAGGTATAAACCATT (SEQ ID NO: 343) | — | SMU.2162c | — | conserved hypothetical protein |
| 4.09059 | −161 | TTTAGAATAGACCATT (SEQ ID NO: 344) | guaB | SMU.2157 | — | inosine monophosphate dehydrogenase |
| 4.07559 | −65 | AATTTGATATTCCAGT (SEQ ID NO: 345) | rmlC | SMU.1460 | — | putative dTDP-4-keto-L-rhamnose reductase |
| 4.06457 | −113 | TTTATTATATACTATT (SEQ ID NO: 346) | — | SMU.624 | — | putative 1-acylglycerol-3-phosphate O-acyltransferase |
| 4.06457 | −42 | AATAGTATATAATAAA (SEQ ID NO: 347) | — | SMU.623c | — | putative deacetylase |

TABLE 7-continued

DasR binding sites in Streptococcus species

| Score | Position | Site | Gene | Synonym | COG | Product |
|---|---|---|---|---|---|---|
| 4.05513 | -256 | AATAGCTTATACTAAT (SEQ ID NO: 348) | — | SMU.40 | — | conserved hypothetical protein |
| 4.05348 | -42 | AGTGTTATATGCTATA (SEQ ID NO: 349) | scnR | SMU.1815 | — | putative response regulator; ScnR homolog |
| 4.0529 | -215 | TGTGGTTTATACCACA (SEQ ID NO: 350) | asd | SMU.989 | — | aspartate-semialdehyde dehydrogenase |

D. S. agalactiae

| Score | Position | Site | Gene | Synonym | COG | Product |
|---|---|---|---|---|---|---|
| 4.67663 | -61 | ATTGGTATATACCATA (SEQ ID NO: 351) | nagB | SAG0799 | — | glucosamine-6-phosphate isomerase |
| 4.57476 | -306 | AATGGAATATACTAAT (SEQ ID NO: 352) | — | SAG0698 | — | beta-glucuronidase |
| 4.43079 | -66 | ATAGGTATATACCATT (SEQ ID NO: 353) | nagA | SAG0266 | — | N-acetylglucosamine-6-phosphate deacetylase |
| 4.42251 | -54 | ATTGGTATATATTAAT (SEQ ID NO: 354) | — | SAG0943 | — | hypothetical protein |
| 4.42251 | -74 | ATTAATATATACCAAT (SEQ ID NO: 355) | glmS | SAG0944 | — | glucosamine--fructose-6-phosphate aminotransferase, isomerizing |
| 4.37914 | -81 | AGTGGTATAATCCAGT (SEQ ID NO: 356) | ksgA | SAG1779 | — | dimethyladenosine transferase |
| 4.37243 | -332 | ATTGGTATATATTATT (SEQ ID NO: 357) | — | SAG1033 | — | FtsK/SpoIIIE family protein |
| 4.33644 | -229 | ATTGGAATATCCGATT (SEQ ID NO: 358) | — | SAG2003 | — | IS1381, transposase OrfA |
| 4.28704 | -61 | AATGGTATATCACAAG (SEQ ID NO: 359) | — | SAG2008 | — | conserved hypothetical protein |
| 4.20258 | -210 | TCTATTATATACCAAT (SEQ ID NO: 360) | — | SAG2170 | — | conserved hypothetical protein |
| 4.20258 | -50 | ATTGGTATATAATAGA (SEQ ID NO: 361) | — | SAG2169 | — | membrane protein, putative |
| 4.13411 | -232 | AATATGATATACTAAT (SEQ ID NO: 362) | — | SAG1186 | — | metallo-beta-lactamase superfamily protein |
| 4.13259 | -292 | CTTGGAATATTCCATA (SEQ ID NO: 363) | — | SAG0699 | — | transcriptional regulator, GntR family |
| 4.10916 | -124 | AGTAGAATAGTCCATT (SEQ ID NO: 364) | — | SAG1951 | — | PTS system, IIA component, putative |
| 4.09376 | -202 | AGTGGAATAGACAAGT (SEQ ID NO: 365) | cglB | SAG0164 | — | competence protein CglB |
| 4.09142 | -270 | AGTGGTATAATCCAGG (SEQ ID NO: 366) | — | SAG1307 | — | hypothetical protein |
| 4.09022 | -9 | ATTGGGCTATGCGAAT (SEQ ID NO: 367) | — | SAG0277 | — | conserved hypothetical protein |
| 4.08873 | -44 | ATTAGGATAAACTAAT (SEQ ID NO: 368) | — | SAG0021 | — | protease, putative |

TABLE 7-continued

DasR binding sites in Streptococcus species

| Score | Position | Site | Gene | Synonym | COG | Product |
|---|---|---|---|---|---|---|
| 4.08273 | −289 | ACTTGAATATCCTAAT (SEQ ID NO: 369) | — | SAG0626 | — | MutT/nudix family protein |
| 4.07572 | −69 | TATAGTATATAGCATT (SEQ ID NO: 370) | neuB | SAG1161 | — | N-acetyl neuraminic acid synthetase NeuB |
| 4.07402 | −31 | ATTTAATATAACAAT (SEQ ID NO: 371) | pepX | SAG1736 | — | X-pro dipeptidyl-peptidase |
| 4.07379 | −257 | AGTTGAATATGCTAAT (SEQ ID NO: 372) | — | SAG1571 | — | hypothetical protein |
| 4.06691 | −122 | ATTGGTATTTACGAGT (SEQ ID NO: 373) | — | SAG1711 | — | magnesium transporter, CorA family |
| 4.06603 | −120 | AATGGATATATTTATT (SEQ ID NO: 374) | cylF | SAG0670 | — | cylF protein |
| 4.04872 | −169 | CATGGGATATTCAAAT (SEQ ID NO: 375) | — | SAG1260 | — | hypothetical protein |
| 4.04872 | −324 | GTTGGAATATCGCATT (SEQ ID NO: 376) | tkt | SAG0278 | — | transketolase |
| 4.04511 | −103 | ATTGGCTTATTCAAAT (SEQ ID NO: 377) | — | SAG0231 | — | hypothetical protein |
| 4.0417 | −180 | AATGATATATGCAACT (SEQ ID NO: 378) | asd | SAG1051 | — | aspartate-semialdehyde dehydrogenase |
| 4.02438 | −141 | ATTGTCATATAACACC (SEQ ID NO: 379) | — | SAG1569 | — | copper homeostasis protein CutC, putative |
| 4.0221 | −8 | ATTAGTATATGTCAAA (SEQ ID NO: 380) | — | SAG1683 | — | immunogenic secreted protein, putative |
| 4.00725 | −283 | AGTACAATATAACAAT (SEQ ID NO: 381) | — | SAG1982 | — | transcriptional regulator, Cro/CI family |

TABLE 8

DasR binding sites in Listeria species.

A. Listeria innocua

| Score | Position | Site | Gene Synonym | COG | Product |
|---|---|---|---|---|---|
| 5.36566 | −121 | ATTGGTCTATATCAAT (SEQ ID NO: 382) | — | lin1996 COG3469 | similar to chitinases |
| 5.36389 | −38 | ATTGGTATAGACCGAT (SEQ ID NO: 383) | — | lin0955 COG1820 | similar to N-acetylglucosamine-6P-phosphate deacetylase (EC 3.5.1.25) |
| 5.26731 | −173 | AATGGTCTAGACAAAT (SEQ ID NO: 384) | codV | lin1316 COG0582 | similar to integrase/recombinase |
| 5.24253 | −34 | ACTTGTATATACAAGT (SEQ ID NO: 385) | — | lin1223 COG1264 | similar to PTS system trehalose specific enzyme IIBC |
| 5.24253 | −98 | ACTTGTATATACAAGT (SEQ ID NO: 386) | — | lin1224 COG0494 | lin1224 |
| 5.16643 | −44 | ACTGGTATAAACAAGT (SEQ ID NO: 387) | — | lin0296 COG0366 | lin0296 |
| 5.0365 | −143 | AACTGTCTAGACCAAT (SEQ ID NO: 388) | — | lin0780 COG1113 | similar to amino acid transporter |
| 4.98056 | −87 | ATTGGTATAAAGCAGT (SEQ ID NO: 389) | — | lin2570 — | similar to Orf51 [bacteriophage bIL285] |
| 4.97549 | −138 | ATCGGTTTATACCGGT (SEQ ID NO: 390) | — | lin1779 COG0803 | similar to ABC transporter and adhesion proteins |
| 4.96433 | −93 | TTTTGTATAGACCAAT (SEQ ID NO: 391) | fbp | lin0825 COG0639 | highly similar to fructose-1,6-bisphosphatase |
| 4.95402 | −201 | ACAAGTATAGACCAAT (SEQ ID NO: 392) | — | lin1606 COG0205 | lin1606 |
| 4.90623 | −72 | ATTTGTCTATATAATAAT (SEQ ID NO: 393) | pheT | lin1648 COG0073 | similar phenylalanyl-tRNA synthetase (B subunit) |
| 4.89907 | −315 | ACTGTTTTATACAAAT (SEQ ID NO: 394) | pflB | lin1443 COG1882 | pyruvate formate-lyase |
| 4.86345 | −1 | AATGGTCAATACAAAT (SEQ ID NO: 395) | aroA | lin1641 COG1605 | 3-deoxy-D-arabino-heptulosonate 7-phosphate synthase |
| 4.83652 | −129 | AGTGGTCTATATAATT (SEQ ID NO: 396) | — | lin1069 — | lin1069 |

TABLE 8-continued

DasR binding sites in *Listeria* species.

| Score | Position | Site | Gene Synonym | COG | Product |
|---|---|---|---|---|---|
| 4.82408 | −299 | ATCGGTATATACTTGT (SEQ ID NO: 397) | lin1328 | — | internalin like protein (LPXTG motif) |
| 4.80458 | −342 | AATGGTTTATATCACT (SEQ ID NO: 398) | lin0432 | COG0574 | similar to phosphoenolpyruvate synthase |
| 4.79819 | −178 | AATGCTTTATACAAAT (SEQ ID NO: 399) | lin0169 | — | similar to phage proteins |
| 4.78736 | −349 | AATGGAATACACCAAT (SEQ ID NO: 400) | lin0406 | — | lin0406 |
| 4.77453 | −294 | ACAGATCTAGACCAGT (SEQ ID NO: 401) | lin1754 | COG1235 | similar to hypothetical protein 44 - *Staphylococcus aureus* phage phi PVL |
| 4.77453 | −295 | ACAGATCTAGACCAGT (SEQ ID NO: 402) | lin1243 | COG1235 | similar to hypothetical protein 44 - *Staphylococcus aureus* phage phi PVL |
| 4.71781 | −330 | ATTGGTGTAGATCCGT (SEQ ID NO: 403) | lin1990 | COG2759 | similar to formyl-tetrahydrofolate synthetase |
| 4.70658 | −158 | ACTGGTATATATAGCT (SEQ ID NO: 404) | lin2737 | COG0489 | similar to ATP binding proteins |
| 4.70658 | −122 | AGCTATATATACCAGT (SEQ ID NO: 405) | lin2738 | COG1705 | surface protein (GW repeat) similar to N-acetylmuramidase |
| 4.70449 | −132 | ATTAGTATATAGAATT (SEQ ID NO: 406) | lin2295 | COG1393 | similar to unknown proteins |

B. *Listeria monocytogenes*

| Score | Position | Site | Gene Synonym | COG | Product |
|---|---|---|---|---|---|
| 5.38367 | −121 | ATTGGTCTATATCAAT (SEQ ID NO: 407) | lmo1883 | COG3469 | similar to chitinases |
| 5.37731 | −38 | ATTGGTATAGACCGAT (SEQ ID NO: 408) | lmo0956 | COG1820 | similar to N-acetylglucosamine-6P-phosphate deacetylase (EC 3.5.1.25) |
| 5.2828 | −47 | ATTGGTATAAACAAGT (SEQ ID NO: 409) | lmo02270 | — | lmo0270 |
| 5.25914 | −34 | ACTTGTATATACCAAGT (SEQ ID NO: 410) | lmo1255 | COG1264 | similar to PTS system trehalose specific enzyme IIBC |
| 5.25914 | −98 | ACTTGTATATACAAGT (SEQ ID NO: 411) | lmo1256 | COG0494 | lmo1256 |

TABLE 8-continued

DasR binding sites in Listeria species.

| Score | Position | Site | | Gene Synonym | COG | Product |
|---|---|---|---|---|---|---|
| 5.07626 | −156 | ACTTGTATATAACAAT | (SEQ ID NO: 412) | — | lmo1393 COG0612 | similar to putative protease |
| 5.05059 | −173 | AATGGTCTAGACAGAT | (SEQ ID NO: 413) | codV | lmo1277 COG0582 | similar to integrase/recombinase |
| 4.97633 | −93 | TTTTGTATAGACCAAT | (SEQ ID NO: 414) | fbp | lmo0830 COG0639 | highly similar to fructose-1,6-bisphosphatase |
| 4.96887 | −200 | ACAAGTATAGACCAAT | (SEQ ID NO: 415) | pfk | lmo1571 COG0205 | highly similar to 6-phosphofructokinase |
| 4.92791 | −72 | ATTTGTCTATAATAAT | (SEQ ID NO: 416) | pheT | lmo1607 COG0073 | similar phenylalanyl-tRNA synthetase (beta subunit) |
| 4.8688 | −109 | ATTGGTATATACCGGA | (SEQ ID NO: 417) | — | lmo1289 — | similar to internalin proteins, putative peptidoglycan bound protein (LPXTG motif) |
| 4.82689 | −117 | ATTCGTATAGAAAAAT | (SEQ ID NO: 418) | — | lmo1139 — | lmo1139 |
| 4.82474 | −282 | AACTGTATATATCAAT | (SEQ ID NO: 419) | — | lmo2445 — | similar to internalin |
| 4.79049 | −14 | AGGGGTCTACACAAGT | (SEQ ID NO: 420) | — | lmo1351 COG0607 | lmo1351 |
| 4.75049 | −81 | ATTTGTCGATATCAAT | (SEQ ID NO: 421) | — | lmo2691 COG1705 | similar to autolysin, N-acetylmuramidase |
| 4.73024 | −181 | ATTGGTATAAATTATT | (SEQ ID NO: 422) | — | lmo2748 — | similar to B. subtilis stress protein YdaG |
| 4.72697 | −234 | ACTCGTATATCCAAAT | (SEQ ID NO: 423) | — | lmo0475 — | lmo0475 |
| 4.72372 | −143 | AACTATCTAGACCAAT | (SEQ ID NO: 424) | — | lmo0787 COG1113 | similar to amino acid transporter |
| 4.71951 | −62 | ATTAGTATATACTTTT | (SEQ ID NO: 425) | — | lmo2110 COG1482 | similar to mannose-6 phospate isomerase |
| 4.71834 | −1 | AATGGTTAATACAAAT | (SEQ ID NO: 426) | aroA | lmo1600 COG1605 | 3-deoxy-D-arabino-heptulosonate 7-phosphate synthase |
| 4.71724 | −160 | ATTTCGTAGACCATT | (SEQ ID NO: 427) | — | lmo0969 COG0564 | similar to ribosomal large subunit pseudouridine synthetase |
| 4.70973 | −98 | ATGGGAATACACCAAT | (SEQ ID NO: 428) | — | lmo0792 COG0388 | similar to conserved hypothetical protein |
| 4.7002 | −31 | ATCAGTATACACAATT | (SEQ ID NO: 429) | — | lmo1125 — | lmo1125 |
| 4.69794 | −1 | AATGATTTATACAATT | (SEQ ID NO: 430) | fruB | lmo2336 COG1105 | fructose-1-phosphate kinase |
| 4.69157 | −275 | ACTTGTTTAAACCGTT | (SEQ ID NO: 431) | — | lmo1219 — | lmo1219 |

TABLE 9

DasR binding sites in Thermobifido fusca.

| # | Gene | Function | dre | Pos | Scr | Co-transcribed gene | Function |
|---|---|---|---|---|---|---|---|
| 1 | Tfu_1418<br>Tfu_1417c | conserved hypothetical protein<br>phospholipid/glycerol acyltransferase | AGTGGTCTAGACCTAT<br>(SEQ ID NO: 432) | −40<br>−156 | 15.0 | — | — |
| 2 | Tfu_3010<br>Tfu_3009c | ketose-bisphosphate aldolase, class-II: Fructose-bisphosphate aldolase, class II, yeast/E. coli subtype | TGTGGTCTAGACCTTT<br>(SEQ ID NO: 433) | −155<br>−222 | 13.15 | Tfu_3011 | conserved hypothetical protein |
| 3 | Tfu_0555<br>Tfu_0554c | signal transduction histidine kinase<br>dasR, regulatory protein GntR, HTH | ACTGGTCTAGTCCAAT<br>(SEQ ID NO: 434) | −68<br>−113 | 13.03 | — | — |
| 4 | Tfu_0643<br>Tfu_0642c | thiamine-monophosphate kinase<br>conserved hypothetical protein | ACGGGTCTAGACCACT<br>(SEQ ID NO: 435) | −48<br>−108 | 12.88 | Tfu_0644 | cellulose-binding, family II, bacterial type |
| 5 | Tfu_0136c | phosphoserine phosphatase SerB: HAD-superfamily hydrolase subfamily IB, PSPase-like | AGTGGCGTAGACCAGG<br>(SEQ ID NO: 436) | 23 | 12.61 | — | — |
| 6 | Tfu_2555<br>Tfu_2554c | propionyl-CoA carboxylase complex B subunit<br>phosphoenolpyruvate carboxylase | ATTGGTCTACTCCACT<br>(SEQ ID NO: 437) | −206<br>−35 | 12.13 | Tfu_2556/<br>Tfu_2557 | conserved hypothetical protein/<br>putative acyl-CoA carboxylase, alpha subunit |
| 7 | Tfu_2290 | hypothetical protein | GCTGGTCTGCACCACG<br>(SEQ ID NO: 438) | 36 | 11.72 | — | — |
| 8 | Tfu_1037 | phosphofructokinase | TATGGTCTAGACCATA<br>(SEQ ID NO: 439) | −150 | 11.6 | — | — |
| 9 | Tfu_0083 | phosphoenolpyruvate carboxykinase (GTP) | AATGGTCTAGTCCATA<br>(SEQ ID NO: 440)<br>AAAGGTCTAGTCCAAG<br>(SEQ ID NO: 441) | −110<br>−86 | 11.49<br>8.92 | — | — |
| 10 | Tfu_0262c | hypothetical protein | TGTGGTGTCGACCAGC<br>(SEQ ID NO: 442) | −121 | 11.4 | — | — |
| 11 | Tfu_2611 | glmS, glucosamine-fructose-6-phosphate aminotransferase, isomerising | ACTGGTCTATACCGCT<br>(SEQ ID NO: 443) | −71 | 11.24 | — | — |
| 12 | Tfu_2017c | glyceraldehyde-3-phosphate dehydrogenase, type I | AAAGGTATAGACCATT<br>(SEQ ID NO: 444) | −203 | 10.59 | Tfu_2016 | phosphoglycerate kinase |
| 13 | Tfu_1774c | putative Lsr2-like protein | TAAGGTCTATACCTCT<br>(SEQ ID NO: 445) | −169 | 10.28 | — | — |
| 14 | Tfu_1202 | putative partitioning or sporulation protein | GCAGGTCTACACCCTC<br>(SEQ ID NO: 446) | −216 | 10.25 | Tfu_1203/<br>Tfu_1204/<br>Tfu_1205 | conserved hypothetical protein/<br>conserved hypothetical protein/<br>Prokaryotic chromosome segregation and condensation protein ScpB |
| 15 | Tfu_2362c | putative proteinase | CCAGGTGTACACCAGT<br>(SEQ ID NO: 447) | −201 | 10.09 | — | — |
| 16 | Tfu_2741 | phosphate ABC transporter, permease protein PstC | AGGGGTGTACTCCACA<br>(SEQ ID NO: 448) | −111 | 10.03 | Tfu_2742/<br>Tfu_2743 | Phosphate transport system permease protein 2/Phosphate transport system permease protein 1 |
| 17 | Tfu_2234c | putative spermidine synthase | TGTGGTGTCGACCATC<br>(SEQ ID NO: 449) | −2 | 9.74 | — | — |
| 18 | Tfu_0614 | D-3-phosphoglycerate dehydrogenase | GGTGGTCCACACCAAT<br>(SEQ ID NO:450) | −173 | 9.72 | — | — |
| 19 | Tfu_2626c | SecY protein | ATTGGTGTGGACCACC<br>(SEQ ID NO: 451) | −157 | 9.72 | Tfu_2625c/<br>Tfu_2624c | adenylate kinase, subfamily/<br>peptidase M24A, methionine aminopeptidase, subfamily 1 |
| 20 | Tfu_1104 | peptidoglycan glycosyltransferase | ACTGGACCGCACCACT<br>(SEQ ID NO: 452) | −52 | 9.3 | — | — |
| 21 | Tfu_1818 | putative membrane protein | CGTGGTG TACACCTAC<br>(SEQ ID NO: 453) | −276 | 9.16 | — | — |
| 22 | Tfu_2283 | similar to Cell wall-associated hydrolases (invasion-associated proteins) | GCTGGCGCAGACCACA<br>(SEQ ID NO: 454) | −191 | 9.02 | Tfu_2284 | hypothetical protein |
| 23 | Tfu_0863 | pyruvate, phosphate dikinase | AGTGGTCTAAATCTCT<br>(SEQ ID NO: 455)<br>ATTGGTTTATACCATT<br>(SEQ ID NO: 456) | −230<br>−134 | 9.0<br>8.53 | — | — |
| 24 | Tfu_1179 | pyruvate kinase | CTTGGTTTAGACCAAT<br>(SEQ ID NO: 457) | −37 | 8.88 | — | — |
| 25 | Tfu_0697<br>Tfu_0696c | putative ATP/GTP binding protein<br>putative 6-phosphofructokinase: 1-phosphofructokinase | AAAGGTCTAAACCAAT<br>(SEQ ID NO: 458) | −306<br>−116 | 8.8 | — | — |
| 26 | Tfu_0433 | delta-1-pyrroline-5-carboxylate dehydrogenase 1 | ACTGGCCTAGTCCACC<br>(SEQ ID NO: 459) | −42 | 8.69 | Tfu_0434/<br>Tfu_0435 | proline dehydrogenase/<br>conserved hypothetical protein |
| 27 | Tfu_2911c | phosphoglycerate mutase 1 | AATGGTCTACGCCAAT<br>(SEQ ID NO: 460) | −66 | 8.66 | — | — |

TABLE 9-continued

DasR binding sites in Thermobifido fusca.

| # | Gene | Function | dre | Pos | Scr | Co-transcribed gene | Function |
|---|---|---|---|---|---|---|---|
| 28 | Tfu_2361c | Tyrosine protein kinase: Serine/threonine protein kinase | TGTGGGCTGCACCACA (SEQ ID NO: 461) | −178 | 8.59 | — | — |
| 29 | Tfu_1504 | extracellular solute-binding protein, family 3 | CGTGGCCTACACCTCC (SEQ ID NO: 462) | −238 | 8.54 | — | — |
| 30 | Tfu_2622c | translation initiation factor IF-1 | AGTGATGTACACCACG (SEQ ID NO: 463) | −306 | 8.44 | — | — |
| 31 | Tfu_0428 Tfu_0427c | enolase cell division membrane protein | AATGGACTAAACCAAT (SEQ ID NO: 464) | −198 −284 | 8.43 | Tfu_0429/ Tfu_0430/ Tfu_0431 | conserved hypothetical protein/ conserved hypothetical protein/ putative hydrolase |
| 32 | Tfu_1002 | hedgehog/intein hint, N-terminal | AGTGTTCTACGCCATT (SEQ ID NO: 465) | −297 | 8.35 | — | — |
| 33 | Tfu_0600 | hypothetical protein | AGTGGACTACTCAACG (SEQ ID NO: 466) | −62 | 8.18 | Tfu_0601 | serine/threonine protein kinase |
| 34 | Tfu_2195c | trigger factor | CGTGGACTGCACAAGT (SEQ ID NO: 467) | −320 | 8.17 | — | — |
| 35 | Tfu_1033 | glucokinase ROK | AATGGTTTACTCCATT (SEQ ID NO: 468) | −74 | 8.16 | Tfu_1034 | conserved hypothetical protein |
| 36 | Tfu_1242 | putative oxidoreductase | CGTGATCTACACCATA (SEQ ID NO: 469) | −289 | 8.16 | — | — |
| 37 | Tfu_0793 | ATPase | CGTGGTGGAGTCCACC (SEQ ID NO: 470) | −321 | 8.14 | Tfu_0794/ Tfu_0795/ Tfu_0796/ Tfu_0797 | helix-turn-helix motif/ Conserved hypothetical protein/CDP-diacylglycerol--glycerol-3-phosphate 3-phosphatidyltransferase/ CinA, C-terminal |
| 38 | Tfu_0213 | RNA methyltransferase TrmH, group 3 | CAAGGACTACGCCACC (SEQ ID NO: 471) | −181 | 8.1 | — | — |
| 39 | Tfu_0538 | molybdenum cofactor biosynthesis protein E | CGTGGACTGCGCCACC (SEQ ID NO: 472) | −289 | 8.1 | Tfu_0539 | secreted protein containing a PDZ domain |
| 40 | Tfu_1530c | similar to Acetyl/propionyl-CoA carboxylase alpha subunit | GGTGGCGCAGTCCACG (SEQ ID NO: 473) | −307 | 8.1 | — | — |
| 41 | Tfu_1691 | ABC-type nitrate/sulfonate/bicarbonate transport system ATPase component | CGAGGTGTACACCAAC (SEQ ID NO: 474) | −117 | 8.1 | Tfu_1692/ Tfu_1693 | putative ABC transporter membrane protein/ putative monooxygenase |
| 42 | Tfu_0105c | hypothetical protein | GCTGGTGCAGTCCATG (SEQ ID NO: 475) | −247 | 8.07 | — | — |
| 43 | Tfu_2986c | hypothetical protein | GCTGGTCTGCACCGCC (SEQ ID NO: 476) | −253 | 8.06 | — | — |
| 44 | Tfu_0525 | conserved hypothetical protein | AGTGGTTTCGCCCACT (SEQ ID NO: 477) | −160 | 8.05 | Tfu_0526/ Tfu_0527 | putative peptidase/conserved hypothetical protein |
| 45 | Tfu_2802c | putative cytochrome P450 | GGGGGTAAAGACCACT (SEQ ID NO: 478) | −40 | 8.05 | — | — |
| 46 | Tfu_2007 | 6-phosphogluconolactonase | GGTGGTGCAGTCCGAT (SEQ ID NO: 479) | 30 | 7.98 | — | — |
| 47 | Tfu_2348 Tfu_2347c | putative ferredoxin reductase exonuclease | ACAGGTGCAGACCATC (SEQ ID NO: 480) | −4 −263 | 7.96 | — | — |
| 48 | Tfu_2320c | putative membrane transport protein | TGTTGTCTAGAACACA (SEQ ID NO: 481) | −36 | 7.95 | — | — |
| 49 | Tfu_1425 Tfu_1424c | putative integral membrane protein hypothetical protein | AGAGGTCAACACAATC (SEQ ID NO: 482) | −159 −293 | 7.91 | — | — |
| 50 | Tfu_0594 | electron transfer flavoprotein, alpha subunit | GGTGGTCGAGGCCACC (SEQ ID NO: 483) | −313 | 7.88 | — | — |
| 51 | Tfu_3054c | glycosyltransferases involved in cell wall biogenesis | GATGGTGAAGACCTCG (SEQ ID NO: 484) | −81 | 7.87 | — | — |
| 52 | Tfu_0527 | conserved hypothetical protein | CAAGGTCTACTCCACC (SEQ ID NO: 485) | −216 | 7.83 | — | — |
| 53 | Tfu_0658 | cell division transporter substrate-binding protein FtsY | TATGGACTACACGATT (SEQ ID NO: 486) | −1 | 7.77 | — | — |
| 54 | Tfu_0815c | tRNA isopentenyltransferase | AGTGGTCCGGACCAAA (SEQ ID NO: 487) | −247 | 7.75 | — | — |
| 55 | Tfu_1226 | hypothetical protein | CATGGTCTACGCCTCA (SEQ ID NO: 488) | −296 | 7.73 | Tfu_1227/ Tfu_1228/ Tfu_1229/ Tfu_1230/ Tfu_1231 | putative ferredoxin reductase/ putative acyl-CoA carboxylase complex A subunit/putative 3-oxoacyl-ACP synthase III/ conserved hypothetical protein/ modular polyketide synthase |
| 56 | Tfu_2687c | NADH-quinone oxidoreductase, chain I | AGTGATCCAGACCAGC (SEQ ID NO: 489) | −318 | 7.57 | Tfu_2686c/ Tfu_2685c | NADH dehydrogenase I chain J/ NADH dehydrogenase I chain K |

What is claimed is:

1. A method for regulating expression of a gene of interest in a micro-organism comprising a DasR protein, wherein the gene of interest is in operable linkage to a DasR-binding site, the method comprising:
    providing the micro-organism with a compound selected from the group consisting of glucosamine-6-phosphate, N-acetylglucosamine-6-phosphate, N-acetylglucosamine, and multimers thereof, such that the expression of the gene of interest is regulated;
    screening for the production of a secondary metabolite; and
    wherein the DasR-binding site is selected from the group consisting of:
    NN(T/A)GG(T/A)(C/G)T(A/G)N(A/T)C(C/A)(A/C)N (SEQ ID NO:1);
    (A/G)N(T/A)(G/T)(G/A)T(C/A)TA(G/T)A(C/T)(C/A)(A/T)N(T/C) (SEQ ID NO: 4);
    A(T/A)(T/C)(G/A)(G/A)TATATA(C/T)(C/T)(A/G)(A/T)T (SEQ ID NO: 5);
    A(T/C)(T/C)(G/T)(G/A)T(A/C)TA(T/G)A(C/T)(C/A)(A/G)(A/G)T (SEQ ID NO: 6); and
    (A/T)(T/A)T(G/A)(G/T)(A/C)TA(T/G)N(C/A)(C/T)A(A/T)(T/A) (SEQ ID NO: 7).

2. The method according to claim 1 wherein the compound is selected from the group consisting of glucosamine-6-phosphate, N-acetylglucosamine, and multimers thereof.

3. The method according to claim 1, further comprising providing the micro-organism with a polynucleotide encoding a DasR protein.

4. The method according to claim 1, wherein the micro-organism is a Streptomyces, a Nocardia, a Thermobifido, an Amycolatopsis, a Planobispora, a Streptoverticillium, a Rhodococcus, or a Corynebacterium.

5. The method according to claim 1, wherein the micro-organism is a low G+C gram-positive bacterium.

6. The method according to claim 1, further comprising introducing into the micro-organism the DasR-binding site in operable linkage with the gene of interest.

7. The method according to claim 1, wherein the micro-organism is a Streptomyces, a Nocardia, a Thermobifido, a Amycolatopsis, a Planobispora, a Streptoverticillium, a Rhodococcus, a Corynebacterium, or a low G+C gram-positive bacterium.

8. The method according to claim 1, further comprising purifying the secondary metabolite.

\* \* \* \* \*

SEQUENCE LISTING

<160> NUMBER OF SEQ ID NOS: 533

<210> SEQ ID NO 1
<211> LENGTH: 15
<212> TYPE: DNA
<213> ORGANISM: Artificial Sequence
<220> FEATURE:
<223> OTHER INFORMATION: DasR binding site consensus
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (6)..(6)
<223> OTHER INFORMATION: w is a or t
<220> FEATURE:
<221> NAME/KEY: misc_feature
<222> LOCATION: (7)..(7)
<223> OTHER INFORMATION: s is g or c
<220> FEATURE:
<221> NAME/KEY: misc_feature
<222> LOCATION: (9)..(9)
<223> OTHER INFORMATION: r is a or g
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: w is a or t
<220> FEATURE:
<221> NAME/KEY: misc_feature
<222> LOCATION: (13)..(14)
<223> OTHER INFORMATION: m is a or c
<220> FEATURE:
<221> NAME/KEY: misc_feature
<222> LOCATION: (15)..(15)
<223> OTHER INFORMATION: n is a, c, g, or t

<400> SEQUENCE: 1
nnwggwstrn wcmmn                                                  15

<210> SEQ ID NO 2
<211> LENGTH: 15
<212> TYPE: DNA
<213> ORGANISM: Artificial Sequence
<220> FEATURE:
<223> OTHER INFORMATION: DasR binding site preferred 1
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 2

```
wnwggtctan accan                                            15
```

```
<210> SEQ ID NO 3
<211> LENGTH: 15
<212> TYPE: DNA
<213> ORGANISM: Artificial Sequence
<220> FEATURE:
<223> OTHER INFORMATION: DasR binding site consesnus more preferred
<220> FEATURE:
<221> NAME/KEY: misc_feature
<222> LOCATION: (15)..(15)
<223> OTHER INFORMATION: s is g or c

<400> SEQUENCE: 3
actggtctac accas                                            15

<210> SEQ ID NO 4
<211> LENGTH: 16
<212> TYPE: DNA
<213> ORGANISM: Artificial Sequence
<220> FEATURE:
<223> OTHER INFORMATION: Consensus sequence for Bacillus species
<220> FEATURE:
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (4)..(4)
<223> OTHER INFORMATION: k is g or t
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (10)..(10)
<223> OTHER INFORMATION: k is g or t
<220> FEATURE:
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (13)..(13)
<223> OTHER INFORMATION: m is a or c
<220> FEATURE:
<221> NAME/KEY: misc_feature
<222> LOCATION: (14)..(14)
<223> OTHER INFORMATION: w is a or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: y is c or t

<400> SEQUENCE: 4
rnwkrtmtak aymwny                                           16
```

```
<210> SEQ ID NO 5
<211> LENGTH: 16
<212> TYPE: DNA
<213> ORGANISM: Artificial Sequence
<220> FEATURE:
<223> OTHER INFORMATION: Consensus sequence for Lactococcus species
<220> FEATURE:
<221> NAME/KEY: misc_feature
<222> LOCATION: (2)..(2)
<223> OTHER INFORMATION: w is a or t
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (4)..(5)
<223> OTHER INFORMATION: r is a or g
<220> FEATURE:
<221> NAME/KEY: misc_feature
<222> LOCATION: (12)..(13)
<223> OTHER INFORMATION: y is c or t
<220> FEATURE:
<221> NAME/KEY: misc_feature
<222> LOCATION: (14)..(14)
<223> OTHER INFORMATION: r is a or g
<220> FEATURE:
<221> NAME/KEY: misc_feature
<222> LOCATION: (15)..(15)
<223> OTHER INFORMATION: w is a or t

<400> SEQUENCE: 5
awyrrtatat ayyrwt                                               16

<210> SEQ ID NO 6
<211> LENGTH: 16
<212> TYPE: DNA
<213> ORGANISM: Artificial Sequence
<220> FEATURE:
<223> OTHER INFORMATION: Consensus sequence for Listeria species
<220> FEATURE:
<221> NAME/KEY: misc_feature
<222> LOCATION: (2)..(3)
<223> OTHER INFORMATION: y is c or t
<220> FEATURE:
<221> NAME/KEY: misc_feature
<222> LOCATION: (4)..(4)
<223> OTHER INFORMATION: k is g or t
<220> FEATURE:
<221> NAME/KEY: misc_feature
<222> LOCATION: (5)..(5)
<223> OTHER INFORMATION: r is a or g
<220> FEATURE:
<221> NAME/KEY: misc_feature
<222> LOCATION: (7)..(7)
<223> OTHER INFORMATION: m is a or c
<220> FEATURE:
<221> NAME/KEY: misc_feature
<222> LOCATION: (10)..(10)
<223> OTHER INFORMATION: k is g or t
<220> FEATURE:
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (13)..(13)
<223> OTHER INFORMATION: m is a or c
<220> FEATURE:
<221> NAME/KEY: misc_feature
<222> LOCATION: (14)..(15)
<223> OTHER INFORMATION: r is a or g

<400> SEQUENCE: 6
ayykrtmtak aymrrt                                               16
```

```
<210> SEQ ID NO 7
<211> LENGTH: 15
<212> TYPE: DNA
<213> ORGANISM: Artificial Sequence
<220> FEATURE:
<223> OTHER INFORMATION: Consensus sequence for Streptococcus species
<220> FEATURE:
<221> NAME/KEY: misc_feature
<222> LOCATION: (1)..(2)
<223> OTHER INFORMATION: w is a or t
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (5)..(5)
<223> OTHER INFORMATION: k is g or t
<220> FEATURE:
<221> NAME/KEY: misc_feature
<222> LOCATION: (6)..(6)
<223> OTHER INFORMATION: m is a or c
<220> FEATURE:
<221> NAME/KEY: misc_feature
<222> LOCATION: (9)..(9)
<223> OTHER INFORMATION: k is g or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: m is a or c
<220> FEATURE:
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (14)..(15)
<223> OTHER INFORMATION: w is a or t

<400> SEQUENCE: 7
wwtrkmtakn myaww                                              15

<210> SEQ ID NO 8
<211> LENGTH: 16
<212> TYPE: DNA
<213> ORGANISM: Artificial Sequence
<220> FEATURE:
<223> OTHER INFORMATION: dre site of malX2 of S. olivaceoviridis

<400> SEQUENCE: 8
actggtctac accacc                                             16

<210> SEQ ID NO 9
<211> LENGTH: 16
<212> TYPE: DNA
<213> ORGANISM: Artificial Sequence
<220> FEATURE:
<223> OTHER INFORMATION: dre site of S. coelicolor malX2

<400> SEQUENCE: 9
actggtctac accagt                                             16

<210> SEQ ID NO 10
<211> LENGTH: 16
<212> TYPE: DNA
<213> ORGANISM: Artificial Sequence
<220> FEATURE:
```

```
<223> OTHER INFORMATION: Protected sequence

<400> SEQUENCE: 10
tgtggtctag acctct                                                  16

<210> SEQ ID NO 11
<211> LENGTH: 16
<212> TYPE: DNA
<213> ORGANISM: Artificial Sequence
<220> FEATURE:
<223> OTHER INFORMATION: T1 - malX2Sco

<400> SEQUENCE: 11
actggtgtag accagt                                                  16

<210> SEQ ID NO 12
<211> LENGTH: 16
<212> TYPE: DNA
<213> ORGANISM: Artificial Sequence
<220> FEATURE:
<223> OTHER INFORMATION: T1 - nagE2Sco(1)

<400> SEQUENCE: 12
caaggtgtag acctct                                                  16

<210> SEQ ID NO 13
<211> LENGTH: 16
<212> TYPE: DNA
<213> ORGANISM: Artificial Sequence
<220> FEATURE:
<223> OTHER INFORMATION: T1 - nagE2Sco(2)

<400> SEQUENCE: 13
agtggtgtag acctgt                                                  16

<210> SEQ ID NO 14
<211> LENGTH: 16
<212> TYPE: DNA
<213> ORGANISM: Artificial Sequence
<220> FEATURE:
<223> OTHER INFORMATION: T1 - nagE2Sco(3)

<400> SEQUENCE: 14
agtggtgtag accacc                                                  16

<210> SEQ ID NO 15
<211> LENGTH: 16
<212> TYPE: DNA
<213> ORGANISM: Artificial Sequence
<220> FEATURE:
<223> OTHER INFORMATION: T1 - ptsHSco(1)

<400> SEQUENCE: 15
agttgtctag accagt                                                  16

<210> SEQ ID NO 16
<211> LENGTH: 16
<212> TYPE: DNA
<213> ORGANISM: Artificial Sequence
<220> FEATURE:
<223> OTHER INFORMATION: T1 - ptsHSco(2)

<400> SEQUENCE: 16
tcttgtctag accagt                                                  16
```

```
<210> SEQ ID NO 17
<211> LENGTH: 16
<212> TYPE: DNA
<213> ORGANISM: Artificial Sequence
<220> FEATURE:
<223> OTHER INFORMATION: T1 - crr-ptsISco(1)

<400> SEQUENCE: 17
tgtggtctag acctct                                                         16

<210> SEQ ID NO 18
<211> LENGTH: 16
<212> TYPE: DNA
<213> ORGANISM: Artificial Sequence
<220> FEATURE:
<223> OTHER INFORMATION: T1 - msiKSco

<400> SEQUENCE: 18
ggtggtgtag tccaca                                                         16

<210> SEQ ID NO 19
<211> LENGTH: 16
<212> TYPE: DNA
<213> ORGANISM: Artificial Sequence
<220> FEATURE:
<223> OTHER INFORMATION: T1 - nagBSco

<400> SEQUENCE: 19
tgtggtttag accaat                                                         16

<210> SEQ ID NO 20
<211> LENGTH: 16
<212> TYPE: DNA
<213> ORGANISM: Artificial Sequence
<220> FEATURE:
<223> OTHER INFORMATION: T1 - nagKASco(1)

<400> SEQUENCE: 20
ggtggtgtag acctta                                                         16

<210> SEQ ID NO 21
<211> LENGTH: 16
<212> TYPE: DNA
<213> ORGANISM: Artificial Sequence
<220> FEATURE:
<223> OTHER INFORMATION: T1 - nagKASco(2)

<400> SEQUENCE: 21
agtggactag acctct                                                         16

<210> SEQ ID NO 22
<211> LENGTH: 16
<212> TYPE: DNA
<213> ORGANISM: Artificial Sequence
<220> FEATURE:
<223> OTHER INFORMATION: T1 - chiFSco(1)

<400> SEQUENCE: 22
aagggtgtag accagt                                                         16

<210> SEQ ID NO 23
<211> LENGTH: 16
<212> TYPE: DNA
<213> ORGANISM: Artificial Sequence
<220> FEATURE:
<223> OTHER INFORMATION: T1 - chiFSco(2)
```

```
<400> SEQUENCE: 23
actggtacag accaaa                                                        16

<210> SEQ ID NO 24
<211> LENGTH: 16
<212> TYPE: DNA
<213> ORGANISM: Artificial Sequence
<220> FEATURE:
<223> OTHER INFORMATION: T1 - actII-4

<400> SEQUENCE: 24
tgttgagtag gcctgt                                                        16

<210> SEQ ID NO 25
<211> LENGTH: 48
<212> TYPE: DNA
<213> ORGANISM: Artificial Sequence
<220> FEATURE:
<223> OTHER INFORMATION: Target for SCO2907, nagE2

<400> SEQUENCE: 25
acaggtctac accactagtg gtgtagacca cccaaggtgt agacctct                     48

<210> SEQ ID NO 26
<211> LENGTH: 16
<212> TYPE: DNA
<213> ORGANISM: Artificial Sequence
<220> FEATURE:
<223> OTHER INFORMATION: Target for SCO2906, nagE1 and SCO2905c, malX2

<400> SEQUENCE: 26
actggtctac accagt                                                        16

<210> SEQ ID NO 27
<211> LENGTH: 32
<212> TYPE: DNA
<213> ORGANISM: Artificial Sequence
<220> FEATURE:
<223> OTHER INFORMATION: Target for SCO5232, dasA

<400> SEQUENCE: 27
actggtctac accattcttg gtctagtcca ta                                      32

<210> SEQ ID NO 28
<211> LENGTH: 16
<212> TYPE: DNA
<213> ORGANISM: Artificial Sequence
<220> FEATURE:
<223> OTHER INFORMATION: Target for SCO1390, crr

<400> SEQUENCE: 28
tgtggtctag acctct                                                        16

<210> SEQ ID NO 29
<211> LENGTH: 32
<212> TYPE: DNA
<213> ORGANISM: Artificial Sequence
<220> FEATURE:
<223> OTHER INFORMATION: Target for SCO5842 and SCO5841c

<400> SEQUENCE: 29
agttgtctag accagttctt gtctagacca gt                                      32

<210> SEQ ID NO 30
<211> LENGTH: 32
```

```
<212> TYPE: DNA
<213> ORGANISM: Artificial Sequence
<220> FEATURE:
<223> OTHER INFORMATION: Target for SCO4286 and SCO4285c, nagK

<400> SEQUENCE: 30
agaggtctag tccactggtg gtgtagacct ta                                32

<210> SEQ ID NO 31
<211> LENGTH: 16
<212> TYPE: DNA
<213> ORGANISM: Artificial Sequence
<220> FEATURE:
<223> OTHER INFORMATION: Target for SCO5239

<400> SEQUENCE: 31
agtggtctag tccaca                                                  16

<210> SEQ ID NO 32
<211> LENGTH: 16
<212> TYPE: DNA
<213> ORGANISM: Artificial Sequence
<220> FEATURE:
<223> OTHER INFORMATION: Target for SCO5236c, nagB

<400> SEQUENCE: 32
tgtggtttag accaat                                                  16

<210> SEQ ID NO 33
<211> LENGTH: 16
<212> TYPE: DNA
<213> ORGANISM: Artificial Sequence
<220> FEATURE:
<223> OTHER INFORMATION: Target for SCO3563, acsA

<400> SEQUENCE: 33
acaggtctaa accatt                                                  16

<210> SEQ ID NO 34
<211> LENGTH: 32
<212> TYPE: DNA
<213> ORGANISM: Artificial Sequence
<220> FEATURE:
<223> OTHER INFORMATION: Target for SCO7263, chiF

<400> SEQUENCE: 34
actggtctac acccttactg gtacagacca aa                                32

<210> SEQ ID NO 35
<211> LENGTH: 48
<212> TYPE: DNA
<213> ORGANISM: Artificial Sequence
<220> FEATURE:
<223> OTHER INFORMATION: Target for SCO7225 and SCO7224c

<400> SEQUENCE: 35
tatggtctag acctgatcag gtctagacct gtccttgtct agaccaat               48

<210> SEQ ID NO 36
<211> LENGTH: 32
<212> TYPE: DNA
<213> ORGANISM: Artificial Sequence
<220> FEATURE:
<223> OTHER INFORMATION: Target for SCO1444, chiI

<400> SEQUENCE: 36
```

```
actggtctag tcctctattg gtccatacct at                           32
```

<210> SEQ ID NO 37
<211> LENGTH: 16
<212> TYPE: DNA
<213> ORGANISM: Artificial Sequence
<220> FEATURE:
<223> OTHER INFORMATION: Target for SCO4240c, msiK

<400> SEQUENCE: 37

```
ggtggtgtag tccaca                                             16
```

<210> SEQ ID NO 38
<211> LENGTH: 16
<212> TYPE: DNA
<213> ORGANISM: Artificial Sequence
<220> FEATURE:
<223> OTHER INFORMATION: Target for SCO5004 and SCO5003c, chiA

<400> SEQUENCE: 38

```
ggtggtccag accaat                                             16
```

<210> SEQ ID NO 39
<211> LENGTH: 32
<212> TYPE: DNA
<213> ORGANISM: Artificial Sequence
<220> FEATURE:
<223> OTHER INFORMATION: Target for SCO7056c

<400> SEQUENCE: 39

```
attggtctaa accagcgcag gtctggtcct cc                           32
```

<210> SEQ ID NO 40
<211> LENGTH: 16
<212> TYPE: DNA
<213> ORGANISM: Artificial Sequence
<220> FEATURE:
<223> OTHER INFORMATION: Target for SCO6486, dppA

<400> SEQUENCE: 40

```
agtggtccag accacc                                             16
```

<210> SEQ ID NO 41
<211> LENGTH: 16
<212> TYPE: DNA
<213> ORGANISM: Artificial Sequence
<220> FEATURE:
<223> OTHER INFORMATION: Target for SCO2672

<400> SEQUENCE: 41

```
agaggtctgg acaaca                                             16
```

<210> SEQ ID NO 42
<211> LENGTH: 48
<212> TYPE: DNA
<213> ORGANISM: Artificial Sequence
<220> FEATURE:
<223> OTHER INFORMATION: Target for SCO2503, chiJ

<400> SEQUENCE: 42

```
aaaggtctgg accacacttg gtccagacct cttctggacc acagcact          48
```

<210> SEQ ID NO 43
<211> LENGTH: 32
<212> TYPE: DNA
<213> ORGANISM: Artificial Sequence

```
<220> FEATURE:
<223> OTHER INFORMATION: Target for SCO1429, chiD and SCO1428c, acd

<400> SEQUENCE: 43
actggtctag tcctccaatg gtccgaacca tt                                    32

<210> SEQ ID NO 44
<211> LENGTH: 16
<212> TYPE: DNA
<213> ORGANISM: Artificial Sequence
<220> FEATURE:
<223> OTHER INFORMATION: Target for SCO3679

<400> SEQUENCE: 44
tgttgtctag tccaat                                                      16

<210> SEQ ID NO 45
<211> LENGTH: 16
<212> TYPE: DNA
<213> ORGANISM: Artificial Sequence
<220> FEATURE:
<223> OTHER INFORMATION: Target for SCO5085, actII-4

<400> SEQUENCE: 45
tgttgagtag gcctgt                                                      16

<210> SEQ ID NO 46
<211> LENGTH: 48
<212> TYPE: DNA
<213> ORGANISM: Artificial Sequence
<220> FEATURE:
<223> OTHER INFORMATION: Target for SCO6013 and SCO6012c, chiH

<400> SEQUENCE: 46
aatggtctgg accagaggtg gactggacca ccatgggact agaccaat                   48

<210> SEQ ID NO 47
<211> LENGTH: 16
<212> TYPE: DNA
<213> ORGANISM: Artificial Sequence
<220> FEATURE:
<223> OTHER INFORMATION: Target for SCO4315

<400> SEQUENCE: 47
attggactag acctgt                                                      16

<210> SEQ ID NO 48
<211> LENGTH: 16
<212> TYPE: DNA
<213> ORGANISM: Artificial Sequence
<220> FEATURE:
<223> OTHER INFORMATION: Target for SCO4671c

<400> SEQUENCE: 48
gctggtacag accagt                                                      16

<210> SEQ ID NO 49
<211> LENGTH: 32
<212> TYPE: DNA
<213> ORGANISM: Artificial Sequence
<220> FEATURE:
<223> OTHER INFORMATION: Target for SCO6300c

<400> SEQUENCE: 49
agaggtctag acaaaaatag gtctagacaa aa                                    32
```

```
<210> SEQ ID NO 50
<211> LENGTH: 16
<212> TYPE: DNA
<213> ORGANISM: Artificial Sequence
<220> FEATURE:
<223> OTHER INFORMATION: Target for SCO6005, ngcE

<400> SEQUENCE: 50
agtggactat acctgt                                                          16

<210> SEQ ID NO 51
<211> LENGTH: 16
<212> TYPE: DNA
<213> ORGANISM: Artificial Sequence
<220> FEATURE:
<223> OTHER INFORMATION: Target for SCO6004c

<400> SEQUENCE: 51
agtggactat acctgt                                                          16

<210> SEQ ID NO 52
<211> LENGTH: 32
<212> TYPE: DNA
<213> ORGANISM: Artificial Sequence
<220> FEATURE:
<223> OTHER INFORMATION: Target for SCO5376c, chic

<400> SEQUENCE: 52
aaaggtctgg accataatag gtctggacca at                                        32

<210> SEQ ID NO 53
<211> LENGTH: 32
<212> TYPE: DNA
<213> ORGANISM: Artificial Sequence
<220> FEATURE:
<223> OTHER INFORMATION: Target for SCO6345 and SCO6344c

<400> SEQUENCE: 53
taaggtctag acctgcgtag gtctagacct gc                                        32

<210> SEQ ID NO 54
<211> LENGTH: 16
<212> TYPE: DNA
<213> ORGANISM: Artificial Sequence
<220> FEATURE:
<223> OTHER INFORMATION: Target for SCO1212 and SCO1211c

<400> SEQUENCE: 54
tgaggtccac accacg                                                          16

<210> SEQ ID NO 55
<211> LENGTH: 16
<212> TYPE: DNA
<213> ORGANISM: Artificial Sequence
<220> FEATURE:
<223> OTHER INFORMATION: Target for SCO1083c

<400> SEQUENCE: 55
tgtggagaag acctca                                                          16

<210> SEQ ID NO 56
<211> LENGTH: 16
<212> TYPE: DNA
<213> ORGANISM: Artificial Sequence
<220> FEATURE:
<223> OTHER INFORMATION: Target for SCO1433
```

```
<400> SEQUENCE: 56
attggtgtcg accact                                                    16

<210> SEQ ID NO 57
<211> LENGTH: 16
<212> TYPE: DNA
<213> ORGANISM: Artificial Sequence
<220> FEATURE:
<223> OTHER INFORMATION: Target for SCO1432c

<400> SEQUENCE: 57
attggtgtcg accact                                                    16

<210> SEQ ID NO 58
<211> LENGTH: 16
<212> TYPE: DNA
<213> ORGANISM: Artificial Sequence
<220> FEATURE:
<223> OTHER INFORMATION: Target for SCO5266

<400> SEQUENCE: 58
catggtgcag acctcc                                                    16

<210> SEQ ID NO 59
<211> LENGTH: 16
<212> TYPE: DNA
<213> ORGANISM: Artificial Sequence
<220> FEATURE:
<223> OTHER INFORMATION: Target for SCO5265c

<400> SEQUENCE: 59
catggtgcag acctcc                                                    16

<210> SEQ ID NO 60
<211> LENGTH: 16
<212> TYPE: DNA
<213> ORGANISM: Artificial Sequence
<220> FEATURE:
<223> OTHER INFORMATION: Target for SCO0481, chb3

<400> SEQUENCE: 60
tatggtctag tccaac                                                    16

<210> SEQ ID NO 61
<211> LENGTH: 16
<212> TYPE: DNA
<213> ORGANISM: Artificial Sequence
<220> FEATURE:
<223> OTHER INFORMATION: Target for SCO2753 and SCO2752c

<400> SEQUENCE: 61
ggtggtctgg acaaga                                                    16

<210> SEQ ID NO 62
<211> LENGTH: 16
<212> TYPE: DNA
<213> ORGANISM: Artificial Sequence
<220> FEATURE:
<223> OTHER INFORMATION: Target for SCO7250c

<400> SEQUENCE: 62
agtggcgtac acctgt                                                    16

<210> SEQ ID NO 63
```

```
<211> LENGTH: 16
<212> TYPE: DNA
<213> ORGANISM: Artificial Sequence
<220> FEATURE:
<223> OTHER INFORMATION: Target for SCO5673, chiB

<400> SEQUENCE: 63
attggtctgg accaaa                                                    16

<210> SEQ ID NO 64
<211> LENGTH: 16
<212> TYPE: DNA
<213> ORGANISM: Artificial Sequence
<220> FEATURE:
<223> OTHER INFORMATION: Target for SCO7699 and SCO7698c

<400> SEQUENCE: 64
gagggtccag acctct                                                    16

<210> SEQ ID NO 65
<211> LENGTH: 16
<212> TYPE: DNA
<213> ORGANISM: Artificial Sequence
<220> FEATURE:
<223> OTHER INFORMATION: Target for SCO2833c, chb

<400> SEQUENCE: 65
gcaggtctag accaag                                                    16

<210> SEQ ID NO 66
<211> LENGTH: 16
<212> TYPE: DNA
<213> ORGANISM: Artificial Sequence
<220> FEATURE:
<223> OTHER INFORMATION: Target for SCO2946c

<400> SEQUENCE: 66
agaggtctga accaat                                                    16

<210> SEQ ID NO 67
<211> LENGTH: 16
<212> TYPE: DNA
<213> ORGANISM: Artificial Sequence
<220> FEATURE:
<223> OTHER INFORMATION: Target for SCO1117c

<400> SEQUENCE: 67
cgcggtctag accaaa                                                    16

<210> SEQ ID NO 68
<211> LENGTH: 16
<212> TYPE: DNA
<213> ORGANISM: Artificial Sequence
<220> FEATURE:
<223> OTHER INFORMATION: Target for SCO5230c

<400> SEQUENCE: 68
tctggtctag tcctgg                                                    16

<210> SEQ ID NO 69
<211> LENGTH: 16
<212> TYPE: DNA
<213> ORGANISM: Artificial Sequence
<220> FEATURE:
<223> OTHER INFORMATION: Target for SCO6149

<400> SEQUENCE: 69
```

-continued

```
ggaggtgtcg accaat                                                    16

<210> SEQ ID NO 70
<211> LENGTH: 16
<212> TYPE: DNA
<213> ORGANISM: Artificial Sequence
<220> FEATURE:
<223> OTHER INFORMATION: Target for SCO6319

<400> SEQUENCE: 70
attggtctga accatg                                                    16

<210> SEQ ID NO 71
<211> LENGTH: 16
<212> TYPE: DNA
<213> ORGANISM: Artificial Sequence
<220> FEATURE:
<223> OTHER INFORMATION: Target for SCO6033 and SCO6032c

<400> SEQUENCE: 71
cttggtctag tccatt                                                    16

<210> SEQ ID NO 72
<211> LENGTH: 16
<212> TYPE: DNA
<213> ORGANISM: Artificial Sequence
<220> FEATURE:
<223> OTHER INFORMATION: Target for SCOEc, chiE

<400> SEQUENCE: 72
cttggtccag acctgt                                                    16

<210> SEQ ID NO 73
<211> LENGTH: 32
<212> TYPE: DNA
<213> ORGANISM: Artificial Sequence
<220> FEATURE:
<223> OTHER INFORMATION: Target for SCO4394, desR and SCO4393c

<400> SEQUENCE: 73
tgcggtctgg accagtactg atcgacacca cg                                  32

<210> SEQ ID NO 74
<211> LENGTH: 32
<212> TYPE: DNA
<213> ORGANISM: Artificial Sequence
<220> FEATURE:
<223> OTHER INFORMATION: Target for SCO6084

<400> SEQUENCE: 74
gagggtggag accactggtg gtgcagtcct ac                                  32

<210> SEQ ID NO 75
<211> LENGTH: 16
<212> TYPE: DNA
<213> ORGANISM: Artificial Sequence
<220> FEATURE:
<223> OTHER INFORMATION: Target for SCO5046, wblI

<400> SEQUENCE: 75
tcaggagtag acccgt                                                    16

<210> SEQ ID NO 76
<211> LENGTH: 16
<212> TYPE: DNA
```

```
<213> ORGANISM: Artificial Sequence
<220> FEATURE:
<223> OTHER INFORMATION: Target for SCO1954 and SCO1953c

<400> SEQUENCE: 76
ggatgtgaag acctct                                                      16

<210> SEQ ID NO 77
<211> LENGTH: 16
<212> TYPE: DNA
<213> ORGANISM: Artificial Sequence
<220> FEATURE:
<223> OTHER INFORMATION: Target for SCO5231c, dasR

<400> SEQUENCE: 77
cttggtctag tccata                                                      16

<210> SEQ ID NO 78
<211> LENGTH: 16
<212> TYPE: DNA
<213> ORGANISM: Artificial Sequence
<220> FEATURE:
<223> OTHER INFORMATION: Target for SCO4506 and SCO4505c, scoF2

<400> SEQUENCE: 78
agaggtcaag atcact                                                      16

<210> SEQ ID NO 79
<211> LENGTH: 16
<212> TYPE: DNA
<213> ORGANISM: Artificial Sequence
<220> FEATURE:
<223> OTHER INFORMATION: Target for SCO3152c

<400> SEQUENCE: 79
agtggactcc tccacc                                                      16

<210> SEQ ID NO 80
<211> LENGTH: 16
<212> TYPE: DNA
<213> ORGANISM: Artificial Sequence
<220> FEATURE:
<223> OTHER INFORMATION: Target for SCO6232 and SCO6231c

<400> SEQUENCE: 80
tcaggactag accggt                                                      16

<210> SEQ ID NO 81
<211> LENGTH: 16
<212> TYPE: DNA
<213> ORGANISM: Artificial Sequence
<220> FEATURE:
<223> OTHER INFORMATION: Target for SCO1906c

<400> SEQUENCE: 81
actggcggag acctct                                                      16

<210> SEQ ID NO 82
<211> LENGTH: 16
<212> TYPE: DNA
<213> ORGANISM: Artificial Sequence
<220> FEATURE:
<223> OTHER INFORMATION: Target for SCO2119c, pfkA

<400> SEQUENCE: 82
ggtggttgag gccact                                                      16
```

-continued

<210> SEQ ID NO 83
<211> LENGTH: 16
<212> TYPE: DNA
<213> ORGANISM: Artificial Sequence
<220> FEATURE:
<223> OTHER INFORMATION: Target for SCO1971 and SCO1970c

<400> SEQUENCE: 83
tgtggtcgag acgtgt                                                          16

<210> SEQ ID NO 84
<211> LENGTH: 16
<212> TYPE: DNA
<213> ORGANISM: Artificial Sequence
<220> FEATURE:
<223> OTHER INFORMATION: Target for SCO1289 and SCO1288c

<400> SEQUENCE: 84
cgtggtgcag acgtga                                                          16

<210> SEQ ID NO 85
<211> LENGTH: 16
<212> TYPE: DNA
<213> ORGANISM: Artificial Sequence
<220> FEATURE:
<223> OTHER INFORMATION: Target for SCO0073 and SCO0072c

<400> SEQUENCE: 85
ccaggttcag acctgt                                                          16

<210> SEQ ID NO 86
<211> LENGTH: 16
<212> TYPE: DNA
<213> ORGANISM: Artificial Sequence
<220> FEATURE:
<223> OTHER INFORMATION: Target for SCO5463 and SCO5462c

<400> SEQUENCE: 86
actggcccgc accacc                                                          16

<210> SEQ ID NO 87
<211> LENGTH: 16
<212> TYPE: DNA
<213> ORGANISM: Artificial Sequence
<220> FEATURE:
<223> OTHER INFORMATION: Target for SCO5016c

<400> SEQUENCE: 87
ggtggagcag accgga                                                          16

<210> SEQ ID NO 88
<211> LENGTH: 16
<212> TYPE: DNA
<213> ORGANISM: Artificial Sequence
<220> FEATURE:
<223> OTHER INFORMATION: Target for SCO3975c

<400> SEQUENCE: 88
tgtggtcgag accgga                                                          16

<210> SEQ ID NO 89
<211> LENGTH: 16
<212> TYPE: DNA
<213> ORGANISM: Artificial Sequence
<220> FEATURE:

<223> OTHER INFORMATION: Target for SCO5366, atpI

<400> SEQUENCE: 89
agaggtaaag acctca                                                         16

<210> SEQ ID NO 90
<211> LENGTH: 16
<212> TYPE: DNA
<213> ORGANISM: Artificial Sequence
<220> FEATURE:
<223> OTHER INFORMATION: Target for SCO2787 and SCO2786c

<400> SEQUENCE: 90
acgggtgcgg accact                                                         16

<210> SEQ ID NO 91
<211> LENGTH: 16
<212> TYPE: DNA
<213> ORGANISM: Artificial Sequence
<220> FEATURE:
<223> OTHER INFORMATION: Target for SCO4442

<400> SEQUENCE: 91
attggcgtaa accaca                                                         16

<210> SEQ ID NO 92
<211> LENGTH: 16
<212> TYPE: DNA
<213> ORGANISM: Artificial Sequence
<220> FEATURE:
<223> OTHER INFORMATION: Target for SCO1752 and SCO1751c

<400> SEQUENCE: 92
tgtggcatgc accact                                                         16

<210> SEQ ID NO 93
<211> LENGTH: 16
<212> TYPE: DNA
<213> ORGANISM: Artificial Sequence
<220> FEATURE:
<223> OTHER INFORMATION: Target for SCO6003c

<400> SEQUENCE: 93
gccggtgaag accagt                                                         16

<210> SEQ ID NO 94
<211> LENGTH: 16
<212> TYPE: DNA
<213> ORGANISM: Artificial Sequence
<220> FEATURE:
<223> OTHER INFORMATION: Target for SCO5716c

<400> SEQUENCE: 94
attggcgcag accact                                                         16

<210> SEQ ID NO 95
<211> LENGTH: 16
<212> TYPE: DNA
<213> ORGANISM: Artificial Sequence
<220> FEATURE:
<223> OTHER INFORMATION: Target for SCO5330

<400> SEQUENCE: 95
gctggcgtag cccact                                                         16

```
<210> SEQ ID NO 96
<211> LENGTH: 16
<212> TYPE: DNA
<213> ORGANISM: Artificial Sequence
<220> FEATURE:
<223> OTHER INFORMATION: Target for SCO5430c

<400> SEQUENCE: 96
aatggtctag tcaggt                                                     16

<210> SEQ ID NO 97
<211> LENGTH: 16
<212> TYPE: DNA
<213> ORGANISM: Artificial Sequence
<220> FEATURE:
<223> OTHER INFORMATION: Target for SCO2685c

<400> SEQUENCE: 97
agtggacaac acccga                                                     16

<210> SEQ ID NO 98
<211> LENGTH: 16
<212> TYPE: DNA
<213> ORGANISM: Artificial Sequence
<220> FEATURE:
<223> OTHER INFORMATION: Target for SCO4516c

<400> SEQUENCE: 98
actggtctgg atccgt                                                     16

<210> SEQ ID NO 99
<211> LENGTH: 16
<212> TYPE: DNA
<213> ORGANISM: Artificial Sequence
<220> FEATURE:
<223> OTHER INFORMATION: Target for SCO7054 and SCO7053c

<400> SEQUENCE: 99
tgtggagtag agtagt                                                     16

<210> SEQ ID NO 100
<211> LENGTH: 16
<212> TYPE: DNA
<213> ORGANISM: Artificial Sequence
<220> FEATURE:
<223> OTHER INFORMATION: Target for SCO4735

<400> SEQUENCE: 100
cgtggccgag accact                                                     16

<210> SEQ ID NO 101
<211> LENGTH: 16
<212> TYPE: DNA
<213> ORGANISM: Artificial Sequence
<220> FEATURE:
<223> OTHER INFORMATION: Target for SCO4722, secY

<400> SEQUENCE: 101
gctcgtctga accact                                                     16

<210> SEQ ID NO 102
<211> LENGTH: 16
<212> TYPE: DNA
<213> ORGANISM: Artificial Sequence
<220> FEATURE:
<223> OTHER INFORMATION: Target for SCO7509c
```

```
<400> SEQUENCE: 102
gcgggtgaag accagc                                                     16

<210> SEQ ID NO 103
<211> LENGTH: 16
<212> TYPE: DNA
<213> ORGANISM: Artificial Sequence
<220> FEATURE:
<223> OTHER INFORMATION: Target for SCO4646, secE

<400> SEQUENCE: 103
actggtctcc aaaacc                                                     16

<210> SEQ ID NO 104
<211> LENGTH: 16
<212> TYPE: DNA
<213> ORGANISM: Artificial Sequence
<220> FEATURE:
<223> OTHER INFORMATION: Target for SCO4645c

<400> SEQUENCE: 104
actggtctcc aaaacc                                                     16

<210> SEQ ID NO 105
<211> LENGTH: 16
<212> TYPE: DNA
<213> ORGANISM: Artificial Sequence
<220> FEATURE:
<223> OTHER INFORMATION: Target for SCO4562

<400> SEQUENCE: 105
ggtggtggag atcaca                                                     16

<210> SEQ ID NO 106
<211> LENGTH: 16
<212> TYPE: DNA
<213> ORGANISM: Artificial Sequence
<220> FEATURE:
<223> OTHER INFORMATION: Target for SCO1692c

<400> SEQUENCE: 106
cgcggtctac tccatt                                                     16

<210> SEQ ID NO 107
<211> LENGTH: 16
<212> TYPE: DNA
<213> ORGANISM: Artificial Sequence
<220> FEATURE:
<223> OTHER INFORMATION: Target for SCO4904c

<400> SEQUENCE: 107
tgaggcctgc gccaca                                                     16

<210> SEQ ID NO 108
<211> LENGTH: 16
<212> TYPE: DNA
<213> ORGANISM: Artificial Sequence
<220> FEATURE:
<223> OTHER INFORMATION: Target for SCO5954

<400> SEQUENCE: 108
attggtccag accttc                                                     16

<210> SEQ ID NO 109
<211> LENGTH: 16
```

```
<212> TYPE: DNA
<213> ORGANISM: Artificial Sequence
<220> FEATURE:
<223> OTHER INFORMATION: Target for SCO5805, nrdJ

<400> SEQUENCE: 109
agtgaacaag acctgt                                                     16

<210> SEQ ID NO 110
<211> LENGTH: 16
<212> TYPE: DNA
<213> ORGANISM: Artificial Sequence
<220> FEATURE:
<223> OTHER INFORMATION: Target for SCO4609

<400> SEQUENCE: 110
cctggcgttg accagt                                                     16

<210> SEQ ID NO 111
<211> LENGTH: 16
<212> TYPE: DNA
<213> ORGANISM: Artificial Sequence
<220> FEATURE:
<223> OTHER INFORMATION: Target for SCO2547c

<400> SEQUENCE: 111
ggtggtccgg tcctgt                                                     16

<210> SEQ ID NO 112
<211> LENGTH: 16
<212> TYPE: DNA
<213> ORGANISM: Artificial Sequence
<220> FEATURE:
<223> OTHER INFORMATION: Target for SCO4963

<400> SEQUENCE: 112
cctggtgaag accttc                                                     16

<210> SEQ ID NO 113
<211> LENGTH: 16
<212> TYPE: DNA
<213> ORGANISM: Artificial Sequence
<220> FEATURE:
<223> OTHER INFORMATION: Target for SCO2037c, trpB

<400> SEQUENCE: 113
ggtggatcag accgct                                                     16

<210> SEQ ID NO 114
<211> LENGTH: 16
<212> TYPE: DNA
<213> ORGANISM: Artificial Sequence
<220> FEATURE:
<223> OTHER INFORMATION: Target for SCO0915 and SCO0914c

<400> SEQUENCE: 114
tttggtatgg accatt                                                     16

<210> SEQ ID NO 115
<211> LENGTH: 16
<212> TYPE: DNA
<213> ORGANISM: Artificial Sequence
<220> FEATURE:
<223> OTHER INFORMATION: Target for SCO2802

<400> SEQUENCE: 115
```

```
agaggactcg tccacg                                               16
```

\<210\> SEQ ID NO 116
\<211\> LENGTH: 16
\<212\> TYPE: DNA
\<213\> ORGANISM: Artificial Sequence
\<220\> FEATURE:
\<223\> OTHER INFORMATION: Target for SCO6914

\<400\> SEQUENCE: 116

```
ggtgctggag acctca                                               16
```

\<210\> SEQ ID NO 117
\<211\> LENGTH: 16
\<212\> TYPE: DNA
\<213\> ORGANISM: Artificial Sequence
\<220\> FEATURE:
\<223\> OTHER INFORMATION: Target for SCO5609c

\<400\> SEQUENCE: 117

```
actggtcagg accgct                                               16
```

\<210\> SEQ ID NO 118
\<211\> LENGTH: 16
\<212\> TYPE: DNA
\<213\> ORGANISM: Artificial Sequence
\<220\> FEATURE:
\<223\> OTHER INFORMATION: Target for SCO3261

\<400\> SEQUENCE: 118

```
accgggctac acacct                                               16
```

\<210\> SEQ ID NO 119
\<211\> LENGTH: 16
\<212\> TYPE: DNA
\<213\> ORGANISM: Artificial Sequence
\<220\> FEATURE:
\<223\> OTHER INFORMATION: Target for SCO5636c, korSA

\<400\> SEQUENCE: 119

```
actggacgag accccg                                               16
```

\<210\> SEQ ID NO 120
\<211\> LENGTH: 16
\<212\> TYPE: DNA
\<213\> ORGANISM: Artificial Sequence
\<220\> FEATURE:
\<223\> OTHER INFORMATION: Target for SCO7070 and SCO7069c

\<400\> SEQUENCE: 120

```
acaggtccgg accaat                                               16
```

\<210\> SEQ ID NO 121
\<211\> LENGTH: 16
\<212\> TYPE: DNA
\<213\> ORGANISM: Artificial Sequence
\<220\> FEATURE:
\<223\> OTHER INFORMATION: Target for SCO1558c

\<400\> SEQUENCE: 121

```
ggaggcctgc tccagc                                               16
```

\<210\> SEQ ID NO 122
\<211\> LENGTH: 16
\<212\> TYPE: DNA
\<213\> ORGANISM: Artificial Sequence

```
<220> FEATURE:
<223> OTHER INFORMATION: Target for SCO5717c

<400> SEQUENCE: 122
ccgggtgtag cccagc                                                    16

<210> SEQ ID NO 123
<211> LENGTH: 16
<212> TYPE: DNA
<213> ORGANISM: Artificial Sequence
<220> FEATURE:
<223> OTHER INFORMATION: Target for SCO3510c

<400> SEQUENCE: 123
cggggtctgg acctgc                                                    16

<210> SEQ ID NO 124
<211> LENGTH: 16
<212> TYPE: DNA
<213> ORGANISM: Artificial Sequence
<220> FEATURE:
<223> OTHER INFORMATION: Target for SCO4811

<400> SEQUENCE: 124
cgtgatccag accacc                                                    16

<210> SEQ ID NO 125
<211> LENGTH: 16
<212> TYPE: DNA
<213> ORGANISM: Artificial Sequence
<220> FEATURE:
<223> OTHER INFORMATION: Target for SCO3560 and SCO3559c

<400> SEQUENCE: 125
agtggtcttc ttcacc                                                    16

<210> SEQ ID NO 126
<211> LENGTH: 16
<212> TYPE: DNA
<213> ORGANISM: Artificial Sequence
<220> FEATURE:
<223> OTHER INFORMATION: Target for SCO5276

<400> SEQUENCE: 126
acgggtccac tcaaca                                                    16

<210> SEQ ID NO 127
<211> LENGTH: 16
<212> TYPE: DNA
<213> ORGANISM: Artificial Sequence
<220> FEATURE:
<223> OTHER INFORMATION: Target for SCO5881c, redZ

<400> SEQUENCE: 127
agtggtttcc acctca                                                    16

<210> SEQ ID NO 128
<211> LENGTH: 16
<212> TYPE: DNA
<213> ORGANISM: Artificial Sequence
<220> FEATURE:
<223> OTHER INFORMATION: Target for SCO1262c

<400> SEQUENCE: 128
cttggtcaag accaat                                                    16
```

```
<210> SEQ ID NO 129
<211> LENGTH: 16
<212> TYPE: DNA
<213> ORGANISM: Artificial Sequence
<220> FEATURE:
<223> OTHER INFORMATION: Target for SCO2141

<400> SEQUENCE: 129
atcggcctgg acaact                                                    16

<210> SEQ ID NO 130
<211> LENGTH: 16
<212> TYPE: DNA
<213> ORGANISM: Artificial Sequence
<220> FEATURE:
<223> OTHER INFORMATION: dre sequence of S. clavuligerus I

<400> SEQUENCE: 130
attggagtag acctct                                                    16

<210> SEQ ID NO 131
<211> LENGTH: 16
<212> TYPE: DNA
<213> ORGANISM: Artificial Sequence
<220> FEATURE:
<223> OTHER INFORMATION: dre sequence of S. clavuligerus II

<400> SEQUENCE: 131
ggagggctgg accagc                                                    16

<210> SEQ ID NO 132
<211> LENGTH: 16
<212> TYPE: DNA
<213> ORGANISM: Artificial Sequence
<220> FEATURE:
<223> OTHER INFORMATION: dre sequence of S. coelicolor I

<400> SEQUENCE: 132
tgttgagtag gcctgt                                                    16

<210> SEQ ID NO 133
<211> LENGTH: 16
<212> TYPE: DNA
<213> ORGANISM: Artificial Sequence
<220> FEATURE:
<223> OTHER INFORMATION: dre sequence of S. coelicolor II

<400> SEQUENCE: 133
gcaggtggag accacc                                                    16

<210> SEQ ID NO 134
<211> LENGTH: 16
<212> TYPE: DNA
<213> ORGANISM: Artificial Sequence
<220> FEATURE:
<223> OTHER INFORMATION: dre sequence of S. coelicolor III

<400> SEQUENCE: 134
tgaggtggaa accact                                                    16

<210> SEQ ID NO 135
<211> LENGTH: 16
<212> TYPE: DNA
<213> ORGANISM: Artificial Sequence
<220> FEATURE:
<223> OTHER INFORMATION: dre sequence of S. viridifaciens
```

```
<400> SEQUENCE: 135
ctctgagtag gcctgt                                                       16

<210> SEQ ID NO 136
<211> LENGTH: 16
<212> TYPE: DNA
<213> ORGANISM: Artificial Sequence
<220> FEATURE:
<223> OTHER INFORMATION: dre sequence of S. filamentosus 1

<400> SEQUENCE: 136
actggtgtcg accagc                                                       16

<210> SEQ ID NO 137
<211> LENGTH: 16
<212> TYPE: DNA
<213> ORGANISM: Artificial Sequence
<220> FEATURE:
<223> OTHER INFORMATION: dre sequence of S. filamentosus II

<400> SEQUENCE: 137
ggaggtcgag accagt                                                       16

<210> SEQ ID NO 138
<211> LENGTH: 16
<212> TYPE: DNA
<213> ORGANISM: Artificial Sequence
<220> FEATURE:
<223> OTHER INFORMATION: dre sequence of S. filamentosus III

<400> SEQUENCE: 138
tgaggtgtac gccacc                                                       16

<210> SEQ ID NO 139
<211> LENGTH: 16
<212> TYPE: DNA
<213> ORGANISM: Artificial Sequence
<220> FEATURE:
<223> OTHER INFORMATION: dre sequence of S. filamentosus IV

<400> SEQUENCE: 139
tgaggtcgag gccacc                                                       16

<210> SEQ ID NO 140
<211> LENGTH: 16
<212> TYPE: DNA
<213> ORGANISM: Artificial Sequence
<220> FEATURE:
<223> OTHER INFORMATION: dre sequence of S. filamentosus V

<400> SEQUENCE: 140
agtggtgctg cccaat                                                       16

<210> SEQ ID NO 141
<211> LENGTH: 16
<212> TYPE: DNA
<213> ORGANISM: Artificial Sequence
<220> FEATURE:
<223> OTHER INFORMATION: dre sequence of S. filamentosus VI

<400> SEQUENCE: 141
cgtgatctac acctcc                                                       16

<210> SEQ ID NO 142
```

```
<210> SEQ ID NO 142
<211> LENGTH: 16
<212> TYPE: DNA
<213> ORGANISM: Artificial Sequence
<220> FEATURE:
<223> OTHER INFORMATION: dre sequence of S. filamentosus VII

<400> SEQUENCE: 142
cgtgatctac acctcc                                                  16

<210> SEQ ID NO 143
<211> LENGTH: 16
<212> TYPE: DNA
<213> ORGANISM: Artificial Sequence
<220> FEATURE:
<223> OTHER INFORMATION: dre sequence of S. filamentosus VIII

<400> SEQUENCE: 143
acaagtccac accccc                                                  16

<210> SEQ ID NO 144
<211> LENGTH: 16
<212> TYPE: DNA
<213> ORGANISM: Artificial Sequence
<220> FEATURE:
<223> OTHER INFORMATION: dre sequence of S. filamentosus IX

<400> SEQUENCE: 144
cgaggcgtag acctgg                                                  16

<210> SEQ ID NO 145
<211> LENGTH: 16
<212> TYPE: DNA
<213> ORGANISM: Artificial Sequence
<220> FEATURE:
<223> OTHER INFORMATION: dre sequence of S. filamentosus X

<400> SEQUENCE: 145
cgtggcctgg acctca                                                  16

<210> SEQ ID NO 146
<211> LENGTH: 16
<212> TYPE: DNA
<213> ORGANISM: Artificial Sequence
<220> FEATURE:
<223> OTHER INFORMATION: dre sequence of S. filamentosus XI

<400> SEQUENCE: 146
ggtggtcctc accacg                                                  16

<210> SEQ ID NO 147
<211> LENGTH: 16
<212> TYPE: DNA
<213> ORGANISM: Artificial Sequence
<220> FEATURE:
<223> OTHER INFORMATION: dre sequence of S. filamentosus XII

<400> SEQUENCE: 147
actggagtcc acctga                                                  16

<210> SEQ ID NO 148
<211> LENGTH: 16
<212> TYPE: DNA
<213> ORGANISM: Artificial Sequence
<220> FEATURE:
<223> OTHER INFORMATION: dre sequence of S. filamentosus XIII

<400> SEQUENCE: 148
```

-continued cgaggcctac accctc                                         16

<210> SEQ ID NO 149
<211> LENGTH: 16
<212> TYPE: DNA
<213> ORGANISM: Artificial Sequence
<220> FEATURE:
<223> OTHER INFORMATION: dre sequence of S. spheroides

<400> SEQUENCE: 149
ggaggtgtag atcaca                                         16

<210> SEQ ID NO 150
<211> LENGTH: 16
<212> TYPE: DNA
<213> ORGANISM: Artificial Sequence
<220> FEATURE:
<223> OTHER INFORMATION: dre sequence of S. anulatus

<400> SEQUENCE: 150
ggaggtgtag atcaca                                         16

<210> SEQ ID NO 151
<211> LENGTH: 16
<212> TYPE: DNA
<213> ORGANISM: Artificial Sequence
<220> FEATURE:
<223> OTHER INFORMATION: dre sequence of S. toyocaensis I

<400> SEQUENCE: 151
ggaggtgtag atcaca                                         16

<210> SEQ ID NO 152
<211> LENGTH: 16
<212> TYPE: DNA
<213> ORGANISM: Artificial Sequence
<220> FEATURE:
<223> OTHER INFORMATION: dre sequence of S. toyocaensis II

<400> SEQUENCE: 152
tctggtggag accttc                                         16

<210> SEQ ID NO 153
<211> LENGTH: 16
<212> TYPE: DNA
<213> ORGANISM: Artificial Sequence
<220> FEATURE:
<223> OTHER INFORMATION: dre sequence of S. toyocaensis III

<400> SEQUENCE: 153
actggtctgc tcgatg                                         16

<210> SEQ ID NO 154
<211> LENGTH: 16
<212> TYPE: DNA
<213> ORGANISM: Artificial Sequence
<220> FEATURE:
<223> OTHER INFORMATION: dre sequence of S. toyocaensis IV

<400> SEQUENCE: 154
gctggtccag gcccct                                         16

<210> SEQ ID NO 155
<211> LENGTH: 16
<212> TYPE: DNA

```
<213> ORGANISM: Artificial Sequence
<220> FEATURE:
<223> OTHER INFORMATION: dre sequence of S. toyocaensis V

<400> SEQUENCE: 155
ggtggtctcc agcacc                                                    16

<210> SEQ ID NO 156
<211> LENGTH: 16
<212> TYPE: DNA
<213> ORGANISM: Artificial Sequence
<220> FEATURE:
<223> OTHER INFORMATION: dre sequence of S. toyocaensis VI

<400> SEQUENCE: 156
gctggtctcg accctc                                                    16

<210> SEQ ID NO 157
<211> LENGTH: 16
<212> TYPE: DNA
<213> ORGANISM: Artificial Sequence
<220> FEATURE:
<223> OTHER INFORMATION: dre sequence of S. toyocaensis VII

<400> SEQUENCE: 157
catggtctcg tccagc                                                    16

<210> SEQ ID NO 158
<211> LENGTH: 16
<212> TYPE: DNA
<213> ORGANISM: Artificial Sequence
<220> FEATURE:
<223> OTHER INFORMATION: dre sequence of S. griseus I

<400> SEQUENCE: 158
gggggtgtcg accagc                                                    16

<210> SEQ ID NO 159
<211> LENGTH: 16
<212> TYPE: DNA
<213> ORGANISM: Artificial Sequence
<220> FEATURE:
<223> OTHER INFORMATION: dre sequence of S. griseus II

<400> SEQUENCE: 159
cgtggcgcag tccaca                                                    16

<210> SEQ ID NO 160
<211> LENGTH: 16
<212> TYPE: DNA
<213> ORGANISM: Artificial Sequence
<220> FEATURE:
<223> OTHER INFORMATION: dre sequence of S. griseus III

<400> SEQUENCE: 160
cctggtcttc accccg                                                    16

<210> SEQ ID NO 161
<211> LENGTH: 16
<212> TYPE: DNA
<213> ORGANISM: Artificial Sequence
<220> FEATURE:
<223> OTHER INFORMATION: dre sequence of S. griseus IV

<400> SEQUENCE: 161
agtggtctgc gcatgc                                                    16
```

<210> SEQ ID NO 162
<211> LENGTH: 16
<212> TYPE: DNA
<213> ORGANISM: Artificial Sequence
<220> FEATURE:
<223> OTHER INFORMATION: dre sequence of S. griseus V

<400> SEQUENCE: 162
tgacgtctac tccttc                                                 16

<210> SEQ ID NO 163
<211> LENGTH: 16
<212> TYPE: DNA
<213> ORGANISM: Artificial Sequence
<220> FEATURE:
<223> OTHER INFORMATION: dre sequence of S. griseus VI

<400> SEQUENCE: 163
ggtggggcag accatc                                                 16

<210> SEQ ID NO 164
<211> LENGTH: 16
<212> TYPE: DNA
<213> ORGANISM: Artificial Sequence
<220> FEATURE:
<223> OTHER INFORMATION: dre sequence of S. griseus VII

<400> SEQUENCE: 164
agttgtgcag acgggt                                                 16

<210> SEQ ID NO 165
<211> LENGTH: 16
<212> TYPE: DNA
<213> ORGANISM: Artificial Sequence
<220> FEATURE:
<223> OTHER INFORMATION: dre sequence of S. griseus VIII

<400> SEQUENCE: 165
attggcctgc accgcg                                                 16

<210> SEQ ID NO 166
<211> LENGTH: 16
<212> TYPE: DNA
<213> ORGANISM: Artificial Sequence
<220> FEATURE:
<223> OTHER INFORMATION: dre sequence of S. venezuelae I

<400> SEQUENCE: 166
acgggtctac acctcc                                                 16

<210> SEQ ID NO 167
<211> LENGTH: 16
<212> TYPE: DNA
<213> ORGANISM: Artificial Sequence
<220> FEATURE:
<223> OTHER INFORMATION: dre sequence of S. venezuelae II

<400> SEQUENCE: 167
gctggtgtcg accatc                                                 16

<210> SEQ ID NO 168
<211> LENGTH: 16
<212> TYPE: DNA
<213> ORGANISM: Artificial Sequence
<220> FEATURE:

<223> OTHER INFORMATION: dre sequence of S. venezuelae III

<400> SEQUENCE: 168
cgaggtggag acctac                                                        16

<210> SEQ ID NO 169
<211> LENGTH: 16
<212> TYPE: DNA
<213> ORGANISM: Artificial Sequence
<220> FEATURE:
<223> OTHER INFORMATION: dre sequence of S. venezuelae IV

<400> SEQUENCE: 169
cgaggtggag acctac                                                        16

<210> SEQ ID NO 170
<211> LENGTH: 15
<212> TYPE: DNA
<213> ORGANISM: Artificial Sequence
<220> FEATURE:
<223> OTHER INFORMATION: dre sequence of S. virginiae

<400> SEQUENCE: 170
actggtgtcg accag                                                         15

<210> SEQ ID NO 171
<211> LENGTH: 16
<212> TYPE: DNA
<213> ORGANISM: Artificial Sequence
<220> FEATURE:
<223> OTHER INFORMATION: dre site of SCO5085

<400> SEQUENCE: 171
tgttgagtag gcctgt                                                        16

<210> SEQ ID NO 172
<211> LENGTH: 16
<212> TYPE: DNA
<213> ORGANISM: Artificial Sequence
<220> FEATURE:
<223> OTHER INFORMATION: dre site of SCO5090

<400> SEQUENCE: 172
ggtggtccac accctg                                                        16

<210> SEQ ID NO 173
<211> LENGTH: 16
<212> TYPE: DNA
<213> ORGANISM: Artificial Sequence
<220> FEATURE:
<223> OTHER INFORMATION: dre site of SCO5879

<400> SEQUENCE: 173
acaggtctac ggcacg                                                        16

<210> SEQ ID NO 174
<211> LENGTH: 16
<212> TYPE: DNA
<213> ORGANISM: Artificial Sequence
<220> FEATURE:
<223> OTHER INFORMATION: dre site of SCO5881c

<400> SEQUENCE: 174
agtggtttcc acctca                                                        16

```
<210> SEQ ID NO 175
<211> LENGTH: 16
<212> TYPE: DNA
<213> ORGANISM: Artificial Sequence
<220> FEATURE:
<223> OTHER INFORMATION: dre site of SCO5883c

<400> SEQUENCE: 175
gttggcctgc tccagg                                                        16

<210> SEQ ID NO 176
<211> LENGTH: 16
<212> TYPE: DNA
<213> ORGANISM: Artificial Sequence
<220> FEATURE:
<223> OTHER INFORMATION: dre site of SCO3237c

<400> SEQUENCE: 176
gtaggtctcg acctcc                                                        16

<210> SEQ ID NO 177
<211> LENGTH: 16
<212> TYPE: DNA
<213> ORGANISM: Artificial Sequence
<220> FEATURE:
<223> OTHER INFORMATION: dre site of SCO3226

<400> SEQUENCE: 177
agcggtctgc tcgact                                                        16

<210> SEQ ID NO 178
<211> LENGTH: 16
<212> TYPE: DNA
<213> ORGANISM: Artificial Sequence
<220> FEATURE:
<223> OTHER INFORMATION: dre site of SCO3234

<400> SEQUENCE: 178
cgatgtccag accggt                                                        16

<210> SEQ ID NO 179
<211> LENGTH: 16
<212> TYPE: DNA
<213> ORGANISM: Artificial Sequence
<220> FEATURE:
<223> OTHER INFORMATION: dre site of SCO0188

<400> SEQUENCE: 179
gcaggactac accgtg                                                        16

<210> SEQ ID NO 180
<211> LENGTH: 16
<212> TYPE: DNA
<213> ORGANISM: Artificial Sequence
<220> FEATURE:
<223> OTHER INFORMATION: dre site of SCO1206

<400> SEQUENCE: 180
gctggtggag accggc                                                        16

<210> SEQ ID NO 181
<211> LENGTH: 16
<212> TYPE: DNA
<213> ORGANISM: Artificial Sequence
<220> FEATURE:
<223> OTHER INFORMATION: dre site of SCO0387
```

<400> SEQUENCE: 181
ggttgtgcag aactac                                              16

<210> SEQ ID NO 182
<211> LENGTH: 16
<212> TYPE: DNA
<213> ORGANISM: Artificial Sequence
<220> FEATURE:
<223> OTHER INFORMATION: dre site of SCO0388

<400> SEQUENCE: 182
gctggtcgcc accacg                                              16

<210> SEQ ID NO 183
<211> LENGTH: 16
<212> TYPE: DNA
<213> ORGANISM: Artificial Sequence
<220> FEATURE:
<223> OTHER INFORMATION: dre site of SCO6282c

<400> SEQUENCE: 183
gctggacgag tccacc                                              16

<210> SEQ ID NO 184
<211> LENGTH: 16
<212> TYPE: DNA
<213> ORGANISM: Artificial Sequence
<220> FEATURE:
<223> OTHER INFORMATION: dre site of tRNA Gln anticodon CTG

<400> SEQUENCE: 184
actggtctaa accaca                                              16

<210> SEQ ID NO 185
<211> LENGTH: 16
<212> TYPE: DNA
<213> ORGANISM: Artificial Sequence
<220> FEATURE:
<223> OTHER INFORMATION: dre site of tRNA Glu anticodon CTC

<400> SEQUENCE: 185
actggtctaa accaca                                              16

<210> SEQ ID NO 186
<211> LENGTH: 32
<212> TYPE: DNA
<213> ORGANISM: Artificial Sequence
<220> FEATURE:
<223> OTHER INFORMATION: dre site of N-acetylglucosamine kinase

<400> SEQUENCE: 186
agaggtctag tccactggtg gtgtagacct ta                            32

<210> SEQ ID NO 187
<211> LENGTH: 32
<212> TYPE: DNA
<213> ORGANISM: Artificial Sequence
<220> FEATURE:
<223> OTHER INFORMATION: dre site of N-acetylglucosamine-6-phosphate
      deacetylase

<400> SEQUENCE: 187
agaggtctag tccactggtg gtgtagacct ta                            32

<210> SEQ ID NO 188

-continued

```
<211> LENGTH: 16
<212> TYPE: DNA
<213> ORGANISM: Artificial Sequence
<220> FEATURE:
<223> OTHER INFORMATION: dre site of Glucosamine-6 phosphate isomerase

<400> SEQUENCE: 188
tgtggtttag accaat                                                     16

<210> SEQ ID NO 189
<211> LENGTH: 16
<212> TYPE: DNA
<213> ORGANISM: Artificial Sequence
<220> FEATURE:
<223> OTHER INFORMATION: dre site of Glu-tRNAGln amidotransferase A
      subunit

<400> SEQUENCE: 189
taaggtctag acctgc                                                     16

<210> SEQ ID NO 190
<211> LENGTH: 16
<212> TYPE: DNA
<213> ORGANISM: Artificial Sequence
<220> FEATURE:
<223> OTHER INFORMATION: DasR binding site in Bsu 0769

<400> SEQUENCE: 190
agtgatctat accaat                                                     16

<210> SEQ ID NO 191
<211> LENGTH: 16
<212> TYPE: DNA
<213> ORGANISM: Artificial Sequence
<220> FEATURE:
<223> OTHER INFORMATION: DasR binding site in Bsu0770

<400> SEQUENCE: 191
attggtatag atcact                                                     16

<210> SEQ ID NO 192
<211> LENGTH: 16
<212> TYPE: DNA
<213> ORGANISM: Artificial Sequence
<220> FEATURE:
<223> OTHER INFORMATION: DasR binding site in Bsu3995

<400> SEQUENCE: 192
aacggtctag acaaat                                                     16

<210> SEQ ID NO 193
<211> LENGTH: 16
<212> TYPE: DNA
<213> ORGANISM: Artificial Sequence
<220> FEATURE:
<223> OTHER INFORMATION: DasR binding site in Bsu3497

<400> SEQUENCE: 193
agtgatctag accagc                                                     16

<210> SEQ ID NO 194
<211> LENGTH: 16
<212> TYPE: DNA
<213> ORGANISM: Artificial Sequence
<220> FEATURE:
<223> OTHER INFORMATION: DasR binding site in Bsu3498
```

```
<400> SEQUENCE: 194
gctggtctag atcact                                                      16

<210> SEQ ID NO 195
<211> LENGTH: 16
<212> TYPE: DNA
<213> ORGANISM: Artificial Sequence
<220> FEATURE:
<223> OTHER INFORMATION: DasR binding site in Bsu0780

<400> SEQUENCE: 195
agttgtatat acaagt                                                      16

<210> SEQ ID NO 196
<211> LENGTH: 16
<212> TYPE: DNA
<213> ORGANISM: Artificial Sequence
<220> FEATURE:
<223> OTHER INFORMATION: DasR binding site in Bsu0779

<400> SEQUENCE: 196
acttgtatat acaact                                                      16

<210> SEQ ID NO 197
<211> LENGTH: 16
<212> TYPE: DNA
<213> ORGANISM: Artificial Sequence
<220> FEATURE:
<223> OTHER INFORMATION: DasR binding site in Bsu2373

<400> SEQUENCE: 197
atatgtatag acctgt                                                      16

<210> SEQ ID NO 198
<211> LENGTH: 16
<212> TYPE: DNA
<213> ORGANISM: Artificial Sequence
<220> FEATURE:
<223> OTHER INFORMATION: DasR binding site in Bsu2140

<400> SEQUENCE: 198
atctgtctat acctat                                                      16

<210> SEQ ID NO 199
<211> LENGTH: 16
<212> TYPE: DNA
<213> ORGANISM: Artificial Sequence
<220> FEATURE:
<223> OTHER INFORMATION: DasR binding site in Bsu3051

<400> SEQUENCE: 199
aatagtatag actatt                                                      16

<210> SEQ ID NO 200
<211> LENGTH: 16
<212> TYPE: DNA
<213> ORGANISM: Artificial Sequence
<220> FEATURE:
<223> OTHER INFORMATION: DasR binding site in Bsu0454

<400> SEQUENCE: 200
ttttgtatat accatt                                                      16

<210> SEQ ID NO 201
<211> LENGTH: 16
```

-continued

```
<212> TYPE: DNA
<213> ORGANISM: Artificial Sequence
<220> FEATURE:
<223> OTHER INFORMATION: DasR binding site in Bsu0453

<400> SEQUENCE: 201
aatggtatat acaaaa                                                16

<210> SEQ ID NO 202
<211> LENGTH: 16
<212> TYPE: DNA
<213> ORGANISM: Artificial Sequence
<220> FEATURE:
<223> OTHER INFORMATION: DasR binding site in Bsu0023

<400> SEQUENCE: 202
agtggtctaa actcct                                                16

<210> SEQ ID NO 203
<211> LENGTH: 16
<212> TYPE: DNA
<213> ORGANISM: Artificial Sequence
<220> FEATURE:
<223> OTHER INFORMATION: DasR binding site in Bsu1963

<400> SEQUENCE: 203
aatggtatat atcata                                                16

<210> SEQ ID NO 204
<211> LENGTH: 16
<212> TYPE: DNA
<213> ORGANISM: Artificial Sequence
<220> FEATURE:
<223> OTHER INFORMATION: DasR binding site in Bsu1476

<400> SEQUENCE: 204
atggctctac accatt                                                16

<210> SEQ ID NO 205
<211> LENGTH: 16
<212> TYPE: DNA
<213> ORGANISM: Artificial Sequence
<220> FEATURE:
<223> OTHER INFORMATION: DasR binding site in Bsu0953

<400> SEQUENCE: 205
aatggaatat accagt                                                16

<210> SEQ ID NO 206
<211> LENGTH: 16
<212> TYPE: DNA
<213> ORGANISM: Artificial Sequence
<220> FEATURE:
<223> OTHER INFORMATION: DasR binding site in Bsu0952

<400> SEQUENCE: 206
actggtatat tccatt                                                16

<210> SEQ ID NO 207
<211> LENGTH: 16
<212> TYPE: DNA
<213> ORGANISM: Artificial Sequence
<220> FEATURE:
<223> OTHER INFORMATION: DasR binding site in Bsu1167

<400> SEQUENCE: 207
```

```
attggtttag acaaca                                               16

<210> SEQ ID NO 208
<211> LENGTH: 16
<212> TYPE: DNA
<213> ORGANISM: Artificial Sequence
<220> FEATURE:
<223> OTHER INFORMATION: DasR binding site in Bsu1012

<400> SEQUENCE: 208
acatttctat accatt                                               16

<210> SEQ ID NO 209
<211> LENGTH: 16
<212> TYPE: DNA
<213> ORGANISM: Artificial Sequence
<220> FEATURE:
<223> OTHER INFORMATION: DasR binding site in Bsu3589

<400> SEQUENCE: 209
aattatatat acaatt                                               16

<210> SEQ ID NO 210
<211> LENGTH: 16
<212> TYPE: DNA
<213> ORGANISM: Artificial Sequence
<220> FEATURE:
<223> OTHER INFORMATION: DasR binding site in Bsu3257

<400> SEQUENCE: 210
aatgttatat aacatt                                               16

<210> SEQ ID NO 211
<211> LENGTH: 16
<212> TYPE: DNA
<213> ORGANISM: Artificial Sequence
<220> FEATURE:
<223> OTHER INFORMATION: DasR binding site in Bsu1783

<400> SEQUENCE: 211
aatggtatat aatatt                                               16

<210> SEQ ID NO 212
<211> LENGTH: 16
<212> TYPE: DNA
<213> ORGANISM: Artificial Sequence
<220> FEATURE:
<223> OTHER INFORMATION: DasR binding site in Bsu0677

<400> SEQUENCE: 212
attcgtataa acaagt                                               16

<210> SEQ ID NO 213
<211> LENGTH: 16
<212> TYPE: DNA
<213> ORGANISM: Artificial Sequence
<220> FEATURE:
<223> OTHER INFORMATION: DasR binding site in Bsu2559

<400> SEQUENCE: 213
aatggtttat atgaat                                               16

<210> SEQ ID NO 214
<211> LENGTH: 16
<212> TYPE: DNA
<213> ORGANISM: Artificial Sequence
```

```
<220> FEATURE:
<223> OTHER INFORMATION: DasR binding site in Bsu0675

<400> SEQUENCE: 214
acttgtttat acgaat                                                       16

<210> SEQ ID NO 215
<211> LENGTH: 16
<212> TYPE: DNA
<213> ORGANISM: Artificial Sequence
<220> FEATURE:
<223> OTHER INFORMATION: DasR binding site in BH0422

<400> SEQUENCE: 215
atttgtatat accaat                                                       16

<210> SEQ ID NO 216
<211> LENGTH: 16
<212> TYPE: DNA
<213> ORGANISM: Artificial Sequence
<220> FEATURE:
<223> OTHER INFORMATION: DasR binding site in BH3323

<400> SEQUENCE: 216
attgatatat accaat                                                       16

<210> SEQ ID NO 217
<211> LENGTH: 16
<212> TYPE: DNA
<213> ORGANISM: Artificial Sequence
<220> FEATURE:
<223> OTHER INFORMATION: DasR binding site in BH0421

<400> SEQUENCE: 217
attggtatat acaaat                                                       16

<210> SEQ ID NO 218
<211> LENGTH: 16
<212> TYPE: DNA
<213> ORGANISM: Artificial Sequence
<220> FEATURE:
<223> OTHER INFORMATION: DasR binding site in BH3324

<400> SEQUENCE: 218
attggtatat atcaat                                                       16

<210> SEQ ID NO 219
<211> LENGTH: 16
<212> TYPE: DNA
<213> ORGANISM: Artificial Sequence
<220> FEATURE:
<223> OTHER INFORMATION: DasR binding site in BH0419

<400> SEQUENCE: 219
attggtatag acattt                                                       16

<210> SEQ ID NO 220
<211> LENGTH: 16
<212> TYPE: DNA
<213> ORGANISM: Artificial Sequence
<220> FEATURE:
<223> OTHER INFORMATION: DasR binding site in BH0418

<400> SEQUENCE: 220
aaatgtctat accaat                                                       16
```

```
<210> SEQ ID NO 221
<211> LENGTH: 16
<212> TYPE: DNA
<213> ORGANISM: Artificial Sequence
<220> FEATURE:
<223> OTHER INFORMATION: DasR binding site in BH2230

<400> SEQUENCE: 221
tatggtatag accact                                                      16

<210> SEQ ID NO 222
<211> LENGTH: 16
<212> TYPE: DNA
<213> ORGANISM: Artificial Sequence
<220> FEATURE:
<223> OTHER INFORMATION: DasR binding site in BH1924

<400> SEQUENCE: 222
attggtataa acaaat                                                      16

<210> SEQ ID NO 223
<211> LENGTH: 16
<212> TYPE: DNA
<213> ORGANISM: Artificial Sequence
<220> FEATURE:
<223> OTHER INFORMATION: DasR binding site in BH0593

<400> SEQUENCE: 223
attcgtttag accaat                                                      16

<210> SEQ ID NO 224
<211> LENGTH: 16
<212> TYPE: DNA
<213> ORGANISM: Artificial Sequence
<220> FEATURE:
<223> OTHER INFORMATION: DasR binding site in BH2561

<400> SEQUENCE: 224
attgttctag accctt                                                      16

<210> SEQ ID NO 225
<211> LENGTH: 16
<212> TYPE: DNA
<213> ORGANISM: Artificial Sequence
<220> FEATURE:
<223> OTHER INFORMATION: DasR binding site in BH2216

<400> SEQUENCE: 225
acttgtatat acaaat                                                      16

<210> SEQ ID NO 226
<211> LENGTH: 16
<212> TYPE: DNA
<213> ORGANISM: Artificial Sequence
<220> FEATURE:
<223> OTHER INFORMATION: DasR binding site in BH1484

<400> SEQUENCE: 226
aatggtctac accaag                                                      16

<210> SEQ ID NO 227
<211> LENGTH: 16
<212> TYPE: DNA
<213> ORGANISM: Artificial Sequence
<220> FEATURE:
<223> OTHER INFORMATION: DasR binding site in BH1482
```

```
<400> SEQUENCE: 227
cttggtgtag accatt                                                  16

<210> SEQ ID NO 228
<211> LENGTH: 16
<212> TYPE: DNA
<213> ORGANISM: Artificial Sequence
<220> FEATURE:
<223> OTHER INFORMATION: DasR binding site in BH0872

<400> SEQUENCE: 228
acttgtatat acaagt                                                  16

<210> SEQ ID NO 229
<211> LENGTH: 16
<212> TYPE: DNA
<213> ORGANISM: Artificial Sequence
<220> FEATURE:
<223> OTHER INFORMATION: DasR binding site in BH0661

<400> SEQUENCE: 229
aaaggtgtag atcatt                                                  16

<210> SEQ ID NO 230
<211> LENGTH: 16
<212> TYPE: DNA
<213> ORGANISM: Artificial Sequence
<220> FEATURE:
<223> OTHER INFORMATION: DasR binding site in BH0786

<400> SEQUENCE: 230
aatgatttag atcaat                                                  16

<210> SEQ ID NO 231
<211> LENGTH: 16
<212> TYPE: DNA
<213> ORGANISM: Artificial Sequence
<220> FEATURE:
<223> OTHER INFORMATION: DasR binding site in BH0464

<400> SEQUENCE: 231
tatggtctat atcatt                                                  16

<210> SEQ ID NO 232
<211> LENGTH: 16
<212> TYPE: DNA
<213> ORGANISM: Artificial Sequence
<220> FEATURE:
<223> OTHER INFORMATION: DasR binding site in BH3302

<400> SEQUENCE: 232
aatagtatag actatt                                                  16

<210> SEQ ID NO 233
<211> LENGTH: 16
<212> TYPE: DNA
<213> ORGANISM: Artificial Sequence
<220> FEATURE:
<223> OTHER INFORMATION: DasR binding site in BH3024

<400> SEQUENCE: 233
acaggtgtag acattt                                                  16

<210> SEQ ID NO 234
```

```
<211> LENGTH: 16
<212> TYPE: DNA
<213> ORGANISM: Artificial Sequence
<220> FEATURE:
<223> OTHER INFORMATION: DasR binding site in BH2314

<400> SEQUENCE: 234
agttgtttag accaga                                                    16

<210> SEQ ID NO 235
<211> LENGTH: 16
<212> TYPE: DNA
<213> ORGANISM: Artificial Sequence
<220> FEATURE:
<223> OTHER INFORMATION: DasR binding site in BH3244

<400> SEQUENCE: 235
attgatctat acaaac                                                    16

<210> SEQ ID NO 236
<211> LENGTH: 16
<212> TYPE: DNA
<213> ORGANISM: Artificial Sequence
<220> FEATURE:
<223> OTHER INFORMATION: DasR binding site in BH2450

<400> SEQUENCE: 236
attgatatag atgagt                                                    16

<210> SEQ ID NO 237
<211> LENGTH: 16
<212> TYPE: DNA
<213> ORGANISM: Artificial Sequence
<220> FEATURE:
<223> OTHER INFORMATION: DasR binding site in BH3530

<400> SEQUENCE: 237
aatggtgtat agaaat                                                    16

<210> SEQ ID NO 238
<211> LENGTH: 16
<212> TYPE: DNA
<213> ORGANISM: Artificial Sequence
<220> FEATURE:
<223> OTHER INFORMATION: DasR binding site in BH4039

<400> SEQUENCE: 238
attgatttat agcatt                                                    16

<210> SEQ ID NO 239
<211> LENGTH: 16
<212> TYPE: DNA
<213> ORGANISM: Artificial Sequence
<220> FEATURE:
<223> OTHER INFORMATION: DasR binding site in BH3678

<400> SEQUENCE: 239
acatgtctat acatct                                                    16

<210> SEQ ID NO 240
<211> LENGTH: 16
<212> TYPE: DNA
<213> ORGANISM: Artificial Sequence
<220> FEATURE:
<223> OTHER INFORMATION: DasR binding site in BH0126

<400> SEQUENCE: 240
```

```
aatggtgtag aggatt                                                 16

<210> SEQ ID NO 241
<211> LENGTH: 16
<212> TYPE: DNA
<213> ORGANISM: Artificial Sequence
<220> FEATURE:
<223> OTHER INFORMATION: DasR binding site in BH2699

<400> SEQUENCE: 241
attggtttat atatat                                                 16

<210> SEQ ID NO 242
<211> LENGTH: 16
<212> TYPE: DNA
<213> ORGANISM: Artificial Sequence
<220> FEATURE:
<223> OTHER INFORMATION: DasR binding site in BH2403

<400> SEQUENCE: 242
attgatctag agcata                                                 16

<210> SEQ ID NO 243
<211> LENGTH: 16
<212> TYPE: DNA
<213> ORGANISM: Artificial Sequence
<220> FEATURE:
<223> OTHER INFORMATION: DasR binding site in BH0134

<400> SEQUENCE: 243
atcggtttac acaatt                                                 16

<210> SEQ ID NO 244
<211> LENGTH: 16
<212> TYPE: DNA
<213> ORGANISM: Artificial Sequence
<220> FEATURE:
<223> OTHER INFORMATION: DasR binding site in L14408

<400> SEQUENCE: 244
attgatatat accaat                                                 16

<210> SEQ ID NO 245
<211> LENGTH: 16
<212> TYPE: DNA
<213> ORGANISM: Artificial Sequence
<220> FEATURE:
<223> OTHER INFORMATION: DasR binding site in L173068

<400> SEQUENCE: 245
attggtatat actgtt                                                 16

<210> SEQ ID NO 246
<211> LENGTH: 16
<212> TYPE: DNA
<213> ORGANISM: Artificial Sequence
<220> FEATURE:
<223> OTHER INFORMATION: DasR binding site in L141634

<400> SEQUENCE: 246
attggtatat aaaaat                                                 16

<210> SEQ ID NO 247
<211> LENGTH: 16
<212> TYPE: DNA
```

```
<213> ORGANISM: Artificial Sequence
<220> FEATURE:
<223> OTHER INFORMATION: DasR binding site in L127921

<400> SEQUENCE: 247
aacggtatat acgatt                                                       16

<210> SEQ ID NO 248
<211> LENGTH: 16
<212> TYPE: DNA
<213> ORGANISM: Artificial Sequence
<220> FEATURE:
<223> OTHER INFORMATION: DasR binding site in L51784

<400> SEQUENCE: 248
aacagtatat atcatt                                                       16

<210> SEQ ID NO 249
<211> LENGTH: 16
<212> TYPE: DNA
<213> ORGANISM: Artificial Sequence
<220> FEATURE:
<223> OTHER INFORMATION: DasR binding site in L0151

<400> SEQUENCE: 249
agtggtatat attgtt                                                       16

<210> SEQ ID NO 250
<211> LENGTH: 16
<212> TYPE: DNA
<213> ORGANISM: Artificial Sequence
<220> FEATURE:
<223> OTHER INFORMATION: DasR binding site in L61341

<400> SEQUENCE: 250
aatgatatat atcttt                                                       16

<210> SEQ ID NO 251
<211> LENGTH: 16
<212> TYPE: DNA
<213> ORGANISM: Artificial Sequence
<220> FEATURE:
<223> OTHER INFORMATION: DasR binding site in L0407

<400> SEQUENCE: 251
acttgtatat acttat                                                       16

<210> SEQ ID NO 252
<211> LENGTH: 16
<212> TYPE: DNA
<213> ORGANISM: Artificial Sequence
<220> FEATURE:
<223> OTHER INFORMATION: DasR binding site in LL57508

<400> SEQUENCE: 252
atgggtagat aacaat                                                       16

<210> SEQ ID NO 253
<211> LENGTH: 16
<212> TYPE: DNA
<213> ORGANISM: Artificial Sequence
<220> FEATURE:
<223> OTHER INFORMATION: DasR binding site in L166512

<400> SEQUENCE: 253
aatgagatat atcaat                                                       16
```

<210> SEQ ID NO 254
<211> LENGTH: 16
<212> TYPE: DNA
<213> ORGANISM: Artificial Sequence
<220> FEATURE:
<223> OTHER INFORMATION: DasR binding site in L128694

<400> SEQUENCE: 254
attggtttat accgac                                                    16

<210> SEQ ID NO 255
<211> LENGTH: 16
<212> TYPE: DNA
<213> ORGANISM: Artificial Sequence
<220> FEATURE:
<223> OTHER INFORMATION: DasR binding site in L128695

<400> SEQUENCE: 255
gtcggtataa accaat                                                    16

<210> SEQ ID NO 256
<211> LENGTH: 16
<212> TYPE: DNA
<213> ORGANISM: Artificial Sequence
<220> FEATURE:
<223> OTHER INFORMATION: DasR binding site in L163025

<400> SEQUENCE: 256
attggtatac aatatt                                                    16

<210> SEQ ID NO 257
<211> LENGTH: 16
<212> TYPE: DNA
<213> ORGANISM: Artificial Sequence
<220> FEATURE:
<223> OTHER INFORMATION: DasR binding site in L0444

<400> SEQUENCE: 257
attagtctat atctat                                                    16

<210> SEQ ID NO 258
<211> LENGTH: 16
<212> TYPE: DNA
<213> ORGANISM: Artificial Sequence
<220> FEATURE:
<223> OTHER INFORMATION: DasR binding site in L174321

<400> SEQUENCE: 258
ataaataaat accaat                                                    16

<210> SEQ ID NO 259
<211> LENGTH: 16
<212> TYPE: DNA
<213> ORGANISM: Artificial Sequence
<220> FEATURE:
<223> OTHER INFORMATION: DasR binding site in L22900

<400> SEQUENCE: 259
aatgggatat actggt                                                    16

<210> SEQ ID NO 260
<211> LENGTH: 16
<212> TYPE: DNA
<213> ORGANISM: Artificial Sequence
<220> FEATURE:

<223> OTHER INFORMATION: DasR binding site in L11986

<400> SEQUENCE: 260
attgatatat atgtct                                                         16

<210> SEQ ID NO 261
<211> LENGTH: 16
<212> TYPE: DNA
<213> ORGANISM: Artificial Sequence
<220> FEATURE:
<223> OTHER INFORMATION: DasR binding site in L179789

<400> SEQUENCE: 261
acgagtatat ataaat                                                         16

<210> SEQ ID NO 262
<211> LENGTH: 16
<212> TYPE: DNA
<213> ORGANISM: Artificial Sequence
<220> FEATURE:
<223> OTHER INFORMATION: DasR binding site in L176316

<400> SEQUENCE: 262
attggtatag gtcaat                                                         16

<210> SEQ ID NO 263
<211> LENGTH: 16
<212> TYPE: DNA
<213> ORGANISM: Artificial Sequence
<220> FEATURE:
<223> OTHER INFORMATION: DasR binding site in L174076

<400> SEQUENCE: 263
ataagtatat acatct                                                         16

<210> SEQ ID NO 264
<211> LENGTH: 16
<212> TYPE: DNA
<213> ORGANISM: Artificial Sequence
<220> FEATURE:
<223> OTHER INFORMATION: DasR binding site in L191704

<400> SEQUENCE: 264
aatggaagat accatt                                                         16

<210> SEQ ID NO 265
<211> LENGTH: 16
<212> TYPE: DNA
<213> ORGANISM: Artificial Sequence
<220> FEATURE:
<223> OTHER INFORMATION: DasR binding site in L106731

<400> SEQUENCE: 265
acttgtattt atcaat                                                         16

<210> SEQ ID NO 266
<211> LENGTH: 16
<212> TYPE: DNA
<213> ORGANISM: Artificial Sequence
<220> FEATURE:
<223> OTHER INFORMATION: DasR binding site in SP0571

<400> SEQUENCE: 266
agtggtgtat gccaat                                                         16

```
<210> SEQ ID NO 267
<211> LENGTH: 16
<212> TYPE: DNA
<213> ORGANISM: Artificial Sequence
<220> FEATURE:
<223> OTHER INFORMATION: DasR binding site in SP1415

<400> SEQUENCE: 267
attggtctat accata                                                    16

<210> SEQ ID NO 268
<211> LENGTH: 16
<212> TYPE: DNA
<213> ORGANISM: Artificial Sequence
<220> FEATURE:
<223> OTHER INFORMATION: DasR binding site in SP1416

<400> SEQUENCE: 268
tatggtatag accaat                                                    16

<210> SEQ ID NO 269
<211> LENGTH: 16
<212> TYPE: DNA
<213> ORGANISM: Artificial Sequence
<220> FEATURE:
<223> OTHER INFORMATION: DasR binding site in SP0266

<400> SEQUENCE: 269
attagactat accaat                                                    16

<210> SEQ ID NO 270
<211> LENGTH: 16
<212> TYPE: DNA
<213> ORGANISM: Artificial Sequence
<220> FEATURE:
<223> OTHER INFORMATION: DasR binding site in SP0856

<400> SEQUENCE: 270
agtggaatat gacagt                                                    16

<210> SEQ ID NO 271
<211> LENGTH: 16
<212> TYPE: DNA
<213> ORGANISM: Artificial Sequence
<220> FEATURE:
<223> OTHER INFORMATION: DasR binding site in SP1211

<400> SEQUENCE: 271
attataatat tccaat                                                    16

<210> SEQ ID NO 272
<211> LENGTH: 16
<212> TYPE: DNA
<213> ORGANISM: Artificial Sequence
<220> FEATURE:
<223> OTHER INFORMATION: DasR binding site in SP1210

<400> SEQUENCE: 272
attataatat tccaat                                                    16

<210> SEQ ID NO 273
<211> LENGTH: 16
<212> TYPE: DNA
<213> ORGANISM: Artificial Sequence
<220> FEATURE:
<223> OTHER INFORMATION: DasR binding site in SP2103
```

```
<400> SEQUENCE: 273
attattatat agcaat                                                    16

<210> SEQ ID NO 274
<211> LENGTH: 16
<212> TYPE: DNA
<213> ORGANISM: Artificial Sequence
<220> FEATURE:
<223> OTHER INFORMATION: DasR binding site in SP2102

<400> SEQUENCE: 274
attgctatat aataat                                                    16

<210> SEQ ID NO 275
<211> LENGTH: 16
<212> TYPE: DNA
<213> ORGANISM: Artificial Sequence
<220> FEATURE:
<223> OTHER INFORMATION: DasR binding site in SP2101

<400> SEQUENCE: 275
attgctatat aataat                                                    16

<210> SEQ ID NO 276
<211> LENGTH: 16
<212> TYPE: DNA
<213> ORGANISM: Artificial Sequence
<220> FEATURE:
<223> OTHER INFORMATION: DasR binding site in SP0088

<400> SEQUENCE: 276
actgttatat aatact                                                    16

<210> SEQ ID NO 277
<211> LENGTH: 16
<212> TYPE: DNA
<213> ORGANISM: Artificial Sequence
<220> FEATURE:
<223> OTHER INFORMATION: DasR binding site in SP0087

<400> SEQUENCE: 277
agtattatat aacagt                                                    16

<210> SEQ ID NO 278
<211> LENGTH: 16
<212> TYPE: DNA
<213> ORGANISM: Artificial Sequence
<220> FEATURE:
<223> OTHER INFORMATION: DasR binding site in SP1249

<400> SEQUENCE: 278
agtggtctat tcgaat                                                    16

<210> SEQ ID NO 279
<211> LENGTH: 16
<212> TYPE: DNA
<213> ORGANISM: Artificial Sequence
<220> FEATURE:
<223> OTHER INFORMATION: DasR binding site in SP1702

<400> SEQUENCE: 279
cttgggataa accact                                                    16

<210> SEQ ID NO 280
<211> LENGTH: 16
```

```
<212> TYPE: DNA
<213> ORGANISM: Artificial Sequence
<220> FEATURE:
<223> OTHER INFORMATION: DasR binding site in SP1956

<400> SEQUENCE: 280
attagaatat aaaaat                                                     16

<210> SEQ ID NO 281
<211> LENGTH: 16
<212> TYPE: DNA
<213> ORGANISM: Artificial Sequence
<220> FEATURE:
<223> OTHER INFORMATION: DasR binding site in SP2056

<400> SEQUENCE: 281
ataggtctat accatt                                                     16

<210> SEQ ID NO 282
<211> LENGTH: 16
<212> TYPE: DNA
<213> ORGANISM: Artificial Sequence
<220> FEATURE:
<223> OTHER INFORMATION: DasR binding site in SP0056

<400> SEQUENCE: 282
agtgttgtat gccagt                                                     16

<210> SEQ ID NO 283
<211> LENGTH: 16
<212> TYPE: DNA
<213> ORGANISM: Artificial Sequence
<220> FEATURE:
<223> OTHER INFORMATION: DasR binding site in SP1319

<400> SEQUENCE: 283
tttggagtat tccaat                                                     16

<210> SEQ ID NO 284
<211> LENGTH: 16
<212> TYPE: DNA
<213> ORGANISM: Artificial Sequence
<220> FEATURE:
<223> OTHER INFORMATION: DasR binding site in SP1431

<400> SEQUENCE: 284
aaggatatat accaat                                                     16

<210> SEQ ID NO 285
<211> LENGTH: 16
<212> TYPE: DNA
<213> ORGANISM: Artificial Sequence
<220> FEATURE:
<223> OTHER INFORMATION: DasR binding site in SP0474

<400> SEQUENCE: 285
agtggtatat ttaatt                                                     16

<210> SEQ ID NO 286
<211> LENGTH: 16
<212> TYPE: DNA
<213> ORGANISM: Artificial Sequence
<220> FEATURE:
<223> OTHER INFORMATION: DasR binding site in SP0473

<400> SEQUENCE: 286
```
aattaaatat accact                                          16

<210> SEQ ID NO 287
<211> LENGTH: 16
<212> TYPE: DNA
<213> ORGANISM: Artificial Sequence
<220> FEATURE:
<223> OTHER INFORMATION: DasR binding site in SP1810

<400> SEQUENCE: 287
aatggtataa ttcatt                                          16

<210> SEQ ID NO 288
<211> LENGTH: 16
<212> TYPE: DNA
<213> ORGANISM: Artificial Sequence
<220> FEATURE:
<223> OTHER INFORMATION: DasR binding site in SP0839

<400> SEQUENCE: 288
tatactatat accatt                                          16

<210> SEQ ID NO 289
<211> LENGTH: 16
<212> TYPE: DNA
<213> ORGANISM: Artificial Sequence
<220> FEATURE:
<223> OTHER INFORMATION: DasR binding site in SP0840

<400> SEQUENCE: 289
aatggtatat agtata                                          16

<210> SEQ ID NO 290
<211> LENGTH: 16
<212> TYPE: DNA
<213> ORGANISM: Artificial Sequence
<220> FEATURE:
<223> OTHER INFORMATION: DasR binding site in SP1264

<400> SEQUENCE: 290
attggcatat cagact                                          16

<210> SEQ ID NO 291
<211> LENGTH: 16
<212> TYPE: DNA
<213> ORGANISM: Artificial Sequence
<220> FEATURE:
<223> OTHER INFORMATION: DasR binding site in SP1421

<400> SEQUENCE: 291
aatgtgatat aatagt                                          16

<210> SEQ ID NO 292
<211> LENGTH: 16
<212> TYPE: DNA
<213> ORGANISM: Artificial Sequence
<220> FEATURE:
<223> OTHER INFORMATION: DasR binding site in SP0394

<400> SEQUENCE: 292
ctttgtatat actagt                                          16

<210> SEQ ID NO 293
<211> LENGTH: 16
<212> TYPE: DNA
<213> ORGANISM: Artificial Sequence

```
<220> FEATURE:
<223> OTHER INFORMATION: DasR binding site in SP2159

<400> SEQUENCE: 293
atggggatat aacatt                                                    16

<210> SEQ ID NO 294
<211> LENGTH: 16
<212> TYPE: DNA
<213> ORGANISM: Artificial Sequence
<220> FEATURE:
<223> OTHER INFORMATION: DasR binding site in SP0499

<400> SEQUENCE: 294
agtgtgatat aatagt                                                    16

<210> SEQ ID NO 295
<211> LENGTH: 16
<212> TYPE: DNA
<213> ORGANISM: Artificial Sequence
<220> FEATURE:
<223> OTHER INFORMATION: DasR binding site in SP1011

<400> SEQUENCE: 295
actagtatag cacaat                                                    16

<210> SEQ ID NO 296
<211> LENGTH: 16
<212> TYPE: DNA
<213> ORGANISM: Artificial Sequence
<220> FEATURE:
<223> OTHER INFORMATION: DasR binding site in SPy1694

<400> SEQUENCE: 296
agtggtatat accatt                                                    16

<210> SEQ ID NO 297
<211> LENGTH: 16
<212> TYPE: DNA
<213> ORGANISM: Artificial Sequence
<220> FEATURE:
<223> OTHER INFORMATION: DasR binding site in SPy1400

<400> SEQUENCE: 297
tatggtatat accaat                                                    16

<210> SEQ ID NO 298
<211> LENGTH: 16
<212> TYPE: DNA
<213> ORGANISM: Artificial Sequence
<220> FEATURE:
<223> OTHER INFORMATION: DasR binding site in SPy1399

<400> SEQUENCE: 298
attggtatat accata                                                    16

<210> SEQ ID NO 299
<211> LENGTH: 16
<212> TYPE: DNA
<213> ORGANISM: Artificial Sequence
<220> FEATURE:
<223> OTHER INFORMATION: DasR binding site in SPy0433

<400> SEQUENCE: 299
attagcatat cccaat                                                    16
```

```
<210> SEQ ID NO 300
<211> LENGTH: 16
<212> TYPE: DNA
<213> ORGANISM: Artificial Sequence
<220> FEATURE:
<223> OTHER INFORMATION: DasR binding site in SPy1280

<400> SEQUENCE: 300
attagactat accaat                                                     16

<210> SEQ ID NO 301
<211> LENGTH: 16
<212> TYPE: DNA
<213> ORGANISM: Artificial Sequence
<220> FEATURE:
<223> OTHER INFORMATION: DasR binding site in SPy1772

<400> SEQUENCE: 301
attgtgatat aataat                                                     16

<210> SEQ ID NO 302
<211> LENGTH: 16
<212> TYPE: DNA
<213> ORGANISM: Artificial Sequence
<220> FEATURE:
<223> OTHER INFORMATION: DasR binding site in SPy0045

<400> SEQUENCE: 302
aatgatatat aataat                                                     16

<210> SEQ ID NO 303
<211> LENGTH: 16
<212> TYPE: DNA
<213> ORGANISM: Artificial Sequence
<220> FEATURE:
<223> OTHER INFORMATION: DasR binding site in SPy0593

<400> SEQUENCE: 303
aattggatat cacaat                                                     16

<210> SEQ ID NO 304
<211> LENGTH: 16
<212> TYPE: DNA
<213> ORGANISM: Artificial Sequence
<220> FEATURE:
<223> OTHER INFORMATION: DasR binding site in SPy0595

<400> SEQUENCE: 304
agtttaatat cccaat                                                     16

<210> SEQ ID NO 305
<211> LENGTH: 16
<212> TYPE: DNA
<213> ORGANISM: Artificial Sequence
<220> FEATURE:
<223> OTHER INFORMATION: DasR binding site in SPy0596

<400> SEQUENCE: 305
attgggatat taaact                                                     16

<210> SEQ ID NO 306
<211> LENGTH: 16
<212> TYPE: DNA
<213> ORGANISM: Artificial Sequence
<220> FEATURE:
<223> OTHER INFORMATION: DasR binding site in SPy2201
```

```
<400> SEQUENCE: 306
tatggaatat tacact                                                     16

<210> SEQ ID NO 307
<211> LENGTH: 16
<212> TYPE: DNA
<213> ORGANISM: Artificial Sequence
<220> FEATURE:
<223> OTHER INFORMATION: DasR binding site in SPy1744

<400> SEQUENCE: 307
acttgtatat gccaag                                                     16

<210> SEQ ID NO 308
<211> LENGTH: 16
<212> TYPE: DNA
<213> ORGANISM: Artificial Sequence
<220> FEATURE:
<223> OTHER INFORMATION: DasR binding site in SPy1026

<400> SEQUENCE: 308
actgttatat agtatt                                                     16

<210> SEQ ID NO 309
<211> LENGTH: 16
<212> TYPE: DNA
<213> ORGANISM: Artificial Sequence
<220> FEATURE:
<223> OTHER INFORMATION: DasR binding site in SPy1884

<400> SEQUENCE: 309
attgtattat aacaat                                                     16

<210> SEQ ID NO 310
<211> LENGTH: 16
<212> TYPE: DNA
<213> ORGANISM: Artificial Sequence
<220> FEATURE:
<223> OTHER INFORMATION: DasR binding site in SPy1749

<400> SEQUENCE: 310
agtggcataa cacaat                                                     16

<210> SEQ ID NO 311
<211> LENGTH: 16
<212> TYPE: DNA
<213> ORGANISM: Artificial Sequence
<220> FEATURE:
<223> OTHER INFORMATION: DasR binding site in SPy1253

<400> SEQUENCE: 311
tgttggatat tccaat                                                     16

<210> SEQ ID NO 312
<211> LENGTH: 16
<212> TYPE: DNA
<213> ORGANISM: Artificial Sequence
<220> FEATURE:
<223> OTHER INFORMATION: DasR binding site in SPy1297

<400> SEQUENCE: 312
attcggatat aacaaa                                                     16

<210> SEQ ID NO 313
```

```
<211> LENGTH: 16
<212> TYPE: DNA
<213> ORGANISM: Artificial Sequence
<220> FEATURE:
<223> OTHER INFORMATION: DasR binding site in SPy1437

<400> SEQUENCE: 313
attagtatag gctact                                                   16

<210> SEQ ID NO 314
<211> LENGTH: 16
<212> TYPE: DNA
<213> ORGANISM: Artificial Sequence
<220> FEATURE:
<223> OTHER INFORMATION: DasR binding site in SPy0830

<400> SEQUENCE: 314
attgggatat gcaaca                                                   16

<210> SEQ ID NO 315
<211> LENGTH: 16
<212> TYPE: DNA
<213> ORGANISM: Artificial Sequence
<220> FEATURE:
<223> OTHER INFORMATION: DasR binding site in SPy0539

<400> SEQUENCE: 315
aattgtatag accaac                                                   16

<210> SEQ ID NO 316
<211> LENGTH: 16
<212> TYPE: DNA
<213> ORGANISM: Artificial Sequence
<220> FEATURE:
<223> OTHER INFORMATION: DasR binding site in SPy2099

<400> SEQUENCE: 316
aatgaaatat tcaaat                                                   16

<210> SEQ ID NO 317
<211> LENGTH: 16
<212> TYPE: DNA
<213> ORGANISM: Artificial Sequence
<220> FEATURE:
<223> OTHER INFORMATION: DasR binding site in SPy2097

<400> SEQUENCE: 317
atttgaatat ttcatt                                                   16

<210> SEQ ID NO 318
<211> LENGTH: 16
<212> TYPE: DNA
<213> ORGANISM: Artificial Sequence
<220> FEATURE:
<223> OTHER INFORMATION: DasR binding site in SPy1494

<400> SEQUENCE: 318
attgtgctag accatt                                                   16

<210> SEQ ID NO 319
<211> LENGTH: 16
<212> TYPE: DNA
<213> ORGANISM: Artificial Sequence
<220> FEATURE:
<223> OTHER INFORMATION: DasR binding site in SPy1249

<400> SEQUENCE: 319
```

-continued attggaatat gataaa                                      16

<210> SEQ ID NO 320
<211> LENGTH: 16
<212> TYPE: DNA
<213> ORGANISM: Artificial Sequence
<220> FEATURE:
<223> OTHER INFORMATION: DasR binding site in SPy0338

<400> SEQUENCE: 320
aatagtatat tagatt                                      16

<210> SEQ ID NO 321
<211> LENGTH: 16
<212> TYPE: DNA
<213> ORGANISM: Artificial Sequence
<220> FEATURE:
<223> OTHER INFORMATION: DasR binding site in SPy1854

<400> SEQUENCE: 321
attggtacat gtcaat                                      16

<210> SEQ ID NO 322
<211> LENGTH: 16
<212> TYPE: DNA
<213> ORGANISM: Artificial Sequence
<220> FEATURE:
<223> OTHER INFORMATION: DasR binding site in SMU.435

<400> SEQUENCE: 322
tttggtatat accatt                                      16

<210> SEQ ID NO 323
<211> LENGTH: 16
<212> TYPE: DNA
<213> ORGANISM: Artificial Sequence
<220> FEATURE:
<223> OTHER INFORMATION: DasR binding site in SMU.284

<400> SEQUENCE: 323
attggaatac accaat                                      16

<210> SEQ ID NO 324
<211> LENGTH: 16
<212> TYPE: DNA
<213> ORGANISM: Artificial Sequence
<220> FEATURE:
<223> OTHER INFORMATION: DasR binding site in SMU.1187

<400> SEQUENCE: 324
attagactat accaat                                      16

<210> SEQ ID NO 325
<211> LENGTH: 16
<212> TYPE: DNA
<213> ORGANISM: Artificial Sequence
<220> FEATURE:
<223> OTHER INFORMATION: DasR binding site in SMU.881

<400> SEQUENCE: 325
actggtataa accaaa                                      16

<210> SEQ ID NO 326
<211> LENGTH: 16
<212> TYPE: DNA

```
<213> ORGANISM: Artificial Sequence
<220> FEATURE:
<223> OTHER INFORMATION: DasR binding site in SMU.995

<400> SEQUENCE: 326
aatgttatat tacagt                                                        16

<210> SEQ ID NO 327
<211> LENGTH: 16
<212> TYPE: DNA
<213> ORGANISM: Artificial Sequence
<220> FEATURE:
<223> OTHER INFORMATION: DasR binding site in SMU.1499

<400> SEQUENCE: 327
aatgggaaat accatt                                                        16

<210> SEQ ID NO 328
<211> LENGTH: 16
<212> TYPE: DNA
<213> ORGANISM: Artificial Sequence
<220> FEATURE:
<223> OTHER INFORMATION: DasR binding site in SMU.458

<400> SEQUENCE: 328
attggaatat aagact                                                        16

<210> SEQ ID NO 329
<211> LENGTH: 16
<212> TYPE: DNA
<213> ORGANISM: Artificial Sequence
<220> FEATURE:
<223> OTHER INFORMATION: DasR binding site in SMU.1912.c

<400> SEQUENCE: 329
attagtataa aacaat                                                        16

<210> SEQ ID NO 330
<211> LENGTH: 16
<212> TYPE: DNA
<213> ORGANISM: Artificial Sequence
<220> FEATURE:
<223> OTHER INFORMATION: DasR binding site in SMU.137

<400> SEQUENCE: 330
attgatatat ttcaat                                                        16

<210> SEQ ID NO 331
<211> LENGTH: 16
<212> TYPE: DNA
<213> ORGANISM: Artificial Sequence
<220> FEATURE:
<223> OTHER INFORMATION: DasR binding site in SMU.753

<400> SEQUENCE: 331
aatagtttat actaat                                                        16

<210> SEQ ID NO 332
<211> LENGTH: 16
<212> TYPE: DNA
<213> ORGANISM: Artificial Sequence
<220> FEATURE:
<223> OTHER INFORMATION: DasR binding site in SMU.1145c

<400> SEQUENCE: 332
agttttatat aacaat                                                        16
```

```
<210> SEQ ID NO 333
<211> LENGTH: 16
<212> TYPE: DNA
<213> ORGANISM: Artificial Sequence
<220> FEATURE:
<223> OTHER INFORMATION: DasR binding site in SMU.1204

<400> SEQUENCE: 333
tatggaatat aataat                                                       16

<210> SEQ ID NO 334
<211> LENGTH: 16
<212> TYPE: DNA
<213> ORGANISM: Artificial Sequence
<220> FEATURE:
<223> OTHER INFORMATION: DasR binding site in SMU.1349

<400> SEQUENCE: 334
aatagtttat actact                                                       16

<210> SEQ ID NO 335
<211> LENGTH: 16
<212> TYPE: DNA
<213> ORGANISM: Artificial Sequence
<220> FEATURE:
<223> OTHER INFORMATION: DasR binding site in SMU.1348c

<400> SEQUENCE: 335
agtagtataa actatt                                                       16

<210> SEQ ID NO 336
<211> LENGTH: 16
<212> TYPE: DNA
<213> ORGANISM: Artificial Sequence
<220> FEATURE:
<223> OTHER INFORMATION: DasR binding site in SMU.1138

<400> SEQUENCE: 336
attgatatag aacagt                                                       16

<210> SEQ ID NO 337
<211> LENGTH: 16
<212> TYPE: DNA
<213> ORGANISM: Artificial Sequence
<220> FEATURE:
<223> OTHER INFORMATION: DasR binding site in SMU.1539

<400> SEQUENCE: 337
ggtggaatag tccaat                                                       16

<210> SEQ ID NO 338
<211> LENGTH: 16
<212> TYPE: DNA
<213> ORGANISM: Artificial Sequence
<220> FEATURE:
<223> OTHER INFORMATION: DasR binding site in SMU.166

<400> SEQUENCE: 338
tgtggcctat gccaat                                                       16

<210> SEQ ID NO 339
<211> LENGTH: 16
<212> TYPE: DNA
<213> ORGANISM: Artificial Sequence
<220> FEATURE:
```

<223> OTHER INFORMATION: DasR binding site in SMU.878

<400> SEQUENCE: 339
aatggtataa aaaaat                                                    16

<210> SEQ ID NO 340
<211> LENGTH: 16
<212> TYPE: DNA
<213> ORGANISM: Artificial Sequence
<220> FEATURE:
<223> OTHER INFORMATION: DasR binding site in SMU.14

<400> SEQUENCE: 340
attagaatat ggcagt                                                    16

<210> SEQ ID NO 341
<211> LENGTH: 16
<212> TYPE: DNA
<213> ORGANISM: Artificial Sequence
<220> FEATURE:
<223> OTHER INFORMATION: DasR binding site in SMU.1908c

<400> SEQUENCE: 341
attagaatat acctct                                                    16

<210> SEQ ID NO 342
<211> LENGTH: 16
<212> TYPE: DNA
<213> ORGANISM: Artificial Sequence
<220> FEATURE:
<223> OTHER INFORMATION: DasR binding site in SMU.1764c

<400> SEQUENCE: 342
attggtatat taaaaa                                                    16

<210> SEQ ID NO 343
<211> LENGTH: 16
<212> TYPE: DNA
<213> ORGANISM: Artificial Sequence
<220> FEATURE:
<223> OTHER INFORMATION: DasR binding site in SMU.2162c

<400> SEQUENCE: 343
aaaggtataa accatt                                                    16

<210> SEQ ID NO 344
<211> LENGTH: 16
<212> TYPE: DNA
<213> ORGANISM: Artificial Sequence
<220> FEATURE:
<223> OTHER INFORMATION: DasR binding site in SMU.2157

<400> SEQUENCE: 344
tttagaatag accatt                                                    16

<210> SEQ ID NO 345
<211> LENGTH: 16
<212> TYPE: DNA
<213> ORGANISM: Artificial Sequence
<220> FEATURE:
<223> OTHER INFORMATION: DasR binding site in SMU.1460

<400> SEQUENCE: 345
aatttgatat tccagt                                                    16

-continued

```
<210> SEQ ID NO 346
<211> LENGTH: 16
<212> TYPE: DNA
<213> ORGANISM: Artificial Sequence
<220> FEATURE:
<223> OTHER INFORMATION: DasR binding site in SMU.624

<400> SEQUENCE: 346
tttattatat actatt                                                        16

<210> SEQ ID NO 347
<211> LENGTH: 16
<212> TYPE: DNA
<213> ORGANISM: Artificial Sequence
<220> FEATURE:
<223> OTHER INFORMATION: DasR binding site in SMU.623c

<400> SEQUENCE: 347
aatagtatat aataaa                                                        16

<210> SEQ ID NO 348
<211> LENGTH: 16
<212> TYPE: DNA
<213> ORGANISM: Artificial Sequence
<220> FEATURE:
<223> OTHER INFORMATION: DasR binding site in SMU.40

<400> SEQUENCE: 348
aatagcttat actaat                                                        16

<210> SEQ ID NO 349
<211> LENGTH: 16
<212> TYPE: DNA
<213> ORGANISM: Artificial Sequence
<220> FEATURE:
<223> OTHER INFORMATION: DasR binding site in SMU.1815

<400> SEQUENCE: 349
agtgttatat gctata                                                        16

<210> SEQ ID NO 350
<211> LENGTH: 16
<212> TYPE: DNA
<213> ORGANISM: Artificial Sequence
<220> FEATURE:
<223> OTHER INFORMATION: DasR binding site in SMU.989

<400> SEQUENCE: 350
tgtggtttat accaca                                                        16

<210> SEQ ID NO 351
<211> LENGTH: 16
<212> TYPE: DNA
<213> ORGANISM: Artificial Sequence
<220> FEATURE:
<223> OTHER INFORMATION: DasR binding site in SAG0799

<400> SEQUENCE: 351
attggtatat accata                                                        16

<210> SEQ ID NO 352
<211> LENGTH: 16
<212> TYPE: DNA
<213> ORGANISM: Artificial Sequence
<220> FEATURE:
<223> OTHER INFORMATION: DasR binding site in SAG0698
```

```
<400> SEQUENCE: 352
aatggaatat actaat                                                16

<210> SEQ ID NO 353
<211> LENGTH: 16
<212> TYPE: DNA
<213> ORGANISM: Artificial Sequence
<220> FEATURE:
<223> OTHER INFORMATION: DasR binding site in SAG0266

<400> SEQUENCE: 353
ataggtatat accatt                                                16

<210> SEQ ID NO 354
<211> LENGTH: 16
<212> TYPE: DNA
<213> ORGANISM: Artificial Sequence
<220> FEATURE:
<223> OTHER INFORMATION: DasR binding site in SAG0943

<400> SEQUENCE: 354
attggtatat attaat                                                16

<210> SEQ ID NO 355
<211> LENGTH: 16
<212> TYPE: DNA
<213> ORGANISM: Artificial Sequence
<220> FEATURE:
<223> OTHER INFORMATION: DasR binding site in SAG0944

<400> SEQUENCE: 355
attaatatat accaat                                                16

<210> SEQ ID NO 356
<211> LENGTH: 16
<212> TYPE: DNA
<213> ORGANISM: Artificial Sequence
<220> FEATURE:
<223> OTHER INFORMATION: DasR binding site in SAG1779

<400> SEQUENCE: 356
agtggtataa tccagt                                                16

<210> SEQ ID NO 357
<211> LENGTH: 16
<212> TYPE: DNA
<213> ORGANISM: Artificial Sequence
<220> FEATURE:
<223> OTHER INFORMATION: DasR binding site in SAG1033

<400> SEQUENCE: 357
attggtatat attatt                                                16

<210> SEQ ID NO 358
<211> LENGTH: 16
<212> TYPE: DNA
<213> ORGANISM: Artificial Sequence
<220> FEATURE:
<223> OTHER INFORMATION: DasR binding site in SAG2003

<400> SEQUENCE: 358
attggaatat ccgatt                                                16

<210> SEQ ID NO 359
<211> LENGTH: 16
```

-continued

```
<212> TYPE: DNA
<213> ORGANISM: Artificial Sequence
<220> FEATURE:
<223> OTHER INFORMATION: DasR binding site in SAG2008

<400> SEQUENCE: 359
aatggtatat cacaag                                                    16

<210> SEQ ID NO 360
<211> LENGTH: 16
<212> TYPE: DNA
<213> ORGANISM: Artificial Sequence
<220> FEATURE:
<223> OTHER INFORMATION: DasR binding site in SAG2170

<400> SEQUENCE: 360
tctattatat accaat                                                    16

<210> SEQ ID NO 361
<211> LENGTH: 16
<212> TYPE: DNA
<213> ORGANISM: Artificial Sequence
<220> FEATURE:
<223> OTHER INFORMATION: DasR binding site in SAG2169

<400> SEQUENCE: 361
attggtatat aataga                                                    16

<210> SEQ ID NO 362
<211> LENGTH: 16
<212> TYPE: DNA
<213> ORGANISM: Artificial Sequence
<220> FEATURE:
<223> OTHER INFORMATION: DasR binding site in SAG1186

<400> SEQUENCE: 362
aatatgatat actaat                                                    16

<210> SEQ ID NO 363
<211> LENGTH: 16
<212> TYPE: DNA
<213> ORGANISM: Artificial Sequence
<220> FEATURE:
<223> OTHER INFORMATION: DasR binding site in SAG0699

<400> SEQUENCE: 363
cttggaatat tccata                                                    16

<210> SEQ ID NO 364
<211> LENGTH: 16
<212> TYPE: DNA
<213> ORGANISM: Artificial Sequence
<220> FEATURE:
<223> OTHER INFORMATION: DasR binding site in SAG1951

<400> SEQUENCE: 364
agtagaatag tccatt                                                    16

<210> SEQ ID NO 365
<211> LENGTH: 16
<212> TYPE: DNA
<213> ORGANISM: Artificial Sequence
<220> FEATURE:
<223> OTHER INFORMATION: DasR binding site in SAG0164

<400> SEQUENCE: 365
```

-continued agtggaatag acaagt                                                        16

<210> SEQ ID NO 366
<211> LENGTH: 16
<212> TYPE: DNA
<213> ORGANISM: Artificial Sequence
<220> FEATURE:
<223> OTHER INFORMATION: DasR binding site in SAG1307

<400> SEQUENCE: 366
agtggtataa tccagg                                                        16

<210> SEQ ID NO 367
<211> LENGTH: 16
<212> TYPE: DNA
<213> ORGANISM: Artificial Sequence
<220> FEATURE:
<223> OTHER INFORMATION: DasR binding site in SAG0277

<400> SEQUENCE: 367
attgggctat gcgaat                                                        16

<210> SEQ ID NO 368
<211> LENGTH: 16
<212> TYPE: DNA
<213> ORGANISM: Artificial Sequence
<220> FEATURE:
<223> OTHER INFORMATION: DasR binding site in SAG0021

<400> SEQUENCE: 368
attaggataa actaat                                                        16

<210> SEQ ID NO 369
<211> LENGTH: 16
<212> TYPE: DNA
<213> ORGANISM: Artificial Sequence
<220> FEATURE:
<223> OTHER INFORMATION: DasR binding site in SAG0626

<400> SEQUENCE: 369
acttgaatat cctaat                                                        16

<210> SEQ ID NO 370
<211> LENGTH: 16
<212> TYPE: DNA
<213> ORGANISM: Artificial Sequence
<220> FEATURE:
<223> OTHER INFORMATION: DasR binding site in SAG1161

<400> SEQUENCE: 370
tatagtatat agcatt                                                        16

<210> SEQ ID NO 371
<211> LENGTH: 16
<212> TYPE: DNA
<213> ORGANISM: Artificial Sequence
<220> FEATURE:
<223> OTHER INFORMATION: DasR binding site in SAG1736

<400> SEQUENCE: 371
attttaatat aacaat                                                        16

<210> SEQ ID NO 372
<211> LENGTH: 16
<212> TYPE: DNA
<213> ORGANISM: Artificial Sequence

```
<220> FEATURE:
<223> OTHER INFORMATION: DasR binding site in SAG1571

<400> SEQUENCE: 372
agttgaatat gctaat                                                         16

<210> SEQ ID NO 373
<211> LENGTH: 16
<212> TYPE: DNA
<213> ORGANISM: Artificial Sequence
<220> FEATURE:
<223> OTHER INFORMATION: DasR binding site in SAG1711

<400> SEQUENCE: 373
attggtattt acgagt                                                         16

<210> SEQ ID NO 374
<211> LENGTH: 16
<212> TYPE: DNA
<213> ORGANISM: Artificial Sequence
<220> FEATURE:
<223> OTHER INFORMATION: DasR binding site in SAG0670

<400> SEQUENCE: 374
aatggaatat tttatt                                                         16

<210> SEQ ID NO 375
<211> LENGTH: 16
<212> TYPE: DNA
<213> ORGANISM: Artificial Sequence
<220> FEATURE:
<223> OTHER INFORMATION: DasR binding site in SAG1260

<400> SEQUENCE: 375
catgggatat tcaaat                                                         16

<210> SEQ ID NO 376
<211> LENGTH: 16
<212> TYPE: DNA
<213> ORGANISM: Artificial Sequence
<220> FEATURE:
<223> OTHER INFORMATION: DasR binding site in SAG0278

<400> SEQUENCE: 376
gttggaatat cgcatt                                                         16

<210> SEQ ID NO 377
<211> LENGTH: 16
<212> TYPE: DNA
<213> ORGANISM: Artificial Sequence
<220> FEATURE:
<223> OTHER INFORMATION: DasR binding site in SAG0231

<400> SEQUENCE: 377
attggcttat tcaaat                                                         16

<210> SEQ ID NO 378
<211> LENGTH: 16
<212> TYPE: DNA
<213> ORGANISM: Artificial Sequence
<220> FEATURE:
<223> OTHER INFORMATION: DasR binding site in SAG1051

<400> SEQUENCE: 378
aatgatatat gcaact                                                         16
```

<210> SEQ ID NO 379
<211> LENGTH: 16
<212> TYPE: DNA
<213> ORGANISM: Artificial Sequence
<220> FEATURE:
<223> OTHER INFORMATION: DasR binding site in SAG1569

<400> SEQUENCE: 379
attgtcatat aacacc                                                        16

<210> SEQ ID NO 380
<211> LENGTH: 16
<212> TYPE: DNA
<213> ORGANISM: Artificial Sequence
<220> FEATURE:
<223> OTHER INFORMATION: DasR binding site in SAG1683

<400> SEQUENCE: 380
attagtatat gtcaaa                                                        16

<210> SEQ ID NO 381
<211> LENGTH: 16
<212> TYPE: DNA
<213> ORGANISM: Artificial Sequence
<220> FEATURE:
<223> OTHER INFORMATION: DasR binding site in SAG1982

<400> SEQUENCE: 381
agtacaatat aacaat                                                        16

<210> SEQ ID NO 382
<211> LENGTH: 16
<212> TYPE: DNA
<213> ORGANISM: Artificial Sequence
<220> FEATURE:
<223> OTHER INFORMATION: DasR binding site in lin1996

<400> SEQUENCE: 382
attggtctat atcaat                                                        16

<210> SEQ ID NO 383
<211> LENGTH: 16
<212> TYPE: DNA
<213> ORGANISM: Artificial Sequence
<220> FEATURE:
<223> OTHER INFORMATION: DasR binding site in lin0955

<400> SEQUENCE: 383
attggtatag accgat                                                        16

<210> SEQ ID NO 384
<211> LENGTH: 16
<212> TYPE: DNA
<213> ORGANISM: Artificial Sequence
<220> FEATURE:
<223> OTHER INFORMATION: DasR binding site in lin1316

<400> SEQUENCE: 384
aatggtctag acaaat                                                        16

<210> SEQ ID NO 385
<211> LENGTH: 16
<212> TYPE: DNA
<213> ORGANISM: Artificial Sequence
<220> FEATURE:
<223> OTHER INFORMATION: DasR binding site in lin1223

-continued

```
<400> SEQUENCE: 385
acttgtatat acaagt                                                        16

<210> SEQ ID NO 386
<211> LENGTH: 16
<212> TYPE: DNA
<213> ORGANISM: Artificial Sequence
<220> FEATURE:
<223> OTHER INFORMATION: DasR binding site in lin1224

<400> SEQUENCE: 386
acttgtatat acaagt                                                        16

<210> SEQ ID NO 387
<211> LENGTH: 16
<212> TYPE: DNA
<213> ORGANISM: Artificial Sequence
<220> FEATURE:
<223> OTHER INFORMATION: DasR binding site in lin0296

<400> SEQUENCE: 387
actggtataa acaagt                                                        16

<210> SEQ ID NO 388
<211> LENGTH: 16
<212> TYPE: DNA
<213> ORGANISM: Artificial Sequence
<220> FEATURE:
<223> OTHER INFORMATION: DasR binding site in lin0780

<400> SEQUENCE: 388
aactgtctag accaat                                                        16

<210> SEQ ID NO 389
<211> LENGTH: 16
<212> TYPE: DNA
<213> ORGANISM: Artificial Sequence
<220> FEATURE:
<223> OTHER INFORMATION: DasR binding site in lin2570

<400> SEQUENCE: 389
attggtataa agcagt                                                        16

<210> SEQ ID NO 390
<211> LENGTH: 16
<212> TYPE: DNA
<213> ORGANISM: Artificial Sequence
<220> FEATURE:
<223> OTHER INFORMATION: DasR binding site in lin1779

<400> SEQUENCE: 390
atcggtttat accggt                                                        16

<210> SEQ ID NO 391
<211> LENGTH: 16
<212> TYPE: DNA
<213> ORGANISM: Artificial Sequence
<220> FEATURE:
<223> OTHER INFORMATION: DasR binding site in lin0825

<400> SEQUENCE: 391
ttttgtatag accaat                                                        16

<210> SEQ ID NO 392
```

```
<211> LENGTH: 16
<212> TYPE: DNA
<213> ORGANISM: Artificial Sequence
<220> FEATURE:
<223> OTHER INFORMATION: DasR binding site in lin1606

<400> SEQUENCE: 392
acaagtatag accaat                                                         16

<210> SEQ ID NO 393
<211> LENGTH: 16
<212> TYPE: DNA
<213> ORGANISM: Artificial Sequence
<220> FEATURE:
<223> OTHER INFORMATION: DasR binding site in lin1648

<400> SEQUENCE: 393
atttgtctat aataat                                                         16

<210> SEQ ID NO 394
<211> LENGTH: 16
<212> TYPE: DNA
<213> ORGANISM: Artificial Sequence
<220> FEATURE:
<223> OTHER INFORMATION: DasR binding site in lin1443

<400> SEQUENCE: 394
actgttttat acaaat                                                         16

<210> SEQ ID NO 395
<211> LENGTH: 16
<212> TYPE: DNA
<213> ORGANISM: Artificial Sequence
<220> FEATURE:
<223> OTHER INFORMATION: DasR binding site in lin1641

<400> SEQUENCE: 395
aatggtcaat acaaat                                                         16

<210> SEQ ID NO 396
<211> LENGTH: 16
<212> TYPE: DNA
<213> ORGANISM: Artificial Sequence
<220> FEATURE:
<223> OTHER INFORMATION: DasR binding site in lin1069

<400> SEQUENCE: 396
agtggtctat ataatt                                                         16

<210> SEQ ID NO 397
<211> LENGTH: 16
<212> TYPE: DNA
<213> ORGANISM: Artificial Sequence
<220> FEATURE:
<223> OTHER INFORMATION: DasR binding site in lin1328

<400> SEQUENCE: 397
atcggtatat acttgt                                                         16

<210> SEQ ID NO 398
<211> LENGTH: 16
<212> TYPE: DNA
<213> ORGANISM: Artificial Sequence
<220> FEATURE:
<223> OTHER INFORMATION: DasR binding site in lin0432

<400> SEQUENCE: 398
```

```
aatggtttat atcact                                                   16

<210> SEQ ID NO 399
<211> LENGTH: 16
<212> TYPE: DNA
<213> ORGANISM: Artificial Sequence
<220> FEATURE:
<223> OTHER INFORMATION: DasR binding site in lin0169

<400> SEQUENCE: 399
aatgctttat acaaat                                                   16

<210> SEQ ID NO 400
<211> LENGTH: 16
<212> TYPE: DNA
<213> ORGANISM: Artificial Sequence
<220> FEATURE:
<223> OTHER INFORMATION: DasR binding site in lin0406

<400> SEQUENCE: 400
aatggaatac accaat                                                   16

<210> SEQ ID NO 401
<211> LENGTH: 16
<212> TYPE: DNA
<213> ORGANISM: Artificial Sequence
<220> FEATURE:
<223> OTHER INFORMATION: DasR binding site in lin1754

<400> SEQUENCE: 401
acagatctag accagt                                                   16

<210> SEQ ID NO 402
<211> LENGTH: 16
<212> TYPE: DNA
<213> ORGANISM: Artificial Sequence
<220> FEATURE:
<223> OTHER INFORMATION: DasR binding site in lin1243

<400> SEQUENCE: 402
acagatctag accagt                                                   16

<210> SEQ ID NO 403
<211> LENGTH: 16
<212> TYPE: DNA
<213> ORGANISM: Artificial Sequence
<220> FEATURE:
<223> OTHER INFORMATION: DasR binding site in lin1990

<400> SEQUENCE: 403
attggtgtag atccgt                                                   16

<210> SEQ ID NO 404
<211> LENGTH: 16
<212> TYPE: DNA
<213> ORGANISM: Artificial Sequence
<220> FEATURE:
<223> OTHER INFORMATION: DasR binding site in lin2737

<400> SEQUENCE: 404
actggtatat atagct                                                   16

<210> SEQ ID NO 405
<211> LENGTH: 16
<212> TYPE: DNA
```

```
<213> ORGANISM: Artificial Sequence
<220> FEATURE:
<223> OTHER INFORMATION: DasR binding site in lin2738

<400> SEQUENCE: 405
agctatatat accagt                                                        16

<210> SEQ ID NO 406
<211> LENGTH: 16
<212> TYPE: DNA
<213> ORGANISM: Artificial Sequence
<220> FEATURE:
<223> OTHER INFORMATION: DasR binding site in lin2295

<400> SEQUENCE: 406
attagtatat agaatt                                                        16

<210> SEQ ID NO 407
<211> LENGTH: 16
<212> TYPE: DNA
<213> ORGANISM: Artificial Sequence
<220> FEATURE:
<223> OTHER INFORMATION: DasR binding site in lmo1883

<400> SEQUENCE: 407
attggtctat atcaat                                                        16

<210> SEQ ID NO 408
<211> LENGTH: 16
<212> TYPE: DNA
<213> ORGANISM: Artificial Sequence
<220> FEATURE:
<223> OTHER INFORMATION: DasR binding site in lmo0956

<400> SEQUENCE: 408
attggtatag accgat                                                        16

<210> SEQ ID NO 409
<211> LENGTH: 16
<212> TYPE: DNA
<213> ORGANISM: Artificial Sequence
<220> FEATURE:
<223> OTHER INFORMATION: DasR binding site in lmo0270

<400> SEQUENCE: 409
attggtataa acaagt                                                        16

<210> SEQ ID NO 410
<211> LENGTH: 16
<212> TYPE: DNA
<213> ORGANISM: Artificial Sequence
<220> FEATURE:
<223> OTHER INFORMATION: DasR binding site in lmo1255

<400> SEQUENCE: 410
acttgtatat acaagt                                                        16

<210> SEQ ID NO 411
<211> LENGTH: 16
<212> TYPE: DNA
<213> ORGANISM: Artificial Sequence
<220> FEATURE:
<223> OTHER INFORMATION: DasR binding site in lmo1256

<400> SEQUENCE: 411
acttgtatat acaagt                                                        16
```

<210> SEQ ID NO 412
<211> LENGTH: 16
<212> TYPE: DNA
<213> ORGANISM: Artificial Sequence
<220> FEATURE:
<223> OTHER INFORMATION: DasR binding site in lmo1393

<400> SEQUENCE: 412
acttgtatat aacaat                                                     16

<210> SEQ ID NO 413
<211> LENGTH: 16
<212> TYPE: DNA
<213> ORGANISM: Artificial Sequence
<220> FEATURE:
<223> OTHER INFORMATION: DasR binding site in lmo1277

<400> SEQUENCE: 413
aatggtctag acagat                                                     16

<210> SEQ ID NO 414
<211> LENGTH: 16
<212> TYPE: DNA
<213> ORGANISM: Artificial Sequence
<220> FEATURE:
<223> OTHER INFORMATION: DasR binding site in lmo0830

<400> SEQUENCE: 414
ttttgtatag accaat                                                     16

<210> SEQ ID NO 415
<211> LENGTH: 16
<212> TYPE: DNA
<213> ORGANISM: Artificial Sequence
<220> FEATURE:
<223> OTHER INFORMATION: DasR binding site in lmo1571

<400> SEQUENCE: 415
acaagtatag accaat                                                     16

<210> SEQ ID NO 416
<211> LENGTH: 16
<212> TYPE: DNA
<213> ORGANISM: Artificial Sequence
<220> FEATURE:
<223> OTHER INFORMATION: DasR binding site in lmo1607

<400> SEQUENCE: 416
atttgtctat aataat                                                     16

<210> SEQ ID NO 417
<211> LENGTH: 16
<212> TYPE: DNA
<213> ORGANISM: Artificial Sequence
<220> FEATURE:
<223> OTHER INFORMATION: DasR binding site in lmo1289

<400> SEQUENCE: 417
attggtatat accgga                                                     16

<210> SEQ ID NO 418
<211> LENGTH: 16
<212> TYPE: DNA
<213> ORGANISM: Artificial Sequence
<220> FEATURE:

<223> OTHER INFORMATION: DasR binding site in lmo1139

<400> SEQUENCE: 418
attcgtatag aaaaat                                                         16

<210> SEQ ID NO 419
<211> LENGTH: 16
<212> TYPE: DNA
<213> ORGANISM: Artificial Sequence
<220> FEATURE:
<223> OTHER INFORMATION: DasR binding site in lmo2445

<400> SEQUENCE: 419
aactgtatat atcaat                                                         16

<210> SEQ ID NO 420
<211> LENGTH: 16
<212> TYPE: DNA
<213> ORGANISM: Artificial Sequence
<220> FEATURE:
<223> OTHER INFORMATION: DasR binding site in lmo1351

<400> SEQUENCE: 420
aggggtctac acaagt                                                         16

<210> SEQ ID NO 421
<211> LENGTH: 16
<212> TYPE: DNA
<213> ORGANISM: Artificial Sequence
<220> FEATURE:
<223> OTHER INFORMATION: DasR binding site in lmo2691

<400> SEQUENCE: 421
atttgtcgat atcaat                                                         16

<210> SEQ ID NO 422
<211> LENGTH: 16
<212> TYPE: DNA
<213> ORGANISM: Artificial Sequence
<220> FEATURE:
<223> OTHER INFORMATION: DasR binding site in lmo2748

<400> SEQUENCE: 422
attggtataa attatt                                                         16

<210> SEQ ID NO 423
<211> LENGTH: 16
<212> TYPE: DNA
<213> ORGANISM: Artificial Sequence
<220> FEATURE:
<223> OTHER INFORMATION: DasR binding site in lmo0475

<400> SEQUENCE: 423
actcgtatat ccaaat                                                         16

<210> SEQ ID NO 424
<211> LENGTH: 16
<212> TYPE: DNA
<213> ORGANISM: Artificial Sequence
<220> FEATURE:
<223> OTHER INFORMATION: DasR binding site in lmo0787

<400> SEQUENCE: 424
aactatctag accaat                                                         16

-continued

```
<210> SEQ ID NO 425
<211> LENGTH: 16
<212> TYPE: DNA
<213> ORGANISM: Artificial Sequence
<220> FEATURE:
<223> OTHER INFORMATION: DasR binding site in lmo2110

<400> SEQUENCE: 425
attagtatat actttt                                                     16

<210> SEQ ID NO 426
<211> LENGTH: 16
<212> TYPE: DNA
<213> ORGANISM: Artificial Sequence
<220> FEATURE:
<223> OTHER INFORMATION: DasR binding site in lmo1600

<400> SEQUENCE: 426
aatggttaat acaaat                                                     16

<210> SEQ ID NO 427
<211> LENGTH: 16
<212> TYPE: DNA
<213> ORGANISM: Artificial Sequence
<220> FEATURE:
<223> OTHER INFORMATION: DasR binding site in lmo0969

<400> SEQUENCE: 427
atttctgtag accatt                                                     16

<210> SEQ ID NO 428
<211> LENGTH: 16
<212> TYPE: DNA
<213> ORGANISM: Artificial Sequence
<220> FEATURE:
<223> OTHER INFORMATION: DasR binding site in lmo0792

<400> SEQUENCE: 428
atgggaatac accaat                                                     16

<210> SEQ ID NO 429
<211> LENGTH: 16
<212> TYPE: DNA
<213> ORGANISM: Artificial Sequence
<220> FEATURE:
<223> OTHER INFORMATION: DasR binding site in lmo1125

<400> SEQUENCE: 429
atcagtatac acaatt                                                     16

<210> SEQ ID NO 430
<211> LENGTH: 16
<212> TYPE: DNA
<213> ORGANISM: Artificial Sequence
<220> FEATURE:
<223> OTHER INFORMATION: DasR binding site in lmo2336

<400> SEQUENCE: 430
aatgatttat acaatt                                                     16

<210> SEQ ID NO 431
<211> LENGTH: 16
<212> TYPE: DNA
<213> ORGANISM: Artificial Sequence
<220> FEATURE:
<223> OTHER INFORMATION: DasR binding site in lmo1219
```

<400> SEQUENCE: 431
acttgtttaa accgtt                                                             16

<210> SEQ ID NO 432
<211> LENGTH: 16
<212> TYPE: DNA
<213> ORGANISM: Artificial Sequence
<220> FEATURE:
<223> OTHER INFORMATION: DasR binding site in Tfu_1418 and Tfu_1417c

<400> SEQUENCE: 432
agtggtctag acctat                                                             16

<210> SEQ ID NO 433
<211> LENGTH: 16
<212> TYPE: DNA
<213> ORGANISM: Artificial Sequence
<220> FEATURE:
<223> OTHER INFORMATION: DasR binding site in Tfu_3010 and Tfu_3009c

<400> SEQUENCE: 433
tgtggtctag accttt                                                             16

<210> SEQ ID NO 434
<211> LENGTH: 16
<212> TYPE: DNA
<213> ORGANISM: Artificial Sequence
<220> FEATURE:
<223> OTHER INFORMATION: DasR binding site in Tfu_0555 and Tfu_0554c

<400> SEQUENCE: 434
actggtctag tccaat                                                             16

<210> SEQ ID NO 435
<211> LENGTH: 16
<212> TYPE: DNA
<213> ORGANISM: Artificial Sequence
<220> FEATURE:
<223> OTHER INFORMATION: DasR binding site in Tfu_0643 and Tfu_0642c

<400> SEQUENCE: 435
acgggtctag accact                                                             16

<210> SEQ ID NO 436
<211> LENGTH: 16
<212> TYPE: DNA
<213> ORGANISM: Artificial Sequence
<220> FEATURE:
<223> OTHER INFORMATION: DasR binding site in Tfu_0136c

<400> SEQUENCE: 436
agtggcgtag accagg                                                             16

<210> SEQ ID NO 437
<211> LENGTH: 16
<212> TYPE: DNA
<213> ORGANISM: Artificial Sequence
<220> FEATURE:
<223> OTHER INFORMATION: DasR binding site in Tfu_2555 and Tfu_2554c

<400> SEQUENCE: 437
attggtctac tccact                                                             16

<210> SEQ ID NO 438
<211> LENGTH: 16

```
<212> TYPE: DNA
<213> ORGANISM: Artificial Sequence
<220> FEATURE:
<223> OTHER INFORMATION: DasR binding site in Tfu_2290

<400> SEQUENCE: 438
gctggtctgc accacg                                                    16

<210> SEQ ID NO 439
<211> LENGTH: 16
<212> TYPE: DNA
<213> ORGANISM: Artificial Sequence
<220> FEATURE:
<223> OTHER INFORMATION: DasR binding site in Tfu_1037

<400> SEQUENCE: 439
tatggtctag accata                                                    16

<210> SEQ ID NO 440
<211> LENGTH: 16
<212> TYPE: DNA
<213> ORGANISM: Artificial Sequence
<220> FEATURE:
<223> OTHER INFORMATION: DasR binding site in Tfu_0083

<400> SEQUENCE: 440
aatggtctag tccata                                                    16

<210> SEQ ID NO 441
<211> LENGTH: 16
<212> TYPE: DNA
<213> ORGANISM: Artificial Sequence
<220> FEATURE:
<223> OTHER INFORMATION: DasR binding site in Tfu_0083

<400> SEQUENCE: 441
aaaggtctag tccaag                                                    16

<210> SEQ ID NO 442
<211> LENGTH: 16
<212> TYPE: DNA
<213> ORGANISM: Artificial Sequence
<220> FEATURE:
<223> OTHER INFORMATION: DasR binding site in Tfu_0262c

<400> SEQUENCE: 442
tgtggtgtcg accagc                                                    16

<210> SEQ ID NO 443
<211> LENGTH: 16
<212> TYPE: DNA
<213> ORGANISM: Artificial Sequence
<220> FEATURE:
<223> OTHER INFORMATION: DasR binding site in Tfu_2611

<400> SEQUENCE: 443
actggtctat accgct                                                    16

<210> SEQ ID NO 444
<211> LENGTH: 16
<212> TYPE: DNA
<213> ORGANISM: Artificial Sequence
<220> FEATURE:
<223> OTHER INFORMATION: DasR binding site in Tfu_2017c

<400> SEQUENCE: 444
```
aaaggtatag accatt                                          16

<210> SEQ ID NO 445
<211> LENGTH: 16
<212> TYPE: DNA
<213> ORGANISM: Artificial Sequence
<220> FEATURE:
<223> OTHER INFORMATION: DasR binding site in Tfu_1774c

<400> SEQUENCE: 445
taaggtctat acctct                                          16

<210> SEQ ID NO 446
<211> LENGTH: 16
<212> TYPE: DNA
<213> ORGANISM: Artificial Sequence
<220> FEATURE:
<223> OTHER INFORMATION: DasR binding site in Tfu_1202

<400> SEQUENCE: 446
gcaggtctac accctc                                          16

<210> SEQ ID NO 447
<211> LENGTH: 16
<212> TYPE: DNA
<213> ORGANISM: Artificial Sequence
<220> FEATURE:
<223> OTHER INFORMATION: DasR binding site in Tfu_2362c

<400> SEQUENCE: 447
ccaggtgtac accagt                                          16

<210> SEQ ID NO 448
<211> LENGTH: 16
<212> TYPE: DNA
<213> ORGANISM: Artificial Sequence
<220> FEATURE:
<223> OTHER INFORMATION: DasR binding site in Tfu_2741

<400> SEQUENCE: 448
aggggtgtac tccaca                                          16

<210> SEQ ID NO 449
<211> LENGTH: 16
<212> TYPE: DNA
<213> ORGANISM: Artificial Sequence
<220> FEATURE:
<223> OTHER INFORMATION: DasR binding site in Tfu_2234c

<400> SEQUENCE: 449
tgtggtgtcg accatc                                          16

<210> SEQ ID NO 450
<211> LENGTH: 16
<212> TYPE: DNA
<213> ORGANISM: Artificial Sequence
<220> FEATURE:
<223> OTHER INFORMATION: DasR binding site in Tfu_0614

<400> SEQUENCE: 450
ggtggtccac accaat                                          16

<210> SEQ ID NO 451
<211> LENGTH: 16
<212> TYPE: DNA
<213> ORGANISM: Artificial Sequence

```
<220> FEATURE:
<223> OTHER INFORMATION: DasR binding site in Tfu_2626c

<400> SEQUENCE: 451
attggtgtgg accacc                                                    16

<210> SEQ ID NO 452
<211> LENGTH: 16
<212> TYPE: DNA
<213> ORGANISM: Artificial Sequence
<220> FEATURE:
<223> OTHER INFORMATION: DasR binding site in Tfu_1104

<400> SEQUENCE: 452
actggaccgc accact                                                    16

<210> SEQ ID NO 453
<211> LENGTH: 16
<212> TYPE: DNA
<213> ORGANISM: Artificial Sequence
<220> FEATURE:
<223> OTHER INFORMATION: DasR binding site in Tfu_1818

<400> SEQUENCE: 453
cgtggtgtac acctac                                                    16

<210> SEQ ID NO 454
<211> LENGTH: 16
<212> TYPE: DNA
<213> ORGANISM: Artificial Sequence
<220> FEATURE:
<223> OTHER INFORMATION: DasR binding site in Tfu_2283

<400> SEQUENCE: 454
gctggcgcag accaca                                                    16

<210> SEQ ID NO 455
<211> LENGTH: 16
<212> TYPE: DNA
<213> ORGANISM: Artificial Sequence
<220> FEATURE:
<223> OTHER INFORMATION: DasR binding site in Tfu_0863

<400> SEQUENCE: 455
agtggtctaa atctct                                                    16

<210> SEQ ID NO 456
<211> LENGTH: 16
<212> TYPE: DNA
<213> ORGANISM: Artificial Sequence
<220> FEATURE:
<223> OTHER INFORMATION: DasR binding site in Tfu_0863

<400> SEQUENCE: 456
attggtttat accatt                                                    16

<210> SEQ ID NO 457
<211> LENGTH: 16
<212> TYPE: DNA
<213> ORGANISM: Artificial Sequence
<220> FEATURE:
<223> OTHER INFORMATION: DasR binding site in Tfu_1179

<400> SEQUENCE: 457
cttggtttag accaat                                                    16
```

```
<210> SEQ ID NO 458
<211> LENGTH: 16
<212> TYPE: DNA
<213> ORGANISM: Artificial Sequence
<220> FEATURE:
<223> OTHER INFORMATION: DasR binding site in Tfu_0697 and Tfu_0696c

<400> SEQUENCE: 458
aaaggtctaa accaat                                                         16

<210> SEQ ID NO 459
<211> LENGTH: 16
<212> TYPE: DNA
<213> ORGANISM: Artificial Sequence
<220> FEATURE:
<223> OTHER INFORMATION: DasR binding site in Tfu_0433

<400> SEQUENCE: 459
actggcctag tccacc                                                         16

<210> SEQ ID NO 460
<211> LENGTH: 16
<212> TYPE: DNA
<213> ORGANISM: Artificial Sequence
<220> FEATURE:
<223> OTHER INFORMATION: DasR binding site in Tfu_2911c

<400> SEQUENCE: 460
aatggtctac gccaat                                                         16

<210> SEQ ID NO 461
<211> LENGTH: 16
<212> TYPE: DNA
<213> ORGANISM: Artificial Sequence
<220> FEATURE:
<223> OTHER INFORMATION: DasR binding site in Tfu_2361c

<400> SEQUENCE: 461
tgtgggctgc accaca                                                         16

<210> SEQ ID NO 462
<211> LENGTH: 16
<212> TYPE: DNA
<213> ORGANISM: Artificial Sequence
<220> FEATURE:
<223> OTHER INFORMATION: DasR binding site in Tfu_1504

<400> SEQUENCE: 462
cgtggcctac acctcc                                                         16

<210> SEQ ID NO 463
<211> LENGTH: 16
<212> TYPE: DNA
<213> ORGANISM: Artificial Sequence
<220> FEATURE:
<223> OTHER INFORMATION: DasR binding site in Tfu_2622c

<400> SEQUENCE: 463
agtgatgtac accacg                                                         16

<210> SEQ ID NO 464
<211> LENGTH: 16
<212> TYPE: DNA
<213> ORGANISM: Artificial Sequence
<220> FEATURE:
<223> OTHER INFORMATION: DasR binding site in Tfu_0428 and Tfu_0427c
```

```
<400> SEQUENCE: 464
aatggactaa accaat                                                         16

<210> SEQ ID NO 465
<211> LENGTH: 16
<212> TYPE: DNA
<213> ORGANISM: Artificial Sequence
<220> FEATURE:
<223> OTHER INFORMATION: DasR binding site in Tfu_1002

<400> SEQUENCE: 465
agtgttctac gccatt                                                         16

<210> SEQ ID NO 466
<211> LENGTH: 16
<212> TYPE: DNA
<213> ORGANISM: Artificial Sequence
<220> FEATURE:
<223> OTHER INFORMATION: DasR binding site in Tfu_0600

<400> SEQUENCE: 466
agtggactac tcaacg                                                         16

<210> SEQ ID NO 467
<211> LENGTH: 16
<212> TYPE: DNA
<213> ORGANISM: Artificial Sequence
<220> FEATURE:
<223> OTHER INFORMATION: DasR binding site in Tfu_2195c

<400> SEQUENCE: 467
cgtggactgc acaagt                                                         16

<210> SEQ ID NO 468
<211> LENGTH: 16
<212> TYPE: DNA
<213> ORGANISM: Artificial Sequence
<220> FEATURE:
<223> OTHER INFORMATION: DasR binding site in Tfu_1033

<400> SEQUENCE: 468
aatggtttac tccatt                                                         16

<210> SEQ ID NO 469
<211> LENGTH: 16
<212> TYPE: DNA
<213> ORGANISM: Artificial Sequence
<220> FEATURE:
<223> OTHER INFORMATION: DasR binding site in Tfu_1242

<400> SEQUENCE: 469
cgtgatctac accata                                                         16

<210> SEQ ID NO 470
<211> LENGTH: 16
<212> TYPE: DNA
<213> ORGANISM: Artificial Sequence
<220> FEATURE:
<223> OTHER INFORMATION: DasR binding site in Tfu_0793

<400> SEQUENCE: 470
cgtggtggag tccacc                                                         16

<210> SEQ ID NO 471
```

```
<211> LENGTH: 16
<212> TYPE: DNA
<213> ORGANISM: Artificial Sequence
<220> FEATURE:
<223> OTHER INFORMATION: DasR binding site in Tfu_0213

<400> SEQUENCE: 471
caaggactac gccacc                                                    16

<210> SEQ ID NO 472
<211> LENGTH: 16
<212> TYPE: DNA
<213> ORGANISM: Artificial Sequence
<220> FEATURE:
<223> OTHER INFORMATION: DasR binding site in Tfu_0538

<400> SEQUENCE: 472
cgtggactgc gccacc                                                    16

<210> SEQ ID NO 473
<211> LENGTH: 16
<212> TYPE: DNA
<213> ORGANISM: Artificial Sequence
<220> FEATURE:
<223> OTHER INFORMATION: DasR binding site in Tfu_1530c

<400> SEQUENCE: 473
ggtggcgcag tccacg                                                    16

<210> SEQ ID NO 474
<211> LENGTH: 16
<212> TYPE: DNA
<213> ORGANISM: Artificial Sequence
<220> FEATURE:
<223> OTHER INFORMATION: DasR binding site in Tfu_1691

<400> SEQUENCE: 474
cgaggtgtac accaac                                                    16

<210> SEQ ID NO 475
<211> LENGTH: 16
<212> TYPE: DNA
<213> ORGANISM: Artificial Sequence
<220> FEATURE:
<223> OTHER INFORMATION: DasR binding site in Tfu_0105c

<400> SEQUENCE: 475
gctggtgcag tccatg                                                    16

<210> SEQ ID NO 476
<211> LENGTH: 16
<212> TYPE: DNA
<213> ORGANISM: Artificial Sequence
<220> FEATURE:
<223> OTHER INFORMATION: DasR binding site in Tfu_2986c

<400> SEQUENCE: 476
gctggtctgc accgcc                                                    16

<210> SEQ ID NO 477
<211> LENGTH: 16
<212> TYPE: DNA
<213> ORGANISM: Artificial Sequence
<220> FEATURE:
<223> OTHER INFORMATION: DasR binding site in Tfu_0525

<400> SEQUENCE: 477
```
agtggtttcg cccact					16

<210> SEQ ID NO 478
<211> LENGTH: 16
<212> TYPE: DNA
<213> ORGANISM: Artificial Sequence
<220> FEATURE:
<223> OTHER INFORMATION: DasR binding site in Tfu_2802c

<400> SEQUENCE: 478
gggggtaaag accact					16

<210> SEQ ID NO 479
<211> LENGTH: 16
<212> TYPE: DNA
<213> ORGANISM: Artificial Sequence
<220> FEATURE:
<223> OTHER INFORMATION: DasR binding site in Tfu_2007

<400> SEQUENCE: 479
ggtggtgcag tccgat					16

<210> SEQ ID NO 480
<211> LENGTH: 16
<212> TYPE: DNA
<213> ORGANISM: Artificial Sequence
<220> FEATURE:
<223> OTHER INFORMATION: DasR binding site in Tfu_2348 and Tfu_2347c

<400> SEQUENCE: 480
acaggtgcag accatc					16

<210> SEQ ID NO 481
<211> LENGTH: 16
<212> TYPE: DNA
<213> ORGANISM: Artificial Sequence
<220> FEATURE:
<223> OTHER INFORMATION: DasR binding site in Tfu_2320c

<400> SEQUENCE: 481
tgttgtctag aacaca					16

<210> SEQ ID NO 482
<211> LENGTH: 16
<212> TYPE: DNA
<213> ORGANISM: Artificial Sequence
<220> FEATURE:
<223> OTHER INFORMATION: DasR binding site in Tfu_1425 and Tfu_1424c

<400> SEQUENCE: 482
agaggtcaac acaatc					16

<210> SEQ ID NO 483
<211> LENGTH: 16
<212> TYPE: DNA
<213> ORGANISM: Artificial Sequence
<220> FEATURE:
<223> OTHER INFORMATION: DasR binding site in Tfu_0594

<400> SEQUENCE: 483
ggtggtcgag gccacc					16

<210> SEQ ID NO 484
<211> LENGTH: 16
<212> TYPE: DNA

```
<213> ORGANISM: Artificial Sequence
<220> FEATURE:
<223> OTHER INFORMATION: DasR binding site in Tfu_3054c

<400> SEQUENCE: 484
gatggtgaag acctcg                                                       16

<210> SEQ ID NO 485
<211> LENGTH: 16
<212> TYPE: DNA
<213> ORGANISM: Artificial Sequence
<220> FEATURE:
<223> OTHER INFORMATION: DasR binding site in Tfu_0527

<400> SEQUENCE: 485
caaggtctac tccacc                                                       16

<210> SEQ ID NO 486
<211> LENGTH: 16
<212> TYPE: DNA
<213> ORGANISM: Artificial Sequence
<220> FEATURE:
<223> OTHER INFORMATION: DasR binding site in Tfu_0658

<400> SEQUENCE: 486
tatggactac acgatt                                                       16

<210> SEQ ID NO 487
<211> LENGTH: 16
<212> TYPE: DNA
<213> ORGANISM: Artificial Sequence
<220> FEATURE:
<223> OTHER INFORMATION: DasR binding site in Tfu_0815c

<400> SEQUENCE: 487
agtggtccgg accaaa                                                       16

<210> SEQ ID NO 488
<211> LENGTH: 16
<212> TYPE: DNA
<213> ORGANISM: Artificial Sequence
<220> FEATURE:
<223> OTHER INFORMATION: DasR binding site in Tfu_1226

<400> SEQUENCE: 488
catggtctac gcctca                                                       16

<210> SEQ ID NO 489
<211> LENGTH: 16
<212> TYPE: DNA
<213> ORGANISM: Artificial Sequence
<220> FEATURE:
<223> OTHER INFORMATION: DasR binding site in Tfu_2687c

<400> SEQUENCE: 489
agtgatccag accagc                                                       16

<210> SEQ ID NO 490
<211> LENGTH: 241
<212> TYPE: DNA
<213> ORGANISM: Streptomyces coelicolor
<220> FEATURE:
<221> NAME/KEY: misc_feature
<222> LOCATION: (82)..(97)
<223> OTHER INFORMATION: footprint
<220> FEATURE:
<221> NAME/KEY: misc_feature
```

-continued

```
<222> LOCATION: (200)..(205)
<223> OTHER INFORMATION: RBS
<220> FEATURE:
<221> NAME/KEY: misc_feature
<222> LOCATION: (212)..(214)
<223> OTHER INFORMATION: Translation start

<400> SEQUENCE: 490
accttgctac gcatcgctca accccaggca ggagtgacga ctgtacacgg ggccgcggaa     60
cgggtgcaaa tccgtgagga gtgtggtcta gacctctaat cggaacactc atgcggaacc    120
ggtacttcct atgacatacc ctgctgctca gtgtgccgtc cgggacaagg cagtgacggc    180
ccgtacagat ccccgccctg ggaggcttcc catgaccacc gtctcgtccc cgctcgcagg    240
a                                                                    241

<210> SEQ ID NO 491
<211> LENGTH: 16
<212> TYPE: DNA
<213> ORGANISM: Artificial Sequence
<220> FEATURE:
<223> OTHER INFORMATION: Fig. 1A - predicted dre consensus

<400> SEQUENCE: 491
actggtctag accact                                                     16

<210> SEQ ID NO 492
<211> LENGTH: 254
<212> TYPE: PRT
<213> ORGANISM: Streptomyces coelicolor

<400> SEQUENCE: 492

Met Ser Thr Asp Val Ser Ser Ala Glu Asn Glu Gly Gly Ala Thr Val
1               5                   10                  15

Arg Thr Ala Arg Val Pro Lys Tyr Tyr Arg Leu Lys Lys His Leu Leu
            20                  25                  30

Asp Met Thr Arg Thr Gln Thr Pro Gly Thr Pro Val Pro Pro Glu Arg
        35                  40                  45

Thr Leu Ala Ala Glu Phe Asp Thr Ser Arg Thr Thr Val Arg Gln Ala
    50                  55                  60

Leu Gln Glu Leu Val Val Glu Gly Arg Leu Glu Arg Ile Gln Gly Lys
65                  70                  75                  80

Gly Thr Phe Val Ala Lys Pro Lys Val Ser Gln Ala Leu Gln Leu Thr
                85                  90                  95

Ser Tyr Thr Glu Asp Met Arg Ala Gln Gly Leu Glu Pro Thr Ser Gln
            100                 105                 110

Leu Leu Asp Ile Gly Tyr Ile Thr Ala Asp Asp Arg Leu Ala Gly Leu
        115                 120                 125

Leu Asp Ile Thr Ala Gly Gly Arg Val Leu Arg Ile Glu Arg Leu Arg
    130                 135                 140

Met Ala Asn Gly Glu Pro Met Ala Ile Glu Thr Thr His Leu Ser Ala
145                 150                 155                 160

Lys Arg Phe Pro Ala Leu Arg Arg Ser Leu Val Lys Tyr Thr Ser Leu
                165                 170                 175

Tyr Thr Ala Leu Ala Glu Val Tyr Asp Val His Leu Ala Glu Ala Glu
            180                 185                 190

Glu Thr Ile Glu Thr Ser Leu Ala Thr Pro Arg Glu Ala Gly Leu Leu
        195                 200                 205

Gly Thr Asp Val Gly Leu Pro Met Leu Met Leu Ser Arg His Ser Gln
```

Asp Arg Thr Gly Gln Pro Val Glu Trp Val Arg Ser Val Tyr Arg Gly
225                 230                 235                 240

Asp Arg Tyr Lys Phe Val Ala Arg Leu Lys Arg Pro Gln Asp
            245                 250

<210> SEQ ID NO 493
<211> LENGTH: 254
<212> TYPE: PRT
<213> ORGANISM: Streptomyces clavuligerus

<400> SEQUENCE: 493

Met Ser Thr Asp Val Ser Ser Ala Glu Asn Glu Asn Gly Ala Thr Val
1               5                   10                  15

Arg Thr Ala Arg Val Pro Lys Tyr Tyr Arg Leu Lys Lys His Leu Leu
            20                  25                  30

Asp Met Thr Glu Thr Leu Pro Pro Gly Thr Pro Val Pro Pro Glu Arg
        35                  40                  45

Thr Leu Ala Ala Glu Phe Asp Thr Ser Arg Thr Thr Val Arg Gln Ala
    50                  55                  60

Leu Gln Glu Leu Val Val Glu Gly Arg Leu Glu Arg Ile Gln Gly Lys
65                  70                  75                  80

Gly Thr Phe Val Ala Lys Pro Lys Val Ser Gln Ala Leu Gln Leu Thr
                85                  90                  95

Ser Tyr Thr Glu Asp Met Arg Ala Gln Gly Leu Glu Pro Thr Ser Gln
            100                 105                 110

Leu Leu Asp Ile Gly Tyr Ile Thr Ala Asp Arg Leu Ala Gly Leu
        115                 120                 125

Leu Asp Ile Thr Ala Gly Gly Arg Val Leu Arg Ile Glu Arg Leu Arg
130                 135                 140

Met Ala Asn Gly Glu Pro Met Ala Ile Glu Thr Thr His Leu Ser Ala
145                 150                 155                 160

Lys Arg Phe Pro Ala Leu Arg Arg Ser Leu Val Lys Tyr Thr Ser Leu
                165                 170                 175

Tyr Thr Ala Leu Ala Glu Val Tyr Asp Val His Leu Ala Glu Ala Glu
            180                 185                 190

Glu Thr Ile Glu Thr Ser Leu Ala Thr Pro Arg Glu Ala Gly Leu Leu
        195                 200                 205

Gly Thr Asp Val Gly Leu Pro Met Leu Met Leu Ser Arg His Ser Gln
    210                 215                 220

Asp Arg Thr Gly Gln Pro Val Glu Trp Val Arg Ser Val Tyr Arg Gly
225                 230                 235                 240

Asp Arg Tyr Lys Phe Val Ala Arg Leu Lys Arg Pro Gln Asp
            245                 250

<210> SEQ ID NO 494
<211> LENGTH: 254
<212> TYPE: PRT
<213> ORGANISM: Streptomyces scabies

<400> SEQUENCE: 494

Met Ser Thr Asp Val Ser Ser Ala Glu Asn Glu Asn Gly Ala Thr Val
1               5                   10                  15

Arg Thr Ala Arg Val Pro Lys Tyr Tyr Arg Leu Lys Lys His Leu Leu
            20                  25                  30

Asp Met Thr Glu Thr Leu Pro Pro Gly Thr Pro Val Pro Pro Glu Arg

```
                35                  40                  45
Thr Leu Ala Ala Glu Phe Asp Thr Ser Arg Thr Thr Val Arg Gln Ala
 50                  55                  60

Leu Gln Glu Leu Val Val Glu Gly Arg Leu Glu Arg Ile Gln Gly Lys
 65                  70                  75                  80

Gly Thr Phe Val Ala Lys Pro Lys Val Ser Gln Ala Leu Gln Leu Thr
                 85                  90                  95

Ser Tyr Thr Glu Asp Met Arg Ala Gln Gly Leu Glu Pro Thr Ser Gln
                100                 105                 110

Leu Leu Asp Ile Gly Tyr Ile Thr Ala Asp Asp Thr Leu Ala Gly Gln
                115                 120                 125

Leu Asp Ile Thr Ala Gly Gly Arg Val Leu Arg Ile Glu Arg Leu Arg
                130                 135                 140

Met Ala Asn Gly Glu Pro Met Ala Ile Glu Thr Thr His Leu Ser Ala
145                 150                 155                 160

Lys Arg Phe Pro Ala Leu Arg Arg Ser Leu Val Lys Tyr Thr Ser Leu
                165                 170                 175

Tyr Thr Ala Leu Ala Glu Val Tyr Asp Val Arg Leu Ala Glu Ala Glu
                180                 185                 190

Glu Thr Ile Glu Thr Ser Leu Ala Thr Pro Arg Glu Ala Gly Leu Leu
                195                 200                 205

Gly Thr Asp Val Gly Leu Pro Met Leu Met Leu Ser Arg His Ser Leu
210                 215                 220

Asp Met Glu Gly Gln Pro Val Glu Trp Val Arg Ser Val Tyr Arg Gly
225                 230                 235                 240

Asp Arg Tyr Lys Phe Val Ala Arg Leu Lys Arg Pro Gln Asp
                245                 250

<210> SEQ ID NO 495
<211> LENGTH: 254
<212> TYPE: PRT
<213> ORGANISM: Streptomyces avermitilis

<400> SEQUENCE: 495

Met Ser Thr Asp Val Ser Ser Ala Glu Asn Glu Gly Gly Ala Pro Ile
 1               5                  10                  15

Arg Thr Ala Arg Val Pro Lys Tyr Tyr Arg Leu Lys Lys His Leu Leu
                 20                  25                  30

Asp Met Thr Glu Thr Leu Pro Pro Gly Thr Pro Val Pro Pro Glu Arg
                 35                  40                  45

Thr Leu Ala Ala Glu Phe Asp Thr Ser Arg Thr Thr Val Arg Gln Ala
 50                  55                  60

Leu Gln Glu Leu Val Val Glu Gly Arg Leu Glu Arg Ile Gln Gly Lys
 65                  70                  75                  80

Gly Thr Phe Val Ala Lys Pro Lys Val Ser Gln Ala Leu Gln Leu Thr
                 85                  90                  95

Ser Tyr Thr Glu Asp Met Arg Ala Gln Gly Leu Glu Pro Thr Ser Gln
                100                 105                 110

Leu Leu Asp Ile Gly Tyr Ile Thr Ala Asp Asp Thr Leu Ala Gly Leu
                115                 120                 125

Leu Asp Ile Thr Ala Gly Gly Arg Val Leu Arg Ile Glu Arg Leu Arg
                130                 135                 140

Leu Ala Ser Gly Glu Pro Met Ala Ile Glu Thr Thr His Leu Ser Ala
145                 150                 155                 160
```

```
Lys Arg Phe Pro Ala Leu Arg Ser Leu Val Lys Tyr Thr Ser Leu
            165                 170                 175

Tyr Thr Ala Leu Ala Glu Val Tyr Asp Val Arg Leu Ala Glu Ala Glu
        180                 185                 190

Glu Thr Ile Glu Thr Ser Leu Ala Thr Pro Arg Glu Ala Gly Leu Leu
        195                 200                 205

Gly Thr Asp Val Gly Leu Pro Met Leu Met Leu Ser Arg His Ser Leu
        210                 215                 220

Asp Lys Asp Gly Arg Pro Val Glu Trp Val Arg Ser Val Tyr Arg Gly
225                 230                 235                 240

Asp Arg Tyr Lys Phe Val Ala Arg Leu Lys Arg Pro Gln Asp
                245                 250
```

<210> SEQ ID NO 496
<211> LENGTH: 253
<212> TYPE: PRT
<213> ORGANISM: Streptomyces griseus

<400> SEQUENCE: 496

```
Met Gly Ala Glu Gly Ala Val Arg Gly Ala Arg Pro Val Pro Val Arg
1               5                   10                  15

Ala Gln Arg Val Pro Lys Tyr Tyr Arg Leu Lys Arg His Leu Leu Asp
            20                  25                  30

Met Thr Asp Thr Leu Pro Pro Gly Thr Pro Val Pro Pro Glu Arg Thr
        35                  40                  45

Leu Ala Ala Glu Phe Asp Thr Ser Arg Thr Thr Val Pro Gln Ala Leu
    50                  55                  60

Gln Glu Leu Val Val Glu Gly Arg Leu Glu Arg Ile Gln Gly Lys Gly
65                  70                  75                  80

Thr Phe Val Ala Lys Pro Lys Val Ser Gln Ala Leu Gln Leu Thr Ser
                85                  90                  95

Tyr Thr Glu Asp Met Arg Ala Gln Gly Leu Glu Pro Thr Ser Gln Leu
            100                 105                 110

Leu Asp Ile Gly Tyr Val Thr Ala Asp Asp Thr Leu Ala Gly Leu Leu
        115                 120                 125

Asp Ile Ser Thr Gly Gly Arg Val Leu Arg Ile Glu Arg Leu Arg Leu
    130                 135                 140

Ala Ser Gly Glu Pro Met Ala Ile Glu Thr Thr His Leu Ser Ala Lys
145                 150                 155                 160

Arg Phe Pro Ala Leu Arg Arg Ser Leu Val Lys Tyr Thr Ser Leu Tyr
                165                 170                 175

Thr Ala Leu Ala Glu Val Tyr Asp Val Arg Leu Ala Glu Ala Glu Glu
            180                 185                 190

Thr Ile Glu Thr Ser Leu Ala Thr Pro Arg Glu Ala Gly Leu Leu Gly
        195                 200                 205

Thr Asp Val Gly Leu Pro Met Leu Met Leu Ser Arg His Ser Val Asp
    210                 215                 220

Gly Gln Gly Glu Pro Val Glu Trp Val Arg Ser Val Tyr Arg Gly Asp
225                 230                 235                 240

Arg Tyr Lys Phe Val Ala Arg Leu Lys Arg Gly Thr Asp
                245                 250
```

<210> SEQ ID NO 497
<211> LENGTH: 254
<212> TYPE: PRT
<213> ORGANISM: Streptomyces species 139

<400> SEQUENCE: 497

```
Met Ser Thr Asp Val Ser Ser Ala Gly Ala Asp Thr Arg Ala Pro Gly
1               5                   10                  15

Arg Arg Asp Arg Val Pro Lys Tyr Tyr Leu Ile Lys Gln Arg Leu Leu
            20                  25                  30

Gln Met Thr Asp Glu Arg Ala Pro Gly Ser Pro Met Pro Ala Glu Arg
        35                  40                  45

Leu Leu Ala Val Glu Phe Gly Thr Ser Arg Thr Thr Val Arg Lys Ala
    50                  55                  60

Leu Leu Glu Leu Val Ser Glu Gly Arg Leu Asp Arg Ile Gln Gly Lys
65                  70                  75                  80

Gly Thr Phe Val Ala Arg Pro Lys Val Tyr Arg Thr Leu Gln Leu Thr
                85                  90                  95

Ser Tyr Thr Glu Asp Met Arg Ala Gln Gly Leu Ser Pro Ala Ser Gln
            100                 105                 110

Val Leu Asp Ile Gly Tyr Val Pro Ala Asp Ala Glu Leu Ala Ala Leu
        115                 120                 125

Leu Glu Val Glu Pro Glu Asp Arg Val Leu Arg Ile Glu Arg Leu Arg
    130                 135                 140

Leu Ala Gly Gly Glu Pro Met Ala Ile Glu Ala Thr His Leu Ser Ala
145                 150                 155                 160

Arg Arg Phe Pro Gly Leu Arg Arg Asn Leu Thr Arg Tyr Thr Ser Leu
                165                 170                 175

Tyr Thr Thr Leu Ala Glu Val Tyr Gly Val Arg Pro Ala Glu Ala Asp
            180                 185                 190

Glu Thr Ile Glu Thr Ser Pro Ala Thr Pro Arg Glu Ala Gly Leu Leu
        195                 200                 205

Gly Thr Asp Val Gly Leu Pro Met Leu Leu Leu Ser Arg His Ser Arg
    210                 215                 220

Asp Glu Asn Gly Ala Pro Val Glu Trp Val Arg Ser Val Tyr Arg Gly
225                 230                 235                 240

Ser Arg Tyr Lys Phe Thr Ala Arg Leu Arg Arg Pro Arg Gly
                245                 250
```

<210> SEQ ID NO 498
<211> LENGTH: 248
<212> TYPE: PRT
<213> ORGANISM: Thermobifido fusca

<400> SEQUENCE: 498

```
Met Thr Gly Gln Arg Thr Val Glu Asp Ser Pro Arg Val Pro Lys Tyr
1               5                   10                  15

Tyr Gln Val Lys Lys Gln Leu Leu Gln Leu Ile Glu Thr Met Pro Ala
            20                  25                  30

Gly Asn Pro Val Pro Pro Glu Arg Thr Leu Ala Thr Gln Phe Gly Thr
        35                  40                  45

Ser Arg Thr Thr Val Arg Gln Ala Leu Ser Glu Met Val Val Glu Gly
    50                  55                  60

Arg Leu Leu Arg Ile Gln Gly Lys Gly Thr Phe Val Ala Lys Pro Lys
65                  70                  75                  80

Val Thr Gln Val Leu Gln Leu Thr Ser Tyr Thr Gln Glu Met Arg Ser
                85                  90                  95

His Gly Leu Gln Pro Asp Thr Arg Ile Leu Asp Val Gly Tyr Ile Asn
            100                 105                 110
```

```
Ala Asp Glu Glu Leu Ala Gly Leu Leu Ala Ile Arg Leu Gly Gly Arg
        115                 120                 125

Val Leu Arg Ile Glu Arg Leu Arg Leu Ala Asn Gly Glu Pro Met Ala
    130                 135                 140

Val Glu Thr Ala His Leu Pro Ala Arg Arg Phe Pro Gly Leu Arg Arg
145                 150                 155                 160

Arg Leu Asp Arg His Ala Ser Leu Tyr Glu Ala Leu Ala Thr Val Tyr
                165                 170                 175

Asn Val His Leu Ala Glu Ala Glu Ala Thr Ile Glu Thr Val Leu Ala
            180                 185                 190

Thr Pro Lys Glu Ala Gln Leu Leu Gly Val Asp Val Gly Leu Pro Leu
        195                 200                 205

Val Leu His Cys Gln His Ser Phe Asp Asp Glu Gly Asn Pro Val Glu
    210                 215                 220

Trp Val Arg Ser Leu Tyr Arg Gly Asp Arg Tyr Lys Phe Val Thr Arg
225                 230                 235                 240

Leu Arg Pro Pro Lys Glu Arg Thr
                245
```

<210> SEQ ID NO 499
<211> LENGTH: 243
<212> TYPE: PRT
<213> ORGANISM: Nocardia farcinica

<400> SEQUENCE: 499

```
Met Leu Gly Arg Val Thr Ala Arg Ala Glu Pro Arg Val Leu Lys His
1               5                   10                  15

Gln Ile Val Arg Ala Gln Val Asp Lys Leu Leu Asp Glu Leu Asp Glu
            20                  25                  30

Gly Asp Pro Val Pro Ser Glu Arg Glu Leu Ala Leu Arg Phe Asp Val
        35                  40                  45

Ala Arg Glu Thr Val Arg Gln Ala Leu Arg Glu Leu Leu Leu Ala Gly
    50                  55                  60

Arg Ile Gln Arg Arg Gly Arg Ala Thr Val Val Ala Gly Pro Lys Phe
65                  70                  75                  80

Val Gln Pro Leu Ala Leu Gly Ser Tyr Thr Glu Ala Ala Leu Ala Gln
                85                  90                  95

Gly His Arg Ala Gly Arg Ile Leu Val Gly Trp Thr Arg Leu Thr Ala
            100                 105                 110

Asp Pro Ala Leu Ala Gly Asp Leu His Ile Ala Glu Gly Asp Pro Val
        115                 120                 125

Ile Gln Leu Glu Arg Val Leu Thr Thr Asp Asp Leu Arg Val Gly Leu
    130                 135                 140

Glu Thr Thr Arg Leu Pro Ala Tyr Arg Tyr Pro Glu Leu Val Glu Thr
145                 150                 155                 160

Phe Asp His Thr Ala Ser Leu Tyr Ala Glu Ile Arg Arg Gly Ile
                165                 170                 175

Val Phe Asp Arg Ala Val Asp Thr Ile Glu Thr Thr Leu Pro Asp Ala
            180                 185                 190

Arg Glu Ala Ala Leu Leu Thr Ala Asp Ala Arg Thr Pro Met Phe Leu
        195                 200                 205

Leu Asn Arg Val Ser Tyr Asp Pro Asp Gly Val Pro Ile Glu His Arg
    210                 215                 220

Arg Ser Leu Tyr Arg Gly Asp Arg Met Thr Phe Thr Ala Val Gln Thr
```

-continued

```
225                 230                 235                 240

Arg Asp His

<210> SEQ ID NO 500
<211> LENGTH: 281
<212> TYPE: PRT
<213> ORGANISM: Streptomyces coelicolor

<400> SEQUENCE: 500

Met Glu Ile Asp Ala Ala Ser Gly Ala Val Leu Lys Arg Glu Arg
1               5                   10                  15

Val Arg Asp Ala Val Leu Glu Leu Ile Glu Asp Arg Arg Pro Gly Asp
            20                  25                  30

Ala Ile Pro Ser Glu Arg Thr Leu Cys Ala Glu Leu Gly Val Ser Arg
        35                  40                  45

Pro Thr Leu Arg Ala Ala Ile Asp Glu Leu Val Val Ala Gly Leu Leu
    50                  55                  60

Val Arg Glu His Gly Arg Gly Met Phe Val Ala Ala Glu Lys Ile Thr
65              70                  75                  80

Gln Glu Leu Leu Ser Asp Arg Arg Ala Phe Ser Leu Pro Gln Ala Ala
                85                  90                  95

Gly Ala Trp Thr Ser Arg Leu Leu Glu Val Arg Thr Leu Pro Ala Gly
            100                 105                 110

Ala Arg Val Gly Arg Lys Leu Arg Met Ser Pro Ala Ala Gln Ile His
        115                 120                 125

Tyr Val Ala Arg Leu Arg Leu Val Asp Gly Ser Pro Met Ala Ile Glu
    130                 135                 140

Tyr Leu His Val Pro Ala Asp Leu Val Ser Asp Leu Thr Ser Glu Glu
145             150                 155                 160

Leu Glu Gln Gly Asp Leu Tyr Glu His Leu Gly Glu Arg His Asp Val
                165                 170                 175

Arg Val Ser Glu Ala Val Gln Ser Ile Glu Pro Thr Val Val Thr Arg
            180                 185                 190

Ala Glu Ala Asp Leu Leu Asp Val Pro Glu Leu Ser Pro Ala Leu Leu
        195                 200                 205

Phe Glu Arg Leu Thr Thr Asp Thr Arg Gly Arg Pro Val Glu Tyr Val
    210                 215                 220

His Ser Leu Tyr Arg Gly Asp Arg Tyr Arg Ile Val Ser Arg Leu Thr
225             230                 235                 240

Leu Gly Pro Arg Asp Gln Ala Pro Pro Gly Glu Gly His His Pro
                245                 250                 255

Gly Ile Pro Pro Gly Asp Phe Ala Thr Lys Asp Pro Val Thr Leu Ser
            260                 265                 270

Thr Arg Gly Val Val Gln Gly Gly Met
        275                 280

<210> SEQ ID NO 501
<211> LENGTH: 265
<212> TYPE: PRT
<213> ORGANISM: Corynebacterium efficiens

<400> SEQUENCE: 501

Met Thr Arg Cys Ala Arg Val Val Asp Met Ser Ala Ala Glu Arg Thr
1               5                   10                  15

Glu Asp Gly Ala Thr Leu Pro His Arg Val Leu Thr Asp Gly Pro Lys
            20                  25                  30
```

```
Pro Lys His Gln Gln Leu Arg Glu Ile Leu Glu Glu Leu Cys Thr Thr
        35                  40                  45

Gln Leu Gln Pro Gly Asp Met Leu Pro Gly Glu Arg Val Leu Glu Asp
 50                  55                  60

Thr Tyr Gly Val Ser Arg Ile Thr Val Arg Arg Ala Ile Gly Asp Leu
 65                  70                  75                  80

Val Ala Ser Gly Arg Leu Lys Arg Ala Arg Gly Lys Gly Thr Phe Val
                 85                  90                  95

Ala His Ala Pro Leu Val Ser Arg Leu His Leu Ala Ser Phe Ser Ala
            100                 105                 110

Glu Met Ala Ala Gln Asn Leu Val Ala Thr Ser Arg Ile Leu Ser Ser
        115                 120                 125

Ser Arg Gly Ala Ala Pro Asp Glu Ile Ala Glu Phe Phe Gly Thr Glu
130                 135                 140

Arg Gly Ala Gln His Ile Thr Leu Arg Arg Leu Arg Leu Gly Asn Gly
145                 150                 155                 160

Arg Pro Tyr Ala Ile Asp His Gly Trp Tyr Asn Ala Val Tyr Ala Pro
                165                 170                 175

Asp Leu Leu Glu Asn Asp Val Tyr Asn Ser Val Tyr Ala Ile Leu Asp
            180                 185                 190

Arg Val Tyr Asn Val Pro Val Thr His Ala Glu Gln Thr Val Thr Ala
        195                 200                 205

Val Ala Ala Asp Glu Asp Thr Ala Lys Leu Leu Asp Val Pro Thr Gly
210                 215                 220

Ala Pro Leu Leu Arg Ile Leu Arg Gln Ser Met Ser Gly Glu Lys Pro
225                 230                 235                 240

Ile Glu Trp Cys Val Ser Val Tyr Arg Thr Asp Arg Tyr Ser Leu Lys
                245                 250                 255

Thr Met Val Thr Arg Ser Glu Asp Leu
            260                 265

<210> SEQ ID NO 502
<211> LENGTH: 240
<212> TYPE: PRT
<213> ORGANISM: Listeria monocytogenes

<400> SEQUENCE: 502

Met Ile Asp Lys Gln Ser Gly Ile Pro Ile Tyr Ile Gln Ile Gln Ser
 1               5                  10                  15

Glu Ile Lys Lys Lys Met Glu Asp Gly Val Trp Lys Val Gly Thr Ser
                20                  25                  30

Ile Pro Ala Glu Arg Gln Leu Ala Glu Met Phe His Val Ser Arg Met
            35                  40                  45

Thr Val Arg Gln Ala Ile Gln Gly Leu Val Asp Asp Asn Ile Leu Gln
 50                  55                  60

Arg Arg Val Gly Ala Gly Thr Phe Ile Ala Glu Lys Lys Leu Thr Glu
 65                  70                  75                  80

Arg Leu Glu Ala Val Thr Ser Phe Thr Asn Leu Met Leu Gln Glu Gly
                 85                  90                  95

Lys Val Pro Ser Thr Arg Ile Val Ser Tyr Gly Ile Arg Pro Ala Ser
            100                 105                 110

Thr Gln Glu Gln Glu Ala Leu Gln Leu Pro Glu Asn Ser Asn Val Met
        115                 120                 125

Lys Ile Glu Arg Ile Arg Tyr Gly Asp Arg Val Pro Ile Leu Tyr Glu
```

```
        130                 135                 140
Val Ala Ala Ile Pro Glu Lys Ile Ala Ser Leu Leu Thr Lys Glu Asp
145                 150                 155                 160

Ile Met Asp Ser Leu Tyr Lys Ala Ile Glu Leu Lys Leu Gly Gln Pro
                165                 170                 175

Ile Gly Glu Ala Glu Gln Ile Met Glu Ala Ser Leu Val Ser Glu Lys
            180                 185                 190

Ile Ala Pro Tyr Leu Asp Val Lys Leu Gly Ser Pro Val Met Lys Leu
        195                 200                 205

Arg Gln Ile Thr Met Leu Glu Asp Gly Arg Pro Phe Glu Phe Thr Arg
    210                 215                 220

Ser Gln Tyr Val Gly Ser Arg Phe Gln Phe Val Ala Arg Ile Lys Gln
225                 230                 235                 240

<210> SEQ ID NO 503
<211> LENGTH: 232
<212> TYPE: PRT
<213> ORGANISM: Streptococcus thermophilus

<400> SEQUENCE: 503

Met Leu Pro Ala Tyr Ile Arg Ile His Asp Lys Ile Lys Glu Asp Val
1               5                   10                  15

Asp Asp Gly Thr Trp Lys Ile Gly Gln Arg Leu Pro Ser Glu Arg Asp
            20                  25                  30

Leu Cys Glu Thr Phe Asp Val Ser Arg Met Thr Val Arg Gln Ala Ile
        35                  40                  45

Thr Leu Leu Val Asp Glu Gly Ile Leu Glu Arg Lys Pro Gly Ser Gly
    50                  55                  60

Thr Phe Val Ala Ser Ser Arg Val Lys Glu Lys Met Arg Gly Thr Thr
65                  70                  75                  80

Ser Phe Thr Glu Ile Val Lys Ser Gln Gly Arg Lys Pro Ser Ser Glu
                85                  90                  95

Leu Ile Ser Tyr Gln Arg Leu His Pro Asn Glu Phe Glu Ile Lys Asn
            100                 105                 110

Leu Gly Val Leu Pro Gln Ser His Val Ile Arg Met Glu Arg Val Arg
        115                 120                 125

Phe Ala Asp Asp Ile Pro Val Ala Tyr Glu Ile Thr Ser Ile Pro Glu
    130                 135                 140

Lys Ile Ile Arg Gly Phe Lys Glu Ser Glu Ile Thr Glu His Phe Phe
145                 150                 155                 160

Lys Thr Leu Thr Asp Asn Gly Tyr Glu Ile Gly Lys Ser Gln Gln Thr
                165                 170                 175

Ile Ser Ala Ser Leu Ala Asn Ser Ser Leu Ala Lys His Leu Lys Val
            180                 185                 190

Lys Thr Gly Asp Ala Leu Leu Ser Leu Thr Gln Ile Ser Phe Leu Gln
        195                 200                 205

Asp Gly Gln Ala Phe Glu Tyr Val Arg Ser Tyr Tyr Val Gly Asp Arg
    210                 215                 220

Phe Glu Phe Tyr Leu Glu Asn Asn
225                 230

<210> SEQ ID NO 504
<211> LENGTH: 243
<212> TYPE: PRT
<213> ORGANISM: Bacillus subtilis
```

<400> SEQUENCE: 504

```
Met Asn Ile Asn Lys Gln Ser Pro Ile Pro Ile Tyr Tyr Gln Ile Met
1               5                   10                  15

Glu Gln Leu Lys Thr Gln Ile Lys Asn Gly Glu Leu Gln Pro Asp Met
            20                  25                  30

Pro Leu Pro Ser Glu Arg Glu Tyr Ala Glu Gln Phe Gly Ile Ser Arg
        35                  40                  45

Met Thr Val Arg Gln Ala Leu Ser Asn Leu Val Asn Glu Gly Leu Leu
    50                  55                  60

Tyr Arg Leu Lys Gly Arg Gly Thr Phe Val Ser Lys Pro Lys Met Glu
65                  70                  75                  80

Gln Ala Leu Gln Gly Leu Thr Ser Phe Thr Glu Asp Met Lys Ser Arg
                85                  90                  95

Gly Met Thr Pro Gly Ser Arg Leu Ile Asp Tyr Gln Leu Ile Asp Ser
            100                 105                 110

Thr Glu Glu Leu Ala Ala Ile Leu Gly Cys Gly His Pro Ser Ser Ile
        115                 120                 125

His Lys Ile Thr Arg Val Arg Leu Ala Asn Asp Ile Pro Met Ala Ile
    130                 135                 140

Glu Ser Ser His Ile Pro Phe Glu Leu Ala Gly Glu Leu Asn Glu Ser
145                 150                 155                 160

His Phe Gln Ser Ser Ile Tyr Asp His Ile Glu Arg Tyr Asn Ser Ile
                165                 170                 175

Pro Ile Ser Arg Ala Lys Gln Glu Leu Glu Pro Ser Ala Ala Thr Thr
            180                 185                 190

Glu Glu Ala Asn Ile Leu Gly Ile Gln Lys Gly Ala Pro Val Leu Leu
        195                 200                 205

Ile Lys Arg Thr Thr Tyr Leu Gln Asn Gly Thr Ala Phe Glu His Ala
    210                 215                 220

Lys Ser Val Tyr Arg Gly Asp Arg Tyr Thr Phe Val His Tyr Met Asp
225                 230                 235                 240

Arg Leu Ser
```

<210> SEQ ID NO 505
<211> LENGTH: 762
<212> TYPE: DNA
<213> ORGANISM: Streptomyces clavuligerus
<220> FEATURE:
<221> NAME/KEY: CDS
<222> LOCATION: (1)..(762)

<400> SEQUENCE: 505

```
atg agc acc gac gtc agc agt gcg gag aac gag ggt ggg gcg acc gtc      48
Met Ser Thr Asp Val Ser Ser Ala Glu Asn Glu Gly Gly Ala Thr Val
1               5                   10                  15 cgt acc gcg cgc gtg ccc aag tac tac cgt ctg aag aag cat ctg ctc      96
Arg Thr Ala Arg Val Pro Lys Tyr Tyr Arg Leu Lys Lys His Leu Leu
            20                  25                  30 gac atg acc cgg acc cag acg ccg ggc aca ccg gtc ccg ccg gag cgc     144
Asp Met Thr Arg Thr Gln Thr Pro Gly Thr Pro Val Pro Pro Glu Arg
        35                  40                  45 acc ctg gcc gcc gag ttc aac acc tcg cgc acg acg gtg cgc cag gcc     192
Thr Leu Ala Ala Glu Phe Asn Thr Ser Arg Thr Thr Val Arg Gln Ala
    50                  55                  60 ctg cag gag ctg gtg gtc gag ggc cgc ctg gag cgc atc cag ggc aag     240
Leu Gln Glu Leu Val Val Glu Gly Arg Leu Glu Arg Ile Gln Gly Lys
65                  70                  75                  80
```

```
ggc acc ttc gtc gcc aag ccc aag gtg tcg cag gcg ctg caa ctc acc      288
Gly Thr Phe Val Ala Lys Pro Lys Val Ser Gln Ala Leu Gln Leu Thr
                 85                  90                  95 tcg tac acc gag gac atg cgg gcc cag ggc ctc gaa ccg acc tct cag      336
Ser Tyr Thr Glu Asp Met Arg Ala Gln Gly Leu Glu Pro Thr Ser Gln
            100                 105                 110 ctg ctg gac atc ggc tac atc acc gcc gac gac cgg ctc gcc ggg ctg      384
Leu Leu Asp Ile Gly Tyr Ile Thr Ala Asp Asp Arg Leu Ala Gly Leu
        115                 120                 125 ctg gac atc acg gcc ggc ggc cgg gtg ctg cgc atc gag cgg ctg cgc      432
Leu Asp Ile Thr Ala Gly Gly Arg Val Leu Arg Ile Glu Arg Leu Arg
    130                 135                 140 atg gcc aac ggc gag ccg atg gcc atc gag acc acc cac ctc agc gcg      480
Met Ala Asn Gly Glu Pro Met Ala Ile Glu Thr Thr His Leu Ser Ala
145                 150                 155                 160 aag cgc ttc ccc gcc ctg cgc cgc tcc ctg gtg aag tac acg tcc ctc      528
Lys Arg Phe Pro Ala Leu Arg Arg Ser Leu Val Lys Tyr Thr Ser Leu
                165                 170                 175 tac acc gcg ctc gcc gag gtg tac gac gtc cat ctc gcc gag gcc gag      576
Tyr Thr Ala Leu Ala Glu Val Tyr Asp Val His Leu Ala Glu Ala Glu
            180                 185                 190 gag acc atc gag acc tcc ctg gcc acc ccg cgc gag gcc ggt ctg ctc      624
Glu Thr Ile Glu Thr Ser Leu Ala Thr Pro Arg Glu Ala Gly Leu Leu
        195                 200                 205 ggc acc gac gtc ggc ctg ccc atg ctg atg ctc tcc cgg cac tcc cag      672
Gly Thr Asp Val Gly Leu Pro Met Leu Met Leu Ser Arg His Ser Gln
    210                 215                 220 gac cgc acc ggc cag ccg gtg gag tgg gtc cgc tcg gtg tac cgg ggc      720
Asp Arg Thr Gly Gln Pro Val Glu Trp Val Arg Ser Val Tyr Arg Gly
225                 230                 235                 240 gac cgc tac aag ttc gtg gcc cgc ctc aag cgg ccc cag gac              762
Asp Arg Tyr Lys Phe Val Ala Arg Leu Lys Arg Pro Gln Asp
                245                 250

<210> SEQ ID NO 506
<211> LENGTH: 254
<212> TYPE: PRT
<213> ORGANISM: Streptomyces clavuligerus

<400> SEQUENCE: 506

Met Ser Thr Asp Val Ser Ser Ala Glu Asn Glu Gly Gly Ala Thr Val
1               5                   10                  15

Arg Thr Ala Arg Val Pro Lys Tyr Tyr Arg Leu Lys Lys His Leu Leu
            20                  25                  30

Asp Met Thr Arg Thr Gln Thr Pro Gly Thr Pro Val Pro Pro Glu Arg
        35                  40                  45

Thr Leu Ala Ala Glu Phe Asn Thr Ser Arg Thr Val Arg Gln Ala
    50                  55                  60

Leu Gln Glu Leu Val Val Glu Gly Arg Leu Glu Arg Ile Gln Gly Lys
65                  70                  75                  80

Gly Thr Phe Val Ala Lys Pro Lys Val Ser Gln Ala Leu Gln Leu Thr
                85                  90                  95

Ser Tyr Thr Glu Asp Met Arg Ala Gln Gly Leu Glu Pro Thr Ser Gln
            100                 105                 110

Leu Leu Asp Ile Gly Tyr Ile Thr Ala Asp Asp Arg Leu Ala Gly Leu
        115                 120                 125

Leu Asp Ile Thr Ala Gly Gly Arg Val Leu Arg Ile Glu Arg Leu Arg
    130                 135                 140
```

Met Ala Asn Gly Glu Pro Met Ala Ile Glu Thr Thr His Leu Ser Ala
145                 150                 155                 160

Lys Arg Phe Pro Ala Leu Arg Arg Ser Leu Val Lys Tyr Thr Ser Leu
            165                 170                 175

Tyr Thr Ala Leu Ala Glu Val Tyr Asp Val His Leu Ala Glu Ala Glu
        180                 185                 190

Glu Thr Ile Glu Thr Ser Leu Ala Thr Pro Arg Glu Ala Gly Leu Leu
            195                 200                 205

Gly Thr Asp Val Gly Leu Pro Met Leu Met Leu Ser Arg His Ser Gln
        210                 215                 220

Asp Arg Thr Gly Gln Pro Val Glu Trp Val Arg Ser Val Tyr Arg Gly
225                 230                 235                 240

Asp Arg Tyr Lys Phe Val Ala Arg Leu Lys Arg Pro Gln Asp
            245                 250

<210> SEQ ID NO 507
<211> LENGTH: 50
<212> TYPE: PRT
<213> ORGANISM: Artificial
<220> FEATURE:
<223> OTHER INFORMATION: HTH DNA binding motif of DasR from S.
      coelicolor

<400> SEQUENCE: 507

Leu Leu Asp Met Thr Arg Thr Gln Thr Pro Gly Thr Pro Val Pro Pro
1               5                   10                  15

Glu Arg Thr Leu Ala Ala Glu Phe Asp Thr Ser Arg Thr Thr Val Arg
            20                  25                  30

Gln Ala Leu Gln Glu Leu Val Val Glu Gly Arg Leu Glu Arg Ile Gln
        35                  40                  45

Gly Lys
    50

<210> SEQ ID NO 508
<211> LENGTH: 50
<212> TYPE: PRT
<213> ORGANISM: Artificial
<220> FEATURE:
<223> OTHER INFORMATION: HTH DNA binding motif of DasR from S.
      avermitilis

<400> SEQUENCE: 508

Leu Leu Asp Met Thr Glu Thr Leu Pro Pro Gly Thr Pro Val Pro Pro
1               5                   10                  15

Glu Arg Thr Leu Ala Ala Glu Phe Asp Thr Ser Arg Thr Thr Val Arg
            20                  25                  30

Gln Ala Leu Gln Glu Leu Val Val Glu Gly Arg Leu Glu Arg Ile Gln
        35                  40                  45

Gly Lys
    50

<210> SEQ ID NO 509
<211> LENGTH: 50
<212> TYPE: PRT
<213> ORGANISM: Artificial
<220> FEATURE:
<223> OTHER INFORMATION: HTH DNA binding motif of DasR from S. griseus

<400> SEQUENCE: 509

Leu Leu Asp Met Thr Asp Thr Leu Pro Pro Gly Thr Pro Val Pro Pro

```
                1               5                  10                  15
Glu Arg Thr Leu Ala Ala Glu Phe Asp Thr Ser Arg Thr Thr Val Pro
            20                  25                  30

Gln Ala Leu Gln Glu Leu Val Val Glu Gly Arg Leu Glu Arg Ile Gln
        35                  40                  45

Gly Lys
    50

<210> SEQ ID NO 510
<211> LENGTH: 49
<212> TYPE: PRT
<213> ORGANISM: Artificial
<220> FEATURE:
<223> OTHER INFORMATION: HTH DNA binding motif of DasR from S. collinus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 510

Leu Xaa Met Thr Glu Thr Gln Ala Pro Gly Thr Pro Val Pro Pro Glu
1               5                   10                  15

Arg Thr Leu Ala Ala Glu Phe Asp Thr Ser Arg Thr Thr Val Arg Gln
            20                  25                  30

Ala Leu Gln Glu Leu Val Val Glu Gly Arg Leu Glu Arg Ile Gln Gly
        35                  40                  45

Lys

<210> SEQ ID NO 511
<211> LENGTH: 47
<212> TYPE: PRT
<213> ORGANISM: Artificial
<220> FEATURE:
<223> OTHER INFORMATION: HTH DNA binding motif of DasR from S.
      venezuelae

<400> SEQUENCE: 511

Met Thr Glu Thr Leu Pro Pro Gly Thr Pro Val Pro Pro Glu Arg Thr
1               5                   10                  15

Leu Ala Ala Glu Phe Asp Thr Ser Arg Thr Thr Val Arg Gln Ala Leu
            20                  25                  30

Gln Glu Leu Val Val Glu Gly Arg Leu Glu Arg Ile Gln Gly Lys
        35                  40                  45

<210> SEQ ID NO 512
<211> LENGTH: 47
<212> TYPE: PRT
<213> ORGANISM: Artificial
<220> FEATURE:
<223> OTHER INFORMATION: HTH DNA binding motif of DasR from S.
      granaticolor

<400> SEQUENCE: 512

Leu Thr Glu Thr Leu Pro Pro Gly Thr Pro Val Pro Pro Glu Arg Thr
1               5                   10                  15

Leu Ala Ala Glu Phe Asp Thr Ser Arg Thr Thr Val Arg Gln Ala Leu
            20                  25                  30

Gln Glu Leu Val Val Glu Gly Arg Leu Glu Arg Ile Gln Gly Lys
        35                  40                  45

<210> SEQ ID NO 513
<211> LENGTH: 44
```

```
<212> TYPE: PRT
<213> ORGANISM: Artificial
<220> FEATURE:
<223> OTHER INFORMATION: HTH DNA binding motif of DasR from S. limosus

<400> SEQUENCE: 513

Thr Leu Pro Pro Gly Thr Ser Val Pro Glu Arg Thr Leu Ala Ala
1               5                   10                  15

Lys Phe Asp Thr Ser Arg Thr Thr Val Arg Gln Ala Leu Gln Glu Leu
                20                  25                  30

Val Val Glu Gly Arg Leu Glu Arg Ile Gln Gly Lys
            35                  40

<210> SEQ ID NO 514
<211> LENGTH: 41
<212> TYPE: PRT
<213> ORGANISM: Artificial
<220> FEATURE:
<223> OTHER INFORMATION: HTH DNA binding motif of DasR from S.
      diastatochromogenes

<400> SEQUENCE: 514

Pro Gly Thr Pro Val Pro Pro Glu Arg Thr Leu Ala Ala Glu Phe Asp
1               5                   10                  15

Thr Ser Arg Thr Thr Val Arg Gln Ala Leu Gln Glu Leu Val Val Glu
                20                  25                  30

Gly Arg Leu Glu Arg Ile Gln Gly Lys
            35                  40

<210> SEQ ID NO 515
<211> LENGTH: 42
<212> TYPE: PRT
<213> ORGANISM: Artificial
<220> FEATURE:
<223> OTHER INFORMATION: HTH DNA binding motif of DasR from S.
      cinnamoneus

<400> SEQUENCE: 515

Pro Pro Gly Thr Pro Val Pro Pro Glu Arg Thr Leu Ala Ala Lys Gly
1               5                   10                  15

Asp Thr Ser Arg Thr Thr Val Arg Gln Ala Leu Gln Glu Leu Val Val
                20                  25                  30

Glu Gly Arg Leu Glu Arg Ile Gln Gly Lys
            35                  40

<210> SEQ ID NO 516
<211> LENGTH: 40
<212> TYPE: PRT
<213> ORGANISM: Artificial
<220> FEATURE:
<223> OTHER INFORMATION: HTH DNA binding motif of DasR from S.
      goldeniensis

<400> SEQUENCE: 516

Gly Thr Pro Val Pro Pro Glu Arg Thr Leu Ala Ala Glu Phe Asp Thr
1               5                   10                  15

Ser Arg Thr Thr Val Arg Gln Ala Leu Gln Glu Leu Val Val Glu Gly
                20                  25                  30

Arg Leu Glu Arg Ile Gln Gly Lys
            35                  40

<210> SEQ ID NO 517
<211> LENGTH: 39
```

```
<212> TYPE: PRT
<213> ORGANISM: Artificial
<220> FEATURE:
<223> OTHER INFORMATION: HTH DNA binding motif of DasR from S.
      ambofaciens

<400> SEQUENCE: 517

Thr Pro Val Pro Pro Glu Arg Thr Leu Pro Ala Glu Phe Asp Thr Ser
1               5                   10                  15

Arg Thr Thr Val Arg Gln Ala Leu Gln Glu Leu Val Val Glu Gly Arg
            20                  25                  30

Leu Glu Arg Ile Gln Gly Lys
        35

<210> SEQ ID NO 518
<211> LENGTH: 20
<212> TYPE: DNA
<213> ORGANISM: Artificial
<220> FEATURE:
<223> OTHER INFORMATION: redZ PCR oligo

<400> SEQUENCE: 518
cgacatgaaa gtgcaggtgg                                             20

<210> SEQ ID NO 519
<211> LENGTH: 21
<212> TYPE: DNA
<213> ORGANISM: Artificial
<220> FEATURE:
<223> OTHER INFORMATION: redZ PCR oligo

<400> SEQUENCE: 519
tcgggcttgg tcagcaaaag c                                           21

<210> SEQ ID NO 520
<211> LENGTH: 24
<212> TYPE: DNA
<213> ORGANISM: Artificial
<220> FEATURE:
<223> OTHER INFORMATION: actII-ORF4 PCR oligo

<400> SEQUENCE: 520
gctgcagacg tacgtgtacc acac                                        24

<210> SEQ ID NO 521
<211> LENGTH: 23
<212> TYPE: DNA
<213> ORGANISM: Artificial
<220> FEATURE:
<223> OTHER INFORMATION: actII-ORF4 PCR oligo

<400> SEQUENCE: 521
gcgtcgatac ggagctgcat tcc                                         23

<210> SEQ ID NO 522
<211> LENGTH: 22
<212> TYPE: DNA
<213> ORGANISM: Artificial
<220> FEATURE:
<223> OTHER INFORMATION: redD PCR oligo

<400> SEQUENCE: 522
tcatgggagt gcggagaacg cg                                          22

<210> SEQ ID NO 523
```

```
<211> LENGTH: 22
<212> TYPE: DNA
<213> ORGANISM: Artificial
<220> FEATURE:
<223> OTHER INFORMATION: redD PCR oligo

<400> SEQUENCE: 523
cgccccacag ttcgtccacc ag                                              22

<210> SEQ ID NO 524
<211> LENGTH: 22
<212> TYPE: DNA
<213> ORGANISM: Artificial
<220> FEATURE:
<223> OTHER INFORMATION: SCO6273 PCR oligo

<400> SEQUENCE: 524
cgggggcgaa ctcgtcaagg tc                                              22

<210> SEQ ID NO 525
<211> LENGTH: 24
<212> TYPE: DNA
<213> ORGANISM: Artificial
<220> FEATURE:
<223> OTHER INFORMATION: SCO6273 PCR oligo

<400> SEQUENCE: 525
gccgagatgt cgatgaggac gcgg                                            24

<210> SEQ ID NO 526
<211> LENGTH: 22
<212> TYPE: DNA
<213> ORGANISM: Artificial
<220> FEATURE:
<223> OTHER INFORMATION: kasO PCR oligo

<400> SEQUENCE: 526
gcgggatgct cagtgagcac gg                                              22

<210> SEQ ID NO 527
<211> LENGTH: 21
<212> TYPE: DNA
<213> ORGANISM: Artificial
<220> FEATURE:
<223> OTHER INFORMATION: kasO PCR oligo

<400> SEQUENCE: 527
gacgaggtcg gcgaggacgg g                                               21

<210> SEQ ID NO 528
<211> LENGTH: 22
<212> TYPE: DNA
<213> ORGANISM: Artificial
<220> FEATURE:
<223> OTHER INFORMATION: rpsI PCR oligo

<400> SEQUENCE: 528
gagaccactc ccgagcagcc gc                                              22

<210> SEQ ID NO 529
<211> LENGTH: 23
<212> TYPE: DNA
<213> ORGANISM: Artificial
<220> FEATURE:
<223> OTHER INFORMATION: rpsI PCR oligo

<400> SEQUENCE: 529
```

```
gtagcggttg tccagctcga gca                                              23
```

<210> SEQ ID NO 530
<211> LENGTH: 40
<212> TYPE: DNA
<213> ORGANISM: Artificial
<220> FEATURE:
<223> OTHER INFORMATION: SCO5085- promoter region of actII-ORF4

<400> SEQUENCE: 530

```
cacattgaaa tctgttgagt aggcctgtta ttgtcgcccc                            40
```

<210> SEQ ID NO 531
<211> LENGTH: 40
<212> TYPE: DNA
<213> ORGANISM: Artificial
<220> FEATURE:
<223> OTHER INFORMATION: SCO5881- promoter region of redZ

<400> SEQUENCE: 531

```
acaagatctt cttgaggtgg aaaccacttc gtatcagtct                            40
```

<210> SEQ ID NO 532
<211> LENGTH: 36
<212> TYPE: DNA
<213> ORGANISM: Artificial
<220> FEATURE:
<223> OTHER INFORMATION: SCO1390- cis-acting element upstream of crr

<400> SEQUENCE: 532

```
ccgtgaggag tgtggtctag acctctaatc ggaaca                                36
```

<210> SEQ ID NO 533
<211> LENGTH: 36
<212> TYPE: DNA
<213> ORGANISM: Artificial
<220> FEATURE:
<223> OTHER INFORMATION: SCO3571- cis-acting element upstream of crp

<400> SEQUENCE: 533

```
tgcggcatcc ttgtgacaga tcacactgtt tggact                                36
```